(12) United States Patent
Boyle et al.

(10) Patent No.: US 7,005,413 B1
(45) Date of Patent: Feb. 28, 2006

(54) COMBINATION THERAPY FOR CONDITIONS LEADING TO BONE LOSS

(75) Inventors: William J. Boyle, Moorpark, CA (US); David Lee Lacey, Newbury Park, CA (US); Frank J. Calzone, Westlake Village, CA (US); Ming-Shi Chang, Tainan (TW)

(73) Assignee: Amgen Inc., Thousand Oaks, CA (US)

( * ) Notice: Subject to any disclaimer, the term of this patent is extended or adjusted under 35 U.S.C. 154(b) by 265 days.

(21) Appl. No.: 09/613,591

(22) Filed: Jul. 10, 2000

Related U.S. Application Data

(63) Continuation-in-part of application No. 09/457,647, filed on Dec. 9, 1999, now abandoned, which is a continuation-in-part of application No. 09/350,670, filed on Jul. 9, 1999, now abandoned, which is a continuation-in-part of application No. 08/706,945, filed on Sep. 3, 1996, now Pat. No. 6,369,027, which is a continuation-in-part of application No. 08/577,788, filed on Dec. 22, 1995, now Pat. No. 6,613,544.

(51) Int. Cl.
*A61K 38/00* (2006.01)
*C07K 14/51* (2006.01)
*C07K 14/525* (2006.01)
*C07K 14/54* (2006.01)
*C07K 16/46* (2006.01)

(52) U.S. Cl. ............................. 514/2; 514/12; 530/399; 530/351; 530/387.1

(58) Field of Classification Search ...................... 514/2, 514/12; 530/351, 399, 387.1
See application file for complete search history.

(56) References Cited

U.S. PATENT DOCUMENTS 6,288,032 B1 * 9/2001 Boyle et al. .................. 514/12

FOREIGN PATENT DOCUMENTS

| EP | 0 784 093 A1 | 7/1997 |
|---|---|---|
| WO | WO 93/21946 | 11/1993 |
| WO | WO 98/01555 | * 1/1998 |

OTHER PUBLICATIONS

Miyagum K. Cytokines in patients with multiple sclerosis. Abstract Shinshu Igaku Zasshi 40 (6), 567–75 (1992).*
Murray et al. Abstract Recombinant human tumor necrosis factor receptor (p75) Fc fusion protein (TNFR:Fc) in rheumatoid arthritis. Ann Pharmacother Nov. 1997; 31 (11):1335–8.*
Nieves et al. High prevalence of vitamin D deficiency and reduced bone mass in multiple sclerosis. Neurology 44 (9) 1687–92 Sep. 1994.*
Martin et al. (1998), "Interleukins in the Control of Osteoclast Differentiation," *Critical Reviews™ in Eukaryotic Gene Expression* 8(2):107–123.
Roodman (1993), "Role of Cytokines in the Regulation of Bone Resorption," *Calcif Tissue Int.* 53(S1):S94–S98.

* cited by examiner

*Primary Examiner*—Elizabeth Kemmerer
*Assistant Examiner*—Regina M. DeBerry
(74) *Attorney, Agent, or Firm*—Timothy J. Gaw; Ron K. Levy; Stuart L. Watt

(57) ABSTRACT

The present invention discloses a novel secreted polypeptide, termed osteoprotegerin, which is a member of the tumor necrosis factor receptor superfamily and is involved in the regulation of bone metabolism. Also disclosed are nucleic acids encoding osteoprotegerin, polypeptides, recombinant vectors and host cells for expression, antibodies which bind OPG, and pharmaceutical compositions. The polypeptides are used to treat bone diseases characterized by increased resorption such as osteoporosis. Methods of treatment are described using the polypeptides in conjunction with various agents, including IL-1 inhibitors, TNF-α inhibitors, and serine protease inhibitors.

15 Claims, 60 Drawing Sheets

FIG.1A

```
              148    178       208       238       268       298
      FRI-1   ALLVFLDIIEWTTQETFPPKYLHYDPETGRQLLCDKCAPGTYLKQHCTVRRKTLCVPCPD
              |:|   |  ||:||  | |   ||:|| |   ||        |:    |:|  :|  |
SW:TNR2_HUMAN HALPAQVAFTPYAPEPGSTCRLREYYDQTAQMCCSKCSPGQHAKVFCTKTSDTVCDSCED
                     30        40        50        60        70        80

328
      FRI-1   YSYTDSWHTS
              :!|: |:
SW:TNR2_HUMAN STYTQLWNWVPECLSCGSRCSSDQVETQACTREQNRICTCRPGWYCALSKQEGCRLCAPL
                     90       100       110       120       130       140
```

FIG.1B

```
      FRI-1    69  YLHYDPETGRQLLCDKCAPGTYLKQHC.TVRRKTLCV.PCPDY.SYTDSW
                   |.|   |||    :| ||    |  .|  .|  |||  ||  ||.  .
TNFR profile    6  YHYYDQNGRMCEECHMCQPGHFLVKHCKQPKRDTVCHKPCEPGVTYTDDW FRI-1   116  H
                   |
TNFR profile   56  H Z Score = 8.29
```

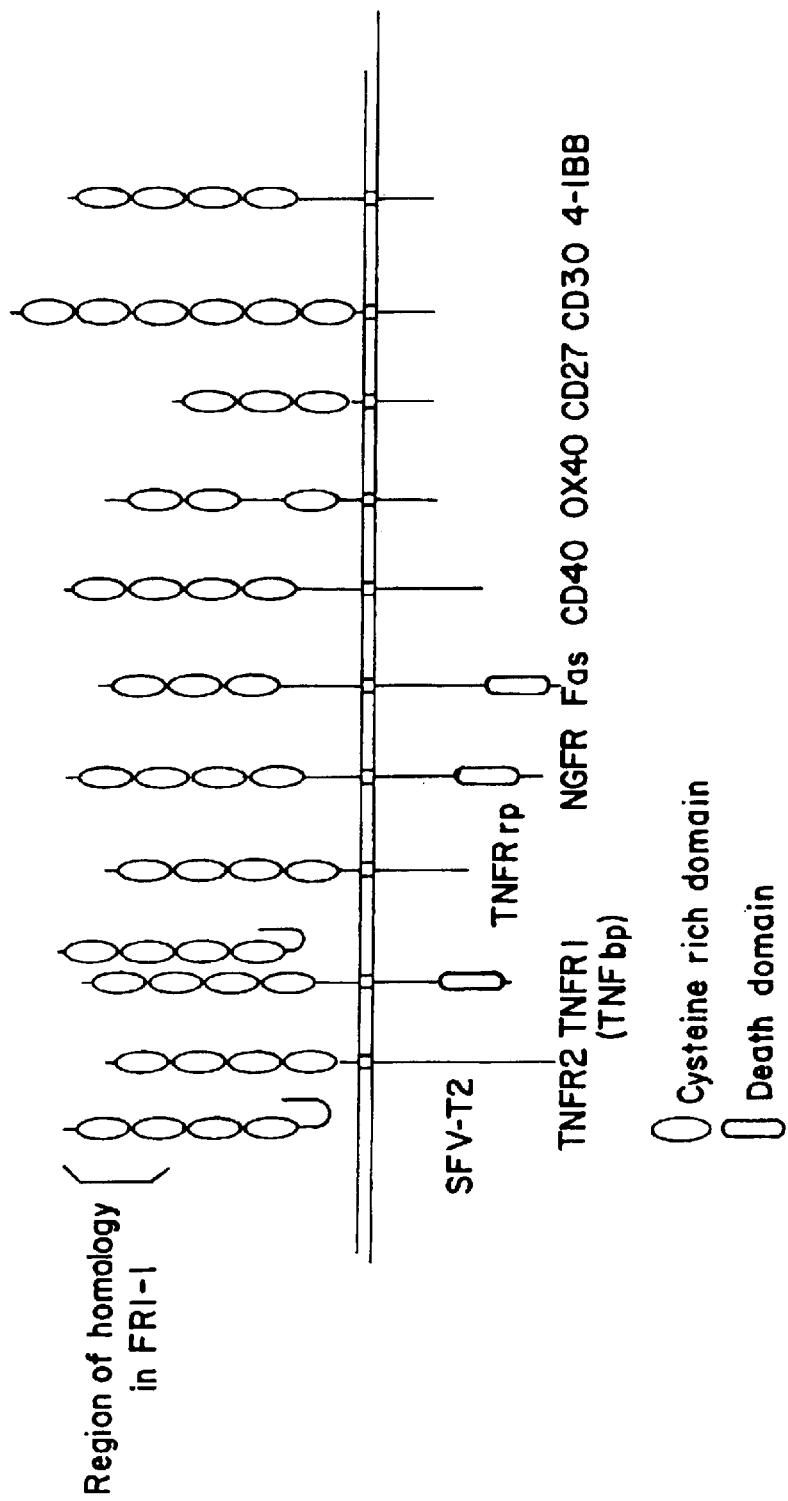

FIG.2A

AUG  TAG

```
           10                  30                   50
ATCAAAGGCAGGGCATACTTCCTGTTGCCCAGACCTTATATAAAACGTCATGTTCGCCTG
           70                  90                  110
GGCAGCAGAGAAGCACCTAGCACTGGCCCAGCGGCTGCCGCCTGAGGTTTCCAGAGGACC
          130                 150                  170
ACAATGAACAAGTGGCTGTGCTGTGCACTCCTGGTGTTCTTGGACATCATTGAATGGACA
    M   N   K   W   L   C   C   A   L   L   V   F   L   D   I   I   E   W   T
          190                 210                  230
ACCCAGGAAACCTTTCCTCCAAAATACTTGCATTATGACCCAGAAACCGGACGTCAGCTC
  T   Q   E   T   F   P   P   K   Y   L   H   Y   D   P   E   T   G   R   Q   L
          250                 270                  290
TTGTGTGACAAATGTGCTCCTGGCACCTACCTAAAACAGCACTGCACAGTCAGGAGGAAG
  L   C   D   K   C   A   P   G   T   Y   L   K   Q   H   C   T   V   R   R   K
          310                 330                  350
ACACTGTGTGTCCCTTGCCCTGACTACTCTTATACAGACAGCTGGCACACGAGTGATGAA
  T   L   C   V   P   C   P   D   Y   S   Y   T   D   S   W   H   T   S   D   E
          370                 390                  410
TGCGTGTACTGCAGCCCCGTGTGCAAGGAACTGCAGACCGTGAAACAGGAGTGCAACCGC
  C   V   Y   C   S   P   V   C   K   E   L   Q   T   V   K   Q   E   C   N   R
          430                 450                  470
ACCCACAACCGAGTGTGCGAATGTGAGGAAGGGCGCTACCTGGAGCTCGAATTCTGCTTG
  T   H   N   R   V   C   E   C   E   E   G   R   Y   L   E   L   E   F   C   L
          490                 510                  530
AAGCACCGGAGCTGTCCCCCAGGCTTGGGTGTGCTGCAGGCTGGGACCCCAGAGCGAAAC
  K   H   R   S   C   P   P   G   L   G   V   L   Q   A   G   T   P   E   R   N
          550                 570                  590
ACGGTTTGCAAAAGATGTCCGGATGGGTTCTTCTCAGGTGAGACGTCATCGAAAGCACCC
  T   V   C   K   R   C   P   D   G   F   F   S   G   E   T   S   S   K   A   P
          610                 630                  650
TGTAGGAAACACACCAACTGCAGCTCACTTGGCCTCCTGCTAATTCAGAAAGGAAATGCA
  C   R   K   H   T   N   C   S   S   L   G   L   L   L   I   Q   K   G   N   A
          670                 690                  710
ACACATGACAATGTATGTTCCGGAAACAGAGAAGCAACTCAAAATTGTGGAATAGATGTC
  T   H   D   N   V   C   S   G   N   R   E   A   T   Q   N   C   G   I   D   V
          730                 750                  770
ACCCTGTGCGAAGAGGCATTCTTCAGGTTTGCTGTGCCTACCAAGATTATACCGAATTGG
  T   L   C   E   E   A   F   F   R   F   A   V   P   T   K   I   I   P   N   W
          790                 810                  830
CTGAGTGTTCTGGTGGACAGTTTGCCTGGGACCAAAGTGAATGCAGAGAGTGTAGAGAGG
  L   S   V   L   V   D   S   L   P   G   T   K   V   N   A   E   S   V   E   R
          850                 870                  890
ATAAAACGGAGACACAGCTCGCAAGAGCAAACTTTCCAGCTACTTAAGCTGTGGAAGCAT
  I   K   R   R   H   S   S   Q   E   Q   T   F   Q   L   L   K   L   W   K   H
          910                 930                  950
CAAAACAGAGACCAGGAAATGGTGAAGAAGATCATCCAAGACATTGACCTCTGTGAAAGC
  Q   N   R   D   Q   E   M   V   K   K   I   I   Q   D   I   D   L   C   E   S
          970                 990                 1010
AGTGTGCAACGGCATATCGGCCACGCGAACCTCACCACAGAGCAGCTCCGCATCTTGATG
  S   V   Q   R   H   I   G   H   A   N   L   T   T   E   Q   L   R   I   L   M
```

FIG. 2C

```
              1030                  1050                  1070
GAGAGCTTGCCTGGGAAGAAGATCAGCCCAGACGAGATTGAGAGAACGAGAAAGACCTGC
 E   S   L   P   G   K   K   I   S   P   D   E   I   E   R   T   R   K   T   C
              1090                  1110                  1130
AAACCCAGCGAGCAGCTCCTGAAGCTACTGAGCTTGTGGAGGATCAAAAATGGAGACCAA
 K   P   S   E   Q   L   L   K   L   L   S   L   W   R   I   K   N   G   D   Q
              1150                  1170                  1190
GACACCTTGAAGGGCCTGATGTACGCACTCAAGCACTTGAAAGCATACCACTTTCCCAAA
 D   T   L   K   G   L   M   Y   A   L   K   H   L   K   A   Y   H   F   P   K
              1210                  1230                  1250
ACCGTCACCCACAGTCTGAGGAAGACCATCAGGTTCTTGCACAGCTTCACCATGTACCGA
 T   V   T   H   S   L   R   K   T   I   R   F   L   H   S   F   T   M   Y   R
              1270                  1290                  1310
TTGTATCAGAAACTCTTTCTAGAAATGATAGGGAATCAGGTTCAATCAGTGAAGATAAGC
 L   Y   Q   K   L   F   L   E   M   I   G   N   Q   V   Q   S   V   K   I   S
              1330                  1350                  1370
TGCTTATAGTTAGGAATGGTCACTGGGCTGTTTCTTCAGGATGGGCCAACACTGATGGAG
 C   L
              1390                  1410                  1430
CAGATGGCTGCTTCTCCGGCTCTTGAAATGGCAGTTGATTCCTTTCTCATCAGTTGGTGG
              1450                  1470                  1490
GAATGAAGATCCTCCAGCCCAACACACACTGGGGAGTCTGAGTCAGGAGAGTGAGGCA
              1510                  1530                  1550
GGCTATTTGATAATTGTGCAAAGCTGCCAGGTGTACACCTAGAAAGTCAAGCACCCTGAG
              1570                  1590                  1610
AAAGAGGATATTTTTATAACCTCAAACATAGGCCCTTTCCTTCCTCTCCTTATGGATGAG
              1630                  1650                  1670
TACTCAGAAGGCTTCTACTATCTTCTGTGTCATCCCTAGATGAAGGCCTCTTTTATTTAT
              1690                  1710                  1730
TTTTTTATTCTTTTTTTCGGAGCTGGGACCGAACCCAGGGCCTTGCGCTTGCGAGGCAA
              1750                  1770                  1790
GTGCTCTACCACTGAGCTAAATCTCCAACCCCTGAAGGCCTCTTTCTTTCTGCCTCTGAT
              1810                  1830                  1850
AGTCTATGACATTCTTTTTTCTACAATTCGTATCAGGTGCACGAGCCTTATCCCATTTGT
              1870                  1890                  1910
AGGTTTCTAGGCAAGTTGACCGTTAGCTATTTTTCCCTCTGAAGATTTGATTCGAGTTGC
              1930                  1950                  1970
AGACTTGGCTAGACAAGCAGGGGTAGGTTATGGTAGTTTATTTAACAGACTGCCACCAGG
              1990                  2010                  2030
AGTCCAGTGTTTCTTGTTCCTCTGTAGTTGTACCTAAGCTGACTCCAAGTACATTTAGTA
              2050                  2070                  2090
TGAAAAATAATCAACAAATTTTATTCCTTCTATCAACATTGGCTAGCTTTGTTTCAGGGC
              2110                  2130                  2150
ACTAAAAGAAACTACTATATGGAGAAAGAATTGATATTGCCCCAACGTTCAACAACCCA
              2170                  2190                  2210
ATAGTTTATCCAGCTGTCATGCCTGGTTCAGTGTCTACTGACTATGCGCCCTCTTATTAC
              2230                  2250                  2270
TGCATGCAGTAATTCAACTGGAAATAGTAATAATAATAATAGAAATAAAATCTAGACTCC
              2290                  2310                  2330
ATTGGATCTCTCTGAATATGGGAATATCTAACTTAAGAAGCTTTGAGATTTCAGTTGTGT
              2350                  2370                  2390
TAAAGGCTTTTATTAAAAAGCTGATGCTCTTCTGTAAAAGTTACTAATATATCTGTAAGA
              2410                  2430
CTATTACAGTATTGCTATTTATATCCATCCAG
```

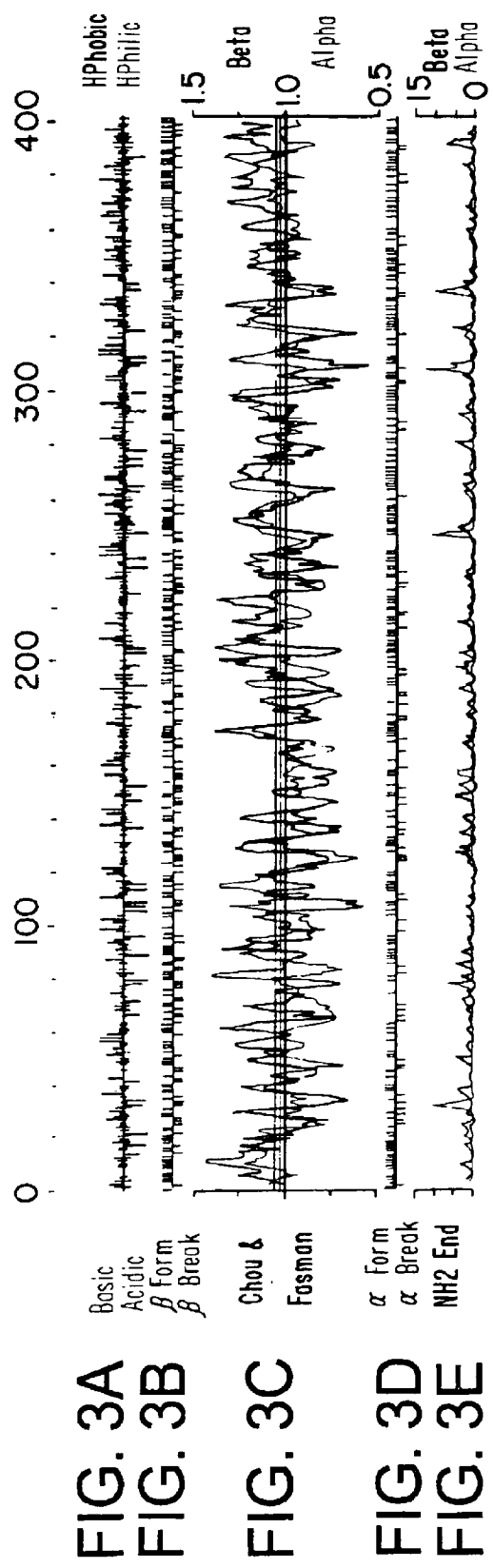

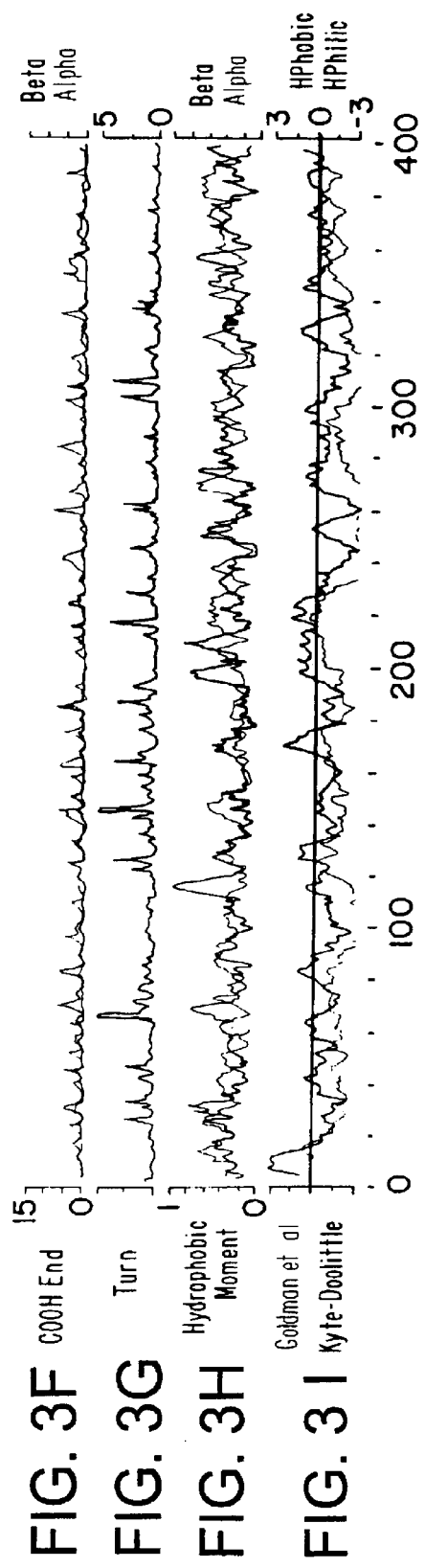

| 2 11 16 17 22 28 33 38 45 | Kb | 1 12 18 30 |

Transgenic Founders          Controls

FIG.9A

```
            10                  30                  50
CCTTATATAARACGTCATGATTGCCTGGGCTGCAGAGACGCACCTAGCACTGACCCAGCG
            70                  90                 110
GCTGCCTCCTGAGGTTTCCCGAGGACCACAATGAACAAGTGGCTGTGCTGCGCACTCCTG
                                       M  N  K  W  L  C  C  A  L  L
           130                 150                 170
GTGCTCCTGGACATCATTGAATGGACAACCCAGGAAACCCTTCCTCCAAAGTACTTGCAT
 V  L  L  D  I  I  E  W  T  T  Q  E  T  L  P  P  K  Y  L  H
           190                 210                 230
TATGACCCAGAAACTGGTCATCAGCTCCTGTGTGACAAATGTGCTCCTGGCACCTACCTA
 Y  D  P  E  T  G  H  Q  L  L  C  D  K  C  A  P  G  T  Y  L
           250                 270                 290
AAACAGCACTGCACAGTGAGGAGGAAGACATTGTGTGTCCCTTGCCCTGACCACTCTTAT
 K  Q  H  C  T  V  R  R  K  T  L  C  V  P  C  P  D  H  S  Y
           310                 330                 350
ACGGACAGCTGGCACACCAGTGATGAGTGTGTGTATTGCAGCCCAGTGTGCAAGGAACTG
 T  D  S  W  H  T  S  D  E  C  V  Y  C  S  P  V  C  K  E  L
           370                 390                 410
CAGTCCGTGAAGCAGGAGTGCAACCGCACCCACAACCGAGTGTGTGAGTGTGAGGAAGGG
 Q  S  V  K  Q  E  C  N  R  T  H  N  R  V  C  E  C  E  E  G
           430                 450                 470
CGTTACCTGGAGATCGAATTCTGCTTGAAGCACCGGAGCTGTCCCCCGGGCTCCGGCGTG
 R  Y  L  E  I  E  F  C  L  K  H  R  S  C  P  P  G  S  G  V
           490                 510                 530
GTGCAAGCTGGAACCCCAGAGCGAAACACAGTTTGCAAAAAATGTCCAGATGGGTTCTTC
 V  Q  A  G  T  P  E  R  N  T  V  C  K  K  C  P  D  G  F  F
           550                 570                 590
TCAGGTGAGACTTCATCGAAAGCACCCTGTATAAAACACACGAACTGCAGCACATTTGGC
 S  G  E  T  S  S  K  A  P  C  I  K  H  T  N  C  S  T  F  G
           610                 630                 650
CTCCTGCTAATTCAGAAAGGAAATGCAACACATGACAACGTGTGTTCCGGAAACAGAGAA
 L  L  L  I  Q  K  G  N  A  T  H  D  N  V  C  S  G  N  R  E
           670                 690                 710
GCCACGCAAAAGTGTGGAATAGATGTCACCCTGTGTGAAGAGGCCTTCTTCAGGTTTGCT
 A  T  Q  K  C  G  I  D  V  T  L  C  E  E  A  F  F  R  F  A
           730                 750                 770
GTTCCTACCAAGATTATACCAAATTGGCTGAGTGTTTTGGTGGACAGTTTGCCTGGGACC
 V  P  T  K  I  I  P  N  W  L  S  V  L  V  D  S  L  P  G  T
```

FIG.9B

```
         790                810                830
AAAGTGAATGCCGAGAGTGTAGAGAGGATAAAACGGAGACACAGCTCACAAGAGCAAACC
  K  V  N  A  E  S  V  E  R  I  K  R  R  H  S  S  Q  E  Q  T
         850                870                890
TTCCAGCTGCTGAAGCTGTGGAAACATCAAAACAGAGACCAGGAAATGGTGAAGAAGATC
  F  Q  L  L  K  L  W  K  H  Q  N  R  D  Q  E  M  V  K  K  I
         910                930                950
ATCCAAGACATTGACCTCTGTGAAAGCAGCGTGCAGCGGCATCTCGGCCACTCGAACCTC
  I  Q  D  I  D  L  C  E  S  S  V  Q  R  H  L  G  H  S  N  L
         970                990               1010
ACCACAGAGCAGCTTCTTGCCTTGATGGAGAGCCTGCCTGGGAAGAAGATCAGCCCAGAA
  T  T  E  Q  L  L  A  L  M  E  S  L  P  G  K  K  I  S  P  E
        1030               1050               1070
GAGATTGAGAGAACGAGAAAGACCTGCAAATCGAGCGAGCAGCTCCTGAAGCTACTCAGT
  E  I  E  R  T  R  K  T  C  K  S  E  Q  L  L  K  L  L  S
        1090               1110               1130
TTATGGAGGATCAAAAATGGTGACCAAGACACCTTGAAGGGCCTGATGTATGCCCTCAAG
  L  W  R  I  K  N  G  D  Q  D  T  L  K  G  L  M  Y  A  L  K
        1150               1170               1190
CACTTGAAAACATCCCACTTTCCCAAAACTGTCACCCACAGTCTGAGGAAGACCATGAGG
  H  L  K  T  S  H  F  P  K  T  V  T  H  S  L  R  K  T  M  R
        1210               1230               1250
TTCCTGCACAGCTTCACAATGTACAGACTGTATCAGAAGCTCTTTTTAGAAATGATAGGG
  F  L  H  S  F  T  M  Y  R  L  Y  Q  K  L  F  L  E  M  I  G
        1270               1290               1310
AATCAGGTTCAATCCGTGAAAATAAGCTGCTTATAACTAGGAATGGTCACTGGGCTGTTT
  N  Q  V  Q  S  V  K  I  S  C  L

CTTCA
```

FIG. 9C

```
       10                 30                  50
GTATATATAACGTGATGAGCGTACGGGTGCGGAGACGCACCGGAGCGCTCGCCCAGCCGC
       70                 90                 110
CGYCTCCAAGCCCCTGAGGTTTCCGGGGACCACAATGAACAAGTTGCTGTGCTGCGCGCT
                                     M  N  K  L  L  C  C  A  L
      130                150                 170
CGTGTTTCTGGACATCTCCATTAAGTGGACCACCCAGGAAACGTTTCCTCCAAAGTACCT
 V  F  L  D  I  S  I  K  W  T  T  Q  E  T  F  P  P  K  Y  L
      190                210                 230
TCATTATGACGAAGAAACCTCTCATCAGCTGTTGTGTGACAAATGTCCTCCTGGTACCTA
 H  Y  D  E  E  T  S  H  Q  L  L  C  D  K  C  P  P  G  T  Y
      250                270                 290
CCTAAAACAACACTGTACAGCAAAGTGGAAGACCGTGTGCGCCCCTTGCCCTGACCACTA
 L  K  Q  H  C  T  A  K  W  K  T  V  C  A  P  C  P  D  H  Y
      310                330                 350
CTACACAGACAGCTGGCACACCAGTGACGAGTGTCTATACTGCAGCCCCGTGTGCAAGGA
 Y  T  D  S  W  H  T  S  D  E  C  L  Y  C  S  P  V  C  K  E
      370                390                 410
GCTGCAGTACGTCAAGCAGGAGTGCAATCGCACCCACAACCGCGTGTGCGAATGCAAGGA
 L  Q  Y  V  K  Q  E  C  N  R  T  H  N  R  V  C  E  C  K  E
      430                450                 470
AGGGCGCTACCTTGAGATAGAGTTCTGCTTGAAACATAGGAGCTGCCCTCCTGGATTTGG
 G  R  Y  L  E  I  E  F  C  L  K  H  R  S  C  P  P  G  F  G
      490                510                 530
AGTGGTGCAAGCTGGAACCCCAGAGCGAAATACAGTTTGCAAAAGATGTCCAGATGGGTT
 V  V  Q  A  G  T  P  E  R  N  T  V  C  K  R  C  P  D  G  F
      550                570                 590
CTTCTCAAATGAGACGTCATCTAAAGCACCCTGTAGAAAACACACAAATTGCAGTGTCTT
 F  S  N  E  T  S  S  K  A  P  C  R  K  H  T  N  C  S  V  F
      610                630                 650
TGGTCTCCTGCTAACTCAGAAAGGAAATGCAACACACGACAACATATGTTCCGGAAACAG
 G  L  L  L  T  Q  K  G  N  A  T  H  D  N  I  C  S  G  N  S
      670                690                 710
TGAATCAACTCAAAAATGTGGAATAGATGTTACCCTGTGTGAGGAGGCATTCTTCAGGTT
 E  S  T  Q  K  C  G  I  D  V  T  L  C  E  E  A  F  F  R  F
      730                750                 770
TGCTGTTCCTACAAAGTTTACGCCTAACTGGCTTAGTGTCTTGGTAGACAATTTGCCTGG
 A  V  P  T  K  F  T  P  N  W  L  S  V  L  V  D  N  L  P  G
```

FIG.9D

```
            790                   810                   830
CACCAAAGTAAACGCAGAGAGTGTAGAGAGGATAAAACGGCAACACAGCTCACAAGAACA
  T  K  V  N  A  E  S  V  E  R  I  K  R  Q  H  S  S  Q  E  Q
            850                   870                   890
GACTTTCCAGCTGCTGAAGTTATGGAAACATCAAAACAAAGACCAAGATATAGTCAAGAA
  T  F  Q  L  L  K  L  W  K  H  Q  N  K  D  Q  D  I  V  K  K
            910                   930                   950
GATCATCCAAGATATTGACCTCTGTGAAAACAGCGTGCAGCGGCACATTGGACATGCTAA
  I  I  Q  D  I  D  L  C  E  N  S  V  Q  R  H  I  G  H  A  N
            970                   990                   1010
CCTCACCTTCGAGCAGCTTCGTAGCTTGATGGAAAGCTTACCGGGAAAGAAAGTGGGAGC
  L  T  F  E  Q  L  R  S  L  M  E  S  L  P  G  K  K  V  G  A
            1030                  1050                  1070
AGAAGACATTGAAAAAACAATAAAGGCATGCAAACCCAGTGACCAGATCCTGAAGCTGCT
  E  D  I  E  K  T  I  K  A  C  K  P  S  D  Q  I  L  K  L  L
            1090                  1110                  1130
CAGTTTGTGGCGAATAAAAAATGGCGACCAAGACACCTTGAAGGGCCTAATGCACGCACT
  S  L  W  R  I  K  N  G  D  Q  D  T  L  K  G  L  M  H  A  L
            1150                  1170                  1190
AAAGCACTCAAAGACGTACCACTTTCCCAAAACTGTCACTCAGAGTCTAAAGAAGACCAT
  K  H  S  K  T  Y  H  F  P  K  T  V  T  Q  S  L  K  K  T  I
            1210                  1230                  1250
CAGGTTCCTTCACAGCTTCACAATGTACAAATTGTATCAGAAGTTATTTTTAGAAATGAT
  R  F  L  H  S  F  T  M  Y  K  L  Y  Q  K  L  F  L  E  M  I
            1270                  1290                  1310
AGGTAACCAGGTCCAATCAGTAAAAATAAGCTGCTTATAACTGGAAATGGCCATTGAGCT
  G  N  Q  V  Q  S  V  K  I  S  C  L
            1330                  1350
GTTTCCTCACAATTGGCGAGATCCCATGGATGATAA
```

FIG. 9E

```
                                                                                                              50
musteo.frg  MNKWLCCALLVLLDIIEWTTQETLPPKYLHYDPETGHQLLCDLCDKCAPGTYL           50
ratosteo.frg MNKWLCCALLVLLDIIEWTTQETLPPKYLHYDPETGRQLLCDLCDKCAPGTYL          50
huosteo.frg  MNKLLCCALVFLDISIKWTQETFPPKYLHYDDEETSHQLLCDLCDKCPPGTYL           50

100
musteo.frg  KQHCTVRRKTLCCVPCPDHSYTDSWHTSDECVYCSPVCKELQSVKQECNRT             100
ratosteo.frg KQHCTVRRKTLCCVPCPDYSYTDSWHTSDECVYCSPVCKELQIVKQECNRT             100
huosteo.frg  KQHCTAKWKTVCAPCPDHYYTDSWHTSDECLYCSPVCKELQYRQECNRT               100

150
musteo.frg  HNRVCECEEGRYLEIEFCLKHRSCPPGSGVVQAGTPERNTVCKKCPDGFF              150
ratosteo.frg HNRVCECEEGRYLEIEFCLKHRSCPPGLGVVQAGTPERNTVCKRCPDGFF              150
huosteo.frg  HNRVCECREGRYLEIEFCLKHRSCPPGEGVVQAGIPERNTVCKRCPDGFF              150

200
musteo.frg  SGETSSKAPCIKHTNCSIFGLLLQLLQKGNATHDNVCSGNREATQKCGIDVT            200
ratosteo.frg SGETSSKAPCRKKHTNCSLLGLLLQLLHQKGNATHDNVCSGNREATQNCGIDVT          200
huosteo.frg  SNETSSKAPCRKKHTNCSVFGLLLTQKGNATHDNICSGNSESTQKCGIDVT             200
```

FIG.9F

```
                                                                                                    250
muosteo.frg   LCEEAFFRFAVPTKIIPNWLSVLVDSLPGTKVNAESVERIKRRHSSQET          250
ratosteo.frg  LCEEAFFRFAVPTKIIPNWLSVLVDSLPGTKVNAESVERIKRRHSSQET          250
huosteo.frg   LCEEAFFRFAVPTKFTPNWLSVLVDNLPGTKVNAESVERIKRQHSSQET          250

300
muosteo.frg   FQLLKLWKHQNRDQEMVKKIIQDIDLCESSVQRHLGHSNLTTEQLLALME         300
ratosteo.frg  FQLLKLWKHQNRDQEMVKKIIQDIDLCESSVQRHIGHANLTTEQLRIHME         300
huosteo.frg   FQLLKLWKHQNKDQDTIVKKIIQDIDLCENSVQRHIGHANLFFEQLRSLME        300

350
muosteo.frg   SLPGKKISPEEIERTRKTCKSSEQLLKLLSLWRIKNGDQDTLKGLMYALK         350
ratosteo.frg  SLPGKKISPDEIERTRKTCKPSSEQLLKLLSLWRIKNGDQDTLKGLMYALK        350
huosteo.frg   SLPGKKVGAEDIEKTIKACKPSDQTLKLLSLWRIKNGDQDTLKGLMHALK         350

400
muosteo.frg   HLKTSHFPKTVTHSLRKTMRFLHSFTMYRLYQKLFLEMIGNQVQSVKISC         400
ratosteo.frg  HLKAYHFPKTVTHSLRKTIRFLHSFTMYRLYQKLFLEMIGNQVQSVKISC         400
huosteo.frg   HSKTYHFPKTVTQSLKKTIRFLHSFTMYKLYQKLFLEMIGNQVQSVKISC         400

401
muosteo.frg   L                                                          401
ratosteo.frg  L                                                          401
huosteo.frg   L                                                          401
```

FIG.10

```
ltnrr   CPQ-GKYIHPQNNSICCTKCHKGTYLYNDCPGPGQDTDCRECESGSFTAS    49
humoste PPKYLHYDEETSHQLLCDKCPPGTYLKQHCTAK-WKTVCAPCPDHYTDS    49 ltnrr   ENHLRHCLSCS-KCRKEMGQVEISSCTVDRDTVCGCRKNQYRHYWSENLF    98
humoste WHTSDECLYCSPVC-KELQYVK-QECNRTHNRVCECKEGRYLEI--E-F    93 ltnrr   QCFNCSLCLNG-TVHLSCQEKQNTVCT-CHAGFFLRE---NECVSC      139
humoste -CLKHRSCPPGFGVVQAGTPERNTVCKRCPDGFFSNETSSKAPCRKH      139
```

FIG. 12B

```
195-CGIDVTLCEEAFFRFAVPTKFTPNWLSVLVDNLPGTKVNAESVERIKRQHSS-246
195-CGIDVTLCEEAFFRFAVPTKFTPNWLSVLVDSLPGTKVNAESVERIKRRHSS-246

247-QEQTFQLLKLWKHQNKDQDIVKKIIQDIDLCENSVQRHIGHANLTPEQLRSL-298
247-QEQTFQLLKLWKHQNRDQEMVKKIIQDIDLCESSVQRHLGHSNLTTEQLLAL-298

299-MESLPGKKVGAEDIEKTIKACKPSDQILKLLSLWRIKNGDQDTLKGLMHALK-350
299-MESLPGKKISPEEIERTRKTCKSSEQLLKLLSLWRIKNGDQDTLKGLMYALK-350

351-HSKTYHFPKTVTQSLKKTIRFLHSFTMYKLYQKLFLEMIGNQVSVKISCL-401
351-HLKTSHFPKTVTHSLRKTMRFLHSFTMYRLYQKLFLEMIGNQVSVKISCL-401
```

C TERMINAL

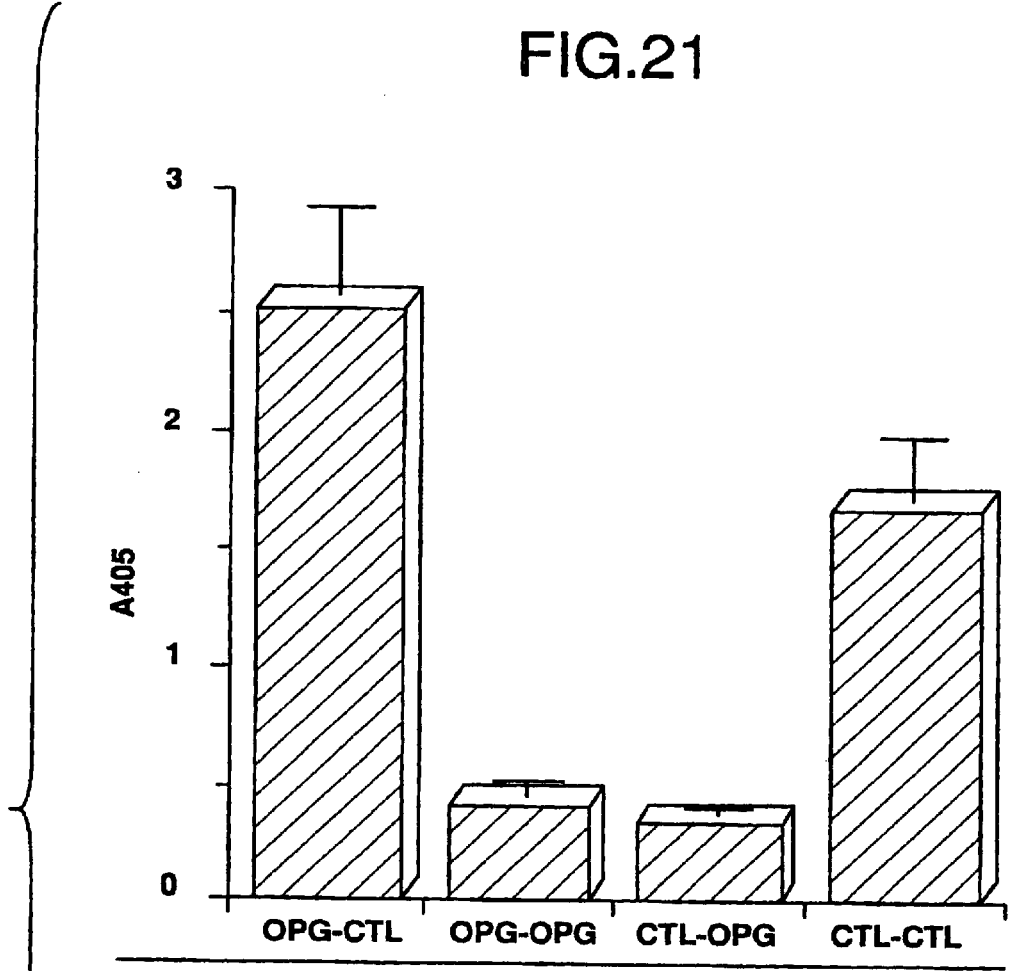

* Different to PBS, p < 0.05
Different to OPG + IL1, p < 0.05

FIG.24A
FIG.24B

* Different to control p < 0.01

* Different to OVX p < 0.05

FIG. 29A

```
           DraIII
              |
     CATGGGAAATGTCAGAGTGGAGAACCACACCGAGTGCCACTGCAGCACTTGTTATTATCA
  1  --------+---------+---------+---------+---------+---------+  60
     GTACCCTTTACAGTCTCACCTCTTGGTGTGGCTCACGGTGACGTCGTGAACAATAATAGT

CAAATCCTAATAGTTTGCAGTGGGCCTTGCTGATGATGGCTGACTTGCTCAAAAGGAAAA
 61  --------+---------+---------+---------+---------+---------+ 120
     GTTTAGGATTATCAAACGTCACCCGGAACGACTACTACCGACTGAACGAGTTTTCCTTTT

TTAATTTGTCCAGTGTCTATGGCTTTGTGAGATAAAACCCTCCTTTTCCTTGCCATACCA
121  --------+---------+---------+---------+---------+---------+ 180
     AATTAAACAGGTCACAGATACCGAAACACTCTATTTTGGGAGGAAAAGGAACGGTATGGT

TTTTTAACCTGCTTTGAGAATATACTGCAGCTTTATTGCTTTTCTCCTTATCCTACAATA
181  --------+---------+---------+---------+---------+---------+ 240
     AAAAATTGGACGAAACTCTTATATGACGTCGAAATAACGAAAAGAGGAATAGGATGTTAT

TAATCAGTAGTCTTGATCTTTTCATTTGGAATGAAATATGGCATTTAGCATGACCATAAA
241  --------+---------+---------+---------+---------+---------+ 300
     ATTAGTCATCAGAACTAGAAAAGTAAACCTTACTTTATACCGTAAATCGTACTGGTATTT

AAGCTGATTCCACTGGAAATAAAGTCTTTTAAATCATCACTCTATCACTGAATTCTAATT
301  --------+---------+---------+---------+---------+---------+ 360
     TTCGACTAAGGTGACCTTTATTTCAGAAAATTTAGTAGTGAGATAGTGACTTAAGATTAA

TTTTCTGAAAAGTTTCAAGCCAGTTACTTTTGATAGGATTAACGGAAGGGAGTGAGCCAG
361  --------+---------+---------+---------+---------+---------+ 420
     AAAAGACTTTTCAAAGTTCGGTCAATGAAAACTATCCTAATTGCCTTCCCTCACTCGGTC

XcmI
              |
     TGGGTGAGGTGGGTTCCCATGTAGTCAATGGCCTAATACTGGAGAATCTTATTCTAACCA
421  --------+---------+---------+---------+---------+---------+ 480
     ACCCACTCCACCCAAGGGTACATCAGTTACCGGATTATGACCTCTTAGAATAAGATTGGT

AGCCTTCCAGAGCAAGCTGTGAGCCCCTCAGACAGTGGGCTACTCATGAGACAGTCCATT
481  --------+---------+---------+---------+---------+---------+ 540
     TCGGAAGGTCTCGTTCGACACTCGGGGAGTCTGTCACCCGATGAGTACTCTGTCAGGTAA

GGGGTAAAGGAAGAAAATATAACTTCTATTTCTATTCATTTGCACATTGTCTTTAGATGC
541  --------+---------+---------+---------+---------+---------+ 600
     CCCCATTTCCTTCTTTTATATTGAAGATAAAGATAAGTAAACGTGTAACAGAAATCTACG

CCATTTGGGTGAGTTTTATAGAAGTACAGCTACATTAAAAAATAGAACTGATAATAGATA
601  --------+---------+---------+---------+---------+---------+ 660
     GGTAAACCCACTCAAAATATCTTCATGTCGATGTAATTTTTATCTTGACTATTATCTAT
```

FIG. 29B

```
        AGGCTTTAAAAAAACTTCATTCATCACCAGTTTGTCAAGATTCCATTTCAAAGTGAAAAA
661     ---------+---------+---------+---------+---------+---------+  720
        TCCGAAATTTTTTTGAAGTAAGTAGTGGTCAAACAGTTCTAAGGTAAAGTTTCACTTTTT

CCAATTTCTAACGGGTTGGTAAACACAGCAGATGGCAGGGTGAAAAATTAAAGTGAGTGC
721     ---------+---------+---------+---------+---------+---------+  780
        GGTTAAAGATTGCCCAACCATTTGTGTCGTCTACCGTCCCACTTTTTAATTTCACTCACG

ATGTACCTTTAAAGAAACACTGAAATGCACACACATTACTTAACCTGCTCATTCATTTAT
781     ---------+---------+---------+---------+---------+---------+  840
        TACATGGAAATTTCTTTGTGACTTTACGTGTGTGTAATGAATTGGACGAGTAAGTAAATA

TTACATATAGTCTTGGGTGTACAAAATTTAGAAATAAATACATATGGGGCGGGGCCTTA
841     ---------+---------+---------+---------+---------+---------+  900
        AATGTATATCAGAACCCACATGTTTTAAATCTTTATTTATGTATACCCCGCCCCGGAAT

GCTGCACAAATAGGATGCGCGGCGGGCCTTGGTAGGGGCGGAGCCTTAGCTGCACAAATA
901     ---------+---------+---------+---------+---------+---------+  960
        CGACGTGTTTATCCTACGCGCCGCCCGGAACCATCCCCGCCTCGGAATCGACGTGTTTAT

GGATGCGCGGCGGGCCTTGGTGGGGCGGGGCCTAAGCTGCGCAAGTGGTACACAGCTCA
961     ---------+---------+---------+---------+---------+---------+  1020
        CCTACGCGCCGCCCGGAACCACCCCCGCCCCGGATTCGACGCGTTCACCATGTGTCGAGT

GGGCTGCGATTTCGCGCCAAACTTGACGGCAATCCTAGCGTGAAGGCTGGTAGGATTTTA
1021    ---------+---------+---------+---------+---------+---------+  1080
        CCCGACGCTAAAGCGCGGTTTGAACTGCCGTTAGGATCGCACTTCCGACCATCCTAAAAT

TCCCCGCTGCCATCATGGTTCGACCATTGAACTGCATCGTCGCCGTGTCCCAAAATATGG
1081    ---------+---------+---------+---------+---------+---------+  1140
        AGGGGCGACGGTAGTACCAAGCTGGTAACTTGACGTAGCAGCGGCACAGGGTTTTATACC

GGATTGGCAAGAACGGAGACCTACCCTGGCCTCCGCTCAGGAACGAGTTCAAGTACTTCC
1141    ---------+---------+---------+---------+---------+---------+  1200
        CCTAACCGTTCTTGCCTCTGGATGGGACCGGAGGCGAGTCCTTGCTCAAGTTCATGAAGG

AAAGAATGACCACAACCTCTTCAGTGGAAGGTAAACAGAATCTGGTGATTATGGGTAGGA
1201    ---------+---------+---------+---------+---------+---------+  1260
        TTTCTTACTGGTGTTGGAGAAGTCACCTTCCATTTGTCTTAGACCACTAATACCCATCCT

AAACCTGGTTCTCCATTCCTGAGAAGAATCGACCTTTAAAGGACAGAATTAATATAGTTC
1261    ---------+---------+---------+---------+---------+---------+  1320
        TTTGGACCAAGAGGTAAGGACTCTTCTTAGCTGGAAATTTCCTGTCTTAATTATATCAAG

SacI         BstXI
                    |             |
        TCAGTAGAGAACTCAAAGAACCACCACGAGGAGCTCATTTTCTTGCCAAAAGTTTGGATG
1321    ---------+---------+---------+---------+---------+---------+  1380
        AGTCATCTCTTGAGTTTCTTGGTGGTGCTCCTCGAGTAAAAGAACGGTTTTCAAACCTAC
```

FIG. 29C

```
AflII
 |
     ATGCCTTAAGACTTATTGAACAACCGGAATTGGCAAGTAAAGTAGACATGGTTTGGATAG
1381 ---------+---------+---------+---------+---------+---------+ 1440
     TACGGAATTCTGAATAACTTGTTGGCCTTAACCGTTCATTTCATCTGTACCAAACCTATC

TCGGAGGCAGTTCTGTTTACCAGGAAGCCATGAATCAACCAGGCCACCTCAGACTCTTTG
1441 ---------+---------+---------+---------+---------+---------+ 1500
     AGCCTCCGTCAAGACAAATGGTCCTTCGGTACTTAGTTGGTCCGGTGGAGTCTGAGAAAC

TGACAAGGATCATGCAGGAATTTGAAAGTGACACGTTTTTCCCAGAAATTGATTTGGGGA
1501 ---------+---------+---------+---------+---------+---------+ 1560
     ACTGTTCCTAGTACGTCCTTAAACTTTCACTGTGCAAAAAGGGTCTTTAACTAAACCCCT

AATATAAACTTCTCCCAGAATACCCAGGCGTCCTCTCTGAGGTCCAGGAGGAAAAAGGCA
1561 ---------+---------+---------+---------+---------+---------+ 1620
     TTATATTTGAAGAGGGTCTTATGGGTCCGCAGGAGAGACTCCAGGTCCTCCTTTTTCCGT

TCAAGTATAAGTTTGAAGTCTACGAGAAGAAAGACTAACAGGAAGATGCTTTCAAGTTCT
1621 ---------+---------+---------+---------+---------+---------+ 1680
     AGTTCATATTCAAACTTCAGATGCTCTTCTTTCTGATTGTCCTTCTACGAAAGTTCAAGA

BglII
                                |
     CTGCTCCCCTCCTAAAGCTATGCATTTTTATAAGACCATGGGACTTTTGCTGGCTTTAGA
1681 ---------+---------+---------+---------+---------+---------+ 1740
     GACGAGGGGAGGATTTCGATACGTAAAAATATTCTGGTACCCTGAAAACGACCGAAATCT

TCTGAAACACTGAAATTGTCTGCTTCTCATCTTCAGTGAGATTCCAAAGGATAGTACAGT
1741 ---------+---------+---------+---------+---------+---------+ 1800
     AGACTTTGTGACTTTAACAGACGAAGAGTAGAAGTCACTCTAAGGTTTCCTATCATGTCA

GACAGAACAAGAATAGGCACTCTCTACAAAAAAAAGAAAGAAAAAACTAAGTAATAGCAA
1801 ---------+---------+---------+---------+---------+---------+ 1860
     CTGTCTTGTTCTTATCCGTGAGAGATGTTTTTTTCTTTCTTTTTGATTCATTATCGTT

GCATAATAGCTACTGTTAAGAACTCAGAGATAATGAATTGAGAATGGATACTGCTTGAAA
1861 ---------+---------+---------+---------+---------+---------+ 1920
     CGTATTATCGATGACAATTCTTGAGTCTCTATTACTTAACTCTTACCTATGACGAACTTT

TGAAAATTTAATAAGTTAGAAACTAAACTTTATAAAAATAAAAAAATGAGCATTAAAAAA
1921 ---------+---------+---------+---------+---------+---------+ 1980
     ACTTTTAAATTATTCAATCTTTGATTTGAAATATTTTATTTTTTACTCGTAATTTTT

NheI
                                                    |
     AAAAAAAAAAAAAAAAAAAAAACCCCCCCCCCCCCCCCTGCAGCCAAGCTAGCTTGGAATC
1981 ---------+---------+---------+---------+---------+---------+ 2040
     TTTTTTTTTTTTTTTTTTTTTTGGGGGGGGGGGGGGGGGACGTCGGTTCGATCGAACCTTAG
```

FIG. 29D

```
     BspLU11I
        |
     AGGGGATAACGCAGGAAAGAACATGTGAGCAAAAGGCCAGCAAAAGGCCAGGAACCGTAA
2041 ---------+---------+---------+---------+---------+---------+ 2100
     TCCCCTATTGCGTCCTTTCTTGTACACTCGTTTTCCGGTCGTTTTCCGGTCCTTGGCATT

AAAGGCCGCGTTGCTGGCGTTTTTCCATAGGCTCCGCCCCCCTGACGAGCATCACAAAAA
2101 ---------+---------+---------+---------+---------+---------+ 2160
     TTTCCGGCGCAACGACCGCAAAAAGGTATCCGAGGCGGGGGGACTGCTCGTAGTGTTTTT

TCGACGCTCAAGTCAGAGGTGGCGAAACCCGACAGGACTATAAAGATACCAGGCGTTTCC
2161 ---------+---------+---------+---------+---------+---------+ 2220
     AGCTGCGAGTTCAGTCTCCACCGCTTTGGGCTGTCCTGATATTTCTATGGTCCGCAAAGG

CCCTGGAAGCTCCCTCGTGCGCTCTCCTGTTCCGACCCTGCCGCTTACCGGATACCTGTC
2221 ---------+---------+---------+---------+---------+---------+ 2280
     GGGACCTTCGAGGGAGCACGCGAGAGGACAAGGCTGGACGGCGAATGGCCTATGGACAG

CGCCTTTCTCCCTTCGGGAAGCGTGGCGCTTTCTCATAGCTCACGCTGTAGGTATCTCAG
2281 ---------+---------+---------+---------+---------+---------+ 2340
     GCGGAAAGAGGGAAGCCCTTCGCACCGCGAAAGAGTATCGAGTGCGACATCCATAGAGTC

TTCGGTGTAGGTCGTTCGCTCCAAGCTGGGCTGTGTGCACGAACCCCCCGTTCAGCCCGA
2341 ---------+---------+---------+---------+---------+---------+ 2400
     AAGCCACATCCAGCAAGCGAGGTTCGACCCGACACACGTGCTTGGGGGGCAAGTCGGGCT

CCGCTGCGCCTTATCCGGTAACTATCGTCTTGAGTCCAACCCGGTAAGACACGACTTATC
2401 ---------+---------+---------+---------+---------+---------+ 2460
     GGCGACGCGGAATAGGCCATTGATAGCAGAACTCAGGTTGGGCCATTCTGTGCTGAATAG

GCCACTGGCAGCAGCCACTGGTAACAGGATTAGCAGAGCGAGGTATGTAGGCGGTGCTAC
2461 ---------+---------+---------+---------+---------+---------+ 2520
     CGGTGACCGTCGTCGGTGACCATTGTCCTAATCGTCTCGCTCCATACATCCGCCACGATG

AGAGTTCTTGAAGTGGTGGCCTAACTACGGCTACACTAGAAGGACAGTATTTGGTATCTG
2521 ---------+---------+---------+---------+---------+---------+ 2580
     TCTCAAGAACTTCACCACCGGATTGATGCCGATGTGATCTTCCTGTCATAAACCATAGAC

CGCTCTGCTGAAGCCAGTTACCTTCGGAAAAAGAGTTGGTAGCTCTTGATCCGGCAAACA
2581 ---------+---------+---------+---------+---------+---------+ 2640
     GCGAGACGACTTCGGTCAATGGAAGCCTTTTCTCAACCATCGAGAACTAGGCCGTTTGT

HgiEII
        |
     AACCACCGCTGGTAGCGGTGGTTTTTTTGTTTGCAAGCAGCAGATTACGCGCAGAAAAAA
2641 ---------+---------+---------+---------+---------+---------+ 2700
     TTGGTGGCGACCATCGCCACCAAAAAAACAAACGTTCGTCGTCTAATGCGCGTCTTTTTT

AGGATCTCAAGAAGATCCTTTGATCTTTTCTACGGGGTCTGACGCTCAGTGGAACGAAAA
2701 ---------+---------+---------+---------+---------+---------+ 2760
     TCCTAGAGTTCTTCTAGGAAACTAGAAAAGATGCCCCAGACTGCGAGTCACCTTGCTTTT
```

FIG. 29E

```
     CTCACGTTAAGGGATTTTGGTCATGAGATTATCAAAAAGGATCTTCACCTAGATCCTTTT
2761 ---------+---------+---------+---------+---------+---------+ 2820
     GAGTGCAATTCCCTAAAACCAGTACTCTAATAGTTTTTCCTAGAAGTGGATCTAGGAAAA

AAATTAAAAATGAAGTTTTAAATCAATCTAAAGTATATATGAGTAAACTTGGTCTGACAG
2821 ---------+---------+---------+---------+---------+---------+ 2880
     TTTAATTTTTACTTCAAAATTTAGTTAGATTTCATATATACTCATTTGAACCAGACTGTC

TTACCAATGCTTAATCAGTGAGGCACCTATCTCAGCGATCTGTCTATTTCGTTCATCCAT
2881 ---------+---------+---------+---------+---------+---------+ 2940
     AATGGTTACGAATTAGTCACTCCGTGGATAGAGTCGCTAGACAGATAAAGCAAGTAGGTA

AGTTGCCTGACTCCCCGTCGTGTAGATAACTACGATACGGGAGGGCTTACCATCTGGCCC
2941 ---------+---------+---------+---------+---------+---------+ 3000
     TCAACGGACTGAGGGGCAGCACATCTATTGATGCTATGCCCTCCCGAATGGTAGACCGGG

CAGTGCTGCAATGATACCGCGAGACCCACGCTCACCGGCTCCAGATTTATCAGCAATAAA
3001 ---------+---------+---------+---------+---------+---------+ 3060
     GTCACGACGTTACTATGGCGCTCTGGGTGCGAGTGGCCGAGGTCTAAATAGTCGTTATTT

CCAGCCAGCCGGAAGGGCCGAGCGCAGAAGTGGTCCTGCAACTTTATCCGCCTCCATCCA
3061 ---------+---------+---------+---------+---------+---------+ 3120
     GGTCGGTCGGCCTTCCCGGCTCGCGTCTTCACCAGGACGTTGAAATAGGCGGAGGTAGGT

GTCTATTAATTGTTGCCGGGAAGCTAGAGTAAGTAGTTCGCCAGTTAATAGTTTGCGCAA
3121 ---------+---------+---------+---------+---------+---------+ 3180
     CAGATAATTAACAACGGCCCTTCGATCTCATTCATCAAGCGGTCAATTATCAAACGCGTT

CGTTGTTGCCATTGCTGCAGGCATCGTGGTGTCACGCTCGTCGTTTGGTATGGCTTCATT
3181 ---------+---------+---------+---------+---------+---------+ 3240
     GCAACAACGGTAACGACGTCCGTAGCACCACAGTGCGAGCAGCAAACCATACCGAAGTAA

CAGCTCCGGTTCCCAACGATCAAGGCGAGTTACATGATCCCCATGTTGTGCAAAAAAGC
3241 ---------+---------+---------+---------+---------+---------+ 3300
     GTCGAGGCCAAGGGTTGCTAGTTCCGCTCAATGTACTAGGGGGTACAACACGTTTTTTCG

EaeI
          PvuI      GdiII
           |        |
     GGTTAGCTCCTTCGGTCCTCCGATCGTTGTCAGAAGTAAGTTGGCCGCAGTGTTATCACT
3301 ---------+---------+---------+---------+---------+---------+ 3360
     CCAATCGAGGAAGCCAGGAGGCTAGCAACAGTCTTCATTCAACCGGCGTCACAATAGTGA

CATGGTTATGGCAGCACTGCATAATTCTCTTACTGTCATGCCATCCGTAAGATGCTTTTC
3361 ---------+---------+---------+---------+---------+---------+ 3420
     GTACCAATACCGTCGTGACGTATTAAGAGAATGACAGTACGGTAGGCATTCTACGAAAAG

BcgI
                 |
     TGTGACTGGTGAGTACTCAACCAAGTCATTCTGAGAATAGTGTATGCGGCGACCGAGTTG
3421 ---------+---------+---------+---------+---------+---------+ 3480
     ACACTGACCACTCATGAGTTGGTTCAGTAAGACTCTTATCACATACGCCGCTGGCTCAAC
```

FIG. 29F

```
     CTCTTGCCCGGCGTCAACACGGGATAATACCGCGCCACATAGCAGAACTTTAAAAGTGCT
3481 ---------+---------+---------+---------+---------+---------+ 3540
     GAGAACGGGCCGCAGTTGTGCCCTATTATGGCGCGGTGTATCGTCTTGAAATTTTCACGA

CATCATTGGAAAACGTTCTTCGGGGCGAAAACTCTCAAGGATCTTACCGCTGTTGAGATC
3541 ---------+---------+---------+---------+---------+---------+ 3600
     GTAGTAACCTTTTGCAAGAAGCCCCGCTTTTGAGAGTTCCTAGAATGGCGACAACTCTAG

CAGTTCGATGTAACCCACTCGTGCACCCAACTGATCTTCAGCATCTTTTACTTTCACCAG
3601 ---------+---------+---------+---------+---------+---------+ 3660
     GTCAAGCTACATTGGGTGAGCACGTGGGTTGACTAGAAGTCGTAGAAAATGAAAGTGGTC

CGTTTCTGGGTGAGCAAAAACAGGAAGGCAAAATGCCGCAAAAAAGGGAATAAGGGCGAC
3661 ---------+---------+---------+---------+---------+---------+ 3720
     GCAAAGACCCACTCGTTTTTGTCCTTCCGTTTTACGGCGTTTTTTCCCTTATTCCCGCTG

SspI
                           |
     ACGGAAATGTTGAATACTCATACTCTTCCTTTTTCAATATTATTGAAGCATTTATCAGGG
3721 ---------+---------+---------+---------+---------+---------+ 3780
     TGCCTTTACAACTTATGAGTATGAGAAGGAAAAAGTTATAATAACTTCGTAAATAGTCCC

TTATTGTCTCATGAGCGGATACATATTTGAATGTATTTAGAAAAATAAACAAATAGGGGT
3781 ---------+---------+---------+---------+---------+---------+ 3840
     AATAACAGAGTACTCGCCTATGTATAAACTTACATAAATCTTTTTATTTGTTTATCCCCA

TCCGCGCACATTTCCCCGAAAAGTGCCACCTGACGTCTAAGAAACCATTATTATCATGAC
3841 ---------+---------+---------+---------+---------+---------+ 3900
     AGGCGCGTGTAAAGGGGCTTTTCACGGTGGACTGCAGATTCTTTGGTAATAATAGTACTG

ATTAACCTATAAAAATAGGCGTATCACGAGGCCCTTTCGTCTTCAAGAATTCCCTGTGGA
3901 ---------+---------+---------+---------+---------+---------+ 3960
     TAATTGGATATTTTTATCCGCATAGTGCTCCGGGAAAGCAGAAGTTCTTAAGGGACACCT

ATGTGTGTCAGTTAGGGTGTGGAAAGTCCCCAGGCTCCCCAGCAGGCAGAAGTATGCAAA
3961 ---------+---------+---------+---------+---------+---------+ 4020
     TACACACAGTCAATCCCACACCTTTCAGGGGTCCGAGGGGTCGTCCGTCTTCATACGTTT

GCATGCATCTCAATTAGTCAGCAACCAGGTGTGGAAAGTCCCCAGGCTCCCCAGCAGGCA
4021 ---------+---------+---------+---------+---------+---------+ 4080
     CGTACGTAGAGTTAATCAGTCGTTGGTCCACACCTTTCAGGGGTCCGAGGGGTCGTCCGT

GAAGTATGCAAAGCATGCATCTCAATTAGTCAGCAACCATAGTCCCGCCCCTAACTCCGC
4081 ---------+---------+---------+---------+---------+---------+ 4140
     CTTCATACGTTTCGTACGTAGAGTTAATCAGTCGTTGGTATCAGGGCGGGGATTGAGGCG

CCATCCCGCCCCTAACTCCGCCCAGTTCCGCCCATTCTCCGCCCCATGGCTGACTAATTT
4141 ---------+---------+---------+---------+---------+---------+ 4200
     GGTAGGGCGGGGATTGAGGCGGGTCAAGGCGGGTAAGAGGCGGGGTACCGACTGATTAAA
```

FIG. 29G

```
            SfiI
             |
      TTTTTATTTATGCAGAGGCCGAGGCCGCCTCGGCCTCTGAGCTATTCCAGAAGTAGTGAG
4201  ---------+---------+---------+---------+---------+---------+ 4260
      AAAAATAAATACGTCTCCGGCTCCGGCGGAGCCGGAGACTCGATAAGGTCTTCATCACTC

AvrII
            |
      GAGGCTTTTTTGGAGGCCTAGGCTTTTGCAAAAAGCTGGTCGAGGCTCGCATCTCTCCTT
4261  ---------+---------+---------+---------+---------+---------+ 4320
      CTCCGAAAAAACCTCCGGATCCGAAAACGTTTTTCGACCAGCTCCGAGCGTAGAGAGGAA

CACGCGCCCGCCGCCCTACCTGAGGCCGCCATCCACGCCGGTTGAGTCGCGTTCTGCCGC
4321  ---------+---------+---------+---------+---------+---------+ 4380
      GTGCGCGGGCGGCGGGATGGACTCCGGCGGTAGGTGCGGCCAACTCAGCGCAAGACGGCG

CTCCCGCCTGTGGTGCCTCCTGAACTGCGTCCGCCGTCTAGGTAAGTTTAAAGCTCAGGT
4381  ---------+---------+---------+---------+---------+---------+ 4440
      GAGGGCGGACACCACGGAGGACTTGACGCAGGCGGCAGATCCATTCAAATTTCGAGTCCA

NgoAIV
                             |
      CGAGACCGGGCCTTTGTCCGGCGCTCCCTTGGAGCCTACCTAGACTCAGCCGGCTCTCCA
4441  ---------+---------+---------+---------+---------+---------+ 4500
      GCTCTGGCCCGGAAACAGGCCGCGAGGGAACCTCGGATGGATCTGAGTCGGCCGAGAGGT

CGCTTTGCCTGACCCTGCTTGCTCAACTCTACGTCTTTGTTTCGTTTTCTGTTCTGCGCC
4501  ---------+---------+---------+---------+---------+---------+ 4560
      GCGAAACGGACTGGGACGAACGAGTTGAGATGCAGAAACAAAGCAAAAGACAAGACGCGG

HpaI
                  |
      GTTACAGATCCGTCGAGGAACTGAAAAACCAGAAAGTTAACTGGTAAGTTTAGTCTTTTT
4561  ---------+---------+---------+---------+---------+---------+ 4620
      CAATGTCTAGGCAGCTCCTTGACTTTTTGGTCTTTCAATTGACCATTCAAATCAGAAAAA

Psp5II BamHI
             |    |
      GTCTTTTATTTCAGGTCCCGGATCCGGTGGTGGTGCAAATCAAAGAACTGCTCCTCAGTG
4621  ---------+---------+---------+---------+---------+---------+ 4680
      CAGAAAATAAAGTCCAGGGCCTAGGCCACCACCACGTTTAGTTTCTTGACGAGGAGTCAC

GATGTTGCCTTTACTTCTAGGCCTGTACGGAAGTGTTACTTCTGCTCTAAAAGCTGCTGC
4681  ---------+---------+---------+---------+---------+---------+ 4740
      CTACAACGGAAATGAAGATCCGGACATGCCTTCACAATGAAGACGAGATTTTCGACGACG

HindIII XbaI       BssHII
       |      |            |
      AACAAGCTTCTAGACCACCATGAACAAGTTGCTGTGCTGCGCGCTCGTGTTTCTGGACAT
4741  ---------+---------+---------+---------+---------+---------+ 4800
      TTGTTCGAAGATCTGGTGGTACTTGTTCAACGACACGACGCGCGAGCACAAAGACCTGTA
   b         M N K L L C C A L V F L D I -
```

FIG. 29H

```
     CTCCATTAAGTGGACCACCCAGGAAACGTTTCCTCCAAAGTACCTTCATTATGACGAAGA
4801 ------------+---------+---------+---------+---------+---------+ 4860
     GAGGTAATTCACCTGGTGGGTCCTTTGCAAAGGAGGTTTCATGGAAGTAATACTGCTTCT
b       S I K W T T Q E T F P P K Y L H Y D E E -
```

```
              KpnI
               |
     AACCTCTCATCAGCTGTTGTGTGACAAATGTCCTCCTGGTACCTACCTAAAACAACACTG
4861 ------------+---------+---------+---------+---------+---------+ 4920
     TTGGAGAGTAGTCGACAACACACTGTTTACAGGAGGACCATGGATGGATTTTGTTGTGAC
b       T S H Q L L C D K C P P G T Y L K Q H C -
```

```
     TACAGCAAAGTGGAAGACCGTGTGCGCCCCTTGCCCTGACCACTACTACACAGACAGCTG
4921 ------------+---------+---------+---------+---------+---------+ 4980
     ATGTCGTTTCACCTTCTGGCACACGCGGGGAACGGGACTGGTGATGATGTGTCTGTCGAC
b       T A K W K T V C A P C P D H Y Y T D S W -
```

```
     GCACACCAGTGACGAGTGTCTATACTGCAGCCCCGTGTGCAAGGAGCTGCAGTACGTCAA
4981 ------------+---------+---------+---------+---------+---------+ 5040
     CGTGTGGTCACTGCTCACAGATATGACGTCGGGGCACACGTTCCTCGACGTCATGCAGTT
b       H T S D E C L Y C S P V C K E L Q Y V K -
```

```
             RleAI BsmI
              |    |
     GCAGGAGTGCAATCGCACCCACAACCGCGTGTGCGAATGCAAGGAAGGGCGCTACCTTGA
5041 ---------+---------+---------+---------+---------+---------+ 5100
     CGTCCTCACGTTAGCGTGGGTGTTGGCGCACACGCTTACGTTCCTTCCCGCGATGGAACT
b       Q E C N R T H N R V C E C K E G R Y L E -
```

```
     GATAGAGTTCTGCTTGAAACATAGGAGCTGCCCTCCTGGATTTGGAGTGGTGCAAGCTGG
5101 ------------+---------+---------+---------+---------+---------+ 5160
     CTATCTCAAGACGAACTTTGTATCCTCGACGGGAGGACCTAAACCTCACCACGTTCGACC
b       I E F C L K H R S C P P G F G V V Q A G -
```

```
              BsmBI
               |
     AACCCCAGAGCGAAATACAGTTTGCAAAAGATGTCCAGATGGGTTCTTCTCAAATGAGAC
5161 ------------+---------+---------+---------+---------+---------+ 5220
     TTGGGGTCTCGCTTTATGTCAAACGTTTTCTACAGGTCTACCCAAGAAGAGTTTACTCTG
b       T P E R N T V C K R C P D G F F S N E T -
```

```
     GTCATCTAAAGCACCCTGTAGAAAACACACAAATTGCAGTGTCTTTGGTCTCCTGCTAAC
5221 ------------+---------+---------+---------+---------+---------+ 5280
     CAGTAGATTTCGTGGGACATCTTTTGTGTGTTTAACGTCACAGAAACCAGAGGACGATTG
b       S S K A P C R K H T N C S V F G L L L T -
```

```
              BspEI
               |
     TCAGAAAGGAAATGCAACACACGACAACATATGTTCCGGAAACAGTGAATCAACTCAAAA
5281 ------------+---------+---------+---------+---------+---------+ 5340
     AGTCTTTCCTTTACGTTGTGTGCTGTTGTATACAAGGCCTTTGTCACTTAGTTGAGTTTT
b       Q K G N A T H D N I C S G N S E S T Q K -
```

FIG. 29 I

```
       SalI              BmgI
        |                 |
       AGTCGACAAAACTCACACATGCCCACCGTGCCCAGCACCTGAACTCCTGGGGGACCGTC
 5341  ---------+---------+---------+---------+---------+---------+ 5400
       TCAGCTGTTTTGAGTGTGTACGGGTGGCACGGGTCGTGGACTTGAGGACCCCCCTGGCAG
  b      V D K T H T C P P C P A P E L L G G P S -

AGTCTTCCTCTTCCCCCCAAAACCCAAGGACACCCTCATGATCTCCCGGACCCCTGAGGT
 5401  ---------+---------+---------+---------+---------+---------+ 5460
       TCAGAAGGAGAAGGGGGGTTTTGGGTTCCTGTGGGAGTACTAGAGGGCCTGGGGACTCCA
  b      V F L F P P K P K D T L M I S R T P E V -

BtrI
                  |
       CACATGCGTGGTGGTGGACGTGAGCCACGAAGACCCTGAGGTCAAGTTCAACTGGTACGT
 5461  ---------+---------+---------+---------+---------+---------+ 5520
       GTGTACGCACCACCACCTGCACTCGGTGCTTCTGGGACTCCAGTTCAAGTTGACCATGCA
  b      T C V V V D V S H E D P E V K F N W Y V -

SacII
                        |
       GGACGGCGTGGAGGTGCATAATGCCAAGACAAAGCCGCGGGAGGAGCAGTACAACAGCAC
 5521  ---------+---------+---------+---------+---------+---------+ 5580
       CCTGCCGCACCTCCACGTATTACGGTTCTGTTTCGGCGCCCTCCTCGTCATGTTGTCGTG
  b      D G V E V H N A K T K P R E E Q Y N S T -

GTACCGTGTGGTCAGCGTCCTCACCGTCCTGCACCAGGACTGGCTGAATGGCAAGGAGTA
 5581  ---------+---------+---------+---------+---------+---------+ 5640
       CATGGCACACCAGTCGCAGGAGTGGCAGGACGTGGTCCTGACCGACTTACCGTTCCTCAT
  b      Y R V V S V L T V L H Q D W L N G K E Y -

CAAGTGCAAGGTCTCCAACAAAGCCCTCCCAGCCCCCATCGAGAAAACCATCTCCAAAGC
 5641  ---------+---------+---------+---------+---------+---------+ 5700
       GTTCACGTTCCAGAGGTTGTTTCGGGAGGGTCGGGGGTAGCTCTTTTGGTAGAGGTTTCG
  b      K C K V S N K A L P A P I E K T I S K A -

SmaI
                            |
       CAAAGGGCAGCCCCGAGAACCACAGGTGTACACCCTGCCCCCATCCCGGGATGAGCTGAC
 5701  ---------+---------+---------+---------+---------+---------+ 5760
       GTTTCCCGTCGGGGCTCTTGGTGTCCACATGTGGGACGGGGGTAGGGCCCTACTCGACTG
  b      K G Q P R E P Q V Y T L P P S R D E L T -

CAAGAACCAGGTCAGCCTGACCTGCCTGGTCAAAGGCTTCTATCCCAGCGACATCGCCGT
 5761  ---------+---------+---------+---------+---------+---------+ 5820
       GTTCTTGGTCCAGTCGGACTGGACGGACCAGTTTCCGAAGATAGGGTCGCTGTAGCGGCA
  b      K N Q V S L T C L V K G F Y P S D I A V -

GGAGTGGGAGAGCAATGGGCAGCCGGAGAACAACTACAAGACCACGCCTCCCGTGCTGGA
 5821  ---------+---------+---------+---------+---------+---------+ 5880
       CCTCACCCTCTCGTTACCCGTCGGCCTCTTGTTGATGTTCTGGTGCGGAGGGCACGACCT
  b      E W E S N G Q P E N N Y K T T P P V L D -
```

FIG. 29J

```
                      AarI
                       |
        CTCCGACGGCTCCTTCTTCCTCTACAGCAAGCTCACCGTGGACAAGAGCAGGTGGCAGCA
  5881  ---------+---------+---------+---------+---------+---------+ 5940
        GAGGCTGCCGAGGAAGAAGGAGATGTCGTTCGAGTGGCACCTGTTCTCGTCCACCGTCGT
    b      S  D  G  S  F  F  L  Y  S  K  L  T  V  D  K  S  R  W  Q  Q  -

SapI
                       |
        GGGGAACGTCTTCTCATGCTCCGTGATGCATGAGGCTCTGCACAACCACTACACGCAGAA
  5941  ---------+---------+---------+---------+---------+---------+ 6000
        CCCCTTGCAGAAGAGTACGAGGCACTACGTACTCCGAGACGTGTTGGTGATGTGCGTCTT
    b      G  N  V  F  S  C  S  V  M  H  E  A  L  H  N  H  Y  T  Q  K  -

GAGCCTCTCCCTGTCTCCGGGTAAATGATAACTCGAC
  6001  ---------+---------+---------+------- 6037
        CTCGGAGAGGGACAGAGGCCCATTTACTATTGAGCTG
    b      S  L  S  L  S  P  G  K  *  *
```

- Normal (NT)
- Normal + 4 mg/kg OPG-Fc (s.c.)
- Normal + 1.0 mg/kg OPG-Fc (s.c.)
- Normal + 0.25 mg/kg OPG-Fc (s.c.)
- AdA Control
- AdA + CSEP (2ML1)
- AdA + OPG Placebo (s.c.)
- AdA + 4 mg/kg OPG-Fc (s.c.)
- AdA + 1.0 mg/kg OPG-Fc (s.c.)
- AdA + 0.25 mg/kg OPG-Fc (s.c.)
- 15.0 mg/kg/hr IL-1ra (2ML1)
- 5.0 mg/kg/hr IL-1ra (2ML1)
- 1.0 mg/kg/hr IL-1ra (2ML1)
- 0.2 mg/kg/hr IL-1ra (2ML1)
- AdA + 0.07 mg/kg Dexamethasone (s.c.)

- Normal
- Normal + 1.0 mg/kg OPG-Fc (s.c.)
- Normal + 0.25 mg/kg OPG-Fc (s.c.)
- Normal + 0.0625 mg/kg OPG-Fc (s.c.)
- Normal + 0.016 mg/kg OPG-Fc (s.c.)
- Normal + 0.004 mg/kg OPG-Fc (s.c.)
- AdA control
- AdA + OPG Placebo (s.c.)
- AdA + 1.0 mg/kg OPG-Fc (s.c.)
- AdA + 0.25 mg/kg OPG-Fc (s.c.)
- AdA + 0.0625 mg/kg OPG-Fc (s.c.)
- AdA + 0.016 mg/kg OPG-Fc (s.c.)
- AdA + 0.004 mg/kg OPG-Fc (s.c.)
- AdA + 5.0 mg/kg/hr IL-1ra (2ML1)
- AdA + 0.07 mg/kg Dexamethasone (s.c.)

SEQUENCE LISTING

```
<160> NUMBER OF SEQ ID NOS: 178

<210> SEQ ID NO 1
<211> LENGTH: 36
<212> TYPE: DNA
<213> ORGANISM: Artificial Sequence
<220> FEATURE:
<223> OTHER INFORMATION: Not I restriction site
<220> FEATURE:
<221> NAME/KEY: misc_feature
<222> LOCATION: (28)..(35)
<223> OTHER INFORMATION: N = any random nucleic acid

<400> SEQUENCE: 1
aaaggaagga aaaaagcggc cgctacannn nnnnnt                              36

<210> SEQ ID NO 2
<211> LENGTH: 16
<212> TYPE: DNA
<213> ORGANISM: Artificial Sequence
<220> FEATURE:
<223> OTHER INFORMATION: Not I restriction site

<400> SEQUENCE: 2
tcgacccacg cgtccg                                                    16

<210> SEQ ID NO 3
<211> LENGTH: 12
<212> TYPE: DNA
<213> ORGANISM: Artificial Sequence
<220> FEATURE:
<223> OTHER INFORMATION: Not I restriction site

<400> SEQUENCE: 3
gggtgcgcag gc                                                        12

<210> SEQ ID NO 4
<211> LENGTH: 18
<212> TYPE: DNA
```

```
<213> ORGANISM: Artificial Sequence
<220> FEATURE:
<223> OTHER INFORMATION: Not I restriction site

<400> SEQUENCE: 4
tgtaaaacga cggccagt                                                 18

<210> SEQ ID NO 5
<211> LENGTH: 18
<212> TYPE: DNA
<213> ORGANISM: Artificial Sequence
<220> FEATURE:
<223> OTHER INFORMATION: Not I restriction site

<400> SEQUENCE: 5
caggaaacag ctatgacc                                                 18

<210> SEQ ID NO 6
<211> LENGTH: 20
<212> TYPE: DNA
<213> ORGANISM: Artificial Sequence
<220> FEATURE:
<223> OTHER INFORMATION: Not I restriction site

<400> SEQUENCE: 6
caattaaccc tcactaaagg                                               20

<210> SEQ ID NO 7
<211> LENGTH: 23
<212> TYPE: DNA
<213> ORGANISM: Rattus rattus

<400> SEQUENCE: 7
gcattatgac ccagaaaccg gac                                           23

<210> SEQ ID NO 8
<211> LENGTH: 23
<212> TYPE: DNA
<213> ORGANISM: Rattus rattus

<400> SEQUENCE: 8
aggtagcgcc cttcctcaca ttc                                           23

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 9
gactagtccc acaatgaaca agtggctgtg                                    30

<210> SEQ ID NO 10
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 10
ataagaatgc ggccgctaaa ctatgaaaca gcccagtgac cattc                   45

<210> SEQ ID NO 11
<211> LENGTH: 21
```

-continued

```
<212> TYPE: DNA
<213> ORGANISM: Artificial Sequence
<220> FEATURE:
<223> OTHER INFORMATION: Oligonucleotide primer

<400> SEQUENCE: 11
gcctctagaa agagctggga c                                              21

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 12
cgccgtgttc catttatgag c                                              21

<210> SEQ ID NO 13
<211> LENGTH: 24
<212> TYPE: DNA
<213> ORGANISM: Rattus rattus

<400> SEQUENCE: 13
atcaaaggca gggcatactt cctg                                           24

<210> SEQ ID NO 14
<211> LENGTH: 24
<212> TYPE: DNA
<213> ORGANISM: Rattus rattus

<400> SEQUENCE: 14
gttgcactcc tgtttcacgg tctg                                           24

<210> SEQ ID NO 15
<211> LENGTH: 24
<212> TYPE: DNA
<213> ORGANISM: Rattus rattus

<400> SEQUENCE: 15
caagacacct tgaagggcct gatg                                           24

<210> SEQ ID NO 16
<211> LENGTH: 24
<212> TYPE: DNA
<213> ORGANISM: Rattus rattus

<400> SEQUENCE: 16 taactttttac agaagagcat cagc                                          24

<210> SEQ ID NO 17
<211> LENGTH: 33
<212> TYPE: DNA
<213> ORGANISM: Rattus rattus

<400> SEQUENCE: 17
agcgcggccg catgaacaag tggctgtgct gcg                                 33

<210> SEQ ID NO 18
<211> LENGTH: 31
<212> TYPE: DNA
<213> ORGANISM: Rattus rattus

<400> SEQUENCE: 18
```

```
agctctagag aaacagccca gtgaccattc c                              31

<210> SEQ ID NO 19
<211> LENGTH: 24
<212> TYPE: DNA
<213> ORGANISM: Rattus rattus

<400> SEQUENCE: 19
gtgaagctgt gcaagaacct gatg                                      24

<210> SEQ ID NO 20
<211> LENGTH: 24
<212> TYPE: DNA
<213> ORGANISM: Rattus rattus

<400> SEQUENCE: 20
atcaaaggca gggcatactt cctg                                      24

<210> SEQ ID NO 21
<211> LENGTH: 24
<212> TYPE: DNA
<213> ORGANISM: Homo sapiens

<400> SEQUENCE: 21
cagatcctga agctgctcag tttg                                      24

<210> SEQ ID NO 22
<211> LENGTH: 33
<212> TYPE: DNA
<213> ORGANISM: Homo sapiens

<400> SEQUENCE: 22
agcgcggccg cggggaccac aatgaacaag ttg                            33

<210> SEQ ID NO 23
<211> LENGTH: 33
<212> TYPE: DNA
<213> ORGANISM: Homo sapiens

<400> SEQUENCE: 23
agctctagaa ttgtgaggaa acagctcaat ggc                            33

<210> SEQ ID NO 24
<211> LENGTH: 39
<212> TYPE: DNA
<213> ORGANISM: Artificial Sequence
<220> FEATURE:
<223> OTHER INFORMATION: Not I restriction site

<400> SEQUENCE: 24
atagcggccg ctgagcccaa atcttgtgac aaaactcac                      39

<210> SEQ ID NO 25
<211> LENGTH: 45
<212> TYPE: DNA
<213> ORGANISM: Artificial Sequence
<220> FEATURE:
<223> OTHER INFORMATION: Not I restriction site

<400> SEQUENCE: 25
tctagagtcg acttatcatt tacccggaga cagggagagg ctctt               45

<210> SEQ ID NO 26
<211> LENGTH: 38
```

```
<212> TYPE: DNA
<213> ORGANISM: Mus musculus

<400> SEQUENCE: 26
cctctgagct caagcttccg aggaccacaa tgaacaag                              38

<210> SEQ ID NO 27
<211> LENGTH: 43
<212> TYPE: DNA
<213> ORGANISM: Mus musculus

<400> SEQUENCE: 27
cctctgcggc cgctaagcag cttattttca cggattgaac ctg                       43

<210> SEQ ID NO 28
<211> LENGTH: 38
<212> TYPE: DNA
<213> ORGANISM: Mus musculus

<400> SEQUENCE: 28
cctctgagct caagcttccg aggaccacaa tgaacaag                              38

<210> SEQ ID NO 29
<211> LENGTH: 24
<212> TYPE: DNA
<213> ORGANISM: Homo sapiens

<400> SEQUENCE: 29
tccgtaagaa acagcccagt gacc                                             24

<210> SEQ ID NO 30
<211> LENGTH: 31
<212> TYPE: DNA
<213> ORGANISM: Mus musculus

<400> SEQUENCE: 30
cctctgcggc cgctgttgca tttcctttct g                                     31

<210> SEQ ID NO 31
<211> LENGTH: 19
<212> TYPE: PRT
<213> ORGANISM: Mus musculus

<400> SEQUENCE: 31

Glu Thr Leu Pro Pro Lys Tyr Leu His Tyr Asp Pro Glu Thr Gly His
1               5                   10                  15

Gln Leu Leu

<210> SEQ ID NO 32
<211> LENGTH: 21
<212> TYPE: DNA
<213> ORGANISM: Mus musculus

<400> SEQUENCE: 32
tcccttgccc tgaccactct t                                                21

<210> SEQ ID NO 33
<211> LENGTH: 34
<212> TYPE: DNA
<213> ORGANISM: Mus musculus

<400> SEQUENCE: 33
cctctgcggc cgcacacacg ttgtcatgtg ttgc                                  34
```

```
<210> SEQ ID NO 34
<211> LENGTH: 21
<212> TYPE: DNA
<213> ORGANISM: Mus musculus

<400> SEQUENCE: 34
tcccttgccc tgaccactct t                                        21

<210> SEQ ID NO 35
<211> LENGTH: 34
<212> TYPE: DNA
<213> ORGANISM: Mus musculus

<400> SEQUENCE: 35
cctctgcggc cgccttttgc gtggcttctc tgtt                          34

<210> SEQ ID NO 36
<211> LENGTH: 37
<212> TYPE: DNA
<213> ORGANISM: Homo sapiens

<400> SEQUENCE: 36
cctctgagct caagcttggt ttccggggac cacaatg                       37

<210> SEQ ID NO 37
<211> LENGTH: 38
<212> TYPE: DNA
<213> ORGANISM: Homo sapiens

<400> SEQUENCE: 37
cctctgcggc cgctaagcag cttattttta ctgaatgg                      38

<210> SEQ ID NO 38
<211> LENGTH: 37
<212> TYPE: DNA
<213> ORGANISM: Homo sapiens

<400> SEQUENCE: 38
cctctgagct caagcttggt ttccggggac cacaatg                       37

<210> SEQ ID NO 39
<211> LENGTH: 33
<212> TYPE: DNA
<213> ORGANISM: Homo sapiens

<400> SEQUENCE: 39
cctctgcggc cgccagggta acatctattc cac                           33

<210> SEQ ID NO 40
<211> LENGTH: 35
<212> TYPE: DNA
<213> ORGANISM: Mus musculus

<400> SEQUENCE: 40
ccgaagcttc caccatgaac aagtggctgt gctgc                         35

<210> SEQ ID NO 41
<211> LENGTH: 40
<212> TYPE: DNA
<213> ORGANISM: Mus musculus

<400> SEQUENCE: 41
```

```
cctctgtcga ctattataag cagcttattt tcacggattg                             40

<210> SEQ ID NO 42
<211> LENGTH: 21
<212> TYPE: DNA
<213> ORGANISM: Mus musculus

<400> SEQUENCE: 42
tcccttgccc tgaccactct t                                                 21

<210> SEQ ID NO 43
<211> LENGTH: 35
<212> TYPE: DNA
<213> ORGANISM: Mus musculus

<400> SEQUENCE: 43
cctctgtcga cttaacacac gttgtcatgt gttgc                                  35

<210> SEQ ID NO 44
<211> LENGTH: 21
<212> TYPE: DNA
<213> ORGANISM: Mus musculus

<400> SEQUENCE: 44
tcccttgccc tgaccactct t                                                 21

<210> SEQ ID NO 45
<211> LENGTH: 35
<212> TYPE: DNA
<213> ORGANISM: Mus musculus

<400> SEQUENCE: 45
cctctgtcga cttacttttg cgtggcttct ctgtt                                  35

<210> SEQ ID NO 46
<211> LENGTH: 1548
<212> TYPE: DNA
<213> ORGANISM: Artificial Sequence
<220> FEATURE:
<223> OTHER INFORMATION: pAMG21

<400> SEQUENCE: 46
tgcacgcatt gcatacgtac cagaggggta cgctctcatc ccttgacggt ccgtagttta       60
ttttgctttc cgagtcagct ttctgacccg gaaagcaaaa tagacaacaa acagccactt      120
gcgagaggac tcatcctgtt taggcggccc tcgcctaaac ttgcaacgct tcgttgccgg      180
gcctcccacc gcccgtcctg cgggcggtat ttgacggtcc gtagtttaat tcgtcttccg      240
gtaggactgc ctaccggaaa aacgcaaaga tgtttgagaa acaaataaa aagatttatg       300 taagtttata cctgcagcat gaattgaaaa tttcataccc gttagttaac gaggacaatt      360
ttaacgaaat cttatgaaa ccgtcgccaa acaacataac tcaaagtaaa cgcgtaacca       420
atttaccttt cactggcacg cgaatgatgt cggattataa aaactttata ggggttctcga     480 aaaaggaagc gtacgggtgc gatttgtaag aaaaagagaa aaccaattta gcaacaaact      540
aaataataaa cgatataaat aaaaagctat taatagttga tctcttcctt gttaattacc      600
atacaagtat gtgcgtacat ttttatttga tagatatatc aacagaaaga gacttacacg      660
ttttgattcg taaggcttcg gtaataatcg tcatacttat ccctttgatt tgggtcacta      720
ttctggacta ctaaagcgaa gaaattaatg taaacctcta aaaaataaat gtcgtaacaa      780
aagtttatat aaggttaatt agccacttac taacctcaat cttattagat gatatcctag      840
```

-continued

```
tataaaataa tttaatcgca gtagtattat aacggaggta aaaaatccca ttaataggtc      900
ttaactttat agtctaaatt ggtatcttac tcctatttac tagcgctcat ttattataag      960
tgttacatgg taaaatcagt atagtctatt cgtaactaat tatagtaata acgaagatgt     1020
ccgaaattaa aataattaat aagacattca cagcagccgt aaatacagaa agtatgggta     1080
gagaaatagg aatggataac aaacagcgtt caaaacgcac aatatatagt aattttgcca     1140
ttatctaact gtaaactaag attatttaac ctaaaaacag tgtgataata tagcgaactt     1200
tatgttaaca aattgtattc atggacatcc tagcatgtcc aaatgcgttc ttttaccaaa     1260
caatatcagc taattagcta aactaagatc taaacaaaat tgattaattt cctccttatt     1320
gtataccaat tgcgcaacct taagctcgag tgatcacagc tggacgtccc atggtacctt     1380
cgaatgagct cctaggcgcc tttcttcttc ttcttcttct ttcgggcttt ccttcgactc     1440
aaccgacgac ggtggcgact cgttattgat cgtattgggg aaccccggag atttgcccag     1500
aactccccaa aaacgacatt cctccttgg cgagaagtgc gagaagtg                  1548
```

```
<210> SEQ ID NO 47
<211> LENGTH: 48
<212> TYPE: DNA
<213> ORGANISM: Homo sapiens

<400> SEQUENCE: 47
ccggcggaca tttatcacac agcagctgat gagaagtttc ttcatcca                   48

<210> SEQ ID NO 48
<211> LENGTH: 55
<212> TYPE: DNA
<213> ORGANISM: Artificial Sequence
<220> FEATURE:
<223> OTHER INFORMATION: pAMG21

<400> SEQUENCE: 48
cgatttgatt ctagaaggag gaataacata tggttaacgc gttggaattc ggtac           55

<210> SEQ ID NO 49
<211> LENGTH: 49
<212> TYPE: DNA
<213> ORGANISM: Artificial Sequence
<220> FEATURE:
<223> OTHER INFORMATION: pAMG21

<400> SEQUENCE: 49
taaactaaga tcttcctcct tattgtatac caattgcgca accttaagc                  49

<210> SEQ ID NO 50
<211> LENGTH: 1546
<212> TYPE: DNA
<213> ORGANISM: Artificial Sequence
<220> FEATURE:
<223> OTHER INFORMATION: pAMG21
<220> FEATURE:
<221> NAME/KEY: misc_feature
<222> LOCATION: (1, 2, 1545 )..(1546)
<223> OTHER INFORMATION: Unique AatII and SacII sticky ends

<400> SEQUENCE: 50
gcgtaacgta tgcatggtct ccccatgcga gagtagggaa ctgccaggca tcaaataaaa       60
cgaaaggctc agtcgaaaga ctgggccttt cgttttatct gttgtttgtc ggtgaacgct      120
ctcctgagta ggacaaatcc gccgggagcg gatttgaacg ttgcgaagca acggcccgga     180
```

```
gggtggcggg caggacgccc gccataaact gccaggcatc aaattaagca gaaggccatc    240
ctgacggatg gccttttgc gtttctacaa actcttttgt ttattttct aaatacattc    300 aaatatggac gtcgtactta acttttaaag tatgggcaat caattgctcc tgttaaaatt    360
gctttagaaa tactttggca gcggtttgtt gtattgagtt tcatttgcgc attggttaaa    420
tggaaagtga ccgtgcgctt actacagcct aatattttg aaatatccca agagcttttt    480
ccttcgcatg cccacgctaa acattctttt tctcttttgg ttaaatcgtt gtttgattta    540
ttatttgcta tatttatttt tcgataatta tcaactagag aaggaacaat taatggtatg    600
ttcatacacg catgtaaaaa taaactatct atatagttgt ctttctctga atgtgcaaaa    660
ctaagcattc cgaagccatt attagcagta tgaataggga aactaaaccc agtgataaga    720
cctgatgatt tcgcttcttt aattacattt ggagattttt tatttacagc attgttttca    780
aatatattcc aattaatcgg tgaatgattg gagttagaat aatctactat aggatcatat    840
tttattaaat tagcgtcatc ataatattgc ctccattttt tagggtaatt atccagaatt    900
gaaatatcag atttaaccat agaatgagga taaatgatcg cgagtaaata atattcacaa    960
tgtaccattt tagtcatatc agataagcat tgattaatat cattattgct tctacaggct   1020
ttaattttat taattattct gtaagtgtcg tcggcattta tgtctttcat acccatctct   1080
ttatccttac ctattgtttg tcgcaagttt tgcgtgttat atatcattaa aacggtaata   1140
gattgacatt tgattctaat aaattggatt tttgtcacac tattatatcg cttgaaatac   1200
aattgtttaa cataagtacc tgtaggatcg tacaggttta cgcaagaaaa tggtttgtta   1260
tagtcgatta atcgatttga ttctagattt gttttaacta attaaaggag gaataacata   1320
tggttaacgc gttggaattc gagctcacta gtgtcgacct gcagggtacc atggaagctt   1380
actcgaggat ccgcggaaag aagaagaaga agaagaaagc ccgaaaggaa gctgagttgg   1440
ctgctgccac cgctgagcaa taactagcat aaccccttgg ggcctctaaa cgggtcttga   1500
ggggtttttt gctgaaagga ggaaccgctc ttcacgctct tcacgc                  1546
```

<210> SEQ ID NO 51
<211> LENGTH: 47
<212> TYPE: DNA
<213> ORGANISM: Artificial Sequence
<220> FEATURE:
<223> OTHER INFORMATION: pAMG22

<400> SEQUENCE: 51

```
tatgaaacat catcaccatc accatcatgc tagcgttaac gcgttgg                 47
```

<210> SEQ ID NO 52
<211> LENGTH: 49
<212> TYPE: DNA
<213> ORGANISM: Artificial Sequence
<220> FEATURE:
<223> OTHER INFORMATION: pAMG22

<400> SEQUENCE: 52

```
actttgtagt agtggtagtg gtagtacgat cgcaattgcg caaccttaa               49
```

<210> SEQ ID NO 53
<211> LENGTH: 141
<212> TYPE: DNA
<213> ORGANISM: Artificial Sequence
<220> FEATURE:
<223> OTHER INFORMATION: pAMG22

<400> SEQUENCE: 53

```
ctaattccgc tctcacctac caaacaatgc cccctgcaa aaataaatt catataaaaa      60 acatacagat aaccatctgc ggtgataaat tatctctggc ggtgttgaca taaataccac    120
tggcggtgat actgagcaca t                                              141

<210> SEQ ID NO 54
<211> LENGTH: 147
<212> TYPE: DNA
<213> ORGANISM: Artificial Sequence
<220> FEATURE:
<223> OTHER INFORMATION: pAMG22

<400> SEQUENCE: 54
tgcagattaa ggcgagagtg gatggtttgt tacgggggga cgttttttat ttaagtatat    60
tttttgtatg tctattggta gacgccacta tttaatagag accgccacaa ctgtatttat   120
ggtgaccgcc actatgactc gtgtagc                                        147

<210> SEQ ID NO 55
<211> LENGTH: 55
<212> TYPE: DNA
<213> ORGANISM: Artificial Sequence
<220> FEATURE:
<223> OTHER INFORMATION: pAMG22

<400> SEQUENCE: 55
cgatttgatt ctagaaggag gaataacata tggttaacgc gttggaattc ggtac         55

<210> SEQ ID NO 56
<211> LENGTH: 49
<212> TYPE: DNA
<213> ORGANISM: Artificial Sequence
<220> FEATURE:
<223> OTHER INFORMATION: pAMG22

<400> SEQUENCE: 56
taaactaaga tcttcctcct tattgtatac caattgcgca accttaagc                49

<210> SEQ ID NO 57
<211> LENGTH: 668
<212> TYPE: DNA
<213> ORGANISM: Artificial Sequence
<220> FEATURE:
<223> OTHER INFORMATION: pAMG22

<400> SEQUENCE: 57
tgcacgcatt gcatacgtac cagaggggta cgctctcatc ccttgacggt ccgtagttta    60
ttttgctttc cgagtcagct ttctgacccg gaaagcaaaa tagacaacaa acagccactt   120
gcgagaggac tcatcctgtt taggcggccc tcgcctaaac ttgcaacgct tcgttgccgg   180
gcctcccacc gcccgtcctg cgggcggtat ttgacggtcc gtagtttaat tcgtcttccg   240
gtaggactgc ctaccggaaa aacgcaaaga tgtttgagaa aacaaataaa aagatttatg   300
taagtttata cctgcagagt attaaaaatt ttttaagtaa actgtttacg attttaagaa   360
ctaattataa gagttaacac tcgcgagtgt taaatagcta aactaagatc taaactcaat   420
tgattaattt cctccttatt gtataccaat tgcgcaacct taagctcgag tgatcacagc   480
tggacgtccc atggtacctt cgaatgagct cctaggcgcc tttcttcttc ttcttcttct   540
ttcgggcttt ccttcgactc aaccgacgac ggtggcgact cgttattgat cgtattgggg   600
aaccccggag atttgcccag aactccccaa aaaacgactt tcctccttgg cgagaagtgc   660
```

-continued gagaagtg                                                          668

<210> SEQ ID NO 58
<211> LENGTH: 726
<212> TYPE: DNA
<213> ORGANISM: Artificial Sequence
<220> FEATURE:
<223> OTHER INFORMATION: pAMG22

<400> SEQUENCE: 58
gcgtaacgta tgcatggtct ccccatgcga gagtagggaa ctgccaggca tcaaataaaa    60
cgaaaggctc agtcgaaaga ctgggccttt cgttttatct gttgtttgtc ggtgaacgct   120
ctcctgagta ggacaaatcc gccgggagcg gatttgaacg ttgcgaagca acggcccgga   180
gggtggcggg caggacgccc gccataaact gccaggcatc aaattaagca gaaggggcct   240
cccaccgccc gtcctgcggg cggtatttga cggtccgtag tttaattcgt cttcgccatc   300
ctgacggatg gcctttttgc gtttctacaa actcttttgt ttattttct aaatacattc    360
aaatatggac gtctcataat ttttaaaaaa ttcatttgac aaatgctaaa attcttgatt   420
aatattctca attgtgagcg ctcacaattt atcgatttga ttctagattt gttttaacta   480
attaaaggag gaataacata tggttaacgc gttggaattc gagctcacta gtgtcgacct   540
gcagggtacc atggaagctt actcgaggat ccgcggaaag aagaagaaga agaagaaagc   600
ccgaaaggaa gctgagttgg ctgctgccac cgctgagcaa taactagcat aaccccttgg   660
ggcctctaaa cgggtcttga ggggttttt gctgaaagga ggaaccgctc ttcacgctct    720
tcacgc                                                              726

<210> SEQ ID NO 59
<211> LENGTH: 44
<212> TYPE: DNA
<213> ORGANISM: Homo sapiens

<400> SEQUENCE: 59
tacgcactgg atccttataa gcagcttatt tttactgatt ggac                     44

<210> SEQ ID NO 60
<211> LENGTH: 27
<212> TYPE: DNA
<213> ORGANISM: Homo sapiens

<400> SEQUENCE: 60
gtcctcctgg tacctaccta aaacaac                                        27

<210> SEQ ID NO 61
<211> LENGTH: 54
<212> TYPE: DNA
<213> ORGANISM: Homo sapiens

<400> SEQUENCE: 61
tatggatgaa gaaacttctc atcagctgct gtgtgataaa tgtccgccgg gtac          54

<210> SEQ ID NO 62
<211> LENGTH: 19
<212> TYPE: PRT
<213> ORGANISM: Homo sapiens

<400> SEQUENCE: 62

Met Asp Glu Glu Thr Ser His Gln Leu Leu Cys Asp Lys Cys Pro Pro
1               5                   10                  15

Gly Thr Tyr

<210> SEQ ID NO 63
<211> LENGTH: 84
<212> TYPE: DNA
<213> ORGANISM: Artificial Sequence
<220> FEATURE:
<223> OTHER INFORMATION: pAMG21

<400> SEQUENCE: 63
tatggaaact tttcctccaa aatatcttca ttatgatgaa gaaacttctc atcagctgct      60
gtgtgataaa tgtccgccgg gtac                                             84

<210> SEQ ID NO 64
<211> LENGTH: 78
<212> TYPE: DNA
<213> ORGANISM: Artificial Sequence
<220> FEATURE:
<223> OTHER INFORMATION: pAMG21

<400> SEQUENCE: 64
ccggcggaca tttatcacac agcagctgat gagaagtttc ttcatcataa tgaagatatt      60
ttggaggaaa agtttcca                                                    78

<210> SEQ ID NO 65
<211> LENGTH: 44
<212> TYPE: DNA
<213> ORGANISM: Artificial Sequence
<220> FEATURE:
<223> OTHER INFORMATION: pAMG21-MuOPG

<400> SEQUENCE: 65
tacgcactgg atccttataa gcagcttatt ttcacggatt gaac                       44

<210> SEQ ID NO 66
<211> LENGTH: 38
<212> TYPE: DNA
<213> ORGANISM: Artificial Sequence
<220> FEATURE:
<223> OTHER INFORMATION: pAMG21-MuOPG

<400> SEQUENCE: 66
gtgctcctgg tacctaccta aaacagcact gcacagtg                              38

<210> SEQ ID NO 67
<211> LENGTH: 84
<212> TYPE: DNA
<213> ORGANISM: Artificial Sequence
<220> FEATURE:
<223> OTHER INFORMATION: pAMG21-MuOPG

<400> SEQUENCE: 67
tatggaaact ctgcctccaa aatacctgca ttacgatccg gaaactggtc atcagctgct      60
gtgtgataaa tgtgctccgg gtac                                             84

<210> SEQ ID NO 68
<211> LENGTH: 78
<212> TYPE: DNA
<213> ORGANISM: Artificial Sequence
<220> FEATURE:
<223> OTHER INFORMATION: pAMG21-MuOPG

<400> SEQUENCE: 68
ccggagcaca tttatcacac agcagctgat gaccagtttc cggatcgtaa tgcaggtatt      60

```
<210> SEQ ID NO 69
<211> LENGTH: 54
<212> TYPE: DNA
<213> ORGANISM: Mus musculus

<400> SEQUENCE: 69
tatggaccca gaaactggtc atcagctgct gtgtgataaa tgtgctccgg gtac       54

<210> SEQ ID NO 70
<211> LENGTH: 48
<212> TYPE: DNA
<213> ORGANISM: Mus musculus

<400> SEQUENCE: 70
ccggagcaca tttatcacac agcagctgat gaccagtttc tgggtcca             48

<210> SEQ ID NO 71
<211> LENGTH: 87
<212> TYPE: DNA
<213> ORGANISM: Artificial Sequence
<220> FEATURE:
<223> OTHER INFORMATION: pAMG21

<400> SEQUENCE: 71
tatgaaagaa actctgcctc caaaatacct gcattacgat ccggaaactg gtcatcagct    60
gctgtgtgat aaatgtgctc cgggtac                                       87

<210> SEQ ID NO 72
<211> LENGTH: 81
<212> TYPE: DNA
<213> ORGANISM: Artificial Sequence
<220> FEATURE:
<223> OTHER INFORMATION: pAMG21

<400> SEQUENCE: 72
ccggagcaca tttatcacac agcagctgat gaccagtttc cggatcgtaa tgcaggtatt    60
ttggaggcag agtttctttc a                                             81

<210> SEQ ID NO 73
<211> LENGTH: 71
<212> TYPE: DNA
<213> ORGANISM: Artificial Sequence
<220> FEATURE:
<223> OTHER INFORMATION: pAMG21

<400> SEQUENCE: 73
gttctcctca tatgaaacat catcaccatc accatcatga aactctgcct ccaaaatacc    60
tgcattacga t                                                        71

<210> SEQ ID NO 74
<211> LENGTH: 43
<212> TYPE: DNA
<213> ORGANISM: Mus musculus

<400> SEQUENCE: 74
gttctcctca tatgaaagaa actctgcctc caaaatacct gca                     43

<210> SEQ ID NO 75
<211> LENGTH: 76
<212> TYPE: DNA
```

```
<213> ORGANISM: Mus musculus

<400> SEQUENCE: 75
tacgcactgg atccttaatg atggtgatgg tgatgatgta agcagcttat tttcacggat    60
tgaacctgat tccta                                                     76

<210> SEQ ID NO 76
<211> LENGTH: 47
<212> TYPE: DNA
<213> ORGANISM: Mus musculus

<400> SEQUENCE: 76
gttctcctca tatgaaatac ctgcattacg atccggaaac tggtcat                  47

<210> SEQ ID NO 77
<211> LENGTH: 43
<212> TYPE: DNA
<213> ORGANISM: Homo sapiens

<400> SEQUENCE: 77
gttctcctat taatgaaata tcttcattat gatgaagaaa ctt                      43

<210> SEQ ID NO 78
<211> LENGTH: 40
<212> TYPE: DNA
<213> ORGANISM: Homo sapiens

<400> SEQUENCE: 78
tacgcactgg atccttataa gcagcttatt tttactgatt                          40

<210> SEQ ID NO 79
<211> LENGTH: 40
<212> TYPE: DNA
<213> ORGANISM: Mus musculus

<400> SEQUENCE: 79
gttctcctca tatggaaact ctgcctccaa aatacctgca                          40

<210> SEQ ID NO 80
<211> LENGTH: 43
<212> TYPE: DNA
<213> ORGANISM: Mus musculus

<400> SEQUENCE: 80
tacgcactgg atccttatgt tgcatttcct ttctgaatta gca                      43

<210> SEQ ID NO 81
<211> LENGTH: 18
<212> TYPE: DNA
<213> ORGANISM: Artificial Sequence
<220> FEATURE:
<223> OTHER INFORMATION: pAMG21

<400> SEQUENCE: 81
ccggaaacag ataatgag                                                  18

<210> SEQ ID NO 82
<211> LENGTH: 18
<212> TYPE: DNA
<213> ORGANISM: Artificial Sequence
<220> FEATURE:
<223> OTHER INFORMATION: pAMG21

<400> SEQUENCE: 82
```

```
gatcctcatt atctgttt                                            18

<210> SEQ ID NO 83
<211> LENGTH: 30
<212> TYPE: DNA
<213> ORGANISM: Artificial Sequence
<220> FEATURE:
<223> OTHER INFORMATION: pAMG21

<400> SEQUENCE: 83
ccggaaacag agaagccacg caaaagtaag                               30

<210> SEQ ID NO 84
<211> LENGTH: 30
<212> TYPE: DNA
<213> ORGANISM: Artificial Sequence
<220> FEATURE:
<223> OTHER INFORMATION: pAMG21

<400> SEQUENCE: 84
gatccttact tttgcgtggc ttctctgttt                               30

<210> SEQ ID NO 85
<211> LENGTH: 12
<212> TYPE: DNA
<213> ORGANISM: Artificial Sequence
<220> FEATURE:
<223> OTHER INFORMATION: pAMG21

<400> SEQUENCE: 85
tatgttaatg ag                                                  12

<210> SEQ ID NO 86
<211> LENGTH: 14
<212> TYPE: DNA
<213> ORGANISM: Artificial Sequence
<220> FEATURE:
<223> OTHER INFORMATION: pAMG21

<400> SEQUENCE: 86
gatcctcatt aaca                                                14

<210> SEQ ID NO 87
<211> LENGTH: 21
<212> TYPE: DNA
<213> ORGANISM: Artificial Sequence
<220> FEATURE:
<223> OTHER INFORMATION: pAMG21

<400> SEQUENCE: 87
tatgttccgg aaacagttaa g                                        21

<210> SEQ ID NO 88
<211> LENGTH: 23
<212> TYPE: DNA
<213> ORGANISM: Artificial Sequence
<220> FEATURE:
<223> OTHER INFORMATION: pAMG21

<400> SEQUENCE: 88
gatccttaac tgtttccgga aca                                      23

<210> SEQ ID NO 89
<211> LENGTH: 36
<212> TYPE: DNA
```

```
<213> ORGANISM: Artificial Sequence
<220> FEATURE:
<223> OTHER INFORMATION: pAMG21

<400> SEQUENCE: 89
tatgttccgg aaacagtgaa tcaactcaaa aataag                          36

<210> SEQ ID NO 90
<211> LENGTH: 38
<212> TYPE: DNA
<213> ORGANISM: Artificial Sequence
<220> FEATURE:
<223> OTHER INFORMATION: pAMG21

<400> SEQUENCE: 90
gatccttatt tttgagttga ttcactgttt ccggaaca                        38

<210> SEQ ID NO 91
<211> LENGTH: 100
<212> TYPE: DNA
<213> ORGANISM: Artificial Sequence
<220> FEATURE:
<223> OTHER INFORMATION: pAMG21

<400> SEQUENCE: 91
ctagcgacga cgacgacaaa gaaactctgc ctccaaaata cctgcattac gatccggaaa    60
ctggtcatca gctgctgtgt cataaatgtg ctccgggtac                         100

<210> SEQ ID NO 92
<211> LENGTH: 92
<212> TYPE: DNA
<213> ORGANISM: Artificial Sequence
<220> FEATURE:
<223> OTHER INFORMATION: pAMG21

<400> SEQUENCE: 92
ccggagcaca tttatcacac agcagctgat gaccagtttc cggatcgtaa tgcaggtatt    60
ttggaggcag agtttctttg tcgtcgtcgt cg                                  92

<210> SEQ ID NO 93
<211> LENGTH: 26
<212> TYPE: DNA
<213> ORGANISM: Artificial Sequence
<220> FEATURE:
<223> OTHER INFORMATION: pAMG21-huOPG

<400> SEQUENCE: 93
acaaacacaa tcgatttgat actaga                                     26

<210> SEQ ID NO 94
<211> LENGTH: 50
<212> TYPE: DNA
<213> ORGANISM: Artificial Sequence
<220> FEATURE:
<223> OTHER INFORMATION: pAMG21-huOPG

<400> SEQUENCE: 94
tttgttttaa ctaattaaag gaggaataaa atatgagagg atcgcatcac            50

<210> SEQ ID NO 95
<211> LENGTH: 50
<212> TYPE: DNA
<213> ORGANISM: Artificial Sequence
<220> FEATURE:
<223> OTHER INFORMATION: pAMG21-huOPG
```

<400> SEQUENCE: 95
catcaccatc acgaaacctt cccgccgaaa tacctgcact acgacgaaga        50

<210> SEQ ID NO 96
<211> LENGTH: 49
<212> TYPE: DNA
<213> ORGANISM: Artificial Sequence
<220> FEATURE:
<223> OTHER INFORMATION: pAMG21-huOPG

<400> SEQUENCE: 96
aacctcccac cagctgctgt gcgacaaatg cccgccgggt acccaaaca         49

<210> SEQ ID NO 97
<211> LENGTH: 26
<212> TYPE: DNA
<213> ORGANISM: Artificial Sequence
<220> FEATURE:
<223> OTHER INFORMATION: pAMG21-huOPG

<400> SEQUENCE: 97
tgtttgggta cccggcgggc atttgt                                  26

<210> SEQ ID NO 98
<211> LENGTH: 50
<212> TYPE: DNA
<213> ORGANISM: Artificial Sequence
<220> FEATURE:
<223> OTHER INFORMATION: pAMG21-huOPG

<400> SEQUENCE: 98
cgcacagcag ctggtgggag gtttcttcgt cgtagtgcag gtatttcggc        50

<210> SEQ ID NO 99
<211> LENGTH: 49
<212> TYPE: DNA
<213> ORGANISM: Artificial Sequence
<220> FEATURE:
<223> OTHER INFORMATION: pAMG21-huOPG

<400> SEQUENCE: 99
gggaaggttt cgtgatggtg atggtgatgc catcctctca tattttatt         49

<210> SEQ ID NO 100
<211> LENGTH: 50
<212> TYPE: DNA
<213> ORGANISM: Artificial Sequence
<220> FEATURE:
<223> OTHER INFORMATION: pAMG21-huOPG

<400> SEQUENCE: 100
cctcctttaa ttagttaaaa caaatctagt atcaaatcga ttgtgtttgt        50

<210> SEQ ID NO 101
<211> LENGTH: 59
<212> TYPE: DNA
<213> ORGANISM: Homo sapiens

<400> SEQUENCE: 101
acaaacacaa tcgatttgat actagatttg ttttaactaa ttaaaggagg aataaaatg    59

<210> SEQ ID NO 102
<211> LENGTH: 48
<212> TYPE: DNA

```
<213> ORGANISM: Homo sapiens

<400> SEQUENCE: 102
ctaattaaag gaggaataaa atgaaagaaa cttttcctcc aaaatatc                    48

<210> SEQ ID NO 103
<211> LENGTH: 31
<212> TYPE: DNA
<213> ORGANISM: Homo sapiens

<400> SEQUENCE: 103
tgtttgggta cccggcggac atttatcaca c                                      31

<210> SEQ ID NO 104
<211> LENGTH: 59
<212> TYPE: DNA
<213> ORGANISM: Homo sapiens

<400> SEQUENCE: 104
acaaacacaa tcgatttgat actagatttg ttttaactaa ttaaaggagg aataaaatg        59

<210> SEQ ID NO 105
<211> LENGTH: 54
<212> TYPE: DNA
<213> ORGANISM: Homo sapiens

<400> SEQUENCE: 105
ctaattaaag gaggaataaa atgaaaaaaa aagaaacttt tcctccaaaa tatc             54

<210> SEQ ID NO 106
<211> LENGTH: 31
<212> TYPE: DNA
<213> ORGANISM: Homo sapiens

<400> SEQUENCE: 106
tgtttgggta cccggcggac atttatcaca c                                      31

<210> SEQ ID NO 107
<211> LENGTH: 44
<212> TYPE: DNA
<213> ORGANISM: Artificial Sequence
<220> FEATURE:
<223> OTHER INFORMATION: PCR primer for Fc-hOPG fusion protein.

<400> SEQUENCE: 107
cagcccgggt aaaatggaaa cgtttcctcc aaaatatctt catt                        44

<210> SEQ ID NO 108
<211> LENGTH: 44
<212> TYPE: DNA
<213> ORGANISM: Artificial Sequence
<220> FEATURE:
<223> OTHER INFORMATION: PCR primer for FchOPG fusion protein.

<400> SEQUENCE: 108
cgtttccatt ttacccgggc tgagcgagag gctcttctgc gtgt                        44

<210> SEQ ID NO 109
<211> LENGTH: 45
<212> TYPE: DNA
<213> ORGANISM: Artificial Sequence
<220> FEATURE:
<223> OTHER INFORMATION: Fc/muOPG

<400> SEQUENCE: 109
```
cgctcagccc gggtaaaatg gaaacgttgc ctccaaaata cctgc          45

<210> SEQ ID NO 110
<211> LENGTH: 39
<212> TYPE: DNA
<213> ORGANISM: Artificial Sequence
<220> FEATURE:
<223> OTHER INFORMATION: Fc/muOPG

<400> SEQUENCE: 110
ccattttacc cgggctgagc gagaggctct tctgcgtgt          39

<210> SEQ ID NO 111
<211> LENGTH: 36
<212> TYPE: DNA
<213> ORGANISM: Artificial Sequence
<220> FEATURE:
<223> OTHER INFORMATION: muOPG

<400> SEQUENCE: 111
gaaaataaga tgcttagctg cagctgaacc aaaatc          36

<210> SEQ ID NO 112
<211> LENGTH: 34
<212> TYPE: DNA
<213> ORGANISM: Artificial Sequence
<220> FEATURE:
<223> OTHER INFORMATION: muOPG

<400> SEQUENCE: 112
cagctgcagc taagcagctt attttcacgg attg          34

<210> SEQ ID NO 113
<211> LENGTH: 36
<212> TYPE: DNA
<213> ORGANISM: Artificial Sequence
<220> FEATURE:
<223> OTHER INFORMATION: huOPG

<400> SEQUENCE: 113
aaaaataagc tgcttagctg cagctgaacc aaaatc          36

<210> SEQ ID NO 114
<211> LENGTH: 35
<212> TYPE: DNA
<213> ORGANISM: Artificial Sequence
<220> FEATURE:
<223> OTHER INFORMATION: huOPG

<400> SEQUENCE: 114
cagctgcagc taagcagctt atttttactg attgg          35

<210> SEQ ID NO 115
<211> LENGTH: 102
<212> TYPE: DNA
<213> ORGANISM: Artificial Sequence
<220> FEATURE:
<223> OTHER INFORMATION: pAMG21-huOPG
<220> FEATURE:
<221> NAME/KEY: misc_feature
<223> OTHER INFORMATION: Linker with XbaI and KpnI sites inserted into
      human sequence.

<400> SEQUENCE: 115
ctagaaggag gaataacata tggaaacttt tgctccaaaa tatcttcatt atgatgaaga          60

```
aactagtcat cagctgctgt gtgataaatg tccgccgggt ac                              102
```

```
<210> SEQ ID NO 116
<211> LENGTH: 94
<212> TYPE: DNA
<213> ORGANISM: Artificial Sequence
<220> FEATURE:
<223> OTHER INFORMATION: huOPG

<400> SEQUENCE: 116
ccggcggaca tttatcacac agcagctgat gactagtttc ttcatcataa tgaagatatt          60
ttggagcaaa agtttccata tgttattcct cctt                                      94

<210> SEQ ID NO 117
<211> LENGTH: 62
<212> TYPE: DNA
<213> ORGANISM: Artificial Sequence
<220> FEATURE:
<223> OTHER INFORMATION: huOPG

<400> SEQUENCE: 117
ctagaaggag gaataacata tggaaacttt tcctgctaaa tatcttcatt atgatgaaga          60
aa                                                                         62

<210> SEQ ID NO 118
<211> LENGTH: 62
<212> TYPE: DNA
<213> ORGANISM: Artificial Sequence
<220> FEATURE:
<223> OTHER INFORMATION: huOPG

<400> SEQUENCE: 118
ctagtttctt catcataatg aagatattta gcaggaaaag tttccatatg ttattcctcc          60
tt                                                                         62

<210> SEQ ID NO 119
<211> LENGTH: 51
<212> TYPE: PRT
<213> ORGANISM: Homo sapiens

<400> SEQUENCE: 119
```

Tyr His Tyr Tyr Asp Gln Asn Gly Arg Met Cys Glu Glu Cys His Met
1               5                   10                  15

Cys Gln Pro Gly His Phe Leu Val Lys His Cys Lys Gln Pro Lys Arg
            20                  25                  30

Asp Thr Val Cys His Lys Pro Cys Glu Pro Gly Val Thr Tyr Thr Asp
        35                  40                  45

Asp Trp His
    50

```
<210> SEQ ID NO 120
<211> LENGTH: 2432
<212> TYPE: DNA
<213> ORGANISM: Rattus rattus
<220> FEATURE:
<221> NAME/KEY: CDS
<222> LOCATION: (124)..(1326)

<400> SEQUENCE: 120
atcaaaggca gggcatactt cctgttgccc agaccttata taaaacgtca tgttcgcctg          60
ggcagcagag aagcacctag cactggccca gcggctgccg cctgaggttt ccagaggacc         120
```

-continued

| | | |
|---|---|---|
| aca atg aac aag tgg ctg tgc tgt gca ctc ctg gtg ttc ttg gac atc<br>Met Asn Lys Trp Leu Cys Cys Ala Leu Leu Val Phe Leu Asp Ile<br>1               5                   10                  15 | | 168 |
| att gaa tgg aca acc cag gaa acc ttt cct cca aaa tac ttg cat tat<br>Ile Glu Trp Thr Thr Gln Glu Thr Phe Pro Pro Lys Tyr Leu His Tyr<br>                20                  25                  30 | | 216 |
| gac cca gaa acc gga cgt cag ctc ttg tgt gac aaa tgt gct cct ggc<br>Asp Pro Glu Thr Gly Arg Gln Leu Leu Cys Asp Lys Cys Ala Pro Gly<br>            35                  40                  45 | | 264 |
| acc tac cta aaa cag cac tgc aca gtc agg agg aag aca ctg tgt gtc<br>Thr Tyr Leu Lys Gln His Cys Thr Val Arg Arg Lys Thr Leu Cys Val<br>        50                  55                  60 | | 312 |
| cct tgc cct gac tac tct tat aca gac agc tgg cac acg agt gat gaa<br>Pro Cys Pro Asp Tyr Ser Tyr Thr Asp Ser Trp His Thr Ser Asp Glu<br>65                  70                  75 | | 360 |
| tgc gtg tac tgc agc ccc gtg tgc aag gaa ctg cag acc gtg aaa cag<br>Cys Val Tyr Cys Ser Pro Val Cys Lys Glu Leu Gln Thr Val Lys Gln<br>80                  85                  90                  95 | | 408 |
| gag tgc aac cgc acc cac aac cga gtg tgc gaa tgt gag gaa ggg cgc<br>Glu Cys Asn Arg Thr His Asn Arg Val Cys Glu Cys Glu Glu Gly Arg<br>                100                 105                 110 | | 456 |
| tac ctg gag ctc gaa ttc tgc ttg aag cac cgg agc tgt ccc cca ggc<br>Tyr Leu Glu Leu Glu Phe Cys Leu Lys His Arg Ser Cys Pro Pro Gly<br>            115                 120                 125 | | 504 |
| ttg ggt gtg ctg cag gct ggg acc cca gag cga aac acg gtt tgc aaa<br>Leu Gly Val Leu Gln Ala Gly Thr Pro Glu Arg Asn Thr Val Cys Lys<br>        130                 135                 140 | | 552 |
| aga tgt ccg gat ggg ttc ttc tca ggt gag acg tca tcg aaa gca ccc<br>Arg Cys Pro Asp Gly Phe Phe Ser Gly Glu Thr Ser Ser Lys Ala Pro<br>145                 150                 155 | | 600 |
| tgt agg aaa cac acc aac tgc agc tca ctt ggc ctc ctg cta att cag<br>Cys Arg Lys His Thr Asn Cys Ser Ser Leu Gly Leu Leu Leu Ile Gln<br>160                 165                 170                 175 | | 648 |
| aaa gga aat gca aca cat gac aat gta tgt tcc gga aac aga gaa gca<br>Lys Gly Asn Ala Thr His Asp Asn Val Cys Ser Gly Asn Arg Glu Ala<br>                180                 185                 190 | | 696 |
| act caa aat tgt gaa ata gat gtc acc ctg tgc gaa gag gca ttc ttc<br>Thr Gln Asn Cys Glu Ile Asp Val Thr Leu Cys Glu Glu Ala Phe Phe<br>            195                 200                 205 | | 744 |
| agg ttt gct gtg cct acc aag att ata ccg aat tgg ctg agt gtt ctg<br>Arg Phe Ala Val Pro Thr Lys Ile Ile Pro Asn Trp Leu Ser Val Leu<br>        210                 215                 220 | | 792 |
| gtg gac agt ttg cct ggg acc aaa gtg aat gca gag agt gta gag agg<br>Val Asp Ser Leu Pro Gly Thr Lys Val Asn Ala Glu Ser Val Glu Arg<br>225                 230                 235 | | 840 |
| ata aaa cgg aga cac agc tcg caa gag caa act ttc cag cta ctt aag<br>Ile Lys Arg Arg His Ser Ser Gln Glu Gln Thr Phe Gln Leu Leu Lys<br>240                 245                 250                 255 | | 888 |
| ctg tgg aag cat caa aac aga gac cag gaa atg gtg aag aag atc atc<br>Leu Trp Lys His Gln Asn Arg Asp Gln Glu Met Val Lys Lys Ile Ile<br>                260                 265                 270 | | 936 |
| caa gac att gac ctc tgt gaa agc agt gtg caa cgg cat atc ggc cac<br>Gln Asp Ile Asp Leu Cys Glu Ser Ser Val Gln Arg His Ile Gly His<br>            275                 280                 285 | | 984 |
| gcg aac ctc acc aca gag cag ctc cgc atc ttg atg gag agc ttg cct<br>Ala Asn Leu Thr Thr Glu Gln Leu Arg Ile Leu Met Glu Ser Leu Pro<br>        290                 295                 300 | | 1032 |
| ggg aag aag atc agc cca gac gag att gag aga acg aga aag acc tgc<br>Gly Lys Lys Ile Ser Pro Asp Glu Ile Glu Arg Thr Arg Lys Thr Cys<br>305                 310                 315 | | 1080 |

-continued

| | |
|---|---|
| aaa ccc agc gag cag ctc ctg aag cta ctg agc ttg tgg agg atc aaa<br>Lys Pro Ser Glu Gln Leu Leu Lys Leu Leu Ser Leu Trp Arg Ile Lys<br>320                        325                          330                          335 | 1128 |
| aat gga gac caa gac acc ttg aag ggc ctg atg tac gca ctc aag cac<br>Asn Gly Asp Gln Asp Thr Leu Lys Gly Leu Met Tyr Ala Leu Lys His<br>                        340                            345                          350 | 1176 |
| ttg aaa gca tac cac ttt ccc aaa acc gtc acc cac agt ctg agg aag<br>Leu Lys Ala Tyr His Phe Pro Lys Thr Val Thr His Ser Leu Arg Lys<br>                        355                            360                          365 | 1224 |
| acc atc agg ttc ttg cac agc ttc acc atg tac cga ttg tat cag aaa<br>Thr Ile Arg Phe Leu His Ser Phe Thr Met Tyr Arg Leu Tyr Gln Lys<br>                    370                            375                          380 | 1272 |
| ctc ttt cta gaa atg ata ggg aat cag gtt caa tca gtg aag ata agc<br>Leu Phe Leu Glu Met Ile Gly Asn Gln Val Gln Ser Val Lys Ile Ser<br>385                        390                          395 | 1320 |
| tgc tta tagttaggaa tggtcactgg gctgtttctt caggatgggc caacactgat<br>Cys Leu<br>400 | 1376 |
| ggagcagatg gctgcttctc cggctcttga aatggcagtt gattcctttc tcatcagttg | 1436 |
| gtgggaatga agatcctcca gcccaacaca cacactgggg agtctgagtc aggagagtga | 1496 |
| ggcaggctat tgataattg tgcaaagctg ccaggtgtac acctagaaag tcaagcaccc | 1556 |
| tgagaaagag gatatttta aacctcaaa cataggccct ttccttcctc tccttatgga | 1616 |
| tgagtactca gaaggcttct actatcttct gtgtcatccc tagatgaagg cctcttttat | 1676 |
| ttattttttt attcttttt tcggagctgg ggaccgaacc cagggccttg cgcttgcgag | 1736 |
| gcaagtgctc taccactgag ctaaatctcc aacccctgaa ggcctctttc tttctgcctc | 1796 |
| tgatagtcta tgcattctt ttttctacaa ttcgtatcag gtgcacgagc cttatcccat | 1856 |
| ttgtaggttt ctaggcaagt tgaccgttag ctattttttcc ctctgaagat ttgattcgag | 1916 |
| ttgcagactt ggctagacaa gcaggggtag gttatggtag tttattttaac agactgccac | 1976 |
| caggagtcca gtgtttcttg ttcctctgta gttgtaccta agctgactcc aagtacattt | 2036 |
| agtatgaaaa ataatcaaca aattttattc cttctatcaa cattggctag ctttgtttca | 2096 |
| gggcactaaa agaaactact atatggagaa agaattgata ttgcccccaa cgttcaacaa | 2156 |
| cccaatagtt tatccagctg tcatgcctgg ttcagtgtct actgactatg cgccctctta | 2216 |
| ttactgcatg cagtaattca actggaaata gtaataataa taatagaaat aaaatctaga | 2276 |
| ctccattgga tctctctgaa tatgggaata tctaacttaa gaagctttga gatttcagtt | 2336 |
| gtgttaaagg cttttattaa aaagctgatg ctcttctgta aaagttacta atatatctgt | 2396 |
| aagactatta cagtattgct atttatatcc atccag | 2432 |

<210> SEQ ID NO 121
<211> LENGTH: 401
<212> TYPE: PRT
<213> ORGANISM: Rattus rattus

<400> SEQUENCE: 121

Met Asn Lys Trp Leu Cys Cys Ala Leu Leu Val Phe Leu Asp Ile Ile
1                  5                        10                        15

Glu Trp Thr Thr Gln Glu Thr Phe Pro Pro Lys Tyr Leu His Tyr Asp
                  20                        25                        30

Pro Glu Thr Gly Arg Gln Leu Leu Cys Asp Lys Cys Ala Pro Gly Thr
                        35                        40                          45

Tyr Leu Lys Gln His Cys Thr Val Arg Arg Lys Thr Leu Cys Val Pro

```
            50                  55                  60
Cys Pro Asp Tyr Ser Tyr Thr Asp Ser Trp His Thr Ser Asp Glu Cys
 65                  70                  75                  80

Val Tyr Cys Ser Pro Val Cys Lys Glu Leu Gln Thr Val Lys Gln Glu
                 85                  90                  95

Cys Asn Arg Thr His Asn Arg Val Cys Glu Cys Glu Glu Gly Arg Tyr
                100                 105                 110

Leu Glu Leu Glu Phe Cys Leu Lys His Arg Ser Cys Pro Pro Gly Leu
            115                 120                 125

Gly Val Leu Gln Ala Gly Thr Pro Glu Arg Asn Thr Val Cys Lys Arg
        130                 135                 140

Cys Pro Asp Gly Phe Phe Ser Gly Glu Thr Ser Ser Lys Ala Pro Cys
145                 150                 155                 160

Arg Lys His Thr Asn Cys Ser Ser Leu Gly Leu Leu Leu Ile Gln Lys
                165                 170                 175

Gly Asn Ala Thr His Asp Asn Val Cys Ser Gly Asn Arg Glu Ala Thr
            180                 185                 190

Gln Asn Cys Glu Ile Asp Val Thr Leu Cys Glu Glu Ala Phe Phe Arg
        195                 200                 205

Phe Ala Val Pro Thr Lys Ile Ile Pro Asn Trp Leu Ser Val Leu Val
210                 215                 220

Asp Ser Leu Pro Gly Thr Lys Val Asn Ala Glu Ser Val Glu Arg Ile
225                 230                 235                 240

Lys Arg Arg His Ser Ser Gln Glu Gln Thr Phe Gln Leu Leu Lys Leu
                245                 250                 255

Trp Lys His Gln Asn Arg Asp Gln Glu Met Val Lys Lys Ile Ile Gln
            260                 265                 270

Asp Ile Asp Leu Cys Glu Ser Ser Val Gln Arg His Ile Gly His Ala
        275                 280                 285

Asn Leu Thr Thr Glu Gln Leu Arg Ile Leu Met Glu Ser Leu Pro Gly
290                 295                 300

Lys Lys Ile Ser Pro Asp Glu Ile Glu Arg Thr Arg Lys Thr Cys Lys
305                 310                 315                 320

Pro Ser Glu Gln Leu Leu Lys Leu Leu Ser Leu Trp Arg Ile Lys Asn
                325                 330                 335

Gly Asp Gln Asp Thr Leu Lys Gly Leu Met Tyr Ala Leu Lys His Leu
            340                 345                 350

Lys Ala Tyr His Phe Pro Lys Thr Val Thr His Ser Leu Arg Lys Thr
        355                 360                 365

Ile Arg Phe Leu His Ser Phe Thr Met Tyr Arg Leu Tyr Gln Lys Leu
370                 375                 380

Phe Leu Glu Met Ile Gly Asn Gln Val Gln Ser Val Lys Ile Ser Cys
385                 390                 395                 400

Leu

<210> SEQ ID NO 122
<211> LENGTH: 1325
<212> TYPE: DNA
<213> ORGANISM: Mus musculus
<220> FEATURE:
<221> NAME/KEY: misc_feature
<222> LOCATION: (11)..(11)
<223> OTHER INFORMATION: At position 11, R is a purine.
<220> FEATURE:
<221> NAME/KEY: CDS
<222> LOCATION: (91)..(1293)
```

<400> SEQUENCE: 122

```
ccttatataa racgtcatga ttgcctgggc tgcagagacg cacctagcac tgacccagcg      60
gctgcctcct gaggtttccc gaggaccaca atg aac aag tgg ctg tgc tgc gca     114
                                Met Asn Lys Trp Leu Cys Cys Ala
                                  1               5 ctc ctg gtg ctc ctg gac atc att gaa tgg aca acc cag gaa acc ctt      162
Leu Leu Val Leu Leu Asp Ile Ile Glu Trp Thr Thr Gln Glu Thr Leu
 10              15                  20 ctt cca aag tac ttg cat tat gac cca gaa act ggt cat cag ctc ctg      210
Leu Pro Lys Tyr Leu His Tyr Asp Pro Glu Thr Gly His Gln Leu Leu
 25              30                  35                  40 tgt gac aaa tgt gct cct ggc acc tac cta aaa cag cac tgc aca gtg      258
Cys Asp Lys Cys Ala Pro Gly Thr Tyr Leu Lys Gln His Cys Thr Val
                 45                  50                  55 agg agg aag aca ttg tgt gtc cct tgc cct gac cac tct tat acg gac      306
Arg Arg Lys Thr Leu Cys Val Pro Cys Pro Asp His Ser Tyr Thr Asp
                 60                  65                  70 agc tgg cac acc agt gat gag tgt gtg tat tgc agc cca gtg tgc aag      354
Ser Trp His Thr Ser Asp Glu Cys Val Tyr Cys Ser Pro Val Cys Lys
                 75                  80                  85 gaa ctg cag tcc gtg aag cag gag tgc aac cgc acc cac aac cga gtg      402
Glu Leu Gln Ser Val Lys Gln Glu Cys Asn Arg Thr His Asn Arg Val
 90                  95                 100 tgt gag tgt gag gaa ggg cgt tac ctg gag atc gaa ttc tgc ttg aag      450
Cys Glu Cys Glu Glu Gly Arg Tyr Leu Glu Ile Glu Phe Cys Leu Lys
105                 110                 115                 120 cac cgg agc tgt ccc ccg ggc tcc ggc gtg gtg caa gct gga acc cca      498
His Arg Ser Cys Pro Pro Gly Ser Gly Val Val Gln Ala Gly Thr Pro
                125                 130                 135 gag cga aac aca gtt tgc aaa aaa tgt cca gat ggg ttc ttc tca ggt      546
Glu Arg Asn Thr Val Cys Lys Lys Cys Pro Asp Gly Phe Phe Ser Gly
                140                 145                 150 gag act tca tcg aaa gca ccc tgt ata aaa cac acg aac tgc agc aca      594
Glu Thr Ser Ser Lys Ala Pro Cys Ile Lys His Thr Asn Cys Ser Thr
                155                 160                 165 ttt ggc ctc ctg cta att cag aaa gga aat gca aca cat gac aac tgt      642
Phe Gly Leu Leu Leu Ile Gln Lys Gly Asn Ala Thr His Asp Asn Cys
170                 175                 180 tgt tcc gga aac aga gaa gcc acg caa aag tgt gga ata gat gtc acc      690
Cys Ser Gly Asn Arg Glu Ala Thr Gln Lys Cys Gly Ile Asp Val Thr
185                 190                 195                 200 ctg tgt gaa gag gcc ttc ttc agg ttt gct gtt cct acc aag att ata      738
Leu Cys Glu Glu Ala Phe Phe Arg Phe Ala Val Pro Thr Lys Ile Ile
                205                 210                 215 cca aat tgg ctg agt gtt ttg gtg gac agt ttg cct ggg acc aaa gtg      786
Pro Asn Trp Leu Ser Val Leu Val Asp Ser Leu Pro Gly Thr Lys Val
                220                 225                 230 aat gcc gag agt gta gag agg ata aaa cgg aga cac agc tca caa gag      834
Asn Ala Glu Ser Val Glu Arg Ile Lys Arg Arg His Ser Ser Gln Glu
                235                 240                 245 caa acc ttc cag ctg ctg aag ctg tgg aaa cat caa aac aga gac cag      882
Gln Thr Phe Gln Leu Leu Lys Leu Trp Lys His Gln Asn Arg Asp Gln
250                 255                 260 gaa atg gtg aag aag atc atc caa gac att gac ctc tgt gaa agc agc      930
Glu Met Val Lys Lys Ile Ile Gln Asp Ile Asp Leu Cys Glu Ser Ser
265                 270                 275                 280 gtg cag cgg cat ctc ggc cac tcg aac ctc acc aca gag cag ctt ctt      978
Val Gln Arg His Leu Gly His Ser Asn Leu Thr Thr Glu Gln Leu Leu
```

```
                    285                 290                 295
gcc ttg atg gag agc ctg cct ggg aag aag atc agc cca gaa gag att        1026
Ala Leu Met Glu Ser Leu Pro Gly Lys Lys Ile Ser Pro Glu Glu Ile
            300                 305                 310 gag aga acg aga aag acc tgc aaa tcg agc gag cag ctc ctg aag cta        1074
Glu Arg Thr Arg Lys Thr Cys Lys Ser Ser Glu Gln Leu Leu Lys Leu
            315                 320                 325 ctc agt tta tgg agg atc aaa aat ggt gac caa gac acc ttg aag ggc        1122
Leu Ser Leu Trp Arg Ile Lys Asn Gly Asp Gln Asp Thr Leu Lys Gly
    330                 335                 340 ctg atg tat gcc ctc aag cac ttg aaa aca tcc cac ttt ccc aaa act        1170
Leu Met Tyr Ala Leu Lys His Leu Lys Thr Ser His Phe Pro Lys Thr
345                 350                 355                 360 gtc acc cac agt ctg agg aag acc atg agg ttc ctg cac agc ttc aca        1218
Val Thr His Ser Leu Arg Lys Thr Met Arg Phe Leu His Ser Phe Thr
                365                 370                 375 atg tac aga ctg tat cag aag ctc ttt tta gaa atg ata ggg aat cag        1266
Met Tyr Arg Leu Tyr Gln Lys Leu Phe Leu Glu Met Ile Gly Asn Gln
            380                 385                 390 gtt caa tcc gtg aaa ata agc tgc tta taactaggaa tggtcactgg             1313
Val Gln Ser Val Lys Ile Ser Cys Leu
            395                 400 gctgtttctt ca                                                          1325

<210> SEQ ID NO 123
<211> LENGTH: 401
<212> TYPE: PRT
<213> ORGANISM: Mus musculus

<400> SEQUENCE: 123

Met Asn Lys Trp Leu Cys Cys Ala Leu Leu Val Leu Leu Asp Ile Ile
1               5                   10                  15

Glu Trp Thr Thr Gln Glu Thr Leu Leu Pro Lys Tyr Leu His Tyr Asp
            20                  25                  30

Pro Glu Thr Gly His Gln Leu Leu Cys Asp Lys Cys Ala Pro Gly Thr
        35                  40                  45

Tyr Leu Lys Gln His Cys Thr Val Arg Arg Lys Thr Leu Cys Val Pro
    50                  55                  60

Cys Pro Asp His Ser Tyr Thr Asp Ser Trp His Thr Ser Asp Glu Cys
65                  70                  75                  80

Val Tyr Cys Ser Pro Val Cys Lys Glu Leu Gln Ser Val Lys Gln Glu
                85                  90                  95

Cys Asn Arg Thr His Asn Arg Val Cys Glu Cys Glu Glu Gly Arg Tyr
            100                 105                 110

Leu Glu Ile Glu Phe Cys Leu Lys His Arg Ser Cys Pro Pro Gly Ser
        115                 120                 125

Gly Val Val Gln Ala Gly Thr Pro Glu Arg Asn Thr Val Cys Lys Lys
    130                 135                 140

Cys Pro Asp Gly Phe Phe Ser Gly Glu Thr Ser Ser Lys Ala Pro Cys
145                 150                 155                 160

Ile Lys His Thr Asn Cys Ser Thr Phe Gly Leu Leu Leu Ile Gln Lys
                165                 170                 175

Gly Asn Ala Thr His Asp Asn Cys Cys Ser Gly Asn Arg Glu Ala Thr
            180                 185                 190

Gln Lys Cys Gly Ile Asp Val Thr Leu Cys Glu Glu Ala Phe Phe Arg
        195                 200                 205
```

-continued

```
Phe Ala Val Pro Thr Lys Ile Ile Pro Asn Trp Leu Ser Val Leu Val
    210             215                 220
Asp Ser Leu Pro Gly Thr Lys Val Asn Ala Glu Ser Val Glu Arg Ile
225                 230                 235                 240
Lys Arg Arg His Ser Ser Gln Glu Gln Thr Phe Gln Leu Leu Lys Leu
                245                 250                 255
Trp Lys His Gln Asn Arg Asp Gln Glu Met Val Lys Lys Ile Ile Gln
            260                 265                 270
Asp Ile Asp Leu Cys Glu Ser Ser Val Gln Arg His Leu Gly His Ser
        275                 280                 285
Asn Leu Thr Thr Glu Gln Leu Leu Ala Leu Met Glu Ser Leu Pro Gly
    290                 295                 300
Lys Lys Ile Ser Pro Glu Glu Ile Glu Arg Thr Arg Lys Thr Cys Lys
305                 310                 315                 320
Ser Ser Glu Gln Leu Leu Lys Leu Leu Ser Leu Trp Arg Ile Lys Asn
                325                 330                 335
Gly Asp Gln Asp Thr Leu Lys Gly Leu Met Tyr Ala Leu Lys His Leu
            340                 345                 350
Lys Thr Ser His Phe Pro Lys Thr Val Thr His Ser Leu Arg Lys Thr
        355                 360                 365
Met Arg Phe Leu His Ser Phe Thr Met Tyr Arg Leu Tyr Gln Lys Leu
    370                 375                 380
Phe Leu Glu Met Ile Gly Asn Gln Val Gln Ser Val Lys Ile Ser Cys
385                 390                 395                 400
Leu
```

```
<210> SEQ ID NO 124
<211> LENGTH: 1356
<212> TYPE: DNA
<213> ORGANISM: Homo sapiens
<220> FEATURE:
<221> NAME/KEY: misc_feature
<222> LOCATION: (63)..(63)
<223> OTHER INFORMATION: At position 63, Y is a pyrimidine.
<220> FEATURE:
<221> NAME/KEY: CDS
<222> LOCATION: (95)..(1297)

<400> SEQUENCE: 124
```

```
gtatatataa cgtgatgagc gtacgggtgc ggagacgcac cggcgcgctc gcccagccgc        60
cgyctccaag cccctgaggt ttccggggac caca atg aac aag ttg ctg tgc tgc       115
                                     Met Asn Lys Leu Leu Cys Cys
                                      1               5 gcg ctc gtg ttt ctg gac atc tcc att aag tgg acc acc cag gaa acg       163
Ala Leu Val Phe Leu Asp Ile Ser Ile Lys Trp Thr Thr Gln Glu Thr
         10                  15                  20 ttt cct cca aag tac ctt cat tat gac gaa gaa acc tct cat cag ctg       211
Phe Pro Pro Lys Tyr Leu His Tyr Asp Glu Glu Thr Ser His Gln Leu
     25                  30                  35 ttg tgt gac aaa tgt cct cct ggt acc tac cta aaa caa cac tgt aca       259
Leu Cys Asp Lys Cys Pro Pro Gly Thr Tyr Leu Lys Gln His Cys Thr
 40                  45                  50                  55 gca aag tgg aag tcc gtg tgc gcc cct tgc cct gac cac tac tac aca       307
Ala Lys Trp Lys Ser Val Cys Ala Pro Cys Pro Asp His Tyr Tyr Thr
                 60                  65                  70 gac agc tgg cac acc agt gac gag tgt cta tac tgc agc ccc gtg tgc       355
Asp Ser Trp His Thr Ser Asp Glu Cys Leu Tyr Cys Ser Pro Val Cys
             75                  80                  85
```

```
aag gag ctg cag tac gtc aag cag gag tgc aat cgc acc cac aac cgc    403
Lys Glu Leu Gln Tyr Val Lys Gln Glu Cys Asn Arg Thr His Asn Arg
         90                  95                 100 gtg tgc gaa tgc aag gaa ggg cgc tac ctt gag ata gag ttc tgc ttg    451
Val Cys Glu Cys Lys Glu Gly Arg Tyr Leu Glu Ile Glu Phe Cys Leu
        105                 110                 115 aaa cat agg agc tgc cct cct gga ttt gga gtg gtg caa gct gga acc    499
Lys His Arg Ser Cys Pro Pro Gly Phe Gly Val Val Gln Ala Gly Thr
120                 125                 130                 135 cca gag cga aat aca gtt tgc aaa aga tgt cca gat ggg ttc ttc tca    547
Pro Glu Arg Asn Thr Val Cys Lys Arg Cys Pro Asp Gly Phe Phe Ser
                140                 145                 150 aat gag acg tca tct aaa gca ccc tgt aga aaa cac aca aat tgc agt    595
Asn Glu Thr Ser Ser Lys Ala Pro Cys Arg Lys His Thr Asn Cys Ser
            155                 160                 165 gtc ttt ggt ctc ctg cta act cag aaa gga aat gca aca cac gac aac    643
Val Phe Gly Leu Leu Leu Thr Gln Lys Gly Asn Ala Thr His Asp Asn
        170                 175                 180 ata tgt tcc gga aac agt gaa tca act caa aaa tgt gga ata gat gtt    691
Ile Cys Ser Gly Asn Ser Glu Ser Thr Gln Lys Cys Gly Ile Asp Val
185                 190                 195 acc ctg tgt gag gag gca ttc ttc agg ttt gct gtt cct aca aag ttt    739
Thr Leu Cys Glu Glu Ala Phe Phe Arg Phe Ala Val Pro Thr Lys Phe
200                 205                 210                 215 acg cct aac tgg ctt agt gtc ttg gta gac aat ttg cct ggc acc aaa    787
Thr Pro Asn Trp Leu Ser Val Leu Val Asp Asn Leu Pro Gly Thr Lys
                220                 225                 230 gta aac gca gag agt gta gag agg ata aaa cgg caa cac agc tca caa    835
Val Asn Ala Glu Ser Val Glu Arg Ile Lys Arg Gln His Ser Ser Gln
            235                 240                 245 gaa cag act ttc cag ctg ctg aag tta tgg aaa cat caa aac aaa gcc    883
Glu Gln Thr Phe Gln Leu Leu Lys Leu Trp Lys His Gln Asn Lys Ala
        250                 255                 260 caa gat ata gtc aag aag atc atc caa gat att gac ctc tgt gaa aac    931
Gln Asp Ile Val Lys Lys Ile Ile Gln Asp Ile Asp Leu Cys Glu Asn
265                 270                 275 agc gtg cag cgg cac att gga cat gct aac ctc acc ttc gag cag ctt    979
Ser Val Gln Arg His Ile Gly His Ala Asn Leu Thr Phe Glu Gln Leu
280                 285                 290                 295 cgt agc ttg atg gaa agc tta ccg gga aag aaa gtg gga gca gaa gac   1027
Arg Ser Leu Met Glu Ser Leu Pro Gly Lys Lys Val Gly Ala Glu Asp
                300                 305                 310 att gaa aaa aca ata aag gca tgc aaa ccc agt gac cag atc ctg aag   1075
Ile Glu Lys Thr Ile Lys Ala Cys Lys Pro Ser Asp Gln Ile Leu Lys
            315                 320                 325 ctg ctc agt ttg tgg cga ata aaa aat ggc gac caa gac acc ttg aag   1123
Leu Leu Ser Leu Trp Arg Ile Lys Asn Gly Asp Gln Asp Thr Leu Lys
        330                 335                 340 ggc cta atg cac gca cta aag cac tca aag acg tac cac ttt ccc aaa   1171
Gly Leu Met His Ala Leu Lys His Ser Lys Thr Tyr His Phe Pro Lys
345                 350                 355 act gtc act cag agt cta aag aag acc atc agg ttc ctt cac agc ttc   1219
Thr Val Thr Gln Ser Leu Lys Lys Thr Ile Arg Phe Leu His Ser Phe
360                 365                 370                 375 aca atg tac aaa ttg tat cag aag tta ttt tta gaa atg ata ggt aac   1267
Thr Met Tyr Lys Leu Tyr Gln Lys Leu Phe Leu Glu Met Ile Gly Asn
                380                 385                 390 cag gtc caa tca gta aaa ata agc tgc tta taactggaaa tggccattga     1317
Gln Val Gln Ser Val Lys Ile Ser Cys Leu
            395                 400
```
gctgtttcct cacaattggc gagatcccat ggatgataa        1356

<210> SEQ ID NO 125
<211> LENGTH: 401
<212> TYPE: PRT
<213> ORGANISM: Homo sapiens

<400> SEQUENCE: 125

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Ser Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Ala Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

```
Ile Arg Phe Leu His Ser Phe Thr Met Tyr Lys Leu Tyr Gln Lys Leu
    370                 375                 380
Phe Leu Glu Met Ile Gly Asn Gln Val Gln Ser Val Lys Ile Ser Cys
385                 390                 395                 400
Leu
```

<210> SEQ ID NO 126
<211> LENGTH: 139
<212> TYPE: PRT
<213> ORGANISM: Homo sapiens

<400> SEQUENCE: 126

```
Cys Pro Gln Gly Lys Tyr Ile His Pro Gln Asn Asn Ser Ile Cys Cys
1               5                   10                  15
Thr Lys Cys His Lys Gly Thr Tyr Leu Tyr Asn Asp Cys Pro Gly Pro
            20                  25                  30
Gly Gln Asp Thr Asp Cys Arg Glu Cys Glu Ser Gly Ser Phe Thr Ala
        35                  40                  45
Ser Glu Asn His Leu Arg His Cys Leu Ser Cys Ser Lys Cys Arg Lys
    50                  55                  60
Glu Met Gly Gln Val Glu Ile Ser Ser Cys Thr Val Asp Arg Asp Thr
65                  70                  75                  80
Val Cys Gly Cys Arg Lys Asn Gln Tyr Arg His Tyr Trp Ser Glu Asn
                85                  90                  95
Leu Phe Gln Cys Phe Asn Cys Ser Leu Cys Leu Asn Gly Thr Val His
            100                 105                 110
Leu Ser Cys Gln Glu Lys Gln Asn Thr Val Cys Thr Cys His Ala Gly
        115                 120                 125
Phe Phe Leu Arg Glu Asn Glu Cys Val Ser Cys
    130                 135
```

<210> SEQ ID NO 127
<211> LENGTH: 48
<212> TYPE: DNA
<213> ORGANISM: Artificial Sequence
<220> FEATURE:
<223> OTHER INFORMATION: huOPG

<400> SEQUENCE: 127

```
acctacttct ttgaagagta gtcgacgaca cactatttac aggcggcc        48
```

<210> SEQ ID NO 128
<211> LENGTH: 219
<212> TYPE: PRT
<213> ORGANISM: Rattus rattus

<400> SEQUENCE: 128

```
Met Leu Gly Ile Trp Thr Leu Leu Pro Leu Val Leu Thr Ser Val Ala
1               5                   10                  15
Arg Leu Ser Ser Lys Ser Val Asn Ala Gln Val Thr Asp Ile Asn Ser
            20                  25                  30
Lys Gly Leu Glu Leu Arg Lys Thr Val Thr Val Glu Thr Gln Asn
        35                  40                  45
Leu Glu Gly Leu His His Asp Gly Gln Phe Cys His Lys Pro Cys Pro
    50                  55                  60
Pro Gly Glu Arg Lys Ala Arg Asp Cys Thr Val Asn Gly Asp Glu Pro
65                  70                  75                  80
```

```
Asp Cys Val Pro Cys Gln Glu Gly Lys Glu Tyr Thr Asp Lys Ala His
                 85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Gly Ser Arg Ser Asn Leu Gly Trp
                165                 170                 175

Leu Cys Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
            195                 200                 205

Ser His Glu Ser Pro Thr Leu Asn Pro Glu Thr
        210                 215
```

<210> SEQ ID NO 129
<211> LENGTH: 280
<212> TYPE: PRT
<213> ORGANISM: Rattus rattus

<400> SEQUENCE: 129

```
Met Gly Leu Ser Thr Val Pro Asp Leu Leu Pro Leu Val Leu Leu
1               5                  10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Thr Arg Thr Gln Arg Trp Lys
225                 230                 235                 240
```

```
Ser Lys Leu Tyr Ser Ile Val Cys Gly Lys Ser Thr Pro Glu Lys Glu
                245                 250                 255
Gly Glu Leu Glu Gly Thr Thr Thr Lys Pro Leu Ala Pro Asn Pro Ser
            260                 265                 270
Phe Ser Pro Thr Pro Gly Phe Thr
        275                 280

<210> SEQ ID NO 130
<211> LENGTH: 207
<212> TYPE: PRT
<213> ORGANISM: Rattus rattus

<400> SEQUENCE: 130

Met Leu Arg Leu Ile Ala Leu Leu Val Cys Val Val Tyr Val Tyr Gly
1               5                   10                  15
Asp Asp Val Pro Tyr Ser Ser Asn Gln Gly Lys Cys Gly Gly His Asp
            20                  25                  30
Tyr Glu Lys Asp Gly Leu Cys Cys Ala Ser Cys His Pro Gly Phe Tyr
        35                  40                  45
Ala Ser Arg Leu Cys Gly Pro Gly Ser Asn Thr Val Cys Ser Pro Cys
    50                  55                  60
Glu Asp Gly Thr Phe Thr Ala Ser Thr Asn His Ala Pro Ala Cys Val
65                  70                  75                  80
Ser Cys Arg Gly Pro Cys Thr Gly His Leu Ser Glu Ser Gln Pro Cys
                85                  90                  95
Asp Arg Thr His Asp Arg Val Cys Asn Cys Ser Thr Gly Asn Tyr Cys
            100                 105                 110
Leu Leu Lys Gly Gln Asn Gly Cys Arg Ile Cys Ala Pro Gln Thr Lys
        115                 120                 125
Cys Pro Ala Gly Tyr Gly Val Ser Gly His Thr Arg Ala Gly Asp Thr
    130                 135                 140
Leu Cys Glu Lys Cys Pro Pro His Thr Tyr Ser Asp Ser Leu Ser Pro
145                 150                 155                 160
Thr Glu Arg Cys Gly Thr Ser Phe Asn Tyr Ile Ser Val Gly Phe Asn
                165                 170                 175
Leu Tyr Pro Val Asn Glu Thr Ser Cys Thr Thr Thr Ala Gly His Asn
            180                 185                 190
Glu Val Ile Lys Thr Lys Glu Phe Thr Val Thr Leu Asn Tyr Thr
        195                 200                 205

<210> SEQ ID NO 131
<211> LENGTH: 227
<212> TYPE: PRT
<213> ORGANISM: Rattus rattus

<400> SEQUENCE: 131

Met Ala Pro Val Ala Val Trp Ala Ala Leu Ala Val Gly Leu Glu Leu
1               5                   10                  15
Trp Ala Ala Ala His Ala Leu Pro Ala Gln Val Ala Phe Thr Pro Tyr
            20                  25                  30
Ala Pro Glu Pro Gly Ser Thr Cys Arg Leu Arg Glu Thr Thr Asp Gln
        35                  40                  45
Thr Ala Gln Met Cys Cys Ser Lys Cys Ser Pro Gly Gln His Ala Lys
    50                  55                  60
Val Phe Cys Thr Lys Thr Ser Asp Thr Val Cys Asp Ser Cys Glu Asp
65                  70                  75                  80
```

```
Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr
225

<210> SEQ ID NO 132
<211> LENGTH: 197
<212> TYPE: PRT
<213> ORGANISM: Rattus rattus

<400> SEQUENCE: 132

Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
        35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
            100                 105                 110

Ser Lys Asp Cys Glu Ala Cys Ala Gln His Thr Pro Cys Ile Pro Gly
        115                 120                 125

Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
                165                 170                 175

Lys Gly Thr Ser Gln Thr Asn Val Ile Cys Gly Leu Lys Ser Arg Met
            180                 185                 190

Arg Ala Leu Leu Val
        195
```

<210> SEQ ID NO 133
<211> LENGTH: 208
<212> TYPE: PRT
<213> ORGANISM: Rattus rattus

<400> SEQUENCE: 133

```
Met Asn Lys Trp Leu Cys Cys Ala Leu Leu Val Phe Leu Asp Ile Ile
1               5                   10                  15

Glu Trp Thr Thr Gln Glu Thr Phe Pro Pro Lys Tyr Leu His Tyr Asp
            20                  25                  30

Pro Glu Thr Gly Arg Gln Leu Leu Cys Asp Lys Cys Ala Pro Gly Thr
        35                  40                  45

Tyr Leu Lys Gln His Cys Thr Val Arg Arg Lys Thr Leu Cys Val Pro
    50                  55                  60

Cys Pro Asp Tyr Ser Tyr Thr Asp Ser Trp His Thr Ser Asp Glu Cys
65                  70                  75                  80

Val Tyr Cys Ser Pro Val Cys Lys Glu Leu Gln Thr Val Lys Gln Glu
                85                  90                  95

Cys Asn Arg Thr His Asn Arg Val Cys Glu Cys Glu Glu Gly Arg Tyr
            100                 105                 110

Leu Glu Leu Glu Phe Cys Leu Lys His Arg Ser Cys Pro Pro Gly Leu
        115                 120                 125

Gly Val Leu Gln Ala Gly Thr Pro Glu Arg Asn Thr Val Cys Lys Arg
    130                 135                 140

Cys Pro Asp Gly Phe Phe Ser Gly Glu Thr Ser Ser Lys Ala Pro Cys
145                 150                 155                 160

Arg Lys His Thr Asn Cys Ser Ser Leu Gly Leu Leu Leu Ile Gln Lys
                165                 170                 175

Gly Asn Ala Thr His Asp Asn Val Cys Ser Gly Asn Arg Glu Ala Thr
            180                 185                 190

Gln Asn Cys Gly Ile Asp Val Thr Leu Cys Glu Glu Ala Phe Phe Arg
        195                 200                 205
```

<210> SEQ ID NO 134
<211> LENGTH: 224
<212> TYPE: PRT
<213> ORGANISM: Rattus rattus

<400> SEQUENCE: 134

```
Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
```

```
            130                 135                 140
Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
                180                 185                 190

Gly Arg Trp Ile Thr Arg Ser Thr Pro Glu Gly Ser Asp Ser Thr
                195                 200                 205

Ala Pro Ser Thr Gln Glu Pro Glu Ala Pro Glu Gln Asp Leu Ile
    210                 215                 220

<210> SEQ ID NO 135
<211> LENGTH: 202
<212> TYPE: PRT
<213> ORGANISM: Rattus rattus

<400> SEQUENCE: 135

Met Tyr Val Trp Val Gln Gln Pro Thr Ala Phe Leu Leu Gly Leu
1               5                   10                  15

Ser Leu Gly Val Thr Val Lys Leu Asn Cys Val Lys Asp Thr Tyr Pro
                20                  25                  30

Ser Gly His Lys Cys Cys Arg Glu Cys Gln Pro Gly His Gly Met Val
            35                  40                  45

Ser Arg Cys Asp His Thr Arg Asp Thr Val Cys His Pro Cys Glu Pro
        50                  55                  60

Gly Phe Tyr Asn Glu Ala Val Asn Tyr Asp Thr Cys Lys Gln Cys Thr
65                  70                  75                  80

Gln Cys Asn His Arg Ser Gly Ser Glu Leu Lys Gln Asn Cys Thr Pro
                85                  90                  95

Thr Glu Asp Thr Val Cys Gln Cys Arg Pro Gly Thr Gln Pro Arg Gln
                100                 105                 110

Asp Ser Ser His Lys Leu Gly Val Asp Cys Val Pro Cys Pro Pro Gly
            115                 120                 125

His Phe Ser Pro Gly Ser Asn Gln Ala Cys Lys Pro Trp Thr Asn Cys
        130                 135                 140

Thr Leu Ser Gly Lys Gln Ile Arg His Pro Ala Ser Asn Ser Val Cys
145                 150                 155                 160

Glu Asp Arg Ser Leu Leu Ala Thr Leu Leu Trp Glu Thr Gln Arg Thr
                165                 170                 175

Thr Phe Arg Pro Thr Thr Val Pro Ser Thr Thr Val Trp Pro Arg Thr
                180                 185                 190

Ser Gln Leu Pro Ser Thr Pro Thr Leu Val
            195                 200

<210> SEQ ID NO 136
<211> LENGTH: 191
<212> TYPE: PRT
<213> ORGANISM: Rattus rattus

<400> SEQUENCE: 136

Met Gly Asn Asn Cys Tyr Asn Val Val Ile Val Leu Leu Leu Val
1               5                   10                  15

Gly Cys Glu Lys Val Gly Ala Val Gln Asn Ser Cys Asp Asn Cys Gln
                20                  25                  30

Pro Gly Thr Phe Cys Arg Lys Tyr Asn Pro Val Cys Lys Ser Cys Pro
```

```
                35                  40                  45
Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
                100                 105                 110

Lys Gln Gly Cys Lys Thr Cys Ser Leu Gly Thr Phe Asn Asp Gln Asn
            115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu
                180                 185                 190

<210> SEQ ID NO 137
<211> LENGTH: 54
<212> TYPE: DNA
<213> ORGANISM: Artificial Sequence
<220> FEATURE:
<223> OTHER INFORMATION: huOPG

<400> SEQUENCE: 137
tatggatgaa gaaacttctc atcagctgct gtgtgataaa tgtccgccgg gtac         54

<210> SEQ ID NO 138
<211> LENGTH: 120
<212> TYPE: PRT
<213> ORGANISM: Homo sapiens

<400> SEQUENCE: 138

His Ala Leu Pro Ala Gln Val Ala Phe Thr Pro Tyr Ala Pro Glu Pro
1               5                   10                  15

Gly Ser Thr Cys Arg Leu Arg Glu Tyr Tyr Asp Gln Thr Ala Gln Met
                20                  25                  30

Cys Cys Ser Lys Cys Ser Pro Gly Gln His Ala Lys Val Phe Cys Thr
            35                  40                  45

Lys Thr Ser Asp Thr Val Cys Asp Ser Cys Glu Asp Ser Thr Tyr Thr
    50                  55                  60

Gln Leu Trp Asn Trp Val Pro Glu Cys Leu Ser Cys Gly Ser Arg Cys
65                  70                  75                  80

Ser Ser Asp Gln Val Glu Thr Gln Ala Cys Thr Arg Glu Gln Asn Arg
                85                  90                  95

Ile Cys Thr Cys Arg Pro Gly Trp Tyr Cys Ala Leu Ser Lys Gln Glu
            100                 105                 110

Gly Cys Arg Leu Cys Ala Pro Leu
        115                 120

<210> SEQ ID NO 139
<211> LENGTH: 380
<212> TYPE: PRT
<213> ORGANISM: Homo sapiens
```

-continued

```
<400> SEQUENCE: 139

Glu Thr Phe Pro Pro Lys Tyr Leu His Tyr Asp Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
        50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys Cys Gly Ile
                165                 170                 175

Asp Val Thr Leu Cys Glu Glu Ala Phe Phe Arg Phe Ala Val Pro Thr
            180                 185                 190

Lys Phe Thr Pro Asn Trp Leu Ser Val Leu Val Asp Asn Leu Pro Gly
            195                 200                 205

Thr Lys Val Asn Ala Glu Ser Val Glu Arg Ile Lys Arg Gln His Ser
            210                 215                 220

Ser Gln Glu Gln Thr Phe Gln Leu Leu Lys Leu Trp Lys His Gln Asn
225                 230                 235                 240

Lys Ala Gln Asp Ile Val Lys Ile Ile Gln Asp Ile Asp Leu Cys
                245                 250                 255

Glu Asn Ser Val Gln Arg His Ile Gly His Ala Asn Leu Thr Phe Glu
            260                 265                 270

Gln Leu Arg Ser Leu Met Glu Ser Leu Pro Gly Lys Lys Val Gly Ala
            275                 280                 285

Glu Asp Ile Glu Lys Thr Ile Lys Ala Cys Lys Pro Ser Asp Gln Ile
290                 295                 300

Leu Lys Leu Leu Ser Leu Trp Arg Ile Lys Asn Gly Asp Gln Asp Thr
305                 310                 315                 320

Leu Lys Gly Leu Met His Ala Leu Lys His Ser Lys Thr Lys His Phe
                325                 330                 335

Pro Lys Thr Val Thr Gln Ser Leu Lys Lys Thr Ile Arg Phe Leu His
            340                 345                 350

Ser Phe Thr Met Tyr Lys Leu Tyr Gln Lys Leu Phe Leu Glu Met Ile
            355                 360                 365

Gly Asn Gln Val Gln Ser Val Lys Ile Ser Cys Leu
        370                 375                 380

<210> SEQ ID NO 140
<211> LENGTH: 30
<212> TYPE: DNA
```

```
<213> ORGANISM: Artificial Sequence
<220> FEATURE:
<223> OTHER INFORMATION: huOPG

<400> SEQUENCE: 140
tggaccaccc agaagtacct tcattatgac                                    30

<210> SEQ ID NO 141
<211> LENGTH: 30
<212> TYPE: DNA
<213> ORGANISM: Artificial Sequence
<220> FEATURE:
<223> OTHER INFORMATION: huOPG

<400> SEQUENCE: 141
gtcataatga aggtacttct gggtggtcca                                    30

<210> SEQ ID NO 142
<211> LENGTH: 31
<212> TYPE: DNA
<213> ORGANISM: Artificial Sequence
<220> FEATURE:
<223> OTHER INFORMATION: huOPG

<400> SEQUENCE: 142
ggaccaccca gcttcattat gacgaagaaa c                                  31

<210> SEQ ID NO 143
<211> LENGTH: 31
<212> TYPE: DNA
<213> ORGANISM: Artificial Sequence
<220> FEATURE:
<223> OTHER INFORMATION: huOPG

<400> SEQUENCE: 143
gtttcttcgt cataatgaag ctgggtggtc c                                  31

<210> SEQ ID NO 144
<211> LENGTH: 29
<212> TYPE: DNA
<213> ORGANISM: Artificial Sequence
<220> FEATURE:
<223> OTHER INFORMATION: huOPG

<400> SEQUENCE: 144
gtggaccacc caggacgaag aaacctctc                                     29

<210> SEQ ID NO 145
<211> LENGTH: 29
<212> TYPE: DNA
<213> ORGANISM: Artificial Sequence
<220> FEATURE:
<223> OTHER INFORMATION: huOPG

<400> SEQUENCE: 145
gagaggtttc ttcgtcctgg gtggtccac                                     29

<210> SEQ ID NO 146
<211> LENGTH: 29
<212> TYPE: DNA
<213> ORGANISM: Artificial Sequence
<220> FEATURE:
<223> OTHER INFORMATION: huOPG

<400> SEQUENCE: 146
cgtttcctcc aaagttcctt cattatgac                                     29
```

<210> SEQ ID NO 147
<211> LENGTH: 29
<212> TYPE: DNA
<213> ORGANISM: Artificial Sequence
<220> FEATURE:
<223> OTHER INFORMATION: huOPG

<400> SEQUENCE: 147
gtcataatga aggaactttg gaggaaacg                               29

<210> SEQ ID NO 148
<211> LENGTH: 32
<212> TYPE: DNA
<213> ORGANISM: Artificial Sequence
<220> FEATURE:
<223> OTHER INFORMATION: huOPG

<400> SEQUENCE: 148
ggaaacgttt cctgcaaagt accttcatta tg                           32

<210> SEQ ID NO 149
<211> LENGTH: 32
<212> TYPE: DNA
<213> ORGANISM: Artificial Sequence
<220> FEATURE:
<223> OTHER INFORMATION: huOPG

<400> SEQUENCE: 149
cataatgaag gtactttgca ggaaacgttt cc                           32

<210> SEQ ID NO 150
<211> LENGTH: 27
<212> TYPE: DNA
<213> ORGANISM: Artificial Sequence
<220> FEATURE:
<223> OTHER INFORMATION: muOPG

<400> SEQUENCE: 150
cacgcaaaag tcgggaatag atgtcac                                 27

<210> SEQ ID NO 151
<211> LENGTH: 27
<212> TYPE: DNA
<213> ORGANISM: Artificial Sequence
<220> FEATURE:
<223> OTHER INFORMATION: muOPG

<400> SEQUENCE: 151
gtgacatcta ttcccgactt ttgcgtg                                 27

<210> SEQ ID NO 152
<211> LENGTH: 25
<212> TYPE: DNA
<213> ORGANISM: Artificial Sequence
<220> FEATURE:
<223> OTHER INFORMATION: muOPG

<400> SEQUENCE: 152
caccctgtcg gaagaggcct tcttc                                   25

<210> SEQ ID NO 153
<211> LENGTH: 25
<212> TYPE: DNA
<213> ORGANISM: Artificial Sequence
<220> FEATURE:

<223> OTHER INFORMATION: muOPG

<400> SEQUENCE: 153
gaagaaggcc tcttccgaca gggtg                                      25

<210> SEQ ID NO 154
<211> LENGTH: 24
<212> TYPE: DNA
<213> ORGANISM: Artificial Sequence
<220> FEATURE:
<223> OTHER INFORMATION: muOPG

<400> SEQUENCE: 154
tgacctctcg gaaagcagcg tgca                                       24

<210> SEQ ID NO 155
<211> LENGTH: 24
<212> TYPE: DNA
<213> ORGANISM: Artificial Sequence
<220> FEATURE:
<223> OTHER INFORMATION: muOPG

<400> SEQUENCE: 155
tgcacgctgc tttccgagag gtca                                       24

<210> SEQ ID NO 156
<211> LENGTH: 24
<212> TYPE: DNA
<213> ORGANISM: Artificial Sequence
<220> FEATURE:
<223> OTHER INFORMATION: muOPG

<400> SEQUENCE: 156
cctcgaaatc gagcgagcag ctcc                                       24

<210> SEQ ID NO 157
<211> LENGTH: 25
<212> TYPE: DNA
<213> ORGANISM: Artificial Sequence
<220> FEATURE:
<223> OTHER INFORMATION: muOPG

<400> SEQUENCE: 157
cgatttcgag gtctttctcg ttctc                                      25

<210> SEQ ID NO 158
<211> LENGTH: 33
<212> TYPE: DNA
<213> ORGANISM: Artificial Sequence
<220> FEATURE:
<223> OTHER INFORMATION: muOPG

<400> SEQUENCE: 158
ccgtgaaaat aagctcgtta taactaggaa tgg                             33

<210> SEQ ID NO 159
<211> LENGTH: 33
<212> TYPE: DNA
<213> ORGANISM: Artificial Sequence
<220> FEATURE:
<223> OTHER INFORMATION: muOPG

<400> SEQUENCE: 159
ccattcctag ttataacgag cttattttca cgg                             33

```
<210> SEQ ID NO 160
<211> LENGTH: 38
<212> TYPE: DNA
<213> ORGANISM: Artificial Sequence
<220> FEATURE:
<223> OTHER INFORMATION: muOPG

<400> SEQUENCE: 160
cctctgagct caagcttccg aggaccacaa tgaacaag                          38

<210> SEQ ID NO 161
<211> LENGTH: 44
<212> TYPE: DNA
<213> ORGANISM: Artificial Sequence
<220> FEATURE:
<223> OTHER INFORMATION: muOPG

<400> SEQUENCE: 161
cctctctcga gtcaggtgac atctattcca cacttttgcg tggc                   44

<210> SEQ ID NO 162
<211> LENGTH: 38
<212> TYPE: DNA
<213> ORGANISM: Artificial Sequence
<220> FEATURE:
<223> OTHER INFORMATION: muOPG

<400> SEQUENCE: 162
cctctgagct caagcttccg aggaccacaa tgaacaag                          38

<210> SEQ ID NO 163
<211> LENGTH: 38
<212> TYPE: DNA
<213> ORGANISM: Artificial Sequence
<220> FEATURE:
<223> OTHER INFORMATION: muOPG

<400> SEQUENCE: 163
cctctctcga gtcaaggaac agcaaacctg aagaaggc                          38

<210> SEQ ID NO 164
<211> LENGTH: 38
<212> TYPE: DNA
<213> ORGANISM: Artificial Sequence
<220> FEATURE:
<223> OTHER INFORMATION: muOPG

<400> SEQUENCE: 164
cctctgagct caagcttccg aggaccacaa tgaacaag                          38

<210> SEQ ID NO 165
<211> LENGTH: 38
<212> TYPE: DNA
<213> ORGANISM: Artificial Sequence
<220> FEATURE:
<223> OTHER INFORMATION: muOPG

<400> SEQUENCE: 165
cctctctcga gtcactctgt ggtgaggttc gagtggcc                          38

<210> SEQ ID NO 166
<211> LENGTH: 38
<212> TYPE: DNA
<213> ORGANISM: Artificial Sequence
<220> FEATURE:
<223> OTHER INFORMATION: muOPG
```

```
<400> SEQUENCE: 166
cctctgagct caagcttccg aggaccacaa tgaacaag                               38

<210> SEQ ID NO 167
<211> LENGTH: 38
<212> TYPE: DNA
<213> ORGANISM: Artificial Sequence
<220> FEATURE:
<223> OTHER INFORMATION: muOPG

<400> SEQUENCE: 167
cctctctcga gtcaggatgt tttcaagtgc ttgagggc                               38

<210> SEQ ID NO 168
<211> LENGTH: 16
<212> TYPE: PRT
<213> ORGANISM: Artificial Sequence
<220> FEATURE:
<223> OTHER INFORMATION: pAMG22

<400> SEQUENCE: 168

Met Lys His His His His His His Ala Ser Val Asn Ala Leu Glu
1               5                   10                  15

<210> SEQ ID NO 169
<211> LENGTH: 70
<212> TYPE: PRT
<213> ORGANISM: Homo sapiens

<400> SEQUENCE: 169

Ala Leu Leu Val Phe Leu Asp Ile Ile Glu Trp Thr Thr Gln Glu Thr
1               5                   10                  15

Phe Pro Pro Lys Tyr Leu His Tyr Asp Pro Glu Thr Gly Arg Gln Leu
                20                  25                  30

Leu Cys Asp Lys Cys Ala Pro Gly Thr Tyr Leu Lys Gln His Cys Thr
            35                  40                  45

Val Arg Arg Lys Thr Leu Cys Val Pro Cys Pro Asp Tyr Ser Tyr Thr
        50                  55                  60

Asp Ser Trp His Thr Ser
65                  70

<210> SEQ ID NO 170
<211> LENGTH: 48
<212> TYPE: PRT
<213> ORGANISM: Homo sapiens

<400> SEQUENCE: 170

Tyr Leu His Tyr Asp Pro Glu Thr Gly Arg Gln Leu Leu Cys Asp Lys
1               5                   10                  15

Cys Ala Pro Gly Thr Tyr Leu Lys Gln His Cys Thr Val Arg Arg Lys
                20                  25                  30

Thr Leu Cys Val Pro Cys Pro Asp Tyr Ser Tyr Thr Asp Ser Trp His
            35                  40                  45

<210> SEQ ID NO 171

<400> SEQUENCE: 171

000

<210> SEQ ID NO 172
```

-continued

<400> SEQUENCE: 172

000

<210> SEQ ID NO 173

<400> SEQUENCE: 173

000

<210> SEQ ID NO 174
<211> LENGTH: 139
<212> TYPE: PRT
<213> ORGANISM: Homo sapiens

<400> SEQUENCE: 174

```
Pro Pro Lys Tyr Leu His Tyr Asp Glu Glu Thr Ser His Gln Leu Leu
1               5                   10                  15

Cys Asp Lys Cys Pro Pro Gly Thr Tyr Leu Lys Gln His Cys Thr Ala
            20                  25                  30

Lys Trp Lys Thr Val Cys Ala Pro Cys Pro Asp His Tyr Tyr Thr Asp
        35                  40                  45

Ser Trp His Thr Ser Asp Glu Cys Leu Tyr Cys Ser Pro Val Cys Lys
    50                  55                  60

Glu Leu Gln Tyr Val Lys Gln Glu Cys Asn Arg Thr His Asn Arg Val
65                  70                  75                  80

Cys Glu Cys Lys Glu Gly Arg Tyr Leu Glu Ile Glu Phe Cys Leu Lys
                85                  90                  95

His Arg Ser Cys Pro Pro Gly Phe Gly Val Val Gln Ala Gly Thr Pro
            100                 105                 110

Glu Arg Asn Thr Val Cys Lys Arg Cys Pro Asp Gly Phe Phe Ser Asn
        115                 120                 125

Glu Thr Ser Ser Lys Ala Pro Cys Arg Lys His
    130                 135
```

<210> SEQ ID NO 175
<211> LENGTH: 380
<212> TYPE: PRT
<213> ORGANISM: Mus musculus

<400> SEQUENCE: 175

```
Glu Thr Leu Pro Pro Lys Tyr Leu His Tyr Asp Pro Glu Thr Gly His
1               5                   10                  15

Gln Leu Leu Cys Asp Lys Cys Ala Pro Gly Thr Tyr Leu Lys Gln His
            20                  25                  30

Cys Thr Val Arg Arg Lys Thr Leu Cys Val Pro Cys Pro Asp His Ser
        35                  40                  45

Tyr Thr Asp Ser Trp His Thr Ser Asp Glu Cys Val Tyr Cys Ser Pro
    50                  55                  60

Val Cys Lys Glu Leu Gln Ser Val Lys Gln Glu Cys Asn Arg Thr His
65                  70                  75                  80

Asn Arg Val Cys Glu Cys Glu Glu Gly Arg Tyr Leu Glu Ile Glu Phe
                85                  90                  95

Cys Leu Lys His Arg Ser Cys Pro Pro Gly Ser Gly Val Val Gln Ala
            100                 105                 110

Gly Thr Pro Glu Arg Asn Thr Val Cys Lys Lys Cys Pro Asp Gly Phe
        115                 120                 125

Phe Ser Gly Glu Thr Ser Ser Lys Ala Pro Cys Ile Lys His Thr Asn
```

-continued

```
            130                 135                 140
Cys Ser Thr Phe Gly Leu Leu Leu Ile Gln Lys Gly Asn Ala Thr His
145                 150                 155                 160

Asp Asn Val Cys Ser Gly Asn Arg Glu Ala Thr Gln Lys Cys Gly Ile
                165                 170                 175

Asp Val Thr Leu Cys Glu Glu Ala Phe Phe Arg Phe Ala Val Pro Thr
            180                 185                 190

Lys Ile Ile Pro Asn Trp Leu Ser Val Leu Val Asp Ser Leu Pro Gly
        195                 200                 205

Thr Lys Val Asn Ala Glu Ser Val Glu Arg Ile Lys Arg Arg His Ser
    210                 215                 220

Ser Gln Glu Gln Thr Phe Gln Leu Leu Lys Leu Trp Lys His Gln Asn
225                 230                 235                 240

Arg Asp Gln Glu Met Val Lys Lys Ile Ile Gln Asp Ile Asp Leu Cys
                245                 250                 255

Glu Ser Ser Val Gln Arg His Leu Gly His Ser Asn Leu Thr Thr Glu
                260                 265                 270

Gln Leu Leu Ala Leu Met Glu Ser Leu Pro Gly Lys Lys Ile Ser Pro
            275                 280                 285

Glu Glu Ile Glu Arg Thr Arg Lys Thr Cys Lys Ser Ser Glu Gln Leu
        290                 295                 300

Leu Lys Leu Leu Ser Leu Trp Arg Ile Lys Asn Gly Asp Gln Asp Thr
305                 310                 315                 320

Leu Lys Gly Leu Met Tyr Ala Leu Lys His Leu Lys Thr Ser His Phe
                325                 330                 335

Pro Lys Thr Val Thr His Ser Leu Arg Lys Thr Met Arg Phe Leu His
            340                 345                 350

Ser Phe Thr Met Tyr Arg Leu Tyr Gln Lys Leu Phe Leu Glu Met Ile
        355                 360                 365

Gly Asn Gln Val Gln Ser Val Lys Ile Ser Cys Leu
    370                 375                 380
```

<210> SEQ ID NO 176
<211> LENGTH: 6037
<212> TYPE: DNA
<213> ORGANISM: Homo sapiens
<220> FEATURE:
<221> NAME/KEY: CDS
<222> LOCATION: (4760)..(6025)

<400> SEQUENCE: 176

| | | | | |
|---|---|---|---|---|
| catgggaaat gtcagagtgg agaaccacac cgagtgccac tgcagcactt gttattatca | 60 |
| caaatcctaa tagtttgcag tgggccttgc tgatgatggc tgacttgctc aaaaggaaaa | 120 |
| ttaatttgtc cagtgtctat ggctttgtga gataaaaccc tccttttcct tgccatacca | 180 |
| tttttaacct gctttgagaa tatactgcag ctttattgct tttctcctta tcctacaata | 240 |
| taatcagtag tcttgatctt ttcatttgga atgaaatatg gcatttagca tgaccataaa | 300 |
| aagctgattc cactggaaat aaagtctttt aaatcatcac tctatcactg aattctaatt | 360 |
| tttttctgaaa agtttcaagc cagttacttt tgataggatt aacggaaggg agtgagccag | 420 |
| tgggtgaggt gggttcccat gtagtcaatg gcctaatact ggagaatctt attctaacca | 480 |
| agccttccag agcaagctgt gagcccctca gacagtgggc tactcatgag acagtccatt | 540 |
| ggggtaaagg aagaaaatat aacttctatt tctattcatt tgcacattgt ctttagatgc | 600 |
| ccatttgggt gagttttata gaagtacagc tacattaaaa aatagaactg ataatagata | 660 |

-continued

```
aggctttaaa aaaacttcat tcatcaccag tttgtcaaga ttccatttca aagtgaaaaa    720
ccaatttcta acgggttggt aaacacagca gatggcaggg tgaaaaatta aagtgagtgc    780
atgtacctttt aaagaaacac tgaaatgcac acacattact taacctgctc attcatttat   840
ttacatatag tcttgggtgt acaaaattta gaaataaata catatggggg cggggcctta    900
gctgcacaaa taggatgcgc ggcgggcctt ggtaggggcg gagccttagc tgcacaaata    960
ggatgcgcgg cgggccttgg tgggggcggg gcctaagctg cgcaagtggt acacagctca   1020
gggctgcgat ttcgcgccaa acttgacggc aatcctagcg tgaaggctgg taggattta    1080
tccccgctgc catcatggtt cgaccattga actgcatcgt cgccgtgtcc caaaatatgg   1140
ggattggcaa gaacggagac ctaccctggc ctccgctcag gaacgagttc aagtacttcc   1200
aaagaatgac cacaacctct tcagtggaag gtaaacagaa tctggtgatt atgggtagga   1260
aaacctggtt ctccattcct gagaagaatc gacctttaaa ggacagaatt aatatagttc   1320
tcagtagaga actcaaagaa ccaccacgag gagctcattt tcttgccaaa agtttggatg   1380
atgccttaag acttattgaa caaccggaat tggcaagtaa agtagacatg gtttggatag   1440
tcggaggcag ttctgtttac caggaagcca tgaatcaacc aggccacctc agactctttg   1500
tgacaaggat catgcaggaa tttgaaagtg acacgttttt cccagaaatt gatttgggga   1560
aatataaact tctcccagaa tacccaggcg tcctctctga ggtccaggag gaaaaaggca   1620
tcaagtataa gttttgaagtc tacgagaaga aagactaaca ggaagatgct ttcaagttct   1680
ctgctcccct cctaaagcta tgcattttta taagaccatg ggactttttgc tggctttaga   1740
tctgaaacac tgaaattgtc tgcttctcat cttcagtgag attccaaagg atagtacagt   1800
gacagaacaa gaataggcac tctctacaaa aaaagaaag aaaaaactaa gtaatagcaa   1860
gcataatagc tactgttaag aactcagaga taatgaattg agaatggata ctgcttgaaa   1920
tgaaaattta ataagttaga aactaaactt tataaaaata aaaaaatgag cattaaaaaa   1980
aaaaaaaaaa aaaaaaaaa accccccccc ccccctgc agccaagcta gcttggaatc   2040
aggggataac gcaggaaaga acatgtgagc aaaaggccag caaaaggcca ggaaccgtaa   2100
aaaggccgcg ttgctggcgt ttttccatag gctccgcccc cctgacgagc atcacaaaaa   2160
tcgacgctca gtcagaggt ggcgaaaccc gacaggacta taaagatacc aggcgtttcc   2220
ccctggaagc tccctcgtgc gctctcctgt tccgaccctg ccgcttaccg gatacctgtc   2280
cgccttttctc ccttcgggaa gcgtggcgct ttctcatagc tcacgctgta ggtatctcag   2340
ttcggtgtag gtcgttcgct ccaagctggg ctgtgtgcac gaaccccccg ttcagcccga   2400
ccgctgcgcc ttatccggta actatcgtct tgagtccaac ccggtaagac acgacttatc   2460
gccactggca gcagccactg gtaacaggat tagcagagcg aggtatgtag gcggtgctac   2520
agagttcttg aagtggtggc ctaactacgg ctacactaga aggacagtat ttggtatctg   2580
cgctctgctg aagccagtta ccttcggaaa aagagttggt agctcttgat ccggcaaaca   2640
aaccaccgct ggtagcggtg gtttttttgt ttgcaagcag cagattacgc gcagaaaaaa   2700
aggatctcaa gaagatcctt tgatcttttc tacgggtct gacgctcagt ggaacgaaaa   2760
ctcacgttaa gggattttgg tcatgagatt atcaaaaagg atcttcacct agatcctttt   2820
aaattaaaaa tgaagtttta atcaatcta agtatatat gagtaaactt ggtctgacag   2880
ttaccaatgc ttaatcagtg aggcaccat ctcagcgatc tgtctatttc gttcatccat   2940
agttgcctga ctccccgtcg tgtagataac tacgatacgg gagggcttac catctggccc   3000
```

-continued

| | |
|---|---|
| cagtgctgca atgataccgc gagacccacg ctcaccggct ccagatttat cagcaataaa | 3060 |
| ccagccagcc ggaagggccg agcgcagaag tggtcctgca actttatccg cctccatcca | 3120 |
| gtctattaat tgttgccggg aagctagagt aagtagttcg ccagttaata gtttgcgcaa | 3180 |
| cgttgttgcc attgctgcag gcatcgtggt gtcacgctcg tcgtttggta tggcttcatt | 3240 |
| cagctccggt tcccaacgat caaggcgagt tacatgatcc cccatgttgt gcaaaaaagc | 3300 |
| ggttagctcc ttcggtcctc cgatcgttgt cagaagtaag ttggccgcag tgttatcact | 3360 |
| catggttatg gcagcactgc ataattctct tactgtcatg ccatccgtaa gatgcttttc | 3420 |
| tgtgactggt gagtactcaa ccaagtcatt ctgagaatag tgtatgcggc gaccgagttg | 3480 |
| ctcttgcccg gcgtcaacac gggataaatac gcgccacat agcagaactt aaaagtgct | 3540 |
| catcattgga aaacgttctt cggggcgaaa actctcaagg atcttaccgc tgttgagatc | 3600 |
| cagttcgatg taacccactc gtgcacccaa ctgatcttca gcatctttta ctttcaccag | 3660 |
| cgtttctggg tgagcaaaaa caggaaggca aatgccgca aaaagggaa taagggcgac | 3720 |
| acggaaatgt tgaatactca tactcttcct ttttcaatat tattgaagca tttatcaggg | 3780 |
| ttattgtctc atgagcggat acatatttga atgtatttag aaaaataaac aaataggggt | 3840 |
| tccgcgcaca tttccccgaa aagtgccacc tgacgtctaa gaaaccatta ttatcatgac | 3900 |
| attaacctat aaaaataggc gtatcacgag gccctttcgt cttcaagaat tcctgtgga | 3960 |
| atgtgtgtca gttagggtgt ggaaagtccc caggctcccc agcaggcaga agtatgcaaa | 4020 |
| gcatgcatct caattagtca gcaaccaggt gtggaaagtc cccaggctcc ccagcaggca | 4080 |
| gaagtatgca aagcatgcat ctcaattagt cagcaaccat agtcccgccc ctaactccgc | 4140 |
| ccatcccgcc cctaactccg cccagttccg cccattctcc gccccatggc tgactaattt | 4200 |
| ttttatttta tgcagaggcc gaggccgcct cggcctctga gctattccag aagtagtgag | 4260 |
| gaggctttt tggaggccta ggcttttgca aaaagctggt cgaggctcgc atctctcctt | 4320 |
| cacgcgcccg ccgccctacc tgaggccgcc atccacgccg gttgagtcgc gttctgccgc | 4380 |
| ctcccgcctg tggtgcctcc tgaactgcgt ccgccgtcta ggtaagttta aagctcaggt | 4440 |
| cgagaccggg cctttgtccg gcgctccctt ggagcctacc tagactcagc cggctctcca | 4500 |
| cgctttgcct gaccctgctt gctcaactct acgtctttgt ttcgttttct gttctgcgcc | 4560 |
| gttacagatc cgtcgaggaa ctgaaaaacc agaaagttaa ctggtaagtt tagtcttttt | 4620 |
| gtctttatt tcaggtcccg gatccggtgg tggtgcaaat caaagaactg ctcctcagtg | 4680 |
| gatgttgcct ttacttctag gcctgtacgg aagtgttact tctgctctaa aagctgctgc | 4740 |
| aacaagcttc tagaccacc atg aac aag ttg ctg tgc tgc gcg ctc gtg ttt | 4792 |
|                                   Met Asn Lys Leu Leu Cys Cys Ala Leu Val Phe<br>                                 1                5                    10 | |
| ctg gac atc tcc att aag tgg acc acc cag gaa acg ttt cct cca aag<br>Leu Asp Ile Ser Ile Lys Trp Thr Thr Gln Glu Thr Phe Pro Pro Lys<br>             15                   20                   25 | 4840 |
| tac ctt cat tat gac gaa gaa acc tct cat cag ctg ttg tgt gac aaa<br>Tyr Leu His Tyr Asp Glu Glu Thr Ser His Gln Leu Leu Cys Asp Lys<br>           30                      35                    40 | 4888 |
| tgt cct cct ggt acc tac cta aaa caa cac tgt aca gca aag tgg aag<br>Cys Pro Pro Gly Thr Tyr Leu Lys Gln His Cys Thr Ala Lys Trp Lys<br>   45                      50                    55 | 4936 |
| acc gtg tgc gcc cct tgc cct gac cac tac tac aca gac agc tgg cac<br>Thr Val Cys Ala Pro Cys Pro Asp His Tyr Tyr Thr Asp Ser Trp His<br>60                        65                    70                    75 | 4984 |
| acc agt gac gag tgt cta tac tgc agc ccc gtg tgc aag gag ctg cag<br>Thr Ser Asp Glu Cys Leu Tyr Cys Ser Pro Val Cys Lys Glu Leu Gln | 5032 |

```
                        80                      85                      90
tac gtc aag cag gag tgc aat cgc acc cac aac cgc gtg tgc gaa tgc         5080
Tyr Val Lys Gln Glu Cys Asn Arg Thr His Asn Arg Val Cys Glu Cys
             95                     100                     105 aag gaa ggg cgc tac ctt gag ata gag ttc tgc ttg aaa cat agg agc         5128
Lys Glu Gly Arg Tyr Leu Glu Ile Glu Phe Cys Leu Lys His Arg Ser
        110                     115                     120 tgc cct cct gga ttt gga gtg gtg caa gct gga acc cca gag cga aat         5176
Cys Pro Pro Gly Phe Gly Val Val Gln Ala Gly Thr Pro Glu Arg Asn
    125                     130                     135 aca gtt tgc aaa aga tgt cca gat ggg ttc ttc tca aat gag acg tca         5224
Thr Val Cys Lys Arg Cys Pro Asp Gly Phe Phe Ser Asn Glu Thr Ser
140                     145                     150                 155 tct aaa gca ccc tgt aga aaa cac aca aat tgc agt gtc ttt ggt ctc         5272
Ser Lys Ala Pro Cys Arg Lys His Thr Asn Cys Ser Val Phe Gly Leu
                    160                     165                     170 ctg cta act cag aaa gga aat gca aca cac gac aac ata tgt tcc gga         5320
Leu Leu Thr Gln Lys Gly Asn Ala Thr His Asp Asn Ile Cys Ser Gly
                175                     180                     185 aac agt gaa tca act caa aaa gtc gac aaa act cac aca tgc cca ccg         5368
Asn Ser Glu Ser Thr Gln Lys Val Asp Lys Thr His Thr Cys Pro Pro
            190                     195                     200 tgc cca gca cct gaa ctc ctg ggg gga ccg tca gtc ttc ctc ttc ccc         5416
Cys Pro Ala Pro Glu Leu Leu Gly Gly Pro Ser Val Phe Leu Phe Pro
        205                     210                     215 cca aaa ccc aag gac acc ctc atg atc tcc cgg acc cct gag gtc aca         5464
Pro Lys Pro Lys Asp Thr Leu Met Ile Ser Arg Thr Pro Glu Val Thr
220                     225                     230                 235 tgc gtg gtg gtg gac gtg agc cac gaa gac cct gag gtc aag ttc aac         5512
Cys Val Val Val Asp Val Ser His Glu Asp Pro Glu Val Lys Phe Asn
                    240                     245                     250 tgg tac gtg gac ggc gtg gag gtg cat aat gcc aag aca aag ccg cgg         5560
Trp Tyr Val Asp Gly Val Glu Val His Asn Ala Lys Thr Lys Pro Arg
                255                     260                     265 gag gag cag tac aac agc acg tac cgt gtg gtc agc gtc ctc acc gtc         5608
Glu Glu Gln Tyr Asn Ser Thr Tyr Arg Val Val Ser Val Leu Thr Val
            270                     275                     280 ctg cac cag gac tgg ctg aat ggc aag gag tac aag tgc aag gtc tcc         5656
Leu His Gln Asp Trp Leu Asn Gly Lys Glu Tyr Lys Cys Lys Val Ser
        285                     290                     295 aac aaa gcc ctc cca gcc ccc atc gag aaa acc atc tcc aaa gcc aaa         5704
Asn Lys Ala Leu Pro Ala Pro Ile Glu Lys Thr Ile Ser Lys Ala Lys
300                     305                     310                 315 ggg cag ccc cga gaa cca cag gtg tac acc ctg ccc cca tcc cgg gat         5752
Gly Gln Pro Arg Glu Pro Gln Val Tyr Thr Leu Pro Pro Ser Arg Asp
                    320                     325                     330 gag ctg acc aag aac cag gtc agc ctg acc tgc ctg gtc aaa ggc ttc         5800
Glu Leu Thr Lys Asn Gln Val Ser Leu Thr Cys Leu Val Lys Gly Phe
                335                     340                     345 tat ccc agc gac atc gcc gtg gag tgg gag agc aat ggg cag ccg gag         5848
Tyr Pro Ser Asp Ile Ala Val Glu Trp Glu Ser Asn Gly Gln Pro Glu
            350                     355                     360 aac aac tac aag acc acg cct ccc gtg ctg gac tcc gac ggc tcc ttc         5896
Asn Asn Tyr Lys Thr Thr Pro Pro Val Leu Asp Ser Asp Gly Ser Phe
        365                     370                     375 ttc ctc tac agc aag ctc acc gtg gac aag agc agg tgg cag cag ggg         5944
Phe Leu Tyr Ser Lys Leu Thr Val Asp Lys Ser Arg Trp Gln Gln Gly
380                     385                     390                 395 aac gtc ttc tca tgc tcc gtg atg cat gag gct ctg cac aac cac tac         5992
```

```
Asn Val Phe Ser Cys Ser Val Met His Glu Ala Leu His Asn His Tyr
                400                 405                 410 acg cag aag agc ctc tcc ctg tct ccg ggt aaa tgataactcg ac            6037
Thr Gln Lys Ser Leu Ser Leu Ser Pro Gly Lys
            415                 420

<210> SEQ ID NO 177
<211> LENGTH: 422
<212> TYPE: PRT
<213> ORGANISM: Homo sapiens

<400> SEQUENCE: 177

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Thr Gln Lys
                165                 170                 175

Gly Asn Ala Thr His Asp Asn Ile Cys Ser Gly Asn Ser Glu Ser Thr
            180                 185                 190

Gln Lys Val Asp Lys Thr His Thr Cys Pro Pro Cys Pro Ala Pro Glu
        195                 200                 205

Leu Leu Gly Gly Pro Ser Val Phe Leu Phe Pro Pro Lys Pro Lys Asp
    210                 215                 220

Thr Leu Met Ile Ser Arg Thr Pro Glu Val Thr Cys Val Val Val Asp
225                 230                 235                 240

Val Ser His Glu Asp Pro Glu Val Lys Phe Asn Trp Tyr Val Asp Gly
                245                 250                 255

Val Glu Val His Asn Ala Lys Thr Lys Pro Arg Glu Glu Gln Tyr Asn
            260                 265                 270

Ser Thr Tyr Arg Val Val Ser Val Leu Thr Val Leu His Gln Asp Trp
        275                 280                 285

Leu Asn Gly Lys Glu Tyr Lys Cys Lys Val Ser Asn Lys Ala Leu Pro
    290                 295                 300

Ala Pro Ile Glu Lys Thr Ile Ser Lys Ala Lys Gly Gln Pro Arg Glu
305                 310                 315                 320

Pro Gln Val Tyr Thr Leu Pro Pro Ser Arg Asp Glu Leu Thr Lys Asn
                325                 330                 335

Gln Val Ser Leu Thr Cys Leu Val Lys Gly Phe Tyr Pro Ser Asp Ile
```

-continued

```
                       340                 345                 350

Ala Val Glu Trp Glu Ser Asn Gly Gln Pro Glu Asn Asn Tyr Lys Thr
            355                 360                 365

Thr Pro Pro Val Leu Asp Ser Asp Gly Ser Phe Phe Leu Tyr Ser Lys
        370                 375                 380

Leu Thr Val Asp Lys Ser Arg Trp Gln Gln Gly Asn Val Phe Ser Cys
385                 390                 395                 400

Ser Val Met His Glu Ala Leu His Asn His Tyr Thr Gln Lys Ser Leu
                405                 410                 415

Ser Leu Ser Pro Gly Lys
            420

<210> SEQ ID NO 178
<211> LENGTH: 51
<212> TYPE: PRT
<213> ORGANISM: Homo sapiens

<400> SEQUENCE: 178

Tyr His Tyr Tyr Asp Gln Asn Gly Arg Met Cys Glu Glu Cys His Met
1               5                   10                  15

Cys Gln Pro Gly His Phe Leu Val Lys His Cys Lys Gln Pro Lys Arg
            20                  25                  30

Asp Thr Val Cys His Lys Pro Cys Glu Pro Gly Val Thr Tyr Thr Asp
        35                  40                  45

Asp Trp His
    50
```

US 7,005,413 B1

COMBINATION THERAPY FOR CONDITIONS LEADING TO BONE LOSS

CROSS-REFERENCE TO RELATED APPLICATIONS

This application is a continuation-in-part of U.S. Ser. No. 09/457,647, filed Dec. 9, 1999, now abandoned, which is a continuation-in-part of U.S. Ser. No. 09/350,670, filed Jul. 9, 1999, now abandoned, which is a continuation-in-part of U.S. Ser. No. 08/706,945, now U.S. Pat. No. 6,369,027, filed on Sep. 3, 1996, which is continuation-in-part of U.S. Ser. No. 08/577,788, now U.S. Pat. No. 6,613,544, filed Dec. 22, 1995. Each of the foregoing applications is hereby incorporated by reference.

FIELD OF THE INVENTION

The invention relates generally to polypeptides involved in the regulation of bone metabolism. More particularly, the invention relates to a novel polypeptide, termed osteoprotegerin, which is a member of the tumor necrosis factor receptor superfamily. The polypeptide is used to treat bone diseases characterized by increased bone loss such as osteoporosis and arthritis.

BACKGROUND OF THE INVENTION

Polypeptide growth factors and cytokines are secreted factors which signal a wide variety of changes in cell growth, differentiation, and metabolism, by specifically binding to discrete, surface bound receptors. As a class of proteins, receptors vary in their structure and mode of signal transduction. They are characterized by having an extracellular domain that is involved in ligand binding, and cytoplasmic domain which transmits an appropriate intracellular signal. Receptor expression patterns ultimately determine which cells will respond to a given ligand, while the structure of a given receptor dictates the cellular response induced by ligand binding. Receptors have been shown to transmit intracellular signals via their cytoplasmic domains by activating protein tyrosine, or protein serine/threonine phosphorylation (e.g., platelet derived growth factor receptor (PDGFR) or transforming growth factor-β receptor-I (TGFβR-I), by stimulating G-protein activation (e.g., β-adrenergic receptor), and by modulating associations with cytoplasmic signal transducing proteins (e.g., TNFR-I and Fas/APO) (Heldin, Cell 80, 213–223 (1995)).

The tumor necrosis factor receptor (TNFR) superfamily is a group of type I transmembrane proteins which share a conserved cysteine-rich motif which is repeated three to six times in the extracellular domain (Smith, et al. Cell 76, 953–962 (1994)). Collectively, these repeat units form the ligand binding domains of these receptors (Chen et al., Chemistry 270, 2874–2878 (1995)). The ligands for these receptors are a structurally related group of proteins homologous to TNFα. (Goeddel et al. Cold Spring Harbor Symp. Quart. Biol. 51, 597–609 (1986); Nagata et al. Science 267, 1449–1456 (1995)). TNFα binds to distinct, but closely related receptors, TNFR-I and TNFR-II. TNFα produces a variety of biological responses in receptor bearing cells, including, proliferation, differentiation, and cytotoxicity and apoptosis (Beutler et al. Ann. Rev. Biochem. 57, 505–518 (1988)).

TNFα is believed to mediate acute and chronic inflammatory responses (Beutler et al. Ann. Rev. Biochem. 57, 505–508 (1988)). Systemic delivery of TNFα induces toxic shock and widespread tissue necrosis. Because of this, TNFα may be responsible for the severe morbidity and mortality associated with a variety of infectious diseases, including sepsis. Mutations in FasL, the ligand for the TNFR-related receptor Fas/APO (Suda et al. Cell 75, 1169–1178 (1993)), is associated with autoimmunity (Fisher et al. Cell 81, 935–946 (1995)), while overproduction of FasL may be implicated in drug-induced hepatitis. Thus, ligands to the various TNFR-related proteins often mediate the serious effects of many disease states, which suggests that agents that neutralize the activity of these ligands would have therapeutic value. Soluble TNFR-I receptors, and antibodies that bind TNFα, have been tested for their ability to neutralize systemic TNFα (Loetscher et al. Cancer Cells 3 (6), 221–226 (1991)). A naturally occurring form of a secreted TNFR-I mRNA was cloned, and its product tested for its ability to neutralize TNFα activity in vitro and in vivo (Kohno et al. PNAS USA 87, 8331–8335 (1990)). The ability of this protein to neutralize TNFα suggests that soluble TNF receptors function to bind and clear TNF thereby blocking the cytotoxic effects on TNFR- bearing cells.

An object of the invention is to identify new members of the TNFR superfamily. It is anticipated that new family members may be transmembrane proteins or soluble forms thereof comprising extracellular domains and lacking transmembrane and cytoplasmic domains. We have identified a new member of the TNFR superfamily which encodes a secreted protein that is closely related to TNFR-II. By analogy to soluble TNFR-II, the TNFR-II related protein may negatively regulate the activity of its ligand, and thus may be useful in the treatment of certain human diseases.

A further object of this invention is new methods of treatment of inflammatory diseases and medical conditions.

SUMMARY OF THE INVENTION

A novel member of the tumor necrosis factor receptor (TNFR) superfamily has been identified from a fetal rat intestinal cDNA library. A full-length cDNA clone was obtained and sequenced. Expression of the rat cDNA in a transgenic mouse revealed a marked increase in bone density, particularly in long bones, pelvic bone and vertebrae. The polypeptide encoded by the cDNA is termed Osteoprotegerin (OPG) and plays a role in promoting bone accumulation.

The invention provides for nucleic acids encoding a polypeptide having at least one of the biological activities of OPG. Nucleic acids which hybridize to nucleic acids encoding mouse, rat or human OPG as shown in FIGS. 2B–2C (SEQ ID NO:120), 9A–9B (SEQ ID NO: 122), and 9C–9D (SEQ ID NO: 124) are also provided. Preferably, OPG is mammalian OPG and more preferably is human OPG. Recombinant vectors and host cells expressing OPG are also encompassed as are methods of producing recombinant OPG. Antibodies or fragments thereof which specifically bind the polypeptide are also disclosed.

Methods of treating bone diseases are also provided by the invention. The polypeptides are useful for preventing bone resorption and may be used to treat any condition resulting in bone loss such as osteoporosis, hypercalcemia, Paget's disease of bone, and bone loss due to rheumatoid arthritis or osteomyelitis, and the like. Bone diseases may also be treated with anti-sense or gene therapy using nucleic acids of the invention. Pharmaceutical compositions comprising OPG nucleic acids and polypeptides are also encompassed.

The invention relates further to treatment of diseases using combination therapy. In particular, the novel polypeptides described herein may be used in conjunction with bone morphogenic proteins BMP-1 through BMP-12; TGF-β and TGF-β family members; IL-1 inhibitors; TNF-α inhibitors; parathyroid hormone and analogs thereof; parathyroid related protein and analogs thereof; E series prostaglandins; bisphosphonates; bone-enhancing minerals; NSAIDs; immunosuppressants; serine protease inhibitors; IL-6 inhibitors; IL-8 inhibitors (e.g., antibodies to IL-8); IL-18 inhibitors; ICE modulators; FGF-1 to FGF-10; FGF modulators; PAF antagonists; KGF, KGF-related molecules, or KGF modulators; MMP modulators; NOS modulators; modulators of glucocorticoid receptor; modulators of glutamate receptor; modulators of LPS levels; and noradrenaline and modulators and mimetics thereof.

DESCRIPTION OF THE FIGURES

FIG. 3. PepPlot analysis (Wisconsin GCG Package, Version 8.1) of the predicted rat OPG sequence. A. Schematic representation of rat OPG showing hydrophobic (up) and hydrophilic (down) amino acids. Also shown are basic (up) and acidic (down) amino acids. B. Display of amino acid residues that are beta-sheet forming (up) and beta-sheet breaking down) as defined by Chou and Fasman (Adv. Enz. 47, 45–147 (1948)). C. Display of propensity measures for alpha-helix and beta-sheet (Chou and Fasman, ibid). Curves above 1.00 show propensity for alpha-helix or beta-sheet structure. Structure may terminate in regions of protein where curves drop below 1.00. D. Display of residues that are alpha-forming (up) or alpha-breaking (down). E. Display of portions of the protein sequence that resemble sequences typically found at the amino end of alpha and beta structures (Chou and Fasman, ibid). F. Display of portions of the protein sequence that resemble sequences typically found at the carboxyl end of alpha and beta structures (Chou and Fasman, ibid). G. Display of portions of the proteins sequence typically found in turns (Chou and Fasman, ibid) H. Display of the helical hydrophobic moment (Eisenberg et al. Proc. Natl. Acad. Sci. USA 81, 140–144 (1984)) at each position in the sequence. I. Display of average hydrophathy based upon Kyte and Doolittle (J. Mol. Biol. 157, 105–132 (1982)) and Goldman et al. (reviewed in Ann. Rev. Biophys. Biophys. Chem. 15, 321–353 (1986)).

FIG. 9. Structure and sequence of mouse and human OPG cDNA clones. A, B. Mouse cDNA and protein sequence (SEQ ID NO: 122 and 123). C, D. Human cDNA and protein sequence. The predicted signal peptides are underlined, and potential sites of N-linked glycosylation are indicated in bold (SEQ ID NO: 124 and 125). E, F. Sequence alignment and comparison of rat, mouse and human OPG amino acid sequences. Muosteo (SEQ ID NO: 171); ratosteo (SEQ ID NO: 172); huosteo (SEQ ID NO: 173).

FIG. 10. Comparison of conserved sequences in extracellular domain of TNFR-I and human OPG. PrettyPlot (Wisconsin GCG Package, Version 8.1) of the TNFR1 and OPG alignment described in example 6. Top line, human TNFR1 sequences encoding domains 1–4 (SEQ ID NO:

126). Bottom line, human OPG sequences encoding domains 1–4. Conserved residues are highlighted by rectangular boxes (SEQ ID NO: 174).

Figure 4A:
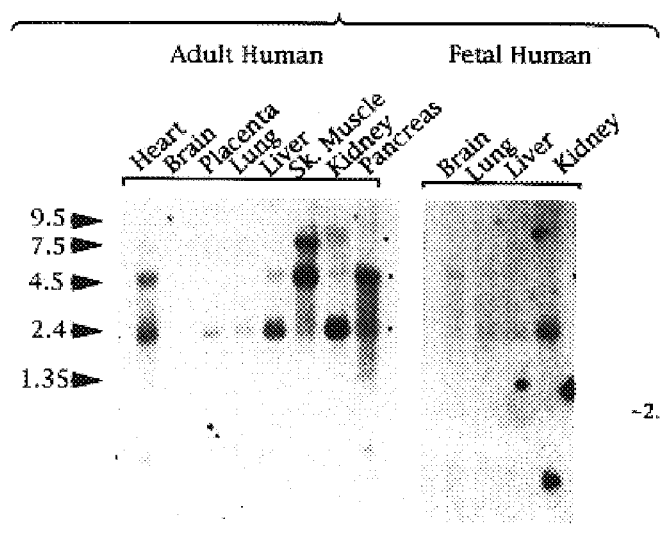
FIG. 4. mRNA expression patterns for the OPG cDNA in human tissues. Northern blots were probed with a 32P-labeled rat cDNA insert (A, left two panels), or with the human cDNA insert (B, right panel).
Figure 4B:
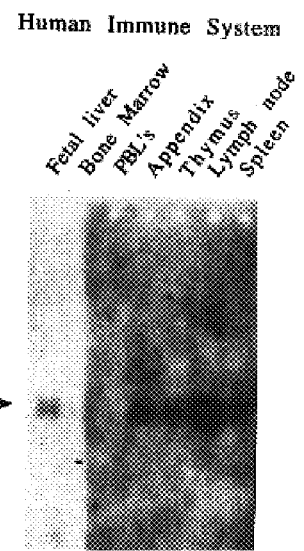
Figure 5:
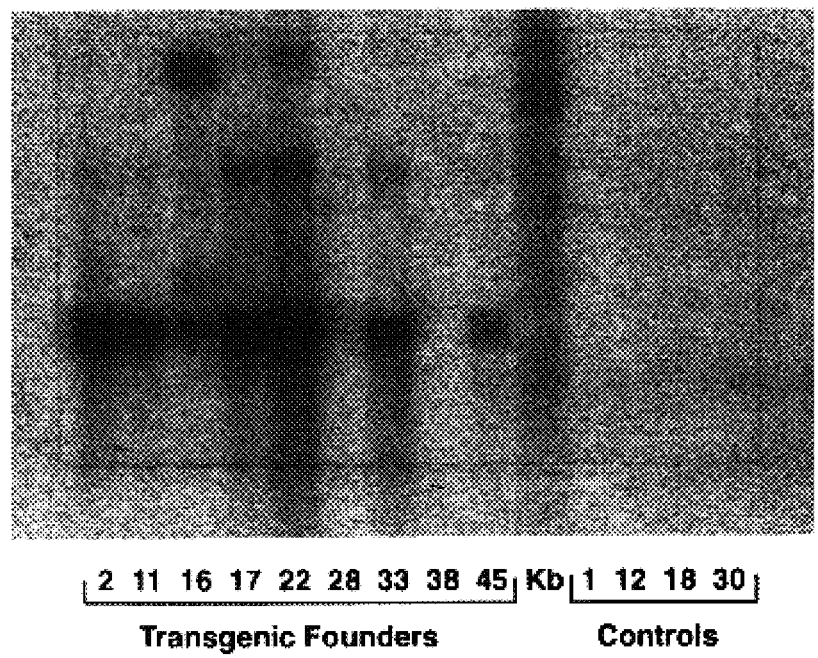
FIG. 5. Creation of transgenic mice expressing the OPG cDNA in hepatocytes. Northern blot expression of HE-OPG transgene in mouse liver.
Figure 6A:
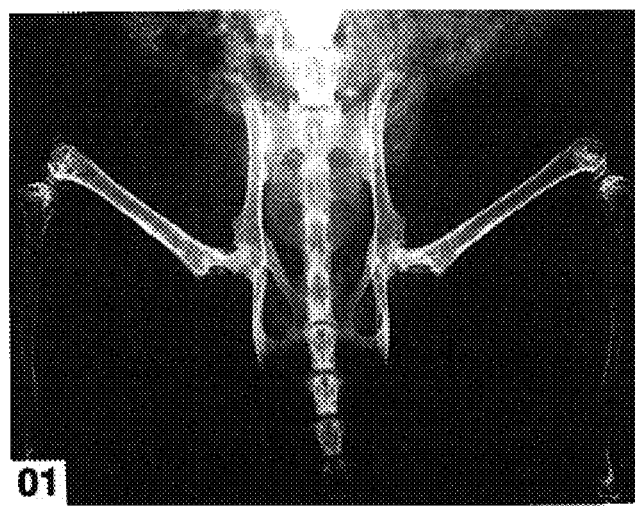
FIG. 6. Increase in bone density in OPG transgenic mice. Panel A–F. Control Mice. G–J, OPG expressing mice. At necropsy, all animals were radiographed and photographs prepared. In A–F, the radiographs of the control animals and the one transgenic non-expressor (#28) are shown. Note that the bones have a clearly defined cortex and a lucent central marrow cavity. In contrast, the OPG (G–J) animals have a poorly defined cortex and increased density in the marrow zone.
Figure 6B:
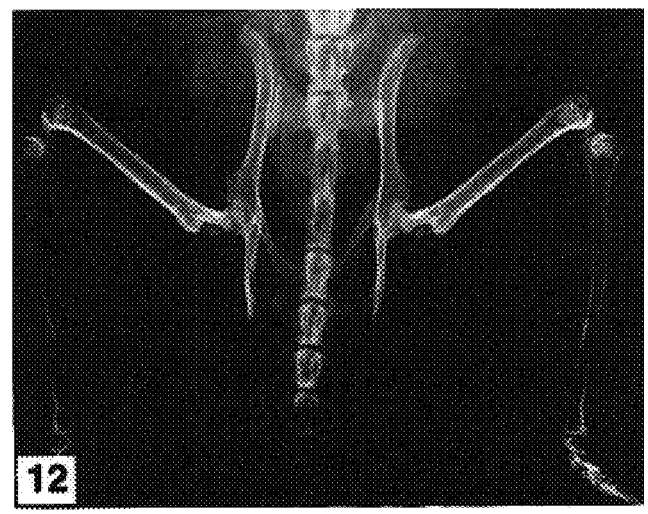
Figure 6C:
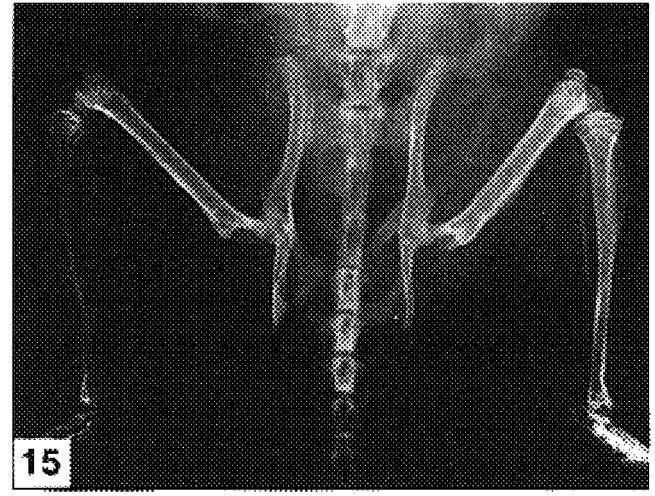
Figure 6D:
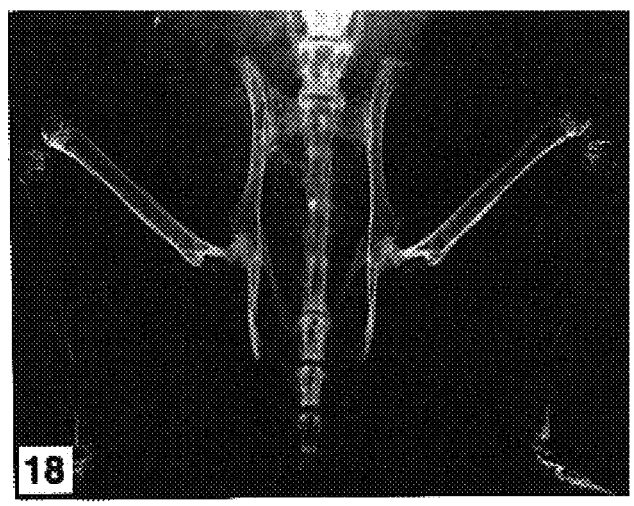
Figure 6E:
Figure 6F:
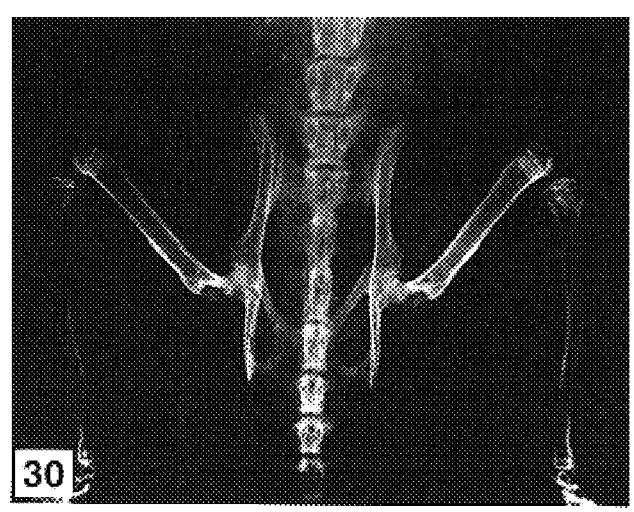
Figure 6G:
Figure 6H:
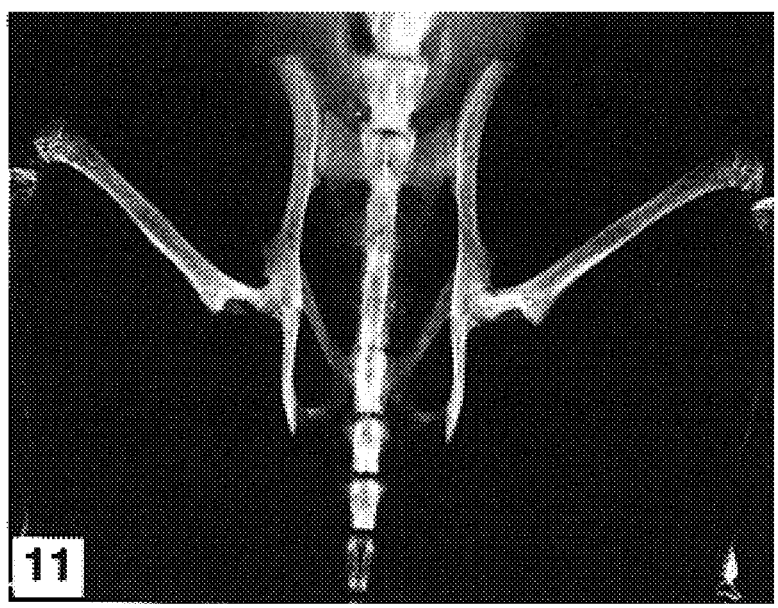
Figure 6I:
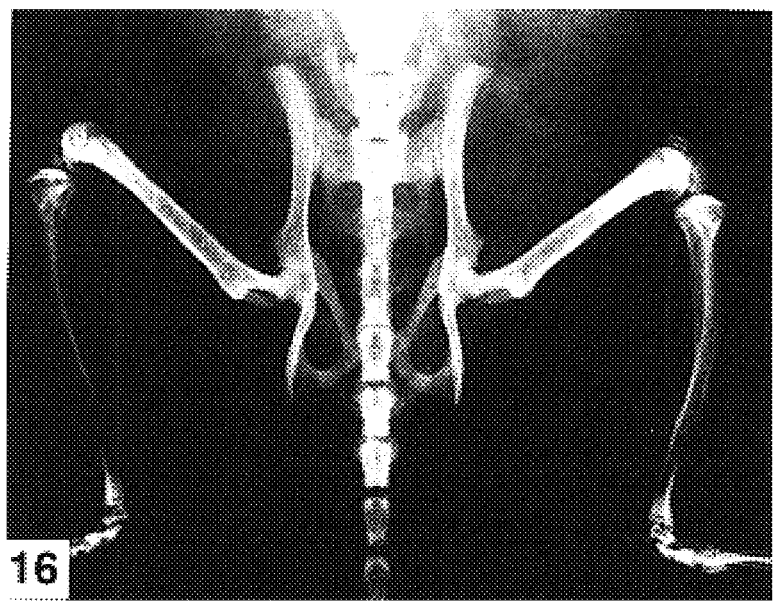
Figure 6J:
Figure 7A:
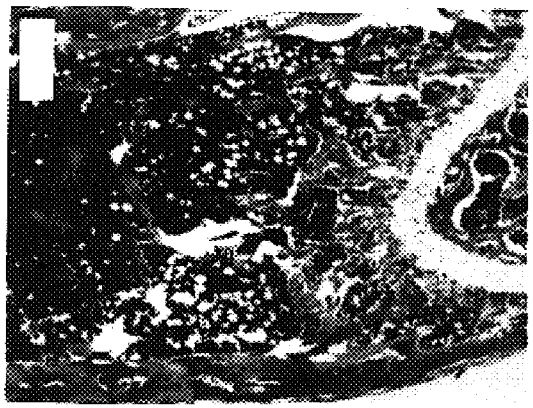
FIG. 7. Increase in trabecular bone in OPG transgenic mice. A–D. Representative photomicrographs of bones from control animals. In A and B, low (4x, 10x) power images of the femurs are shown (Masson Trichrome stain). Stains for tartrate resistant acid phosphatase (TRAP) demonstrate osteoclasts (see arrows) both resorbing cartilage (C) and trabecular bone (D). Note the flattened appearance of osteoclasts on trabecular bone. E–H. Representative photomicrographs of bones from OPG-expressing animals. In E and F, low (4x, 10x) power images of the femurs are shown (Masson Trichrome stain). The clear region is the growth plate cartilage, blue stained area is bone, and the red area is marrow. Note that in contrast to the controls, the trabecular bone has not been resorbed resulting in the absence of the usual marrow cavity. Also, the resulting trabeculae have a variegated appearance with blue and clear areas. The clear areas are remnants of growth plate cartilage that have never been remodelled. Based on TRAP stains, these animals do have osteoclasts (see arrows) at the growth plate (G), which may be reduced in number. However, the surfaces of the trabeculae away from the growth plate are virtually devoid of osteoclasts (H), a finding that stands in direct contrast with the control animals (see D).
Figure 7B:
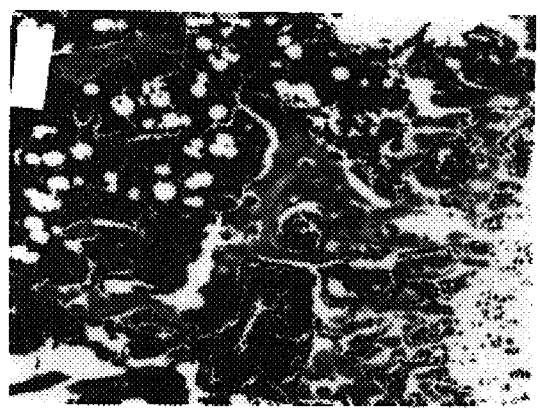
Figure 7C:
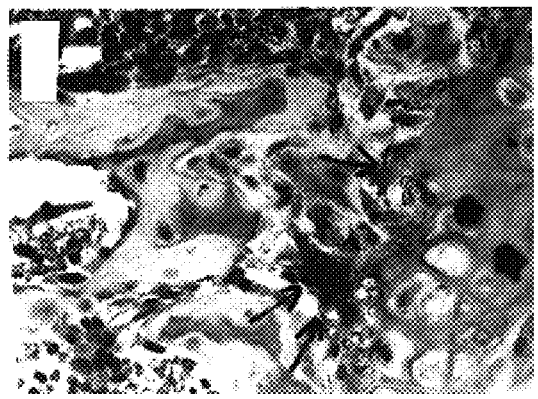
Figure 7D:
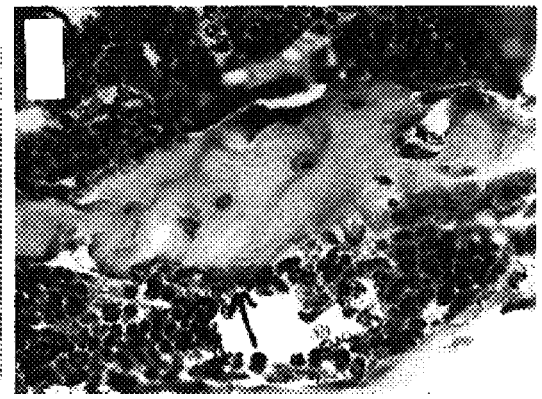
Figure 7E:
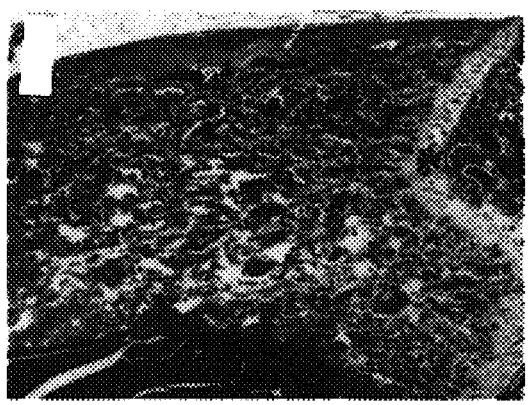
Figure 7F:
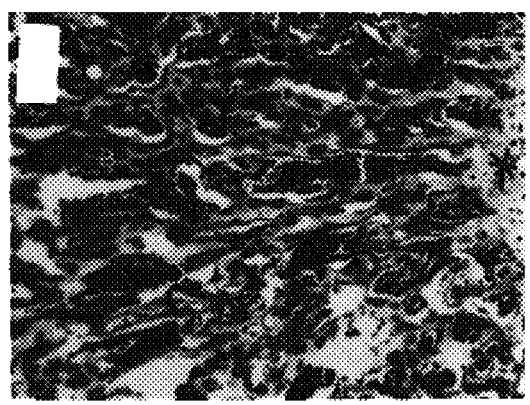
Figure 7G:
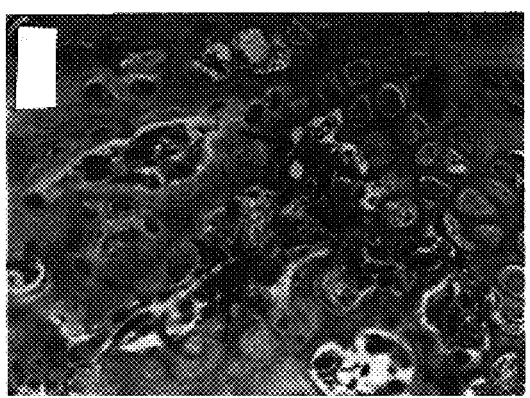
Figure 7H:
Figure 8A:
FIG. 8. HE-OPG expressors do not have a defect in monocyte-macrophage development. One cause for osteopetrosis in mice is defective M-CSF production due to a point mutation in the M-CSF gene. This results in a marked deficit of circulating and tissue based macrophages. The peripheral blood of OPG expressors contained monocytes as assessed by H1E analysis. To affirm the presence of tissue macrophages, immnohistochemistry was performed using F480 antibodies, which recognize a cell surface antigen on murine macrophages. A and C show low power (4x) photomicrographs of the spleens from normal and CR1 overexpressors. Note that both animals have numerous F480 positive cells. Monocyte-macrophages were also present in the marrow of normal (B) and HE-OPG overexpressors (D) (40x).
Figure 8B:
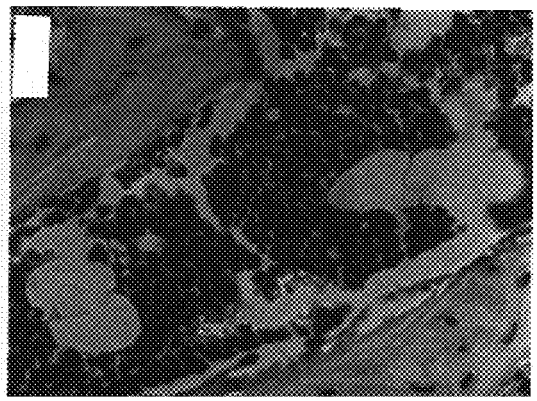
Figure 8C:
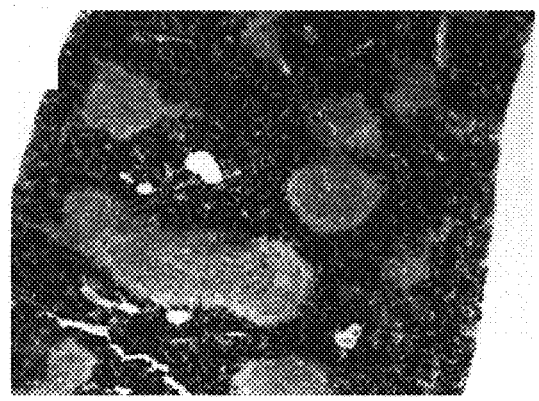
Figure 8D:
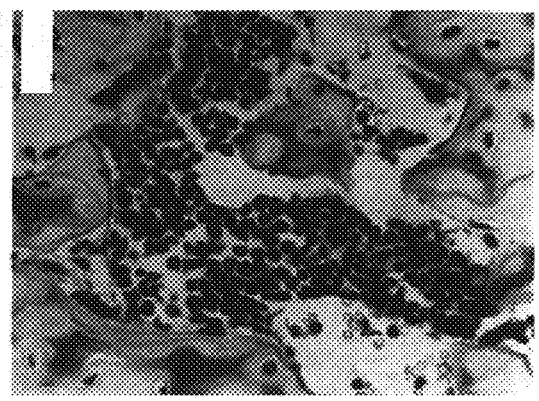
Figure 11:
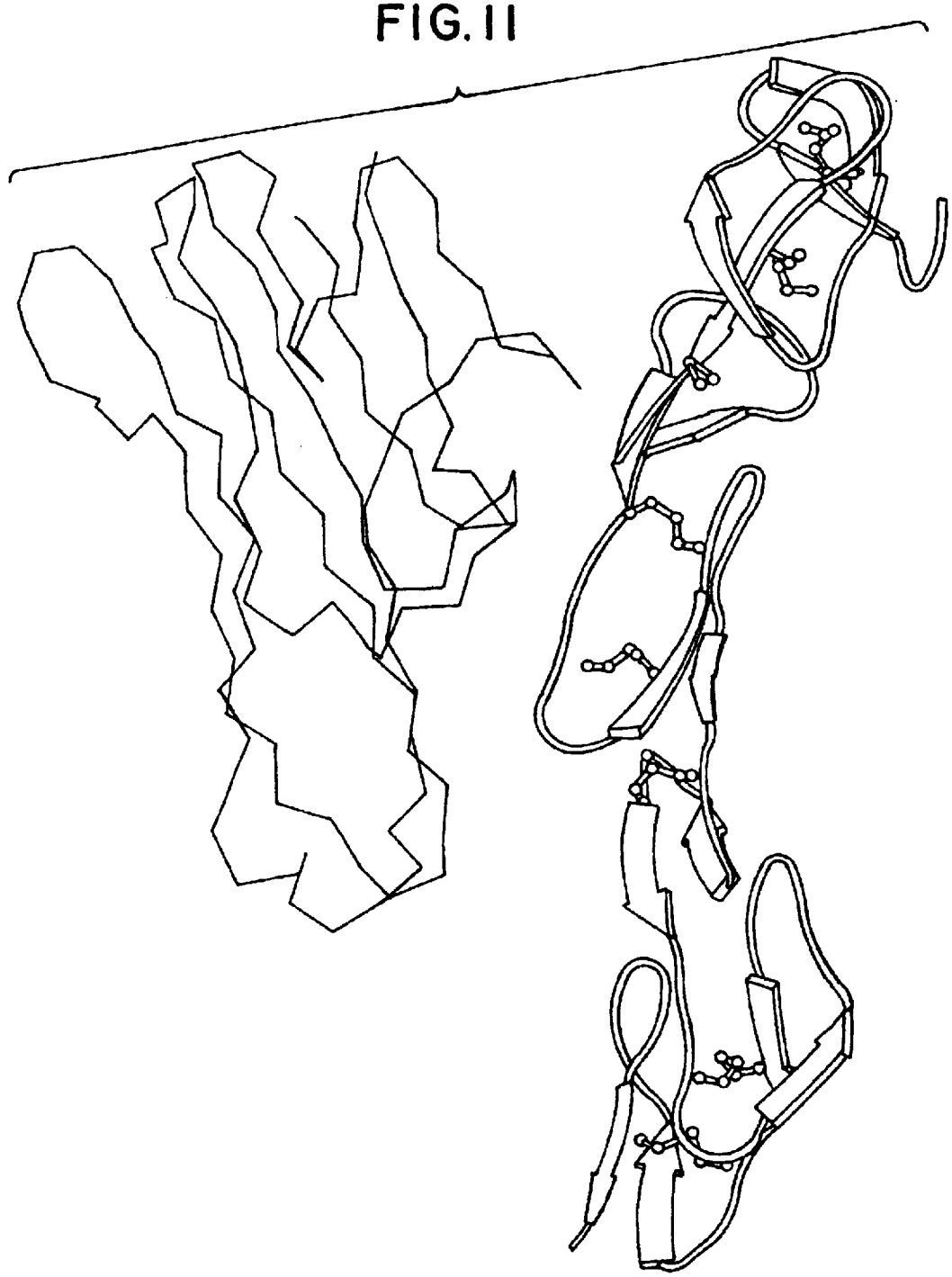

FIG. 11. Three-dimensional representation of human OPG. Side-view of the Molescript display of the predicted 3-dimensional structure of human OPG residues 25 through 163, (wide line), co-crystallized with human TNFβ (thin line). As a reference for orientation, the bold arrows along the OPG polypeptide backbone are pointing in the N-terminal to C-terminal direction. The location of individual cysteine residue side chains are inserted along the polypeptide backbone to help demonstrate the separate cysteine-rich domains. The TNFβ molecule is aligned as described by Banner et al. (1993).

FIG. 12. Structure of OPG cysteine-rich domains. Alignment of the human (top line SEQ ID NO:139) and mouse (bottom line SEQ ID NO:175) OPG amino acid sequences highlighting the predicted domain structure of OPG. The polypeptide is divided into two halves; the N-terminus (A), and C-terminus (B). The N-terminal half is predicted to contain four cysteine rich domains (labeled 1–4). The predicted intrachain disulfide bonds are indicated by bold lines, labeled "SS1", "SS2", or "SS3". Tyrosine 28 and histidine 75 (underlined) are predicted to form an ionic interaction. Those amino acids predicted to interact with an OPG ligand are indicated by bold dots above the appropriate residue. The cysteine residues located in the C-terminal half of OPG are indicated by rectangular boxes.

Figure 13A:
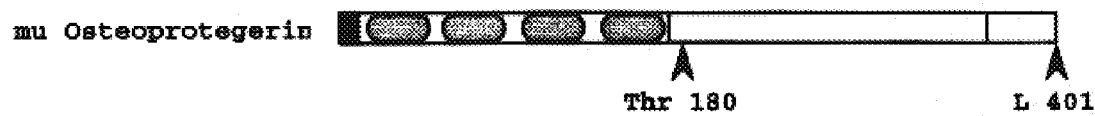
Figure 13B:
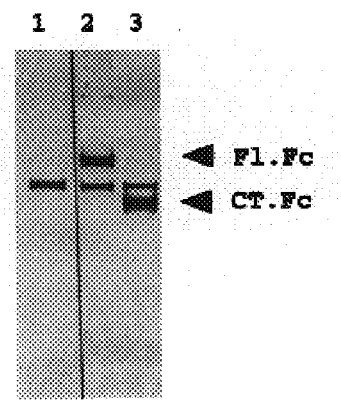
Figure 13C:
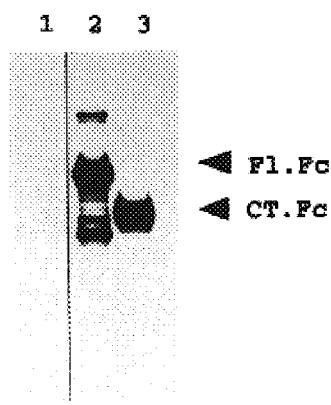

FIG. 13. Expression and secretion of full length and truncated mouse OPG-Fc fusion proteins. A. Map indicating points of fusion to the human IgG1 Fc domain are indicated by arrowheads. B. Silver stain of a SDS-polyacrylamide gel of conditioned media obtained from cells expressing either Fl.Fc (Full length OPG fused to Fc at Leucine 401) or CT.Fc (Carboxy-terminal truncated OPG fused to Fc at threonine 180) fusion protein expression vectors. Lane 1, parent pCEP4 expression vector cell line; Lane 2, Fl.Fc vector cell line; Lane 3, CT.Fc vector cell line. C. Western blot of conditioned media obtained from Fl.Fc and CT.Fc fusion protein expression vectors probed with anti-human IgG1 Fc domain (Pierce). Lane 1, parent pCEP4 expression vector cell line; Lane 2, Fl.Fc vector cell line; Lane 3, CT.Fc vector cell line.

Figure 14A:
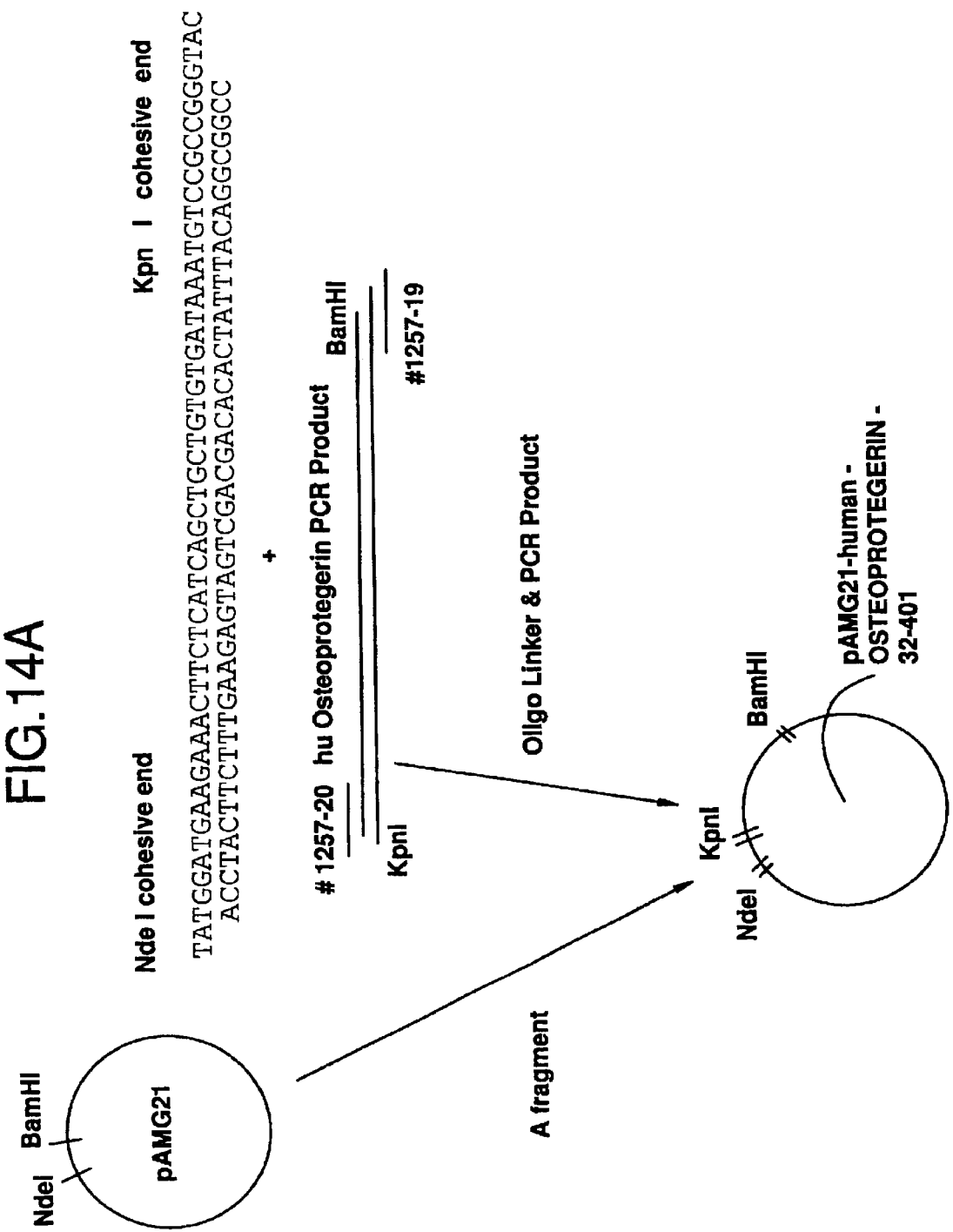

FIG. 14. Expression of human OPG in E. coli. A. Construction of a bacterial expression vector. The LORF of the human OPG gene was amplified by PCR, then joined to a oligonucleotide linker fragment (top strand is SEQ ID NO:137; bottom strand is SEQ ID NO:127), and ligated into pAMG21 vector DNA. The resulting vector is capable of expressing OPG residues 32–401 linked to a N-terminal methionine residue. B SDS-PAGE analysis of uninduced and induced bacterial harboring the pAMG21-human OPG-32–401 plasmid. Lane 1, MW standards; lane 2, uninduced bacteria; lane 3, 30° C. induction; lane 4, 37° C. induction; lane 5, whole cell lysate from 37° C. induction; lane 6, soluble fraction of whole cell lysate; lane 7, insoluble fraction of whole cell lysate; lane 8, purified inclusion bodies obtained from whole cell lysate.

Figure 15:
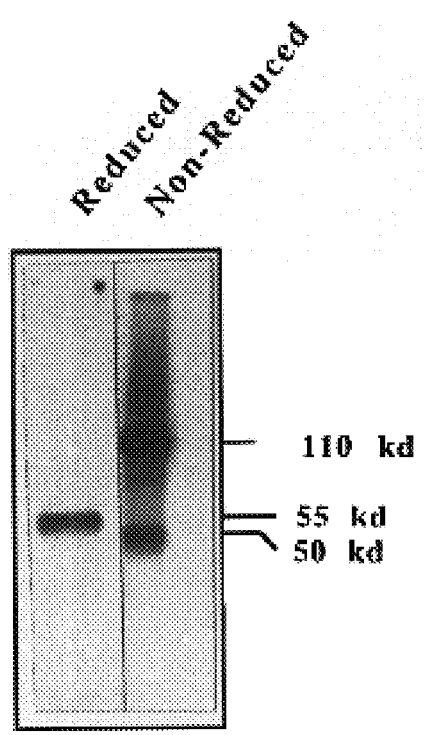

FIG. 15. Analysis of recombinant murine OPG produced in CHO cells by SDS-PAGE and western blotting. An equal amount of CHO conditioned media was applied to each lane shown, and was prepared by treatment with either reducing sample buffer (left lane), or non-reducing sample buffer (right lane). After electrophoresis, the resolved proteins were transferred to a nylon membrane, then probed with anti-OPG antibodies. The relative positions of the 55 kd monomeric and 100 kd dimeric forms of OPG are indicated by arrowheads.

Figure 16A:
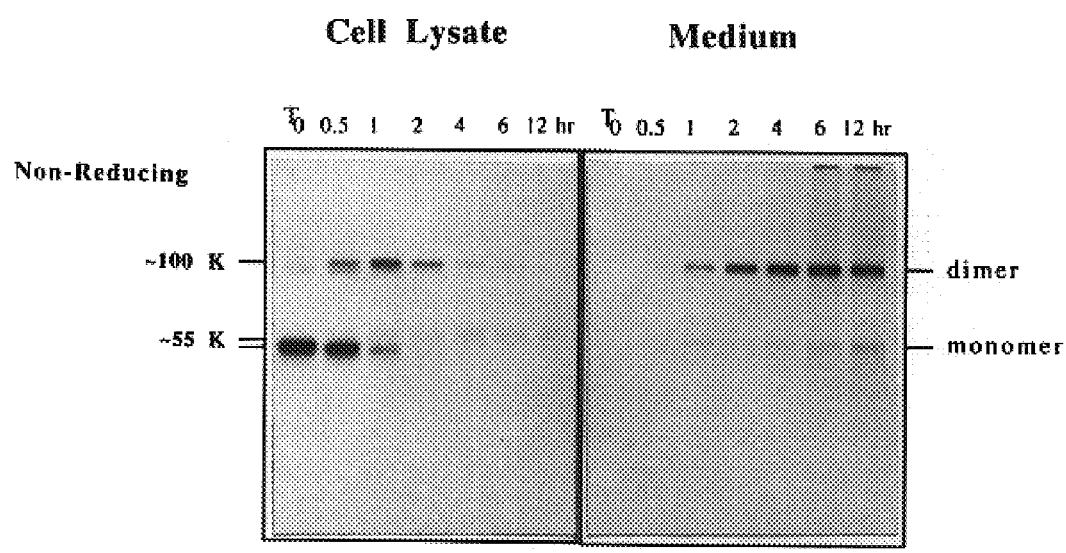
Figure 16B:
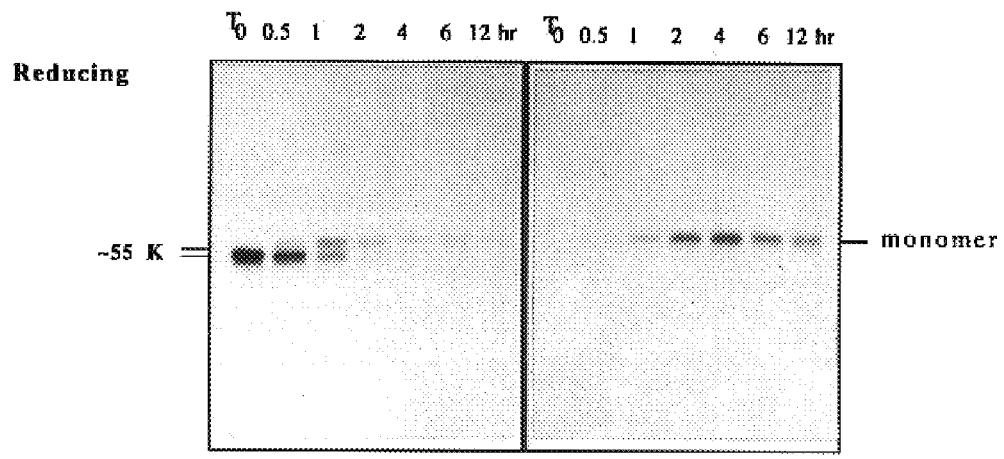

FIG. 16. Pulse-chase analysis of recombinant murine OPG produced in CHO cells. CHO cells were pulse-labeled with $^{35}$S-methionine/cysteine, then chased for the indicated time. Metabolically labeled cultures were separated into both conditioned media and cells, and detergent extracts were prepared from each, clarified, then immunoprecipitated with anti-OPG antibodies. The immunoprecipitates were the resolved by SDS-PAGE, and exposed to film. Top left and right panels; samples analyzed under non-reducing conditions. Lower left and right panels; samples analyzed under reducing conditions. Top and bottom left panels; Cell extracts. Top and bottom right panels; Conditioned media extracts. The relative mobility of the 55 kd monomeric and 100 kd dimeric forms of OPG are indicated by arrowheads.

Figure 17:
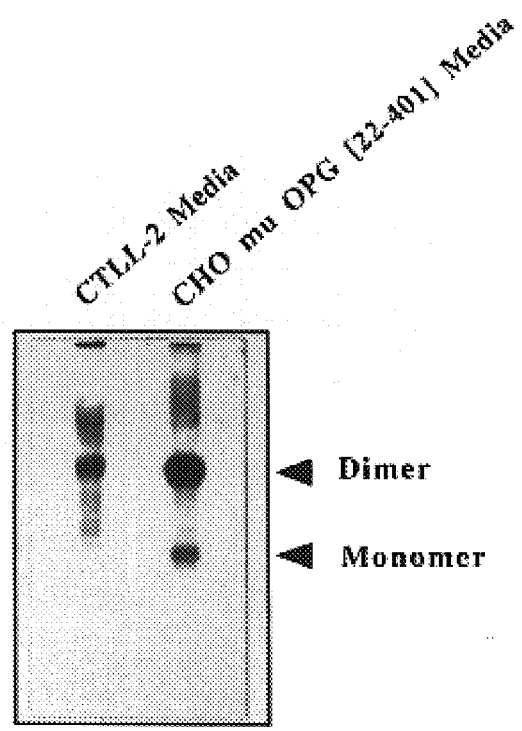

FIG. 17. Expression of OPG in the CTLL-2 cell line. Serum-free conditioned media from CTLL-2 cells and CHO-mu OPG [1–401] transfected cells was prepared, concentrated, then analyzed by non-reducing SDS-PAGE and western blotting. Left lane; CTLL-2 conditioned media. Right lane; CHO-muOPG conditioned media. The relative mobility of the 55 kd monomeric and 100 kd dimeric forms of OPG are indicated by arrowheads.

Figure 18:
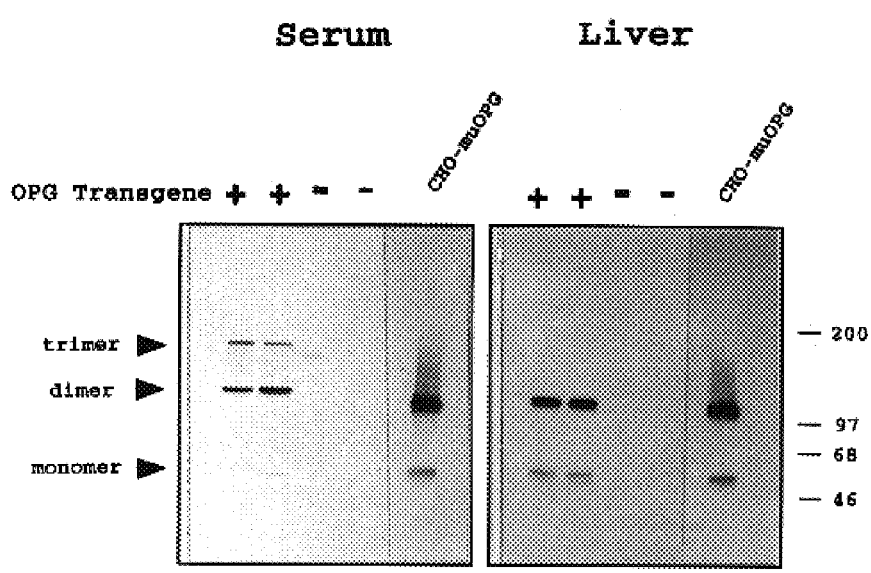

FIG. 18. Detection of OPG expression in serum samples and liver extracts obtained from control and OPG transgenic mice. Transgenic mice were constructed as described in Example 4. OPG expression was visualized after SDS-PAGE followed by Western blotting using anti-OPG antibodies.

FIG. 19. Effects of huOPG [22–401]-Fc fusion protein on osteoclast formation in vitro. The osteoclast forming assay was performed as described in Example 11A in the absence (control) or presence of the indicated amounts of huOPG [22–401]-Fc fusion. Osteoclast formation was visualized by histochemical staining for tartrate acid phosphatase (TRAP). ). A. OPG added to 100 ng/ml. D. OPG added to 0.1 ng/ml. E. OPG added to 0.01 ng/ml. F. OPG added to 0.001 ng/ml. G. Control. No OPG added.

Figure 20:
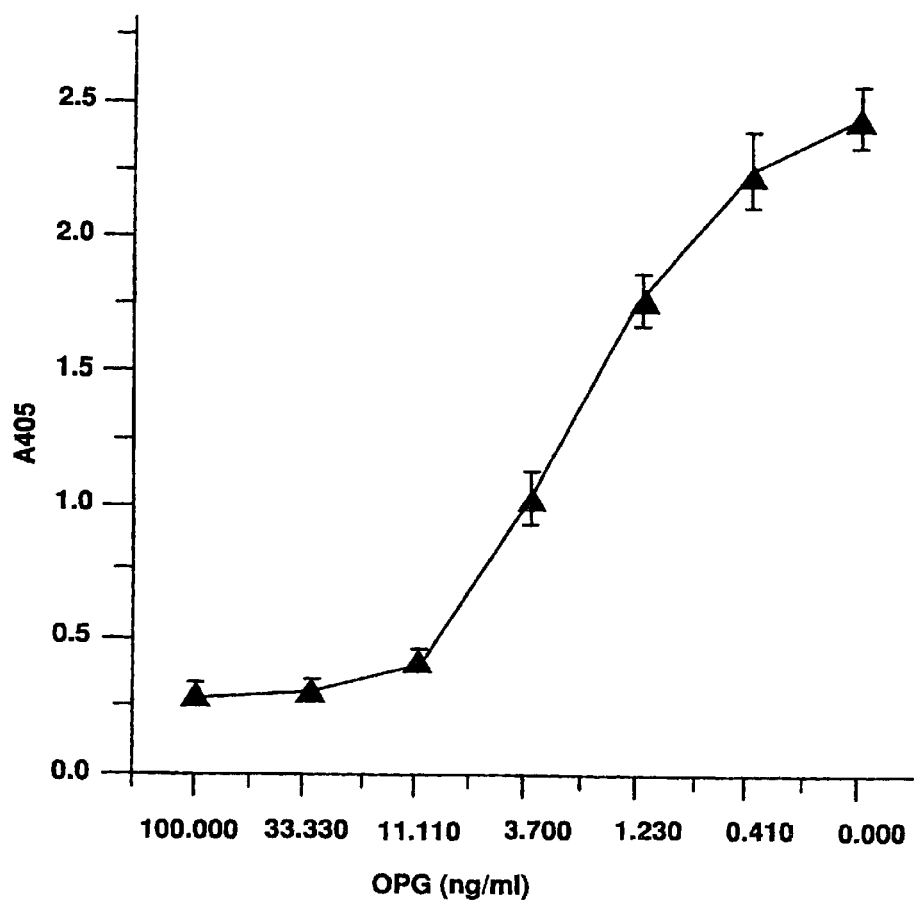

FIG. 20. Decrease in osteoclast culture TRAP activity with increasing amounts of OPG. Indicated concentrations of huOPG [22–401]-Fc fusion protein were added to osteoclast forming assay and TRAP activity quantitated as described in Example 11A.

FIG. 21. Effect of OPG on a terminal stage of osteoclast differentiation. huOPG [22–401]-Fc fusion was added to the osteoclast forming assay during the intermediate stage of osteoclast maturation (days 5–6; OPG-CTL) or during the terminal stage of osteoclast maturation (days 7–15; CTL-OPG). TRAP activity was quantitated and compared with the activity observed in the absence of OPG (CTL-CTL) in the presence of OPG throughout (OPG-OPG).

FIG. 22. Effects of IL-1β, IL-1α and OPG on blood ionized calcium in mice. Levels of blood ionized calcium were monitored after injection of IL-1β alone, IL-1α alone, IL-1β plus muOPG [22–401]-Fc, IL-1α plus MuOPG [22–401]-Fc, and muOPG [22–401]-Fc alone. Control mice received injections of phosphate buffered saline (PBS) only. IL-1β experiment shown in A; IL-1α experiment shown in B.

FIG. 23. Effects of OPG on calvarial osteoclasts in control and IL-1-treated mice. Histological methods for analyzing mice calvarial bone samples are described in Example 11B. Arrows indicate osteoclasts present in day 2-treated mice. Calvarial samples of mice receiving four PBS injections daily (A), one injection of IL-1 and three injections of PBS daily (B), one injection of PBS and three injections of OPG daily (C), one injection of IL-1 and three injections of OPG daily.

FIG. 24. Radiographic analysis of bone accumulation in marrow cavity of normal mice. Mice were injected subcutaneously with saline (A) or muOPG [22–401]-Fc fusion (5 mg/kg/d) for 14 days (B) and bone density determined as described in Example 11C.

Figure 25:
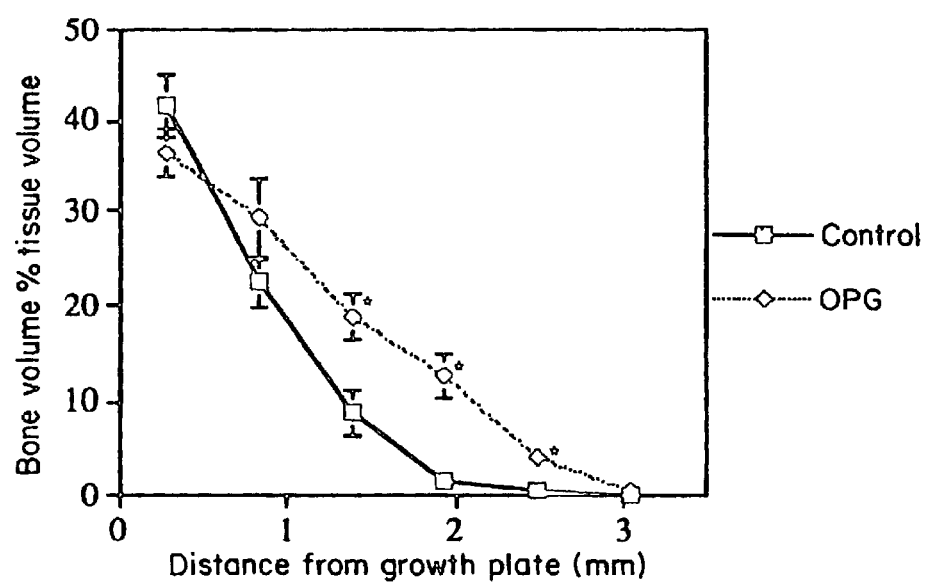

FIG. 25. Histomorphometric analysis of bone accumulation in marrow cavity of normal mice. Injection experiments and bone histology performed as described in Example 11C.

FIG. 26. Histology analysis of bone accumulation in marrow cavity of normal mice. Injection experiments and bone histology performed as described in Example 11C. A. Saline injection B. Injection of muOPG [22–401]-Fc fusion.

Figure 27:
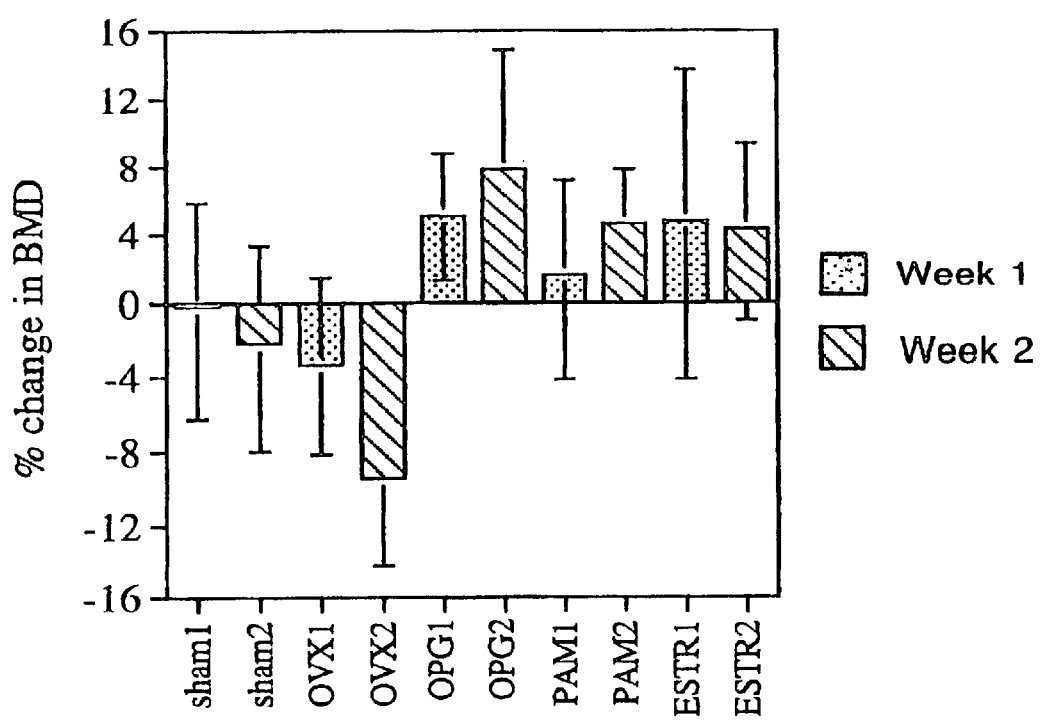

FIG. 27. Activity of OPG administered to ovariectomized rats. In this two week experiment the trend to reduced bone density appears to be blocked by OPG or other anti-resorptive therapies. DEXA measurements were taken at time of ovariectomy and at week 1 and week 2 of treatment. The results are expressed as % change from the initial bone density (Mean+/–SEM).

Figure 28:
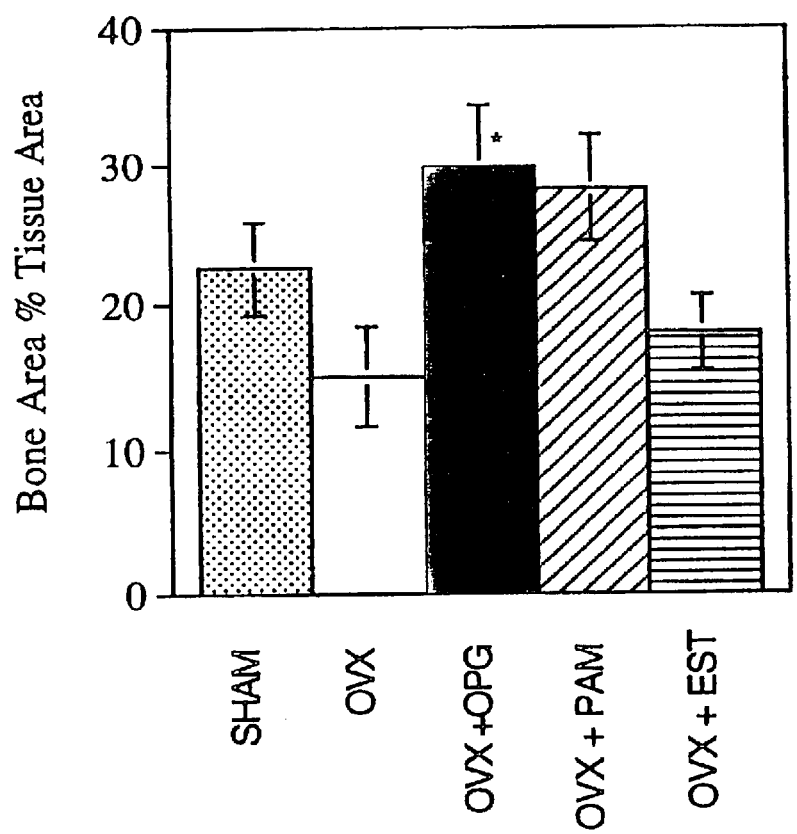

FIG. 28. Bone density in the femoral metaphysis, measured by histomorphometric methods, tends to be lower in ovariectomized rats (OVX) than sham operated animals (SHAM) 17 days following ovariectomy. This effect was blocked by OPG-Fc, with OPG-Fc treated ovariectomized rats (OVX+OPG) having significantly higher bone density than vehicle treated ovariectomized rats (OVX). (Mean +/–SEM).

FIGS. 29A through 29J. Sequence of OPG-Fc. DNA and encoded protein sequences are shown. Restriction sites for various nucleases are noted above the DNA sequence (SEQ ID NO:176 and 177).

FIGS. 30A-1 through 30B-2. Effects of OPG-Fc during the course of adjuvant arthritis I male Lewis rats. Paws from rats with adjuvant arthritis induced by 0.5 mg *mycobacteria* in oil were analyzed by DEXA for bone mineral density (BMD). Evaluation of BMD, a 29 mm×25 mm box was centered at the calcaneus (expt AdA-14 2/99, Amgen nb#22957 p47–49). * compared to normal, # compared to vehicle P<0.05 Mann-Whitney U test.

Figures 1, 30A:
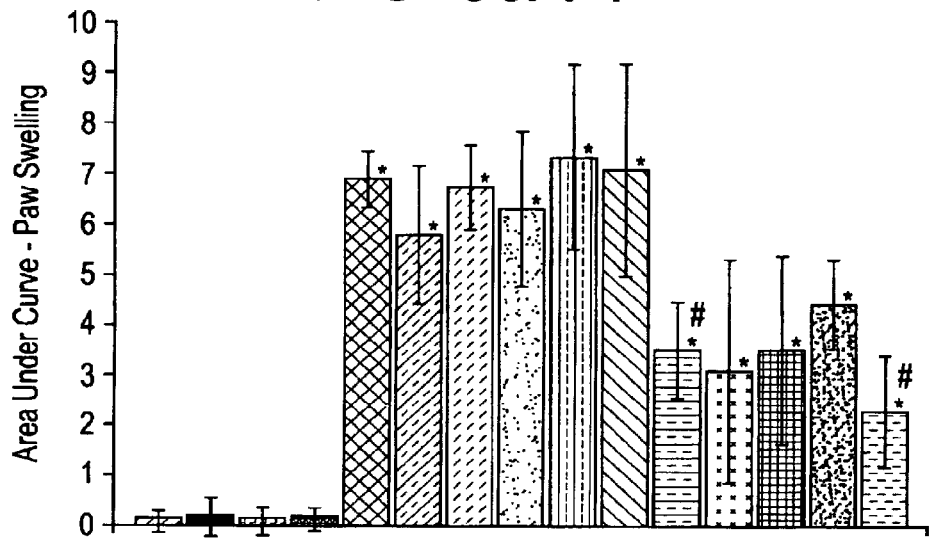
FIG. 1. A. FASTA analysis of novel EST LORF. Shown is the deduced FRI-1 amino acid sequence aligned to the human TNFR-II sequence (SEQ ID NO: 169 and SEQ ID NO: 138). B. Profile analysis of the novel EST LORF shown is the deduced FRI-1 amino acid sequence aligned to the TNFR-profile (SEQ ID NO: 170 and SEQ ID NO: 178). C. Structural view of TNFR superfamily indicating region which is homologous to the novel FRI-1.
Figures 2, 30A:
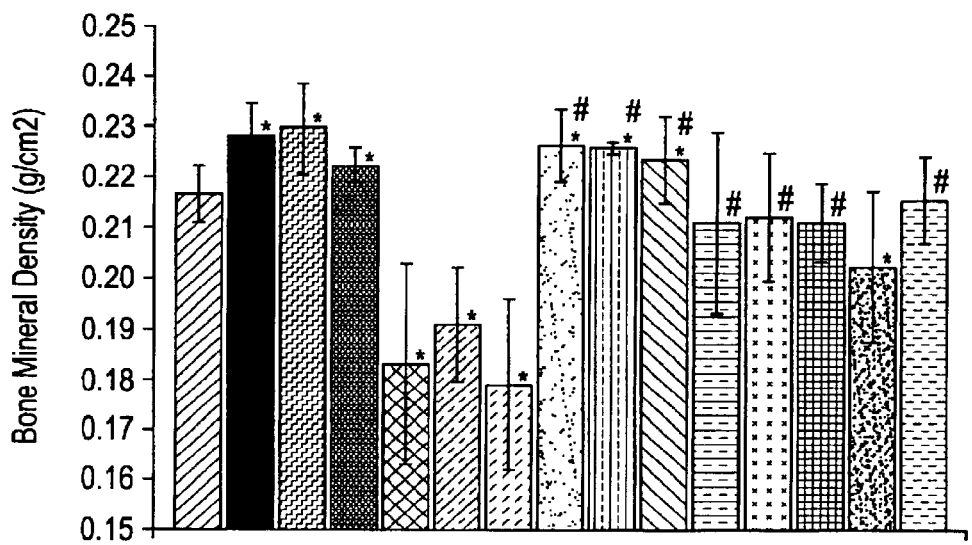
FIG. 2. Structure and sequence of full length rat OPG gene, a novel member of the TNFR superfamily. A. Map of pMOB-B1.1 insert. Box indicates position of LORF within the cDNA sequence (bold line). Black box indicates signal peptide, and gray ellipses indicate position of cysteine-rich repeat sequences. B, C. Nucleic acid and protein sequence of the Rat OPG cDNA The predicted signal peptide is underlined, and potential sites of N-linked glycosylation are indicated in bold, underlined letters (SEQ ID NO: 120 and 121). D, E. Pileup sequence comparison (Wisconsin GCG Package, Version 8.1) of OPG with other members of the TNFR superfamily, fas (SEQ ID NO:128); tnfr1 (SEQ ID NO: 129); sfu-t2 (SEQ ID NO:130); tnfr2 (SEQ ID NO:131); cd40 (SEQ ID NO:132); osteo (SEQ ID NO:133); ngfr (SEQ ID NO:134); ox40 (SEQ ID NO:135); 41bb (SEQ ID NO:136).
Figures 1, 30B:
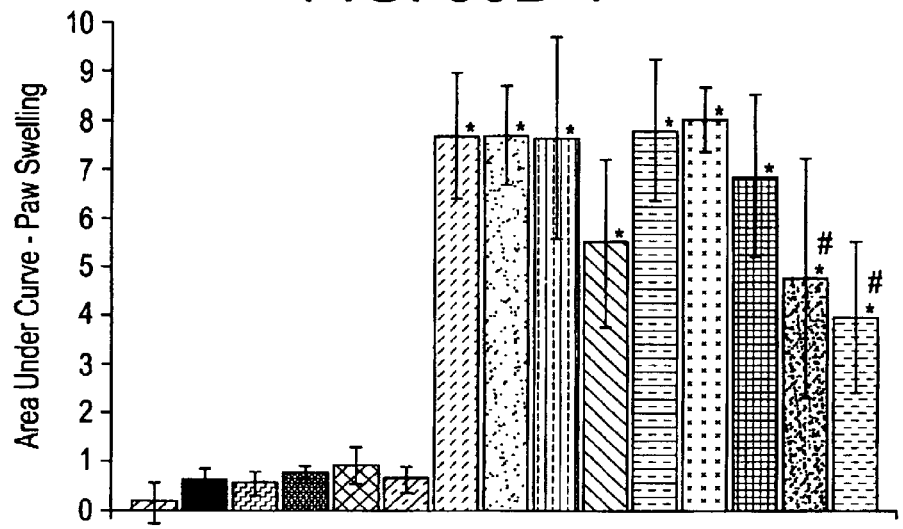
Figures 2, 30B:
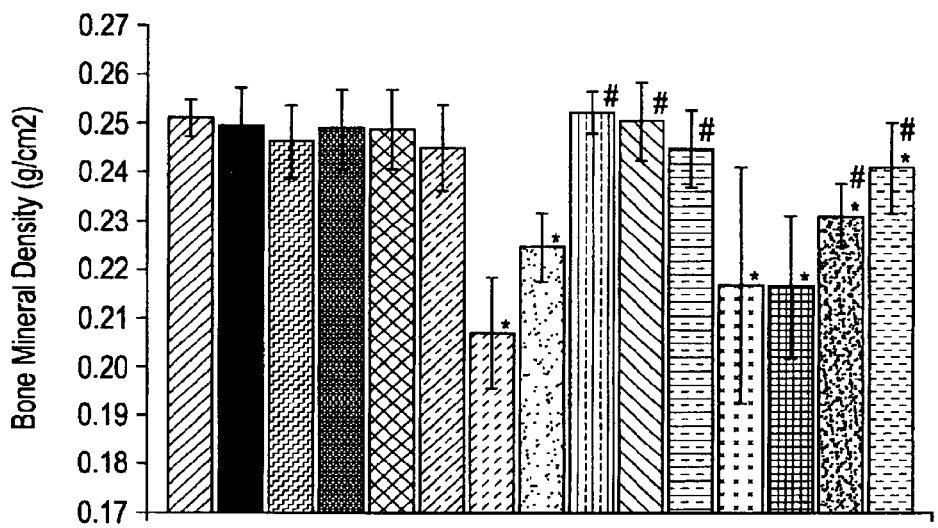
Figure 31A:
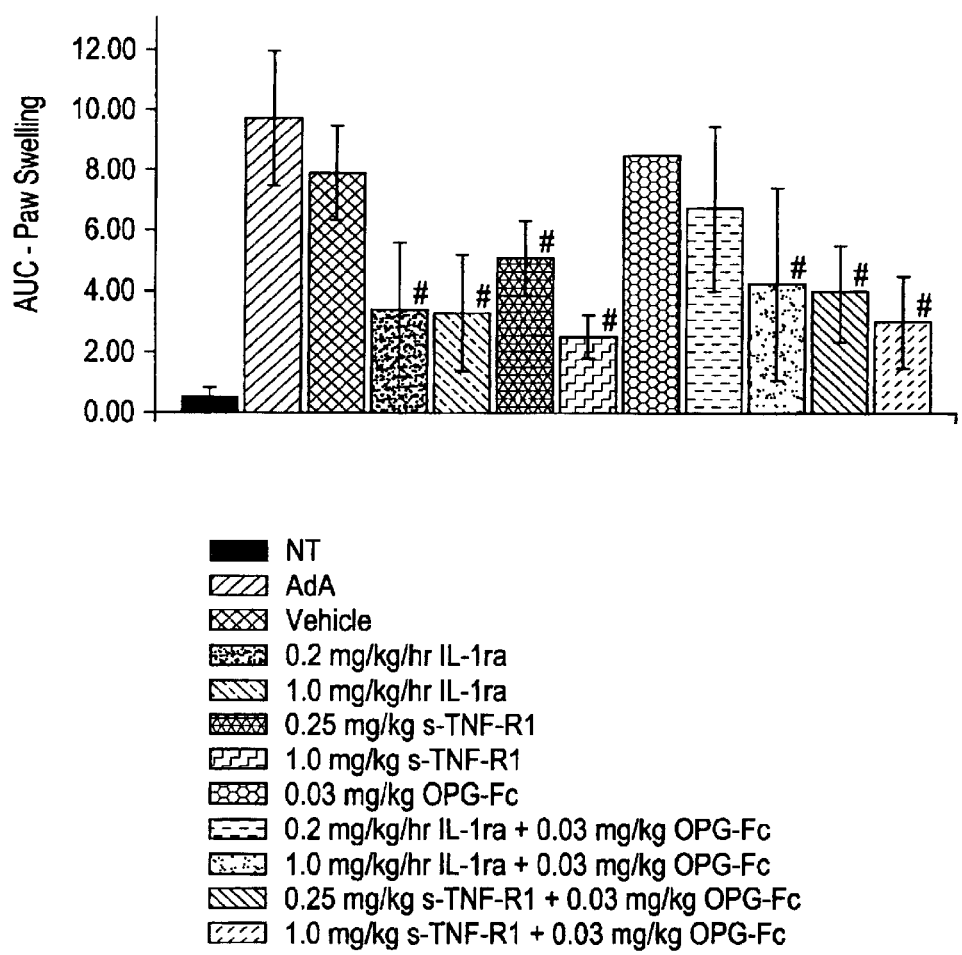
Figure 31B:
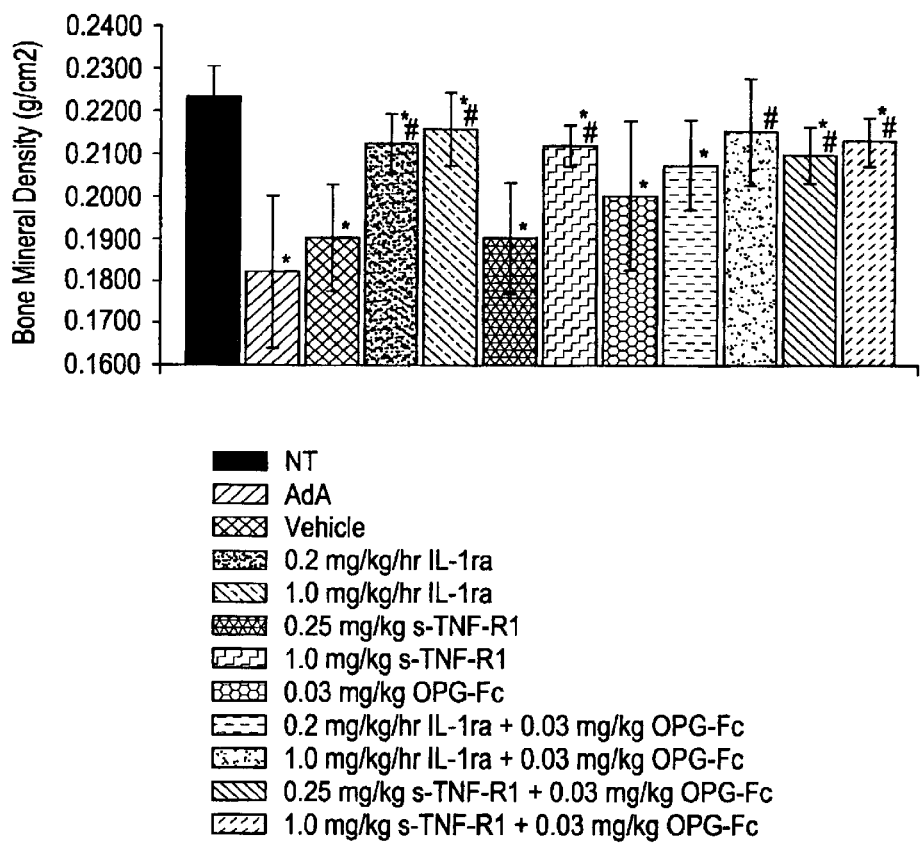

FIGS. 31A and 31B. Combination treatment with OPG-FC and sTNFR-I on Adjuvant Arthritis in Male Lewis Rats. Area under the curve (AUC) for measurement of paw swelling and BMD were measured as described above for FIG. 30 and in the examples hereinafter.

DETAILED DESCRIPTION OF THE INVENTION

OPG Proteins

The term "OPG protein" refers collectively to the novel member of the tumor necrosis factor receptor family described hereinafter, variants and truncations thereof that maintain OPG's activity in increasing bone density, and antibodies to OPG ligand that maintain OPG's activity in increasing bone density. An exemplary assay for measuring such activity is shown in FIG. 6 and the accompanying text. Exemplary OPG proteins are polypeptides comprising the consensus of the rat, mouse and human sequences (FIG. 9C), OPG-Fc fusions (FIGS. 13, 29), or the rat, mouse or human OPG sequences (FIGS. 2, 9).

Figure 2D:
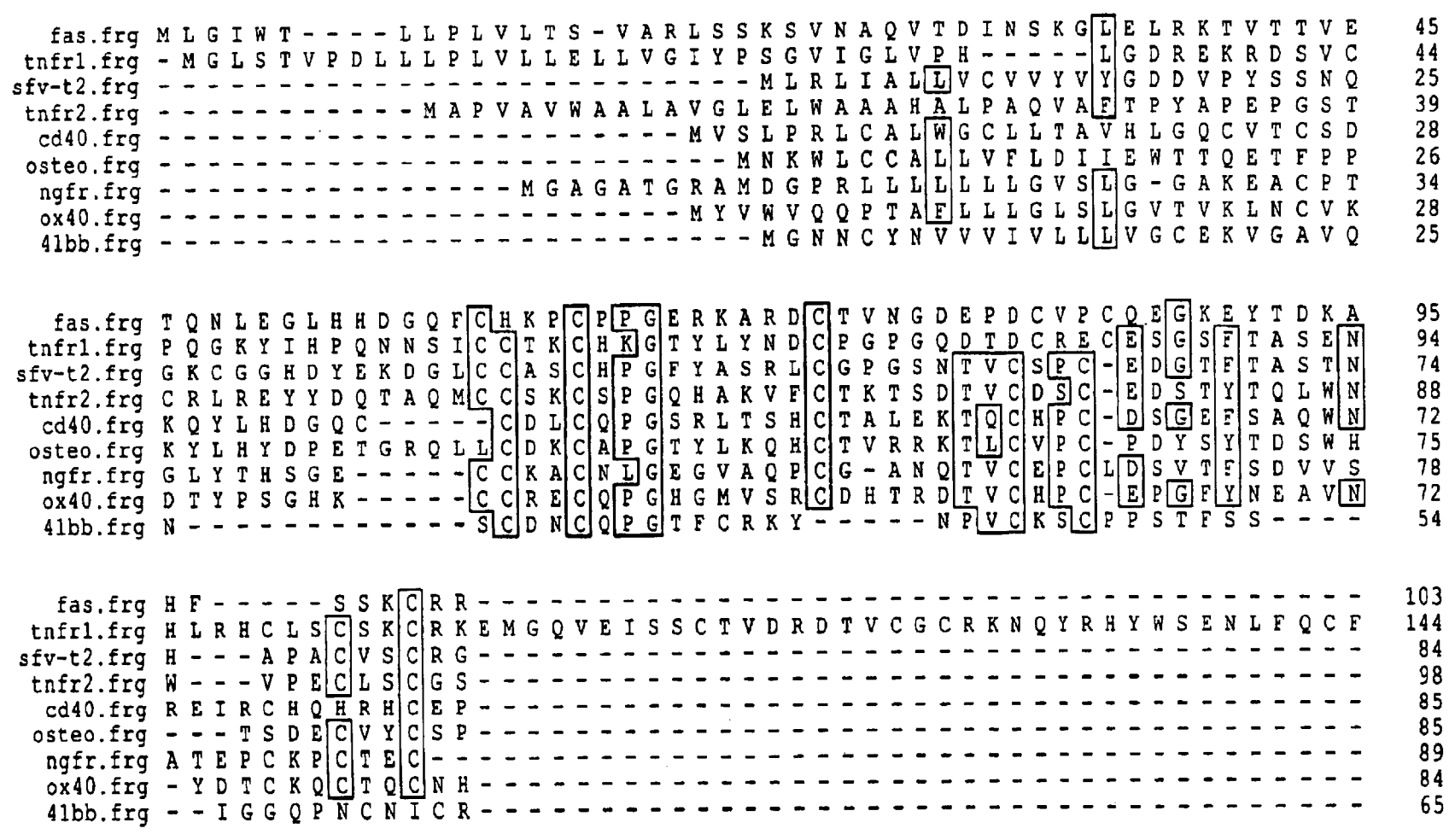
Figure 2E:
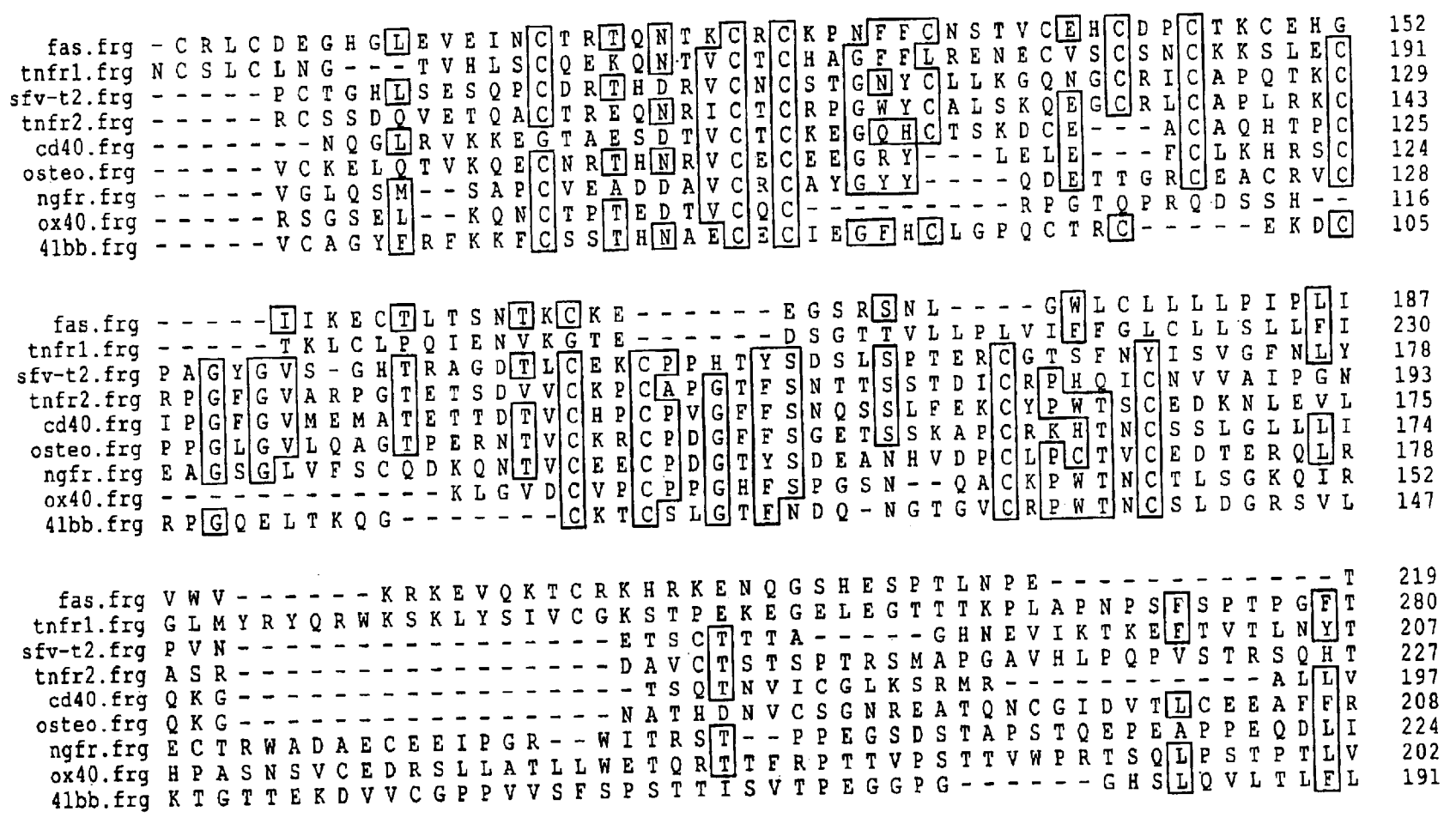

OPG was identified as follows. A novel member of the tumor necrosis factor receptor (TNFR) superfamily was identified as an expressed sequence tag (EST) isolated from a fetal rat intestinal cDNA library . The structures of the full-length rat cDNA clones and the corresponding mouse and human cDNA clones were determined as described in Examples 1 and 6. The rat, mouse and human genes are shown in FIGS. 2B–2C (SEQ ID NO:120), 9A–9B (SEQ ID NO:122), and 9C–9D (SEQ ID NO:124), respectively. All three sequences showed strong similarity to the extracellular domains of TNFR family members. None of the full-length cDNA clones isolated encoded transmembrane and cytoplasmic domains that would be expected for membrane-bound receptors, suggesting that these cDNAs encode soluble, secreted proteins rather than cell surface receptors. A portion of the human gene spanning nucleotides 1200–1353 shown in FIG. 9D was deposited in the Genebank database on Nov. 22, 1995 under accession no. 17188769.

The tissue distribution of the rat and human mRNA was determined as described in Example 2. In rat, mRNA expression was detected in kidney, liver, placenta and heart with the highest expression in the kidney. Expression in skeletal muscle and pancreas was also detected. In humans, expression was detected. in the same tissues along with lymph node, thymus, spleen and appendix.

The rat cDNA was expressed in transgenic mice (Example 3) using the liver-specific APOE promoter expression system. Analysis of expressors showed a marked increase in bone density, particularly in long bones (femurs), vertebrae and flat bones (pelvis). Histological analysis of stained sections of bone showed severe osteopetrosis (see Example 4) indicating a marked imbalance between bone formation and resorption which has led to a marked accumulation of bone and cartilage. A decrease in the number of trabecular osteoclasts in the bones of OPG expressor animals indicate that a significant portion of the activity of the TNFR-related protein may be to prevent bone resorption, a process mediated by osteoclasts. In view of the activity in transgenic expressors, the TNFR-related proteins described herein are termed OPGs.

Using the rat cDNA sequence, mouse and human cDNA clones were isolated (Example 5). Expression of mouse OPG in 293 cells and human OPG in *E. coli* is described in Examples 7 and 8. Mouse OPG was produced as an Fc fusion which was purified by Protein A affinity chromatography. Also described in Example 7 is the expression of full-length and truncated human and mouse OPG polypeptides in CHO and 293 cells either as fusion polypeptides to the Fc region of human IgG1 or as unfused polypeptides. The expression of full-length and truncated human and mouse OPGs in *E. coli* either as Fc fusion polypeptides or as unfused polypeptides is described in Example 8. Purification of recombinantly produced mammalian and bacterial OPG is described in Example 10.

The biological activity of OPG was determined using an in vitro osteoclast maturation assay, an in vivo model of interleukin-1 (IL-1) induced hypercalcemia, and injection studies of bone density in normal mice (see Example 11). The following OPG recombinant proteins produced in CHO or 293 cells demonstrated activity in the in *E. coli* osteoclast maturation assay: muOPG [22–185]-Fc, muOPG [22–194]-Fc, muOPG [22–401]Fc, muOPG [22–401], huOPG [22–201]-Fc, huOPG [22–401]-Fc. muOPG [22–180]-Fc produced in CHO cells and huOPG met[32–401] produced in *E. coli* did not demonstrate activity in the in vitro assay.

OPG from several sources was produced as a dimer and to some extent as a higher multimer. Rat OPG [22–401) produced in transgenic mice, muOPG [22–401) and huOPG [22–401] produced as a recombinant polypeptide in CHO cells, and OPG expressed as a naturally occurring product from a cytotoxic T cell line were predominantly dimers and trimers when analyzed on nonreducing SDS gels (see Example 9). Truncated OPG polypeptides having deletions in the region of amino acids 186–401 (e.g., OPG [1–185] and OPG [1–194]) were predominantly monomeric suggesting that the region 186–401 may be involved in self-association of OPG polypeptides. However, huOPG met [32–401] produced in E. coli was largely monomeric.

OPG may be important in regulating bone resorption. The protein appears to act as a soluble receptor of the TNF family and may prevent a receptor-ligand interaction involved in the osteolytic pathway. One aspect of the regulation appears to be a reduction in the number of osteoclasts.

OPG proteins encompassed by the invention include rat [1–401], rat [22–180], rat [22–401], rat [22–401])-Fc fusion, rat [1–180]-Fc fusion, mouse [1–401], mouse [1–180], mouse [22–401], human [1–401], mouse [22–180], human [22–401], human [22–180], human [1–180], human [22–180]-Fc fusion and human met-32–401. Amino acid numbering is as shown in SEQ ID NO:121 (rat), SEQ ID NO:123 (mouse) and SEQ ID NO:125 (human). Also encompassed are polypeptide derivatives having deletions or carboxy-terminal truncations of part or all of amino acids residues 180–401 of OPG; one or more amino acid changes in residues 180–401; deletion of part or all of a cysteine-rich domain of OPG, in particular deletion of the distal (carboxy-terminal) cysteine-rich domain; and one or more amino acid changes in a cysteine-rich domain, in particular in the distal (carboxy-terminal) cysteine-rich domain. In one embodiment, OPG has from 1 to about 216 amino acids deleted from the carboxy terminus. In another embodiment, OPG has from 1 to about 10 amino acids deleted from the mature amino terminus (wherein the mature amino terminus is at residue 22) and, optionally, has from 1 to about 216 amino acids deleted from the carboxy terminus.

Additional OPG proteins encompassed by the invention include the following: human [22–180]-Fc fusion, human [22–201]-Fc fusion, human (22–401]-Fc fusion, mouse [22–185]-Fc fusion, mouse [22–194]-Fc fusion. These polypeptides are produced in mammalian host cells, such as CHO or 293 cells, Additional OPG polypeptides encompassed by the invention which are expressed in procaryotic host cells include the following: human met[22–401], Fc-human met[22–401] fusion (Fc region is fused at the amino terminus of the full-length OPG coding sequence as described in Example 8), human met[22–401]-Fc fusion (Fc region fused to the full-length OPG sequence), Fc-mouse met[22–401] fusion, mouse met[22–401]-FC fusion, human met[27–401], human met[22–185], human met[22–189], human met(22–194], human met[22–194] (P25A), human met [22–194] (P26A), human met[27–185], human met [27–189], human met[27–194], human met-arg-gly-ser-(his)$_6$ [22–401], human met-lys [22–401], human met-(lys)$_3$-[22–401], human met[22–401]-Fc (P25A), human met [22–401] (P25A), human met[22–401] (P26A), human met [22–401] (P26D), mouse met[22–401], mouse met[27–401], mouse met[32–401], mouse met[27–180], mouse met [22–189], mouse met[22–194], mouse met[27–189], mouse met[27–194], mouse met-lys[22–401], mouse HEK [22–401] (A45T), mouse met-lys-(his)$_7$ [22–401], mouse met-lys[22–401]-(his)$_7$ and mouse met[27–401] (P33E, G36S, A45P). It is understood that the above OPG polypeptides produced in procaryotic host cells have an amino-terminal methionine residue, if such a residue is not indicated. In specific examples, OPG-Fc fusion were produced using a 227 amino acid region of human IgG1-γ1 was used having the sequence as shown in Ellison et al. (1982) Nuc. Acids Res. 10: 4071–9. However, variants of the Fc region of human IgG may also be used.

Analysis of the biological activity of carboxy-terminal OPG truncations fused to the human IgG1 Fc region indicates a portion of OPG of about 164 amino acids which is required for activity. This region encompasses amino acids 22–185, preferably those in FIGS. 9C–9D (SEQ ID NO:125), and comprises four cysteine-rich domains characteristic of the cysteine-rich domains of TNFR extraceullular domains. Proteins comprising this 164 amino acid sequence are within the meaning of "OPG protein" in this invention.

OPG proteins of the invention also may be isolated and purified from other polypeptides present in tissues, cell lines and transformed host cells expressing OPG, or purified from components in cell cultures containing the secreted protein. In one embodiment, the polypeptide is free from association with other human proteins, such as the expression product of a bacterial host cell.

A method for the purification of OPG from natural sources and from transfected host cells is also included. The purification process may employ one or more standard protein purification steps in an appropriate order to obtain purified protein. The chromatography steps can include ion exchange, gel filtration, hydrophobic interaction, reverse phase, chromatofocusing, affinity chromatography employing an anti-OPG antibody or biotin-streptavidin affinity complex and the like.

IL-1 Inhibitors

One of the most potent inflammatory cytokines yet discovered is interleukin-1 (IL-1). IL-1 is thought to be a key mediator in many diseases and medical conditions. It is manufactured (though not exclusively) by cells of the macrophage/monocyte lineage and may be produced in two forms: IL-1 alpha (IL-1α) and IL-1 beta (IL-1β).

A disease or medical condition is considered to be an "interleukin-1 mediated disease" if the spontaneous or experimental disease or medical condition is associated with elevated levels of IL-1 in bodily fluids or tissue or if cells or tissues taken from the body produce elevated levels of IL-1 in culture. In many cases, such interleukin-1 mediated diseases are also recognized by the following additional two conditions: (1) pathological findings associated with the disease or medical condition can be mimicked experimentally in animals by administration of IL-1 or upregulation of expression of IL-1; and (2) a pathology induced in experimental animal models of the disease or medical condition can be inhibited or abolished by treatment with agents that inhibit the action of IL-1. In most interleukin-1 mediated diseases at least two of the three conditions are met, and in many interleukin-1 mediated diseases all three conditions are met.

A non-exclusive list of acute and chronic interleukin-1 (IL-1)-mediated diseases includes but is not limited to the following:

acute pancreatitis;

ALS;

Alzheimer's disease;

cachexia/anorexia, including AIDS-induced cachexia;

asthma and other pulmonary diseases; atherosclerosis;

autoimmune vasculitis;

chronic fatigue syndrome;

Clostridium associated illnesses, including Clostridium-associated diarrhea;

coronary conditions and indications, including congestive heart failure, coronary restenosis, myocardial infarction, myocardial dysfunction (e.g., related to sepsis), and coronary artery bypass graft;

cancer, such as multiple myeloma and myelogenous (e.g., AML and CML) and other leukemias, as well as tumor metastasis;

diabetes (e.g., insulin diabetes);
endometriosis;
fever;
fibromyalgia;
glomerulonephritis;
graft versus host disease/transplant rejection;
hemohorragic shock;
hyperalgesia;
inflammatory bowel disease;
inflammatory conditions of a joint, including osteoarthritis, psoriatic arthritis and rheumatoid arthritis;
inflammatory eye disease, as may be associated with, for example, corneal transplant;
ischemia, including cerebral ischemia (e.g., brain injury as a result of trauma, epilepsy, hemorrhage or stroke, each of which may lead to neurodegeneration);
Kawasaki's disease;
learning impairment;
lung diseases (e.g., ARDS);
multiple sclerosis;
myopathies (e.g., muscle protein metabolism, esp. in sepsis);
neurotoxicity (e.g., as induced by HIV);
osteoporosis;
pain, including cancer-related pain;
Parkinson's disease;
periodontal disease;
pre-term labor;
psoriasis;
reperfusion injury;
septic shock;
side effects from radiation therapy;
temporal mandibular joint disease;
sleep disturbance;
uveitis;
or an inflammatory condition resulting from strain, sprain, cartilage damage, trauma, orthopedic surgery, infection or other disease processes. interleukin-1 inhibitors may be from any protein capable of specifically preventing activation of cellular receptors to IL-1, which may result from any number of mechanisms. Such mechanisms include downregulating IL-1 production, binding free IL-1, interfering with IL-1 binding to its receptor, interfering with formation of the IL-1 receptor complex (i.e., association of IL-1 receptor with IL-1 receptor accessory protein), or interfering with modulation of IL-1 signaling after binding to its receptor. Classes of interleukin-1 inhibitors include:

interleukin-1 receptor antagonists such as IL-1ra, as described below;

anti-IL-1 receptor monoclonal antibodies (e.g., EP 623674), the disclosure of which is hereby incorporated by reference;

IL-1 binding proteins such as soluble IL-1 receptors (e.g., U.S. Pat. Nos. 5,492,888, 5,488,032, and 5,464,937, 5,319,071, and 5,180,812, the disclosures of which are hereby incorporated by reference);

anti-IL-1 monoclonal antibodies (e.g., WO 9501997, WO 9402627, WO 9006371, U.S. Pat. No. 4,935,343, EP 364778, EP 267611 and EP 220063, the disclosures of which are hereby incorporated by reference);

IL-1 receptor accessory proteins and antibodies thereto (e.g., WO 96/23067 and WO 99/37773, the disclosure of which is hereby incorporated by reference);

inhibitors of interleukin-1 beta converting enzyme (ICE) or caspase I (e.g., WO 99/46248, WO 99/47545, and WO 99/47154, the disclosures of which are hereby incorporated by reference), which can be used to inhibit IL-1 beta production and secretion;

interleukin-1beta protease inhibitors;

and other compounds and proteins which block in vivo synthesis or extracellular release of IL-1.

Exemplary IL-1 inhibitors are disclosed in the following references:

U.S. Pat. Nos. 5,747,444; 5,359,032; 5,608,035; 5,843,905; 5,359,032; 5,866,576; 5,869,660; 5,869,315; 5,872,095; 5,955,480; 5,965,564;

International (WO) patent applications 98/21957, 96/09323, 91/17184, 96/40907, 98/32733, 98/42325, 98/44940, 98/47892, 98/56377, 99/03837, 99/06426, 99/06042, 91/17249, 98/32733, 98/17661, 97/08174, 95/34326, 99/36426, 99/36415

European (EP) patent applications 534978 and 894795.

French patent application FR 2762514.

The disclosures of all of the aforementioned references are hereby incorporated by reference.

For purposes of the present invention, IL-1ra and variants and derivatives thereof as discussed hereinafter are collectively termed "IL-1ra protein(s)". The molecules described in the above references and the variants and derivatives thereof discussed hereinafter are collectively termed "IL-1 inhibitors."

Interleukin-1 receptor antagonist (IL-1ra) is a human protein that acts as a natural inhibitor of interleukin-1 and which is a member of the IL-1 family member which includes IL-1α and IL-1β. Preferred receptor antagonists (including IL-1ra and variants and derivatives thereof), as well as methods of making and using thereof, are described in U.S. Pat. No. 5,075,222; WO 91/08285; WO 91/17184; AU 9173636; WO 92/16221; WO93/21946; WO 94/06457; WO 94/21275; FR 2706772; WO 94/21235; DE 4219626, WO 94/20517; WO 96/22793;WO 97/28828; and WO 99/36541, the disclosures of which are incorporated herein by reference. The proteins include glycosylated as well as non-glycosylated IL-1 receptor antagonists.

Specifically, three useful forms of IL-1ra and variants thereof are disclosed and described in the U.S. Pat. No. 5,075,222. The first of these, called "IL-1i" in the '222 patent, is characterized as a 22–23 kD molecule on SDS-PAGE with an approximate isoelectric point of 4.8, eluting from a Mono Q FPLC column at around 52 mM NaCl in Tris buffer, pH 7.6. The second, IL-1raβ, is characterized as a 22–23 kD protein, eluting from a Mono Q column at 48 mM NaCl. Both IL-1raα and IL-1raβ are glycosylated. The third, IL-1rax, is characterized as a 20 kD protein, eluting from a Mono Q column at 48 mM NaCl, and is non-glycosylated. U.S. Pat. No. 5,075,222 also discloses methods for isolating the genes responsible for coding the inhibitors, cloning the gene in suitable vectors and cell types, and expressing the gene to produce the inhibitors.

Those skilled in the. art understand that many combinations of deletions, insertions and substitutions (individually or collectively "variant(s)") can be made within the amino acid sequences of IL-1ra, provided that the resulting molecule is biologically active (e.g., possesses the ability to inhibit IL-1). See "Variants of Proteins" hereinafter.

TNF-α Inhibitors

Many diseases and medical conditions are mediated by TNF and are usually categorized as inflammatory conditions. A "TNF-mediated disease" is a spontaneous or experimental disease or medical condition is associated with elevated levels of TNF in bodily fluids or tissue or if cells or tissues taken from the body produce elevated levels of TNF in culture. In many cases, such TNF-mediated diseases may also be recognized by (1) pathological findings associated with the disease or medical condition can be mimicked experimentally in animals by the administration or upregulation of expression of TNF or (2) a pathology induced in experimental animal models of the disease or medical condition can be inhibited or abolished by treatment with agents that inhibit the action of TNF. A non-exclusive list of acute and chronic TNF-mediated diseases includes but is not limited to the following:

cachexia/anorexia;
cancer (e.g., leukemias);
chronic fatigue syndrome;
coronary conditions and indications, including congestive heart failure, coronary restenosis, myocardial infarction, myocardial dysfunction (e.g., related to sepsis), and coronary artery bypass graft;
depression;
diabetes, including juvenile onset Type 1, diabetes mellitus, and insulin resistance (e.g., as associated with obesity);
endometriosis, endometritis, and related conditions;
fibromyalgia or analgesia;
graft versus host rejection;
hyperalgesia;
inflammatory bowel diseases, including Crohn's disease and *Clostridium difficile*-associated diarrhea;
ischemia, including cerebral ischemia (brain injury as a result of trauma, epilepsy, hemorrhage or stroke, each of which may lead to neurodegeneration);
lung diseases (e.g., adult respiratory distress syndrome, asthma, and pulmonary fibrosis);
multiple sclerosis;
neuroinflammatory diseases;
ocular diseases and conditions, including corneal transplant, ocular degeneration and uveitis;
pain, including cancer-related pain;
pancreatitis;
periodontal diseases;
Pityriasis rubra pilaris (PRP);
prostatitis (bacterial or non-bacterial) and related conditions;
psoriasis and related conditions;
pulmonary fibrosis;
reperfusion injury;
rheumatic diseases, including rheumatoid arthritis, osteoarthritis, juvenile (rheumatoid) arthritis, seronegative polyarthritis, ankylosing spondylitis, Reiter's syndrome and reactive arthritis, Still's disease, psoriatic arthritis, enteropathic arthritis, polymyositis, dermatomyositis, scleroderma, systemic sclerosis, vasculitis (e.g., Kawasaki's disease), cerebral vasculitis, Lyme disease, staphylococcal-induced ("septic") arthritis, Sjogren's syndrome, rheumatic fever, polychondritis and polymyalgia rheumatica and giant cell arteritis);
septic shock;
side effects from radiation therapy;
systemic lupus erythematosus (SLE);
temporal mandibular joint disease;
thyroiditis;
tissue transplantation or an inflammatory condition resulting from strain, sprain, cartilage damage, trauma, orthopedic surgery, infection (e.g., HIV, *Clostridium difficile* and related species) or other disease process.

TNF-α inhibitors may act by downregulating or inhibiting TNF production, binding free TNF, interfering with TNF binding to its receptor, or interfering with modulation of TNF signaling after binding to its receptor. The term "TNF-α inhibitor" thus includes solubilized TNF receptors, antibodies to TNF, antibodies to TNF receptor, inhibitors of TNF-α converting enzyme (TACE), and other molecules that affect TNF activity.

TNF-α inhibitors of various kinds are disclosed in the art, including the following references:

European patent applications 308 378; 422 339; 393 438; 398 327; 412 486; 418 014, 417 563, 433 900; 464 533; 512 528; 526 905; 568 928; EP 607 776 (use of leflunomide for inhibition of TNF-α); 663 210; 542 795; 818 439; 664 128; 542 795; 741 707; 874 819 ; 882 714; 880 970; 648 783; 731 791; 895 988; 550 376; 882 714; 853 083; 550 376; 943 616; 939 121; 614 984 ; 853 083

U.S. Pat. Nos. 5,136,021; 5,929,117; 5,948,638; 5,807,862; 5,695,953; 5,834,435; 5,817,822; 5830742; 5,834,435; 5,851,556; 5,853,977; 5,359,037; 5,512,544; 5,695,953; 5,811,261; 5,633,145; 5,863,926; 5,866,616; 5,641,673; 5,869,677; 5,869,511; 5,872,146; 5,854,003; 5,856,161; 5,877,222; 5,877,200; 5,877,151; 5,886,010; 5,869,660; 5,859,207; 5,891,883; 5,877,180; 5,955,480; 5,955,476; 5,955,435; 5,994,351; 5,990,119; 5,952,320; 5,962,481;

International(WO)patent applications 90/13575, 91/03553, 92/01002, 92/13095, 92/16221, 93/07863, 93/21946, 93/19777, 95/34326, 96/28546, 98/27298, 98/30541, 96/38150, 96/38150, 97/18207, 97/15561, 97/12902, 96/25861, 96/12735, 96/11209, 98/39326, 98/39316, 98/38859, 98/39315, 98/42659, 98/39329, 98/43959, 98/45268, 98/47863, 96/33172, 96/20926, 97/37974, 97/37973, 97/47599, 96/35711, 98/51665, 98/43946, 95/04045, 98/56377, 97/12244, 99/00364, 99/00363, 98/57936, 99/01449, 99/01139, 98/56788, 98/56756, 98/53842, 98/52948, 98/52937, 99/02510, 97/43250, 99/06410, 99/06042, 99/09022, 99/08688, 99/07679, 99/09965, 99/07704, 99/06041, 99/37818, 99/37625, 97/11668, 99/50238, 99/47672, 99/48491;

Japanese (JP) patent applications 10147531, 10231285, 10259140, and 10130149, 10316570, 11001481, and 127, 800/1991;

German (DE) application 19731521;

British (GB) applications 2 218 101, 2 326 881, 2 246 569.

The disclosures of all of the aforementioned references are hereby incorporated by reference.

For purposes of this invention, the molecules disclosed in these references and the sTNFRs and variants and derivatives of the sTNFRs and the molecules disclosed in the references (see below) are collectively termed "TNF-α inhibitors."

For example, EP 393 438 and EP 422 339 teach the amino acid and nucleic acid sequences of a soluble TNF receptor type I (also known as sTNFR-I or 30 kDa TNF inhibitor) and a soluble TNF receptor type II (also known as sTNFR-II or 40 kDa TNF inhibitor), collectively termed "sTNFRs", as well as modified forms thereof (e.g., fragments, functional derivatives and variants). EP 393 438 and EP 422 339 also disclose methods for isolating the genes responsible for coding the inhibitors, cloning the gene in suitable vectors and cell types, and expressing the gene to produce the inhibitors.

sTNFR-I and sTNFR-II are members of the nerve growth factor/TNF receptor superfamily of receptors which includes the nerve growth factor receptor (NGF), the B cell antigen CD40, 4-1BB, the rat T-cell antigen MRC OX40, the fas antigen, and the CD27 and CD30 antigens (Smith et al. (1990), *Science,* 248:1019–1023). The most conserved feature amongst this group of cell surface receptors is the cysteine-rich extracellular ligand binding domain, which can be divided into four repeating motifs of about forty amino acids and which contains 4–6 cysteine residues at positions which are well conserved (Smith et al. (1990), supra).

EP 393 438 teaches a 40 kDa TNF inhibitor Δ51 and a 40 kDa TNF inhibitor Δ53, which are truncated versions of the full-length recombinant 40 kDa TNF inhibitor protein wherein 51 or 53 amino acid residues, respectively, at the carboxyl terminus of the mature protein are removed.

PCT Application No. PCT/US97/12244 teaches truncated forms of sTNFR-I and sTNFR-II which do not contain the fourth domain (amino acid residues $Thr^{127}$-$Asn^{161}$ of sTNFR-I and amino acid residues $Pro^{141}$-$Thr^{179}$ of sTNFR-II); a portion of the third domain (amino acid residues $Asn^{111}$-$Cys^{126}$ of sTNFR-I and amino acid residues $Pro^{123}$-$Lys^{140}$ of sTNFR-II); and, optionally, which do not contain a portion of the first domain (amino acid residues $Asp^1$-$Cys^{19}$ of sTNFR-I and amino acid residues $Leu^1$-$Cys^{32}$ of sTNFR-II). The truncated sTNFRs of the present invention include the proteins represented by the formula $R_1$-$[Cys^{19}$-$Cys^{103}]$-$R_2$ and $R_4$-$[Cys^{32}$-$Cys^{115}]$-$R_5$. These proteins are truncated forms of sTNFR-I and sTNFR-II, respectively.

By "$R_1$-$[Cys^{19}$-$Cys^{103}]$-$R_2$" is meant one or more proteins wherein $[Cys^{19}$-$Cys^{103}]$ represents residues 19 through 103 of sTNFR-I, the amino acid residue numbering scheme of which is provided in FIG. 1 to facilitate the comparison; wherein $R_1$ represents a methionylated or nonmethionylated amine group of $Cys^{19}$ or of amino-terminus amino acid residue(s) selected from any one of $Cys^{18}$ to $Asp^1$ and wherein $R_2$ represents a carboxy group of $Cys^{103}$ or of carboxy-terminal amino acid residues selected from any one of $Phe^{104}$ to $Leu^{110}$.

Exemplary truncated sTNFR-I of the present invention include the following molecules (collectively termed 2.6D sTNFR-I): $NH_2$-$[Asp^1$-$Cys^{105}]$-COOH (also referred to as sTNFR-I 2.6D/C105); $NH_2$-$[Asp^1$-$Leu^{108}]$-COOH (also referred to as sTNFR-I 2.6D/C106); $NH_2$-$[Asp^1$-$Asn^{105}]$-COOH (also referred to as sTNFR-I 2.6D/N105); $NH_2$-$[Tyr^9$-$Leu^{108}]$-COOH (also referred to as sTNFR-I 2.3D/d8); $NH_2$-$[Cys^{19}$-$Leu^{108}]$-COOH (also referred to as sTNFR-I 2.3D/d18); and $NH_2$-$[Ser^{16}$-$Leu^{108}]$-COOH (also referred to as sTNFR-I 2.3D/d15), either methionylated or nonmethionylated, and variants and derivatives thereof.

By "$R_3$-$[Cys^{32}$-$Cys^{115}]$-$R_4$" is meant one or more proteins wherein $[Cys^{32}$-$Cys^{115}]$ represents residues $Cys^{32}$ through $Cys^{115}$ of sTNFR-II, the amino acid residue numbering scheme of which is provided in FIG. 2 to facilitate the comparison; wherein $R_3$ represents a methionylated or nonmethionylated amine group of $Cys^{32}$ or of amino-terminus amino acid residue(s) selected from any one of $Cys^{31}$ to $Leu^1$ and wherein $R_4$ represents a carboxy group of $Cys^{115}$ or of carboxy-terminal amino acid residue(s) selected from any one of $Ala^{116}$ to $Arg^{122}$.

Serine Protease Inhibitors

Endogenous proteolytic enzymes degrade invading organisms, antigen-antibody complexes, and certain tissue proteins that are no longer necessary or useful. Infective agents may introduce additional proteolytic enzymes into the organism. Protease inhibitors regulate both endogenous and invading proteolytic enzymes.

A large number of naturally occurring protease inhibitors serve to control the endogenous proteases by limiting their reactions locally and temporally. In addition, the protease inhibitors may inhibit proteases introduced into the body by infective agents. Tissues that are particularly prone to proteolytic attack and infection, e.g. those of the respiratory tract, are rich in protease inhibitors.

Protease inhibitors comprise approximately 10% of the human plasma proteins. At least eight inhibitors have been isolated from this source and characterized in the literature. These include alpha 2-macroglobulin (alpha 2M), alpha 1-protease inhibitor (alpha 1PI), alpha 1-antichymotrypsin (alpha 1Achy), alpha 1-anticollagenase (alpha 1AC), and inter-alpha-trypsin inhibitor (I-alpha-I).

A disturbance of the protease/protease inhibitor balance can lead to protease-mediated tissue destruction, including emphysema, arthritis, glomerulonephritis, periodontitis, muscular dystrophy, tumor invasion and various other pathological conditions. In certain situations, e.g. severe pathological processes such as sepsis or acute leukemia, the amount of free proteolytic enzymes present increases due to the release of enzyme from the secretory cells. In addition, or separately in other situations, a diminished regulating inhibitor capacity of the organism may also cause alterations in the protease/protease inhibitor balance. An example of such a diminished regulating inhibitor capacity is an alpha 1-protease inhibitor deficiency, which is highly correlated with the development of pulmonary emphysema.

In organisms where such aberrant conditions are present, serious damage to the organism can occur unless measures can be taken to control the proteolytic enzymes. Therefore, protease inhibitors have been sought which are capable of being administered to an organism to control the proteolytic enzymes.

One protease that is of particular pharmacological interest is leukocyte elastase. Leukocyte elastase, when released extracellularly, degrades connective tissue and other valuable proteins. While it is necessary for a normally functioning organism to degrade a certain amount of connective tissue and other proteins, the presence of an excessive amount of leukocyte elastase has been associated with various pathological states, such as emphysema and rheumatoid arthritis. To counteract the effects of leukocyte elastase when it is present in amounts greater than normal, a protease inhibitor has been sought which is specific for leukocyte elastase. Such a protease inhibitor would be especially useful if it were capable of being isolated or prepared in a purified form and in sufficient quantities to be pharmaceutically useful In the past, at least two leukocyte elastase inhibitors have been identified in the literature. One protein, described in Schiessler et al., "Acid-Stable Inhibitors of Granulocyte Neutral Proteases in Human Mucous Secretions: Biochemistry and Possible Biological Function", in *Neutral Proteases of Human Polymorphoneuclear Leucocytes,* Havemann et al. (eds), Urban and Schwarzenberg, Inc. (1978), was isolated from human seminal plasma and sputum and was characterized as being approximately 11 Kda in size with tyrosine as the N-terminal amino acid. The literature reports of this protein have only furnished a partial amino acid sequence, but even this partial sequence indicates that this protein varies substantially from the proteins of the present invention. The reports of the sequence of this protein, in combination with the complete amino acid sequence data for proteins of the present invention, indicate to the present inventors that the product sequenced by Schiessler et al. may have been a degraded protein which was not a single-polypeptide chain.

A second protein, isolated in one instance from human plasma, has been named alpha 1-protease inhibitor. Work on this protein has been summarized in a review by Travis and Salvesen, *Ann. Rev. Biochem.* 52: 655–709 (1983). The reports of the amino acid sequence of this protein indicate that it too differs substantially from the proteins of the present invention.

Trypsin is another protease of particular interest from a pharmacological standpoint. Trypsin is known to initiate degradation of certain soft organ tissue, such as pancreatic tissue, during a variety of acute conditions, such as pancreatitis. A variety of efforts have been directed toward the treatment of these conditions, without marked success, through the use of proteins which it was hoped would inhibit the action of trypsin. Illustrative of such efforts are attempts to use exogenous bovine trypsin inhibitors in treatment of human pancreatitis. While such techniques have been attempted in Europe, they have not been approved as effective by the U.S. Food and Drug Administration.

Thus, there is a need for a protease inhibitor effective in neutralizing excess trypsin in a variety of acute and chronic conditions. As was the case with the leukocyte elastase inhibitor discussed above, a trypsin inhibitor would be particularly useful if it could be isolated and prepared in a purified form and in sufficient quantities to be pharmaceutically useful.

Cathepsin G is another protease present in large quantities in leukocytes. Cathepsin G is known to be capable of degrading in vitro a variety of valuable proteins, including those of the complement pathway pancreatic elastase is another protease which may have a role in pancreatitis. Thus, inhibitors for these proteases are also of pharmaceutical value.

Leukocyte elastase, trypsin, cathepsin G and pancreatic elastase are examples of a class of proteases known as serine proteases, which have elements of common structure and mechanism. Their activity against different substrates and their sensitivity to different inhibitors are believed to result from changes in only a few amino acid residues. By analogy, it is possible to conceive of a class of serine protease inhibitors, also having common elements of structure and mechanism, in which changes in a relatively few amino acids will result in inhibition of different proteases, and that at least one member of this class will inhibit every serine protease of the former class.

A particularly preferred serine protease inhibitor is secretory leukocyte protease inhibitor (SLPI) and fragments and analogues thereof. Also preferred are anti-leukoprotease (ALP), mucous protease inhibitor (MPI), human seminal plasma inhibitor-I (HUSI-I), bronchial mucus inhibitor (BMI), cervical mucus inhibitor (CUSI). These molecules are especially well-suited for use in conditions leading to bone loss because they are preferentially directed to the cartilage. Exemplary serine protease inhibitors are described in the following, each of which is hereby incorporated by reference: U.S. Pat. No. 4,760,130, issued Jul. 26, 1988; U.S. Pat. No. 5,900,400, issued May 4, 1999, which discloses preferred SLPI analogues; and U.S. Pat. No. 5,633,227, issued May 27, 1997, which discloses preferred SLPI fragments. The molecules disclosed in the foregoing references as well as any variants or analogues thereof as described hereinafter are collectively termed "serine protease inhibitors."

IL-18 Inhibitors

IL-18 is a pro-inflammatory cytokine of somewhat recent discovery. IL-18 was found to induce interferon-γ and was originally named interferon gamma inducing factor (IGIF). IL-1 upregulates IL-18 production, and IL-18 induces production of a number of proinflammatory cytokines, including IL-6 and MMP-1. Dinarello et al. (1998), *J. Leukocyte Biol.* 63: 658–64. Caspase I is also critical for IL-18 production. The art also suggested that TNF-α regulates IL-18 production, and it was found that simultaneous inhibition of TNF-α and IL-18 protected against liver toxicity. Faggioni et al. (2000), *PNAS* 97: 2367–72.

IL-18 acts in vivo through a receptor system reminiscent of the IL-1 system. IL-18 interacts with a cell surface receptor (IL-18R), which interacts with an accessory protein (IL-18RAcP). IL-18-mediated signaling proceeds upon formation of the complex of IL-18, IL-18R, and IL-18RAcP. A natural inhibitor for IL-18 is IL-18 bp. Although it bears insignificant sequence homology with IL-18R, IL-18 bp's act as a "decoy receptors" by binding to IL-18 molecules and preventing interaction with IL-18 and subsequent IL-18-mediated signaling.

The present invention concerns methods of treatment using IL-18 inhibitors in combination with the other classes of molecules described herein. Such combination therapy is useful for treating inflammation and autoimmune diseases generally, as well as IL-1 mediated diseases and TNF-mediated diseases as defined hereinabove. In particular, combination therapy using IL-18 inhibitors is useful for treating arthritis (particularly rheumatoid arthritis), systemic lupus erythematosus (SLE), graft versus host disease (GvHD), hepatitis and sepsis.

A number of classes of IL-18 inhibitors are known in the art, and all are useful in the present invention. Suitable IL-18 inhibitors include antibodies binding to IL-18; antibodies binding to IL-18R; antibodies binding to IL-18RAcP; IL-18 bp; IL-18R fragments (e.g., a solubilized extracellular domain of the IL-18 receptor), peptides binding to IL-18 and preventing its interaction with IL-18R; peptides binding to IL-18R and preventing its interaction with IL-18 or with IL-18RAcP; peptides binding to IL-18RAcP and preventing its interaction with IL-18R; and small molecules preventing IL-18 production or interaction between any of IL-18, IL-18R, and IL-18RAcP. Any of the foregoing, with the exception of small molecules, may be linked to half-life extending vehicles known in the art. Such vehicles include the Fc domain, polyethylene glycol, and dextran. These vehicles are reviewed in a patent application entitled, "Modified Peptides as Therapeutic Agents," U.S. Ser. No. 09/428,082, PCT appl. no. WO 99/25044, which is hereby incorporated by reference in its entirety.

Useful IL-18 inhibitors are described in the following references, which are hereby incorporated by reference: U.S. Pat. No. 5,912,324, issued Jul. 14, 1994; EP 0 962 531, published Dec. 8, 1999; EP 712 931, published Nov. 15, 1994; U.S. Pat. No. 5,914,253, issued Jul. 14, 1994; WO 97/24441, published Jul. 10, 1997; U.S. Pat. No. 6,060,283, issued May 9, 2000; EP 850 952, published Dec. 26, 1996; EP 864 585, published Sep. 16, 1998; WO 98/41232, published Sep. 24, 1998; U.S. Pat. No. 6,054,487, issued Apr. 25, 2000; WO 99/09063, published Aug. 14, 1997; WO 99/22760, published Nov. 3, 1997; WO 99/37772, published Jan. 23, 1998; WO 99/37773, published Mar. 20, 1998; EP 0 974 600, published Jan. 26, 2000; WO 00/12555, published Mar. 9, 2000; Japanese patent application JP 111,399/94, published Oct. 31, 1997; Israel patent application IL 121554 A0, published Feb. 8, 1998.

Variants of Proteins

Those skilled in the art will understand that one may make many molecules derived in sequence from the aforementioned molecules in which amino acids have been deleted ("deletion variants"), inserted ("addition variants"), or substituted ("substitution variants"). Molecules having such substitutions, additions, deletions, or any combination thereof are termed individually or collectively "variant(s)").

Such variants should, however, maintain at some level (including a reduced level) the relevant activity of the unmodified or "parent" molecule (e.g., an sTNFR variant possesses the ability to bind TNF). Hereinafter, "parent molecule" refers to an unmodified molecule or a variant molecule lacking the particular variation under discussion; for example, when discussing substitution below, the parent molecule may be a deletion variant.

Variants may be rapidly screened to assess their physical properties. It will be appreciated that such variant(s) will demonstrate similar properties to the unmodified molecule, but not necessarily all of the same properties and not necessarily to the same degree as the corresponding parent molecule.

There are two principal variables in the construction of amino acid sequence variant(s): the location of the mutation site and the nature of the mutation. In designing variant(s), the location of each mutation site and the nature of each mutation will depend on the biochemical characteristic(s) to be modified. Each mutation site can be modified individually or in series, e.g., by (1) deleting the target amino acid residue, (2) inserting one or more amino acid residues adjacent to the located site or (3) substituting first with conservative amino acid choices and, depending upon the results achieved, then with more radical selections.

Amino acid sequence deletions generally range from about 1 to 30 amino acid residues, preferably from about 1 to 20 amino acid residues, more preferably from about 1 to 10 amino acid residues and most preferably from about 1 to 5 contiguous residues. Amino-terminal, carboxy-terminal and internal intrasequence deletions are contemplated. Deletions within the amino acid sequences of OPG or the sTNFRs may be made, for example, in regions of low homology with the sequences of other members of the NGF/TNF receptor family. In the case of IL-1ra, deletions may be made in regions of low homology in the IL-1 family (which comprises IL-1α, IL-1β, and IL-1ra). Deletions in areas of substantial homology with other members of the family will be more likely to significantly modify the biological activity. Specifically, the sequence similarity among NGF/TNF receptor family members is particularly high in the region corresponding to the first two disulfide loops of domain 1, the whole of domain 2, and the first disulfide loop of domain 3 (Banner et al. (1993), *Cell*, 73:431–445). The number of total deletions and/or consecutive deletions preferably will be selected so as to preserve the tertiary structure in the affected domain, e.g., cysteine crosslinking.

An amino acid sequence addition may include insertions of an amino- and/or carboxyl-terminal fusion ranging in length from one residue to one hundred or more residues, as well as internal intrasequence insertions of single or multiple amino acid residues. Internal additions may range generally from about 1 to 20 amino acid residues, preferably from about 1 to 10 amino acid residues, more preferably from about 1 to 5 amino acid residues, and most preferably from about 1 to 3 amino acid residues. Additions within the amino acid sequences of OPG or the sTNFRs may be made in regions of low homology with the sequences of other members of the NGF/TNF receptor family. Additions within the amino acid sequence of OPG or the sTNFRs in areas of substantial homology with the sequences of other members of the NGF/TNF receptor family will be more likely to significantly modify the biological activity. Additions preferably include amino acid sequences derived from the sequences of the NGF/TNF receptor family members.

An amino-terminus addition is contemplated to include the addition of a methionine (for example, as an artifact of the direct expression in bacterial recombinant cell culture). A further example of an amino-terminal addition includes the fusion of a signal sequence to the amino-terminus of a mature molecule in order to facilitate its secretion from recombinant host cells. Such signal sequences generally will be obtained from and thus be homologous to the intended host cell species. For prokaryotic host cells that do not recognize and process the native signal sequence of the mature molecule, the signal sequence may be substituted by a prokaryotic signal sequence selected, for example, from the group of the alkaline phosphatase, penicillinase or heat-stable enterotoxin II leader sequences. For expression in yeast cells the signal sequence may be selected, for example, from the group of the yeast invertase, alpha factor or acid phosphatase leader sequences. For mammalian cell expression, the native signal sequences (see, e.g., EP 393 438 and EP 422 339 for sTNFRs) are satisfactory, although other mammalian signal sequences may be suitable; for example, sequences derived from other NGF/TNF receptor family members.

An example of an amino- or a carboxy-terminus addition includes chimeric proteins comprising the amino-terminal or carboxy-terminal fusion of the parent molecules with all or part of the constant domain of the heavy or light chain of human immunoglobulin (individually or collectively, ("Fc variant(s)"). Such chimeric polypeptides are preferred wherein the immunoglobulin portion of each comprises all of the domains except the first domain of the constant region of the heavy chain of human immunoglobulin such as IgG (e.g., IgG1 or IgG3), IgA, IgM or IgE. A skilled artisan will appreciate that any amino acid of the immunoglobulin portion can be deleted or substituted with one or more amino acids, or one or more amino acids can be added as long as the parent molecule still maintains some level of its relevant activity and the immunoglobulin portion shows one or more of its characteristic properties.

Another group of variant(s) is amino acid substitution variant(s). These are variant(s) wherein at least one amino acid residue in a parent molecule is removed and a different residue inserted in its place. Substitution variant(s) include allelic variant(s) which are characterized by naturally-occurring nucleotide sequence changes in the species population that may or may not result in an amino acid change. One skilled in the art can use any information known about the binding or active site of the polypeptide in the selection of possible mutation sites.

One method for identifying amino acid residues or regions for mutagenesis of a protein is called "alanine scanning mutagenesis", as described by Cunningham and Wells (1989), *Science*, 244:1081–1085, the disclosure of which is hereby incorporated by reference. In this method, an amino acid residue or group of target residues is identified (e.g., charged residues such as Arg, Asp, His, Lys and Glu) and replaced by a neutral or negatively-charged amino acid (most preferably alanine or polyalanine) to affect the interaction of the amino acids with the surrounding aqueous environment in or outside the cell. Those domains/residues demonstrating functional sensitivity to the substitutions are then refined by introducing additional or alternate residues at the sites of substitution. Thus, the site for introducing an amino acid sequence modification is predetermined. To optimize the performance of a mutation at a given site, alanine scanning or random mutagenesis may be conducted and the variant(s) may be screened for the optimal combination of desired activity and degree of activity.

The sites of greatest interest for substitutional mutagenesis include sites in which particular amino acid residues within a parent molecule are substantially different from other species or other family members in terms of side-chain bulk, charge and/or hydrophobicity. Other sites of interest include those in which particular residues of a parent molecule are identical among other species or other family members, as such positions are generally important for the biological activity of a protein.

Other sites of interest include those in which particular residues are similar or identical with proteins with similar structure or activity to the parent molecule. For sTNFR-I, for example, information has been elucidated relevant to sTNFR-I-like molecules (Banner et al. (1993), supra, and Fu et al. (1995), *Protein Engineering*, 8(12):1233–1241). Residues $Tyr^9$, $Thr^{39}$, $His^{55}$ in Domain 1, residues $Phe^{49}$, $Ser^{63}$, $Asp^{82}$ in Domain 2 and residues $Tyr^{92}$ and $Ser^{107}$ in Domain 3 have been identified as being potentially important for the stabilization of the structure of Domains 1, 2 and 3, respectively. Residues $Pro^{12}$ and $His^{55}$ have been identified as potentially interacting with $Ser^{86}$-$Tyr^{87}$ on subunit C of TNF-α. Residues $Glu^{45}$-$Phe^{49}$ have been identified as being in a loop which potentially interacts with residues $Leu^{29}$-$Arg^{32}$ of TNF-α subunit A. Residues $Gly^{48}$ has been identified as potentially interacting with $Asn^{19}$-$Pro^{20}$ on subunit A of TNF-α. Residue $His^{58}$-$Leu^{60}$ have been identified as being in an extended strand conformation and side chain interactions with residues $Arg^{31}$-$Ala^{33}$ on subunit A of TNF-α have been potentially identified with residue $His^{58}$ of sTNFR-I specifically interacting with residue $Arg^{31}$. Residues $Lys^{64}$-$Arg^{66}$ have been identified as being in an extended strand conformation and have been identified as having side chain and main chain interactions with residues $Ala^{145}$-$Glu^{146}$ and residue $Glu^{46}$ on subunit A of TNF-α. Residue $Met^{69}$ has been identified as potentially interacting with residue $Tyr^{115}$ on subunit A of TNF-α. Residues $His^{94}$-$Phe^{101}$ have been identified as forming a loop which interacts with residues $Thr^{72}$-$Leu^{75}$ and $Asn^{137}$ of subunit C of TNF-α, with residue $Trp^{96}$ of sTNFR-I specifically interacting with residues $Ser^{71}$-$Thr^{72}$ on subunit C of TNF-α, $Leu^{100}$ of sTNFR-I being in close proximity with residue $Asn^{137}$ on subunit C of TNF-αand residue $Gln^{102}$ of sTNFR-I specifically interacting with residue $Pro^{113}$ on subunit A of TNF-α.

In addition to the cysteines forming the 3 pairs of disulfide bonds within each of the four domains of the molecule, there are several other conserved residues that contribute to the stabilization of the tertiary fold of each domain.

There are two main classes into which these stabilizing residues fall. The first type contributes to the shielding of the disulfide bond sulfur atoms from solvent. An example of this residues in domain 3 is $Tyr^{92}$. In domain 4 $Phe^{133}$ helps to shield the $Cys^{128}$-$Cys^{139}$ disulfide bond. All four domains have either a Tyr or Phe at these same structurally conserved locations. The second class of stabilizing residues form hydrogen bonds within their respective domains. Within domain 3 $Asn^{123}$ and $Ser^{107}$ form a hydrogen bond and $Ser^{107}$ forms an additional hydrogen bond with $Thr^{124}$. For domain 4 these residues include $Asn^{144}$ and $Ser^{141}$.

In addition there are hydrogen bonds between domain 3 and 4 that are not seen between other domains. These hydrogens bonds are (1) $Asn^{105}$ main-chain oxygen and $Asn^{137}$ side-chain nitrogen and (2) $Ser^{107}$ side-chain oxygen and $Asn^{137}$ main-chain nitrogen.

Figure 12A:
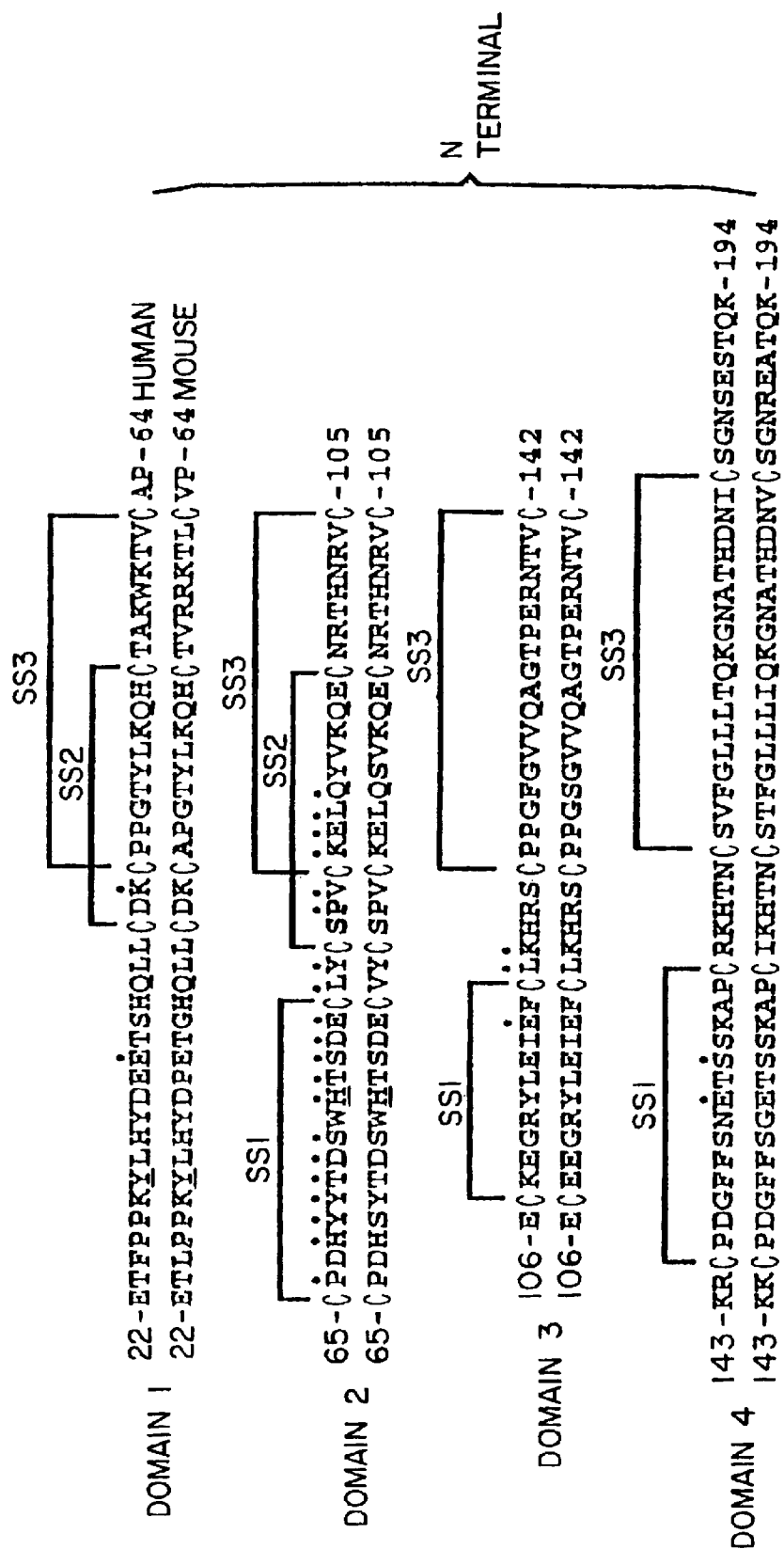

Another useful tool in identifying sites suitable for substitution is molecular modeling. One example of this technique is OPG. Using the homology between OPG and the extracellular ligand binding domains of TNF receptor family members, a three-dimensional model of OPG was generated based upon the known crystal structure of the extracellular domain of TNFR-I (see Example 6). This model was used to identify those residues within OPG which may be important for biological activity. Cysteine residues that are involved in maintaining the structure of the four cysteine-rich domains were identified. The following disulfide bonds were identified in the model: Domain 1: cys4l to cys54, cys44 to cys62, tyr23 and his 66 may act to stabilize the structure of this domain; Domain 2: cys65 to cys80, cys83 to cys98, cys87 to cys105; Domain 3: cys107 to cys118, cys124 to cys142; Domain 4: cys145 to cys160, cys166 to cys185. Residues were also identified which were in close proximity to TNFβ as shown in FIGS. 11 and 12A–12B. In this model, it is assumed that OPG binds to a corresponding ligand; TNFβ was used as a model ligand to simulate the interaction of OPG with its ligand. Based upon this modeling, the following residues in OPG may be important for ligand binding: glu34, lys43, pro66 to gln91 (in particular, pro66, his68, tyr69, tyr70, thr71, asp72, ser73, his76, ser77, asp78, glu79, leu81, tyr82, pro85, val86, lys88, glu90 and gln91), glu153 and ser155.

Alterations in these amino acid residues, either singly or in combination, may alter the biological activity of OPG. For example, changes in specific cysteine residues may alter the structure of individual cysteine-rich domains, whereas changes in residues important for ligand binding may affect physical interactions of OPG with ligand. Structural models can aid in identifying analogs which have more desirable properties, such as enhanced biological activity, greater stability, or greater ease of formulation.

A skilled artisan will appreciate that initially sites should be modified by substitution in a relatively conservative manner. Such conservative substitutions are shown in Table 1 under the heading of "Preferred Substitutions". If such substitutions result in a change in biological activity, then more substantial changes (Exemplary Substitutions) may be introduced and/or other additions/deletions may be made and the resulting products screened.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

In making such changes, the hydropathic index of amino acids may be considered. The importance of the hydropathic amino acid index in conferring interactive biological function on a protein is generally understood in the art (Kyte and Doolittle (1982), *J. Mol. Biol.*, 157:105–131, the disclosure of which is incorporated herein by reference). It is known that certain amino acids may be substituted for other amino acids having a similar hydropathic index or score and still retain a similar biological activity.

It is also understood in the art that the substitution of like amino acids can be made effectively on the basis of hydrophilicity, particularly where the functionally equivalent protein or peptide thereby created is intended for use in immunological embodiments, as in the present case. U.S. Pat. No. 4,554,101, the disclosure of which is incorporated herein by reference, states that the greatest local average hydrophilicity of a protein, as governed by the hydrophilicity of its adjacent amino acids, correlates with its immunogenicity and antigenicity, i.e., with a biological property of the protein.

U.S. Pat. No. 4,554,101 also teaches the identification and preparation of epitopes from primary amino acid sequences on the basis of hydrophilicity. Through the methods disclosed in U.S. Pat. No. 4,554,101 a skilled artisan would be able to identify epitopes, for example, within the amino acid sequence of an sTNFR. These regions are also referred to as "epitopic core regions". Numerous scientific publications have been devoted to the prediction of secondary structure, and to the identification of epitopes, from analyses of amino acid sequences (Chou and Fasman (1974), *Biochemistry*, 13(2):222–245; Chou and Fasman (1974), *Biochemistry*, 13(2):211–222; Chou and Fasman (1978), *Adv. Enzymol. Relat. Areas Mol. Biol.*, 47:45–148; Chou and Fasman (1978), *Ann. Rev. Biochem.*, 47:251–276 and Chou and Fasman (1979), *Biophys. J.*, 26:367–384, the disclosures of which are incorporated herein by reference). Moreover, computer programs are currently available to assist with predicting antigenic portions and epitopic core regions of proteins. Examples include those programs based upon the Jameson-Wolf analysis (Jameson and Wolf (1988), *Comput. Appl. Biosci.*, 4(1):181–186 and Wolf et al. (1988), *Comput. Appl. Biosci.*, 4(1):187–191, the disclosures of which are incorporated herein by reference); the program PepPlot® (Brutlag et al. (1990), *CABS*, 6:237–245 and Weinberger et al. (1985), *Science*, 228:740–742, the disclosures of which are incorporated herein by reference); and other programs for protein tertiary structure prediction (Fetrow and Bryant (1993), *BIOTECHNOLOGY*, 11:479–483, the disclosure of which is incorporated herein by reference).

In contrast, substantial modifications in the functional and/or chemical characteristics of a parent molecule may be accomplished by selecting substitutions that differ significantly in their effect on maintaining (a) the structure of the polypeptide backbone in the area of the substitution, for example, as a sheet or helical conformation, (b) the relative charge or hydrophobicity of the protein at the target site or (c) the bulk of the side chain. Naturally-occurring residues are divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) aromatic: Trp, Tyr, Phe; and
6) residues that influence chain orientation: Gly, Pro.

Non-conservative substitutions may involve the exchange of a member of one of these groups for another. For example, substituted residues may be introduced into regions of OPG or the sTNFRs that are homologous with other NGF/TNF receptor family members or into non-homologous regions of the protein.

A variety of amino acid substitutions or deletions may be made to modify or add N-linked or O-linked glycosylation sites, resulting in a protein with altered glycosylation. The sequence may be modified to add glycosylation sites to or to delete N-linked or O-linked glycosylation sites from the parent molecule. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where xaa can be any amino acid other than Pro. In the 30 kDa TNF inhibitor, for example, proven or predicted asparagine residues exist at positions 14, 105 and 111.

Specific mutations of the sequences of the parent molecules may involve substitution of a non-native amino acid at the amino-terminus, carboxy-terminus or at any site of the protein that is modified by the addition of an N-linked or O-linked carbohydrate. Such modifications may be of particular utility in the addition of an amino acid (e.g., cysteine), which is advantageous for the linking of a water-soluble polymer to form a derivative. For example, WO 92/16221 describes the preparation of sTNFR-I muteins, e.g., wherein an asparagine residue at position 105 of the native human protein is changed to cysteine (c105 sTNFR-I).

In a specific embodiment, a variant polypeptide will preferably be substantially homologous to the amino acid of the parent molecule from which it is derived. The term "substantially homologous" as used herein means a degree of homology that is in excess of 80%, preferably in excess of 90%, more preferably in excess of 95% or most preferably even 99%. The percentage of homology as described herein is calculated as the percentage of amino acid residues found in the smaller of the two sequences which align with identical amino acid residues in the sequence being compared when four gaps in a length of 100 amino acids may be introduced to assist in that alignment, as set forth by Dayhoff (1972), *Atlas of Protein Sequence and Structure*, 5:124, National Biochemical Research Foundation, Washington, D.C., the disclosure of which is hereby incorporated by reference. Also included within the term "substantially homologous" are variant(s) of parent molecules that may be isolated by cross-reactivity with antibodies to the parent molecule amino acid sequences or whose genes may be isolated through hybridization with the DNA of parent molecules or segments thereof.

Polypeptide Derivatives

This invention also comprises chemically modified derivatives of the parent molecule(s) in which the protein is linked to a nonproteinaceous moiety (e.g., a polymer) in order to modify properties. These chemically modified parent molecules are referred to herein as "derivatives". Such derivatives may be prepared by one skilled in the art given the disclosures herein. Conjugates may be prepared using glycosylated, non-glycosylated or de-glycosylated parent molecule(s) and suitable chemical moieties. Typically non-glycosylated parent molecules and water-soluble polymers will be used. Other derivatives encompassed by the invention include post-translational modifications (e.g., N-linked or O-linked carbohydrate chains, processing of N-terminal or C-terminal ends), attachment of chemical moieties to the amino acid backbone, and chemical modifications of N-linked or O-linked carbohydrate chains. The polypeptides may also be modified with a detectable label, such as an enzymatic, fluorescent, isotopic or affinity label to allow for detection and isolation of the protein.

Water-soluble polymers are desirable because the protein to which each is attached will not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically and, if so, the therapeutic profile of the protein (e.g., duration of sustained release; resistance to proteolysis; effects, if any, on dosage; biological activity; ease of handling; degree or lack of antigenicity and other known effects of a water-soluble polymer on a therapeutic proteins).

Suitable, clinically acceptable, water-soluble polymers include but are not limited to polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1, 3-dioxolane, poly-1, 3,6-trioxane, ethylene/maleic anhydride copolymer, poly (β-amino acids) (either homopolymers or random copolymers), poly(n-vinyl pyrrolidone)polyethylene glycol, polypropylene glycol homopolymers (PPG) and other polyalkylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof. As used herein, polyethylene glycol is meant to encompass any of the forms that have been used to derivatize other proteins, such as mono-(C1–C10) alkoxy- or aryloxy-polyethylene glycol. Polyethylene glycol propionaldehyde may have advantages in manufacturing due to its stability in water.

The water-soluble polymers each may be of any molecular weight and may be branched or unbranched. Generally, the higher the molecular weight or the more branches, the higher the polymer:protein ratio. The water-soluble polymers each typically have an average molecular weight of between about 2 kDa to about 100 kDa (the term "about" indicating that in preparations of a water-soluble polymer, some molecules will weigh more, some less, than the stated molecular weight). The average molecular weight of each water-soluble polymer preferably is between about 5 kDa and about 40 kDa, more preferably between about 10 kDa and about 35 kDa and most preferably between about 15 kDa and about 30 kDa.

There are a number of attachment methods available to those skilled in the art, including acylation reactions or alkylation reactions (preferably to generate an amino-terminal chemically modified protein) with a reactive water-soluble molecule. See, for example, EP 0 401 384; Malik et al. (1992), *Exp. Hematol.*, 20:1028–1035; Francis (1992), *Focus on Growth Factors*, 3(2):4–10, published by Mediscript, Mountain Court, Friern Barnet Lane, London N20 OLD, UK; EP 0 154 316; EP 0 401 384; WO 92/16221; WO 95/34326; WO 95/13312; WO 96/11953; WO 96/19459 and WO 96/19459 and the other publications cited herein that relate to pegylation, the disclosures of which are hereby incorporated by reference.

Pegylation also may be specifically carried out using water-soluble polymers having at least one reactive hydroxy group (e.g. polyethylene glycol). The water-soluble polymer can be reacted with an activating group, thereby forming an "activated linker" useful in modifying various proteins. The activated linkers can be monofunctional, bifunctional, or multifunctional.

Activating groups which can be used to link the water-soluble polymer to two or more proteins include the following: sulfone, maleimide, sulfhydryl, thiol, triflate, tresylate, azidirine, oxirane and 5-pyridyl. Useful reagents having a reactive sulfone group that can be used in the methods include, without limitation, chlorosulfone, vinylsulfone and divinylsulfone. These PEG derivatives are stable against hydrolysis for extended periods in aqueous environments at pHs of about 11 or less, and can form linkages with molecules to form conjugates which are also hydrolytically stable. Useful homobifunctional derivatives are PEG-bis-chlorosulfone and PEG-bis-vinylsulfone (see WO 95/13312).

WO 97/04003, the disclosure of which is hereby incorporated by reference, teaches methods of making sulfone-activated linkers by obtaining a compound having a reactive hydroxyl group and converting the hydroxyl group to a reactive Michael acceptor to form an activated linker, with tetrahydrofuran as the solvent for the conversion. The application also teaches a process for purifying the activated linkers which utilizes hydrophobic interaction chromatography to separate the linkers based on size and end-group functionality.

As an example, chemically modified derivatives of OPG may provide such advantages as increased stability, increased time in circulation, or decreased immunogenicity (see U.S. Pat. No. 4,179,337). The chemical moieties for derivitization may be selected from water-soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

One may specifically desire N-terminally chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemically modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Polyvalent Forms

Polyvalent forms, i.e., molecules comprising more than one active moiety, may be constructed. In one embodiment, an sTNFR variant may possess multiple tumor necrosis factor binding sites for the TNF ligand. Additionally, the molecule may possess at least one tumor necrosis factor binding site and, depending upon the desired characteristic of polyvalent form, at least one site of another molecule (e.g., a TNF-α inhibitor(s), and an OPG).

Active moieties may be linked using conventional coupling techniques (see WO 92/16221, WO 95/13312 and WO 95/34326, the disclosures of which are hereby incorporated by reference). For example, WO 92/16221 and WO 95/34326 describe the preparation of various dimerized sTNFR-I molecules, e.g., dimerized c105 sTNFR-I. Techniques for formation of polyvalent forms include photochemical crosslinking (e.g., exposure to ultraviolet light), chemical crosslinking (e.g., with bifunctional linker molecules such as polyethylene glycol), and mutagenesis (e.g., introduction of additional cysteine residues).

Polyvalent forms may be constructed by chemically coupling at least one parent molecule and another moiety with any clinically accepted linker (e.g., a water-soluble polymer). In principle, the linker must not impart new immunogenicity. The linker also must not, by virtue of the new amino acid residues, alter the hydrophobicity and charge balance of the structure, which affects its biodistribution and clearance. A variety of chemical crosslinkers may be used depending upon which properties of the protein dimer are desired. For example, crosslinkers may be short and relatively rigid or longer and more flexible, may be biologically reversible, and may provide reduced immunogenicity or longer pharmacokinetic half-life.

In one example, OPG molecules are linked through the amino terminus by a two step synthesis (see Example 12). In the first step, OPG is chemically modified at the amino terminus to introduce a protected thiol, which after purification is deprotected and used as a point of attachment for site-specific conjugation through a variety of crosslinkers with a second OPG molecule. Amino-terminal crosslinks include, but are not limited to, a disulfide bond, thioether linkages using short-chain, bis-functional aliphatic crosslinkers, and thioether linkages to variable length, bifunctional polyethylene glycol crosslinkers (PEG "dumbbells"). Also encompassed by PEG dumbbell synthesis of OPG dimers is a byproduct of such synthesis, termed a "monobell". An OPG monobell consists of a monomer coupled to a linear bifunctional PEG with a free polymer terminus. Alternatively, OPG may be crosslinked directly through a variety of amine specific homobifunctional crosslinking techniques which include reagents such as: diethylenetriaminepentaacetic dianhydride (DTPA), p-benzoquinone (pBQ) or bis(sulfosuccinimidyl) suberate (BS$^3$) as well as others known in the art. It is also possible to thiolate OPG directly with reagents such as iminothiolane in the presence of a variety of bifunctional, thiol specific crosslinkers, such as PEG bismaleimide, and achieve dimerization and/or dumbbells in a one step process.

The water-soluble polymers for this polyvalent form can be, based on the monomers listed herein, homopolymers, random or block copolymers, terpolymers straight chain or branched, substituted or unsubstituted. The polymer can be of any length or molecular weight, but these characteristics can affect the biological properties. Polymer average molecular weights particularly useful for decreasing clearance rates in pharmaceutical applications are in the range of 2,000 to 35,000 daltons. In addition, the length of the polymer can be varied to optimize or confer the desired biological activity.

Alternatively, a bivalent molecule may consist of two tandem repeats of parent molecules separated by a polypeptide linker region. The design of the polypeptide linkers is similar in design to the insertion of short loop sequences between domains in the de novo design of proteins (Mutter (1988), *TIBS*, 13:260–265 and Regan and DeGrado (1988), *Science*, 241:976–978, the disclosures of which are hereby incorporated by reference). Several different linker constructs have been assembled and shown to be useful for forming single chain antibodies; the most functional linkers vary in size from 12 to 25 amino acids (amino acids having unreactive side groups, e.g., alanine, serine and glycine) which together constitute a hydrophilic sequence, have a few oppositely charged residues to enhance solubility and are flexible (Whitlow and Filpula (1991), *Methods: A Companion to Methods in Enzymology*, 2:97–105; and Brigido et al. (1993), *J. Immunol.*, 150:469–479, the disclosures of which are hereby incorporated by reference). It has been shown that a linker suitable for single chain antibodies is effective to produce a dimeric form of the human sTNFR-II (Neve et al. (1996), *Cytokine*, 8(5):365–370, the disclosure of which is hereby incorporated by reference).

Self-associating variants are another example of polyvalent forms. Such self-associating variants may be bound covalently (typically by disulfide bonds) or noncovalently. Analysis of carboxy-terminal deletions of OPG, for example, suggest that at least a portion of the region 186–401 is involved in association of OPG polypeptides. Substitution of part or all of the region of OPG amino acids 186–401 with an amino acid sequence capable of self-association is also encompassed by the invention.

Polyvalent forms may also be formed using substitution variants. Parent molecules may be modified to form dimers or multimers by site-directed mutagenesis to create unpaired cysteine residues for interchain disulfide bond formation.

Additionally, a parent molecule may be chemically coupled to biotin, and the resulting conjugate may then be allowed to bind to avidin, resulting in tetravalent avidin/biotin/parent molecules. A parent molecule may also be covalently coupled to dinitrophenol (DNP) or trinitrophenol (TNP) and the resulting conjugates precipitated with anti-DNP or anti-TNP-IgM to form decameric conjugates.

In yet another embodiment, recombinant fusion proteins may also be produced wherein each recombinant chimeric molecule has a parent molecule(s) sequence amino-terminally or carboxy-terminally fused to all or part of the constant domains, but at least one constant domain, of the heavy or light chain of human immunoglobulin. For example, a chimeric TNF-α inhibitor(s)/IgG1 (or IgG1/TNF-α inhibitor(s)) fusion protein may be produced from a light chain-containing chimeric gene: a TNF-α inhibitor(s)/human kappa light chain chimera (TNF-α inhibitor(s)/Ck) or a human kappa light chain/TNF-α inhibitors chimera (Ck/TNF-α inhibitor(s)); or a heavy chain-containing chimeric gene: a TNF-α inhibitor(s)/human gamma-1 heavy chain chimera (TNF-α inhibitor(s)/Cg-1) or a human gamma-1 heavy chain/TNF-α inhibitor(s) chimera (Cg-1/TNF-α inhibitor(s)). Alternatively, an OPG-Fc chimera may be formed as described in WO 97/23614, which is hereby incorporated by reference. Following transcription and translation of a heavy-chain chimeric gene, or of a light chain-containing gene and a heavy-chain chimeric gene, the gene products may be assembled into a single chimeric molecule having a parent molecule(s) displayed bivalently. Additional details relating to the construction of such chimeric molecules are disclosed in U.S. Pat. No. 5,116,964, WO 89/09622, WO 91/16437, WO 97/23614 and EP 315062, the disclosures of which are hereby incorporated by reference.

In yet a further embodiment, recombinant fusion proteins may also be produced wherein each recombinant chimeric molecule has at least one TNF-α inhibitor(s), as described herein, and at least a portion of the region 186–401 of osteoprotogerin or a variant thereof, as described in European Patent Application No. 96309363.8, the disclosures of which are hereby incorporated by reference. Either the TNF-α inhibitor(s) or the portion of osteoprotogerin may be at the amino-terminus or the carboxy-terminus of the chimeric molecule.

Nucleic Acids

The invention provides for an isolated nucleic acid encoding a polypeptide having at least one of the biological activities of OPG. As described herein, the biological activities of OPG include, but are not limited to, any activity involving bone metabolism and in particular, include increasing bone density. The nucleic acids of the invention are selected from the following:

a) the nucleic acid sequences as shown in FIGS. 2B–2C (SEQ ID NO:120), 9A–9B (SEQ ID NO:122), and 9C–9D (SEQ ID NO:124) or complementary strands thereof;

b) the nucleic acids which hybridize under stringent conditions with the polypeptide-encoding region in FIGS. 2B–2C (SEQ ID NO:120), 9A–9B (SEQ ID NO:122), and 9C–9D (SEQ ID NO:124); and C) nucleic acids which hybridize under stringent conditions with nucleotides 148 through 337 inclusive as shown in FIG. 1A.

d) the nucleic acid sequences which are degenerate to the sequences in (a) and (b).

The invention provides for nucleic acids which encode rat, mouse and human OPG as well as nucleic acid sequences hybridizing thereto which encode a polypeptide having at least one of the biological activities of OPG. Also provided for are nucleic acids which hybridize to a rat OPG EST encompassing nucleotides 148–337 as shown in FIG. 1A. The conditions for hybridization are generally of high stringency such as 5×SSC, 50% formamide and 42° C. described in Example 1 of the specification. Equivalent stringency to these conditions may be readily obtained by adjusting salt and organic solvent concentrations and temperature. The nucleic acids in (b) encompass sequences encoding OPG-related polypeptides which do not undergo detectable hybridization with other known members of the TNF receptor superfamily. In a preferred embodiment, the nucleic acids are as shown in FIGS. 2B–2C (SEQ ID NO:120), 9A–9B (SEQ ID NO:122), and 9C–9D (SEQ ID NO:124).

The length of hybridizing nucleic acids of the invention may be variable since hybridization may occur in part or all of the polypeptide-encoding regions as shown in FIGS. 2B–2C (SEQ ID NO:120), 9A–9B (SEQ ID NO:122), and 9C–9D (SEQ ID NO:124), and may also occur in adjacent noncoding regions. Therefore, hybridizing nucleic acids may be truncations or extensions of the sequences shown in FIGS. 2B–2C (SEQ ID NO:120), 9A–9B (SEQ ID NO:122), and 9C–9D (SEQ ID NO:124). Truncated or extended nucleic acids are encompassed by the invention provided they retain one or more of the biological properties of OPG. The hybridizing nucleic acids may also include adjacent noncoding regions which are 5' and/or 3' to the OPG coding region. The noncoding regions include regulatory regions involved in OPG expression, such as promoters, enhance, translational initiation sites, transcription termination sites and the like.

Hybridization conditions for nucleic acids are described in Sambrook et al., *Molecular Cloning: A Laboratory Manual*, 2$^{nd}$ ed. Cold Spring Harbor Laboratory Press, Cold Spring Harbor, N.Y. (1989)

DNA encoding rat OPG was provided in plasmid pMO-B1.1 deposited with the American Type Culture Collection, Rockville, Md. on Dec. 27, 1995 under ATCC accession no. 69970. DNA encoding mouse OPG was provided in plasmid pRcCMV-murine OPG deposited with the American Type Culture Collection, Rockville, Md. on Dec. 27, 1995 under accession no. 69971. DNA encoding human OPG was provided in plasmid pRcCMV-human OPG deposited with the American Type Culture Collection, Rockville, Md. on Dec. 27, 1995 under accession no. 69969. The nucleic acids of the invention will hybridize under stringent conditions to the DNA inserts of ATCC accession nos. 69969, 69970, and 69971 and have at least one of the biological activities of OPG.

Also provided by the invention are derivatives of the nucleic acid sequences as shown in FIGS. 2B, 9A and 9B. As used herein, derivatives include nucleic acid sequences having addition, substitution, insertion or deletion of one or more residues such that the resulting sequences encode polypeptides having one or more amino acid residues which have been added, deleted, inserted or substituted and the resulting polypeptide has the activity of OPG. The nucleic acid derivatives may be naturally occurring, such as by splice variation or polymorphism, or may be constructed using site-directed mutagenesis techniques available to the skilled worker. One example of a naturally occurring variant of OPG is a nucleic acid encoding a lys to asn change at residue 3 within the leader sequence (see Example 5). It is anticipated that nucleic acid derivatives will encode amino acid changes in regions of the molecule which are least likely to disrupt biological activity. other derivatives include a nucleic acid encoding a membrane-bound form of OPG having an extracellular domain as shown in FIGS. 2B–2C (SEQ ID NO:120), 9A–9B (SEQ ID NO:122), and 9C–9D (SEQ ID NO:124) along with transmembrane and cytoplasmic domains.

In one embodiment, derivatives of OPG include nucleic acids encoding truncated forms of OPG having one or more amino acids deleted from the carboxy terminus. Nucleic acids encoding OPG may have from 1 to 216 amino acids deleted from the carboxy terminus. Optionally, an antibody Fc region may extend from the new carboxy terminus to yield a biologically active OPG-Fc fusion polypeptide. (see Example 11). In preferred embodiments, nucleic acids encode OPG having the amino acid sequence from residues 22–185, 22–189, 22–194 or 22–201 (using numbering in FIGS. 9E–F) and optionally, encoding an Fc region of human IgG.

Also included are nucleic acids encoding truncated forms of OPG having one or more amino acids deleted from the amino terminus. Truncated forms include those lacking part or all the 21 amino acids comprising the leader sequence. Additionally, the invention provides for nucleic acids encoding OPG having from 1 to 10 amino acids deleted from the mature amino terminus (at residue 22) and optionally, having from 1 to 216 amino acids deleted from the carboxy terminus (at residue 401). Optionally, the nucleic acids may encode a methionine residue at the amino terminus. Examples of such OPG truncated polypeptides are described in Example 8.

Examples of the nucleic acids of the invention include cDNA, genomic DNA, synthetic DNA and RNA. cDNA is obtained from libraries prepared from mRNA isolated from various tissues expressing OPG. In humans, tissue sources for OPG include kidney, liver, placenta and heart. Genomic DNA encoding OPG is obtained from genomic libraries which are commercially available from a variety of species. Synthetic DNA is obtained by chemical synthesis of overlapping oligonucleotide fragments followed by assembly of the fragments to reconstitute part or all of the coding region and flanking sequences (see U.S. Pat. No. 4,695,623 describing the chemical synthesis of interferon genes). RNA is obtained most easily by procaryotic expression vectors which direct high-level synthesis of mRNA, such as vectors using T7 promoters and RNA polymerase.

Nucleic acid sequences of the invention are used for the detection of OPG sequences in biological samples in order to determine which cells and tissues are expressing OPG mRNA. The sequences may also be used to screen cDNA and genomic libraries for sequences related to OPG. Such screening is well within the capabilities of one skilled in the art using appropriate hybridization conditions to detect homologus sequences. The nucleic acids are also useful for modulating the expression of OPG levels by anti-sense therapy or gene therapy. The nucleic acids are also used for the development of transgenic animals which may be used for the production of the polypeptide and for the study of biological activity (see Example 3).

Vectors and Host Cells

Expression vectors containing nucleic acid sequences encoding OPG, host cells transformed with said vectors and methods for the production of OPG are also provided by the invention. An overview of expression of recombinant proteins is found in *Methods of Enzymology* v. 185, Goeddel, D. V. ed. Academic Press (1990).

Host cells for the production of OPG include procaryotic host cells, such as *E. coli,* yeast, plant, insect and mammalian host cells. *E. coli* strains such as HB101 or JM101 are suitable for expression. Preferred mammalian host cells include COS, CHOd-, 293, CV-1, 3T3, baby hamster kidney (BHK) cells and others. Mammalian host cells are preferred when post-translational modifications, such as glycosylation and polypeptide processing, are important for OPG activity. Mammalian expression allows for the production of secreted polypeptides which may be recovered from the growth medium.

Vectors for the expression of OPG contain at a minimum sequences required for vector propagation and for expression of the cloned insert. These sequences include a replication origin, selection marker, promoter, ribosome binding site, enhancer sequences, RNA splice sites and transcription termination site. Vectors suitable for expression in the aforementioned host cells are readily available and the nucleic acids of the invention are inserted into the vectors using standard recombinant DNA techniques. Vectors for tissue-specific expression of OPG are also included. Such vectors include promoters which function specifically in liver, kidney or other organs for production in mice, and viral vectors for the expression of OPG in targeted human cells.

Using an appropriate host-vector system, OPG is produced recombinantly by culturing a host cell transformed with an expression vector containing nucleic acid sequences encoding OPG under conditions such that OPG is produced, and isolating the product of expression. OPG is produced in the supernatant of transfected mammalian cells or in inclusion bodies of transformed bacterial host cells. OPG so produced may be purified by procedures known to one skilled in the art as described below. The expression of OPG in mammalian and bacterial host systems is described in Examples 7 and 8. Expression vectors for mammalian hosts are exemplified by plasmids such as pDSRa described in PCT Application No. 90/14363. Expression vectors for bacterial host cells are exemplified by plasmids pAMG21 and pAMG22-His described in Example 8. Plasmid pAMG21 was deposited with the American Type Culture Collection, Rockville, Md. on Jul. 24, 1996 under accession no. 98113. Plasmid pAMG22-His was deposited with the American Type Culture Collection, Rockville, Md. on Jul. 24, 1996 under accession no. 98112. It is anticipated that the specific plasmids and host cells described are for illustrative purposes and that other available plasmids and host cells could also be used to express the polypeptides.

The invention also provides for expression of OPG from endogenous nucleic acids by in vivo or ex vivo recombination events to allow modulation of OPG from the host chromosome. Expression of OPG by the introduction of exogenous regulatory sequences (e.g. promoters or enhancers) capable of directing the production of OPG from endogenous OPG coding regions is also encompassed. Stimulation of endogenous regulatory sequences capable of directing OPG production (e.g. by exposure to transcriptional enhancing factors) is also provided by the invention.

Antibodies

Also encompassed by the invention are antibodies specifically binding to OPG. Antigens for the generation of antibodies may be full-length polypeptides or peptides spanning a portion of the OPG sequence. Immunological procedures for the generation of polyclonal or monoclonal antibodies reactive with OPG are known to one skilled in the art (see, for example, Harlow and Lane, *Antibodies: A Laboratory Manual* Cold Spring Harbor Laboratory Press, Cold Spring Harbor N.Y. (1988)). Antibodies so produced are characterized for binding specificity and epitope recognition using standard enzyme-linked immunosorbent assays. Antibodies also include chimeric antibodies having variable and constant domain regions derived from different species. In one embodiment, the chimeric antibodies are humanized antibodies having murine variable domains and human constant domains. Also encompassed are complementary determining regions grafted to a human framework (so-called CDR-grafted antibodies). Chimeric and CDR-grafted antibodies are made by recombinant methods known to one skilled in the art. Also encompassed are human antibodies made in mice.

Anti-OPG antibodies of the invention may be used as an affinity reagent to purify OPG from biological samples (see Example 10). In one method, the antibody is immobilized on CnBr-activated Sepharose and a column of antibody-Sepharose conjugate is used to remove OPG from liquid samples. Antibodies are also used as diagnostic reagents to detect and quantitate OPG in biological samples by methods described below.

Pharmaceutical Compositions

The invention also provides for pharmaceutical compositions comprising a therapeutically effective amount of a polypeptide comprising OPG or the other therapeutic molecules used (e.g., IL-1ra, sTNF-RI, or SLPI) together with a pharmaceutically acceptable diluent, carrier, solubilizer, emulsifier, preservative and/or adjuvant. Two or more of the therapeutic molecules (e.g., OPG, IL-1ra, sTNF-RI, or SLPI) can be formulated together or packaged together in a kit. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascrobic acid or sodium metabisulfite. Also encompassed are compositions comprising any of the therapeutic molecules modified with water-soluble polymers to increase solubility or stability. Compositions may also comprise incorporation of any of the therapeutic molecules into liposomes, microemulsions, micelles or vesicles for controlled delivery over an extended period of time.

Specifically, compositions herein may comprise incorporation into polymer matrices such as hydrogels, silicones, polyethylenes, ethylene-vinyl acetate copolymers, or biodegradable polymers. Examples of hydrogels include polyhydroxyalkylmethacrylates (p-HEMA), polyacrylamide, polymethacrylamide, polyvinylpyrrolidone, polyvinyl alcohol and various polyelectrolyte complexes. Examples of biodegradable polymers include polylactic acid (PLA), polyglycolic acid (PGA), copolymers of PLA and PGA, polyamides and copolymers of polyamides and polyesters. Other controlled release formulations include microcapsules, microspheres, macromolecular complexes and polymeric beads which may be administered by injection.

Selection of a particular composition will depend upon a number of factors, including the condition being treated, the route of administration and the pharmacokinetic parameters desired. A more extensive survey of component suitable for pharmaceutical compositions is found in *Remington's Pharmaceutical Sciences,* 18$^{th}$ ed. A. R. Gennaro, ed. Mack, Easton, Pa. (1980).

Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The invention also provides for pharmaceutical compositions comprising a therapeutically effective amount of the nucleic acids of the invention together with a pharmaceutically acceptable adjuvant. Nucleic acid compositions will be suitable for the delivery of part or all of the therapeutic molecule coding region to cells and tissues as part of an anti-sense or gene therapy regimen.

Methods of Treatment

Bone tissue provides support for the body and consists of mineral (largely calcium and phosphorous), a matrix of collagenous and noncollagenous proteins, and cells. Three types of cells found in bone, osteocytes, osteoblasts and osteoclasts, are involved in the dynamic process by which bone is continually formed and resorbed. Osteoblasts promote formation of bone tissue whereas osteoclasts are associated with resorption. Resorption, or the dissolution of bone matrix and mineral, is a fast and efficient process compared to bone formation and can release large amounts of mineral from bone. Osteoclasts are involved in the regulation of the normal remodeling of skeletal tissue and in resorption induced by hormones. For instance, resorption is stimulated by the secretion of parathyroid hormone in response to decreasing concentrations of calcium ion in extracellular fluids. In contrast, inhibition of resorption is the principal function of calcitonin. In addition, metabolites of vitamin D alter the responsiveness of bone to parathyroid hormone and calcitonin.

After skeletal maturity, the amount of bone in the skeleton reflects the balance (or imbalance) of bone formation and bone resorption. Peak bone mass occurs after skeletal maturity prior to the fourth decade. Between the fourth and fifth decades, the equilibrium shifts and bone resorption dominates. The inevitable decrease in bone mass with advancing years starts earlier in females than males and is distinctly accelerated after menopause in some females (principally those of Caucasian and Asian descent).

Osteopenia is a condition relating generally to any decrease in bone mass to below normal levels. Such a condition may arise from a decrease in the rate of bone synthesis or an increase in the rate of bone destruction or both. The most common form of osteopenia is primary osteoporosis, also referred to as postmenopausal and senile osteoporosis. This form of osteoporosis is a consequence of the universal loss of bone with age and is usually a result of increase in bone resorption with a normal rate of bone formation. About 25 to 30 percent of all white females in the United States develop symptomatic osteoporosis. A direct relationship exists between osteoporosis and the incidence of hip, femoral, neck and inter-trochanteric fracture in women 45 years and older. Elderly males develop symptomatic osteoporosis between the ages of 50 and 70, but the disease primarily affects females.

The cause of postmenopausal and senile osteoporosis is unknown. Several factors have been identified which may contribute to the condition. They include alteration in hormone levels accompanying aging and inadequate calcium consumption attributed to decreased intestinal absorption of calcium and other minerals. Treatments have usually included hormone therapy or dietary supplements in an attempt to retard the process. To date, however, an effective treatment for bone loss does not exist.

The invention provides for a method of treating a bone disorder using a therapeutically effective amount of OPG. The bone disorder may be any disorder characterized by a net bone loss (osteopenia or osteolysis). In general, treatment with OPG is anticipated when it is necessary to suppress the rate of bone resorption. Thus treatment may be done to reduce the rate of bone resorption where the resorption rate is above normal or to reduce bone resorption to below normal levels in order to compensate for below normal levels of bone formation.

Conditions which are treatable with OPG include the following:

Osteoporosis, such as primary osteoporosis, endocrine osteoporosis (hyperthyroidism, hyperparathyroidism, Cushing's syndrome, and acromegaly), hereditary and congenital forms of osteoporosis (osteogenesis imperfecta, homocystinuria, Menkes' syndrome, and Riley-Day syndrome) and osteoporosis due to immobilization of extremities.

Paget's disease of bone (osteitis deformans) in adults and juveniles

Osteomyelitis, or an infectious lesion in bone, leading to bone loss.

Hypercalcemia resulting from solid tumors (breast, lung and kidney) and hematologic malignacies (multiple myeloma, lymphoma and leukemia), idiopathic hypercalcemia, and hypercalcemia associated with hyperthyroidism and renal function disorders.

Osteopenia following surgery, induced by steroid administration, and associated with disorders of the small and large intestine and with chronic hepatic and renal diseases.

Osteonecrosis, or bone cell death, associated with traumatic injury or nontraumatic necrosis associated with Gaucher's disease, sickle cell anemia, systemic lupus erythematosus, rheumatoid arthritis, periodontal disease, osteolytic metastasis, and other conditions It is understood that OPG may be used alone or in conjunction with other factors for the treatment of bone disorders. In one embodiment, osteoprotegerin is used in conjunction with a therapeutically effective amount of a factor which stimulates bone formation. Such factors include but are not limited to the bone morphogenic factors designated BMP-1 through BMP-12; transforming growth factor-β (TGF-β) and TGF-β family members; interleukin-1

(IL-1) inhibitors; TNFα inhibitors; parathyroid hormone and analogs thereof, parathyroid related protein and analogs thereof; E series prostaglandins; bisphosphonates (such as alendronate and others); bone-enhancing minerals such as fluoride and calcium; non-steroidal anti-inflammatory drugs (NSAIDs), including COX-2 inhibitors, such as Celebrex™ and Vioxx™; immunosuppressants, such as methotrexate or leflunomide; serine protease inhibitors such as secretory leukocyte protease inhibitor (SLPI); IL-6 inhibitors (e.g., antibodies to IL-6), IL-8 inhibitors (e.g., antibodies to IL-8); IL-18 inhibitors (e.g., IL-18 binding protein or IL-18 antibodies); Interleukin-1 converting enzyme (ICE) modulators; fibroblast growth factors FGF-1 to FGF-10 and FGF modulators; PAF antagonists; keratinocyte growth factor (KGF), KGF-related molecules, or KGF modulators; matrix metalloproteinase (MMP) modulators; Nitric oxide synthase (NOS) modulators, including modulators of inducible NOS; modulators of glucocorticoid receptor; modulators of glutamate receptor; modulators of lipopolysaccharide (LPS) levels; and noradrenaline and modulators and mimetics thereof.

The invention also relates to treatment of IL-1 mediated disease by treatment with an IL-1 inhibitor in conjunction with a serine protease inhibitor. In particular, this method is useful for treatment of asthma and rheumatoid arthritis.

The invention relates further to treatment of TNF-mediated disease by treatment with a TNF inhibitor in conjunction with a serine protease inhibitor. In particular, this method is useful for treatment of rheumatoid arthritis.

In preferred embodiments, a polypeptide comprising OPG is used in conjunction with particular therapeutic molecules to treat various inflammatory conditions, autoimmune conditions, and other conditions leading to bone loss. Depending on the condition and the desired level of treatment, two, three, or more agents may be administered. These agents may be provided together by inclusion in the same formulation or inclusion in a treatment kit, or they may be provided separately. When administered by gene therapy, the genes encoding the protein agents may be included in the same vector, optionally under the control of the same promoter region, or in separate vectors. Particularly preferred molecules in the aforementioned classes are as follows.

IL-1 inhibitors: IL-1ra proteins and soluble IL-1 receptors. The most preferred IL-1 inhibitor is anakinra.

TNF-α inhibitors: soluble tumor necrosis factor receptor type I (sTNF-RI; -RI is also called the p55 receptor); soluble tumor necrosis factor receptor type II (also called the p75 receptor); and monoclonal antibodies that bind the TNF receptor. Most preferred is sTNF-RI as described in WO 98/24463, etanercept (Enbrel®), and Avakine®.

Exemplary TNF-α inhibitors are described in EP 422 339, EP 308 378, EP 393 438, EP 398 327, and EP 418 014.

serine protease inhibitors: SLPI, ALP, MPI, HUSI-I, BMI, and CUSI. These inhibitors also may be viewed as exemplary LPS modulators, as SLPI has been shown to inhibit LPS responses. Jin et al. (1997), *Cell* 88(3): 417–26 (incorporated by reference).

Particularly preferred methods of treatment concern use of TNF-α inhibitors and IL-1 inhibitors in conjunction with polypeptides comprising OPG. Such polypeptides may be used with either or both TNF-α inhibitors and IL-1 inhibitors for treatment of conditions such as rheumatoid arthritis and multiple sclerosis.

The following examples are offered to more fully illustrate the invention, but are not construed as limiting the scope thereof.

EXAMPLE 1

Identification and Isolation of the Rat OPG cDNA

Materials and methods for cDNA cloning and analysis are described in Maniatis et al, ibid. Polymerase chain reactions (PCR) were performed using a Perkin-Elmer 9600 thermocycler using PCR reaction mixture (Boehringer-Mannheim) and primer concentrations specified by the manufacturer. In general, 25–50 μl reactions were denatured at 94° C., followed by 20–40 cycles of 94° C. for 5 seconds, 50–60° C. for 5 seconds, and 72° C. for 3–5 minutes. Reactions were the treated for 72° C. for 3–5 minutes. Reactions were then analyzed by gel electrophoresis as described in Maniatis et al., ibid.

A cDNA library was constructed using mRNA isolated from embryonic d20 intestine for EST analysis (Adams et al. Science 252, 1651–1656 (1991)). Rat embryos were dissected, and the entire developing small and large intestine removed and washed in PBS. Total cell RNA was purified by acid guanidinium thiocyanate-phenol-chloroform extraction (Chomczynski and Sacchi Anal. Biochem. 162. 156–159, (1987)). The poly (A+) mRNA fraction was obtained from the total RNA preparation by adsorption to, and elution from, Dynabeads Oligo (dT)25 (Dynal Corp) using the manufacturer's recommended procedures. A random primed cDNA library was prepared using the Superscript Plasmid System (Gibco BRL, Gaithersburg, Md.). The random cDNA primer containing an internal Not I restriction site was used to initiate first strand synthesis and had the following sequence:

5'-AAAGGAAGGAAAAAA<u>GCGGCCGC</u>TACANNNNNNNNT-3' (SEQ ID NO:1)

Not I

For the first strand synthesis three separate reactions were assembled that contained 2.5 μg of poly(A) RNA and 120 ng, 360 ng or 1,080 ng of random primer. After second strand synthesis, the reaction products were separately extracted with a mixture of phenol:choroform:isoamyl alcohol (25:24:1 ratio), and then ethanol precipitated. The double strand (ds) cDNA products of the three reactions were combined and ligated to the following ds oligonucleotide adapter:

5'-TCGACCCACGCGTCCG-3' (SEQ ID NO:2)
3'-GGGTGCGCAGGCp-5' (SEQ ID NO:3)

After ligation the cDNA was digested to completion with Not I, extracted with phenol:chloroform:isoamyl (25:24:1) alcohol and ethanol precipitated. The resuspended cDNA was then size fractionated by gel filtration using premade columns provided with the Superscript Plasmid System (Gibco BRL, Gaithersburg, Md.) as recommended by the manufacturer. The two fractions containing the largest cDNA products were pooled, ethanol precipitated and then directionally ligated into Not I and Sal I digested pMOB vector DNA (Strathmann et al, 1991). The ligated cDNA was introduced into competent ElectroMAX DH10B *E. coli* (Gibco BRL, Gaithersburg, Md.) by electroporation. For automated sequence analysis approximately 10,000 transformants were plated on 20 cm×20 cm agar plates containing ampicillin supplemented LB nutrient media. The colonies that arose were picked and arrayed onto 96 well microtiter plates containing 200 ml of L-broth, 7.5% glycerol, and 50 μg/ml ampicillin. The cultures were grown overnight at 37° C., a duplicate set of microtiter plates were made using a sterile 96 pin replicating tool, then both sets were stored at −80° C. for further analysis. For full-length cDNA cloning approximately one million transformants were plated on 96 bacterial ampicillin plates containing about 10,000 clones each. The plasmid DNA from each pool was separately isolated using the Qiagen Plasmid Maxi Kit (Qiagen Corp., Germany) and arrayed into 96 microtiter plates for PCR analyses.

To sequence random fetal rat intestine cDNA clones, glycerol stocks were thawed, and small aliquots diluted 1:25 in distilled. Approximately 3.0 ul of diluted bacterial cultures were added to PCR reaction mixture (Boehringer-Mannheim) containing the following oligonucleotides:

5'-TGTAAAACGACGGCCAGT-3' (SEQ ID NO:4)

5'-CAGGAAACAGCTATGACC-3' (SEQ ID NO:5)

The reactions were incubated in a thermocycler (Perkin-Elmer 9600) with the following cycle conditions: 94 C for 2 minutes; 30 cycles of 94° C. for 5 seconds, 50° C. for 5 seconds, and 72° C. for 3 minutes.; 72° C. for 4 minutes. After incubation in the thermocycler, the reactions were diluted with 2.0 mL of water. The amplified DNA fragments were further purified using Centricon columns (Princeton Separations) using the manufacturer's recommended procedures. The PCR reaction products were sequenced on an Applied Biosystems 373A automated DNA sequencer using T3 primer (oligonucleotide 353-23; 5'-CAATTAACCCTCACTAAAGG-3') (SEQ ID NO:6) Taq dye-terminator reactions (Applied Biosystems) following the manufacturer's recommended procedures.

The resulting 5' nucleotide sequence obtained from randomly picked cDNA clones translated and then compared to the existing database of known protein sequences using a modified version of the FASTA program (Pearson et al. *Meth. Enzymol.* 183, (1990)). Translated sequences were also analysed for the presence of a specific cysteine-rich protein motif found in all known members of the tumor necrosis factor receptor (TNFR) superfamily (Smith et al. (1994) *Cell* 76: 959–62), using the sequence profile method of Gribskov et al. (1987), *Proc. Natl. Acad. Sci. USA* 83: 4355–9), as modified by Luethy et al. (1994), *Protein Science* 3: 139–46.

Using the FASTA and Profile search data, an EST, FRI-1 (Fetal Rat Intestine-1), was identified as a possible new member of the TNFR superfamily. FRI-1 contained an approximately 600 bp insert with a LORF of about 150 amino acids. The closest match in the database was the human type II TNFR (TNFR-II). The region compared showed an about 43% homology between TNFR-II and FRI-1 over this 150 aa LORF. Profile analysis using the first and second cysteine-rich repeats of the TNFR superfamily yielded a Z score of about 8, indicating that the FRI-1 gene possibly encodes a new family member.

To deduce the structure of the FRI-1 product, the fetal rat intestine cDNA library was screened for full length clones. The following oligonucleotides were derived from the original FRI-1 sequence:

5'-GCATTATGACCCAGAAACCGGAC-3' (SEQ ID NO:7)

5'-AGGTAGCGCCCTTCCTCACATTC-3' (SEQ ID NO:8)

These primers were used in PCR reactions to screen 96 pools of plasmid DNA, each pool containing plasmid DNA from 10,000 independent cDNA clones. Approximately 1 ug of plasmid pool DNA was amplified in a PCR reaction mixture (Boehringer-Mannheim) using a Perkin-Elmer 96 well thermal cycler with the following cycle conditions: 2 min at 94° C., 1 cycle; 15 sec at 94° C., then 45 sec at 65° C., 30 cycles; 7 min at 65° C., 1 cycle. PCR reaction products were analysed by gel electrophoresis. 13 out of 96 plasmid DNA pools gave rise to amplified DNA products with the expected relative molecular mass.

DNA from one positive pool was used to transform competent ElectroMAX DH10B *E. coli* (Gibco BRL, Gaithersburg, Md.) as described above. Approximately 40,000 transformants were plated onto sterile nitrocellulose filters (BA-85, Schleicher and Schuell), and then screened by colony hybridization using a $^{32}$p-dCTP labeled version of the PCR product obtained above. Filters were prehybridized in 5×SSC, 50% deionized formamide, 5×Denhardt's solution, 0.5% SDS, and 100 ug/ml denatured salmon sperm DNA for 2–4 hours at 42° C. Filters were then hybridized in 5×SSC, 50% deionized formamide, 2×Denhardt's solution, 0.1% SDS, 100 $\mu$g/ml denatured salmon sperm DNA, and about 5 ng/ml of labelled probe for about 18 hours at 42° C. The filters were then washed in 2×SSC for 10 min at RT, 1×SSC for 10 minutes at 55° C., and finally in 0.5×SSC for 10–15 min at 55° C. Hybridizing clones were detected following autoradiography, and then replated onto nitrocellulose filters for secondary screening. Upon secondary screening, a plasmid clone (pB1.1) was isolated, then amplified in L-broth media containing 100 ug/ml ampicillin and the plasmid DNA obtained. Both strands of the 2.4 kb pB1.1 insert were sequenced.

The pB1.1 insert sequence was used for a FASTA search of the public database to detect any existing sequence matches and/or similarities. No matches to any known genes or EST's were found, although there was an approximate 45% similarity to the human and mouse TNFR-II genes. A methionine start codon is found at bp 124 of the nucleotide sequence, followed by a LORF encoding 401 aa residues that terminates at bp 1327. The 401 aa residue product is predicted to have a hydrophobic signal peptide of approximately 31 residues at its N-terminus, and 4 potential sites of N-linked glycosylation. No hydrophobic transmembrane spanning sequence was identified using the PepPlot program (Wisconsin GCG package, version 8.1). The deduced 401 aa sequence was then used to search the protein database. Again, there were no existing matches, although there appeared to be a strong similarity to many members of the TNFR superfamily, most notably the human and mouse TNFR-II. A sequence alignment of this novel protein with known members of the TNFR-superfamily was prepared using the Pileup program, and then modified by PrettyPlot (Wisconsin GCG package, version 8.1). This alignment shows a clear homology between the full length FRI-1 gene product and all other TNFR family members. The homologus region maps to the extracellular domain of TNFR family members, and corresponds to the three or four cysteine-rich repeats found in the ligand binding domain of these proteins. This suggested that the FRI-1 gene encoded a novel TNFR family member. Since no transmembrane spanning region was detected we predicted that this may be a secreted receptor, similar to TNFR-I derived soluble receptors (Kohno et al. (1990), *Proc. Natl. Acad. Sci. USA* 87: 8331–5). Due to the apparent biological activity of the FRI-1 gene (vide infra), the product was named Osteoprotegerin (OPG).

EXAMPLE 2

OPG mRNA Expression Patterns in Tissues

Multiple human tissue northern blots (Clonetech) were probed with a $^{32}$P-dCTP labelled FRI-1 PCR product to detect the size of the human transcript and to determine patterns of expression. Northern blots were prehybridized in 5×SSPE, 50% formamide, 5×Denhardt's solution, 0.5% SDS, and 100 μg/ml denatured salmon sperm DNA for 2–4 hr at 42° C. The blots were then hybridized in 5×SSPE, 50% formamide, 2×Denhardt's solution, 0.1% SDS, 100 μg/ml denatured salmon sperm DNA, and 5 ng/ml labelled probe for 18–24 hr at 42° C. The blots were then washed in 2×SSC for 10 min at room temperature, 1×SSC for 10 min at 50° C., then in 0.5×SSC for 10–15 min.

Using a probe derived from the rat gene, a predominant mRNA species with a relative molecular mass of about 2.4 kb is detected in several tissues, including kidney, liver, placenta, and heart. Highest levels are detected in the kidney. A large mRNA species of Mr 4.5 and 7.5 kb was detected in skeletal muscle and pancreas. In human fetal tissue, kidney was found to express relatively high levels of the 2.4 kb mRNA. Using a human probe (vide infra), only the 2.4 kb transcript is detected in these same tissues. In addition, relatively high levels of the 2.4 kb transcript was detected in the lymph node, thymus, spleen and appendix. The size of the transcript detected by both the rat and human Osteoprotegerin gene is almost identical to the length of the rat pB1.1 FRI-1 insert, suggesting it was a full length cDNA clone.

EXAMPLE 3

Systemic Delivery of OPG in Transgenic Mice

The rat OPG clone pB1.1 was used as template to PCR amplify the coding region for subcloning into an ApoE-liver specific expression vector (Simonet et al. J. Clin. Invest. 94, 1310–1319 (1994), and PCT Application No. US94/11675 and co-owned U.S. Ser. No. 08/221,767. The following 5' and 3' oligonucleotide primers were used for PCR amplification, respectively:

5'-GACTAGTCCCACAATGAACAAGTGGCTGTG-3' (SEQ ID NO:9)

5'-ATAAGAATGCGGCCGCTAAACTATGAAACAGC CCAGTGACCATTC-3' (SEQ ID NO:10)

The PCR reaction mixture (Boehringer-Mannheim) was treated as follows: 94° C. for 1 minute, 1 cycle; 94° C. for 20 sec, 62° C. for 30 sec, and 74 C for 1 minute, 25 cycles. Following amplification, the samples were purified over Qiagen PCR columns and digested overnight with SpeI and NotI restriction enzymes. The digested products were extracted and precipitated and subcloned into the APOE promoter expression vector. Prior to microinjecting the resulting clone, HE-OPG, it was sequenced to ensure it was mutation-free.

The HE-OPG plasmid was purified through two rounds of CsCl density gradient centrifugation. The purified plasmid DNA was digested with XhoI and Ase I, and the 3.6 kb transgene insert was purified by gel electrophoresis. The purified fragment was diluted to a stock injection solution of 1 μg/ml in 5 mM Tris, pH 7.4, 0.2 mM EDTA. Single-cell embryos from BDF1×BDF1-bred mice were injected essentially as described (Brinster et al. (1985), Proc. Natl. Acad. Sci. USA 82: 4338), except that injection needles were beveled and siliconized before use. Embryos were cultured overnight in a $CO_2$ incubator and 15 to 20 2-cell embryos were transferred to the oviducts of pseudopregnant CD1 female mice.

Following term pregnancy, 49 offspring were obtained from implantation of microinjected embryos. The offspring were screened by PCR amplification of the integrated transgene in genomic DNA samples. The target region for amplification was a 369 bp region of the human Apo E intron which was included in the expression vector. The oligos used for PCR amplification were:

5'-GCC TCT AGA AAG AGC TGG GAC-3' (SEQ ID NO:11)

5'-CGC CGT GTT CCA TTT ATG AGC-3' (SEQ ID NO:12)

The conditions for PCR were: 94° C. for 2 minute, 1 cycle; 94° C. for 1 min, 63° C. for 20 sec, and 72° C. for 30 sec, 30 cycles. Of the 49 original offspring, 9 were identified as PCR positive transgenic founders.

At 8–10 weeks of age, five transgenic founders (2, 11, 16, 17, and 28) and five controls ( 1, 12, 15, 18, and 30) were sacrificed for necropsy and pathological analysis. Liver was isolated from the remaining 4 founders by partial hepatectomy. For partial hepatectomy, the mice were anesthetized and a lobe of liver was surgically removed. Total cellular RNA was isolated from livers of all transgenic founders, and 5 negative control littermates as described (McDonald et al. Meth. Enzymol. 152, 219 (1987)). Northern blot analysis was performed on these samples to assess the level of transgene expression. Approximately 10 ug of total RNA from each animal liver was resolved by electrophoresis denaturing gels (Ogden et al. Meth. Enzymol 152, 61 (1987)), then transferred to HYBOND-N nylon membrane (Amersham), and probed with $^{32}p$ dCTP-labelled pB1.1 insert DNA. Hybridization was performed overnight at 42° C. in 50% Formamide, 5×SSPE, 0.5% SDS, 5 ×Denhardt's solution, 100 μg/ml denatured salmon sperm DNA and 2–4'$10^6$ cpm of labeled probe/ml of hybridization buffer. Following hybridization, blots were washed twice in 2×SSC, 0.1% SDS at room temperature for 5 min each, and then twice in 0.1×SSC, 0.1% SDS at 55° C. for 5–10 min each. Expression of the transgene in founder and control littermates was determined following autoradiography.

The northern blot data indicate that 7 of the transgenic founders express detectable levels of the transgene mRNA (animal #'s 2,11,16,17,22,33,and 45). The negative control mice and one of the founders (#28) expressed no transgenerelated mRNA. Since OPG is predicted to be a secreted protein, overexpression of transgene mRNA should be a proxy for the level of systemically delivered gene product. Of the PCR and northern blot positive mice, animal 2, 17 and 22 expressed the highest levels of transgene mRNA, and may show more extensive biological effects on host cells and tissues.

EXAMPLE 4

Biological Activity of OPG

Five of the transgenic mice (animals 2,11,16,17 and 28) and 5 control littermates (animals 1,12,15,18, and 30) were sacrificed for necropsy and pathological analysis using the following procedures:

Prior to euthanasia, all animals had their identification numbers verified, then were weighed, anesthetized and blood drawn. The blood was saved as both serum and whole blood for a complete serum chemistry and hematology panel. Radiography was performed just after terminal anesthesia by lethal CO2 inhalation, and prior to the gross dissection. Following this, tissues were removed and fixed in 10% buffered Zn-Formalin for histological examination. The tissues collected included the liver, spleen, pancreas, stomach, duodenum, ileum, colon, kidney, reproductive organs, skin and mammary glands, bone, brain, heart, lung, thymus, trachea, eosphagus, thyroid, jejunem, cecum, rectum, adrenals, urinary bladder, and skeletal muscle. Prior to fixation the whole organ weights were determined for the liver, stomach, kidney, adrenals, spleen, and thymus. After fixation the tissues were processed into paraffin blocks, and 3 um sections were obtained. Bone tissue was decalcified using a formic acid solution, and all sections were stained with hematoxylin and eosin. In addition, staining with Gomori's reticulin and Masson's trichrome were performed on certain tissues. Enzyme histochemistry was performed to determine the expression of tartrate resistant acid phosphatase (TRAP), an enyzme highly expressed by osteoclasts, multinucleated bone-resorbing cells of monocyte-macrophage lineage.

Immunohistochemistry for BrdU and F480 monocyte-macrophage surface antigen was also performed to detect replicating cells and cells of the monocyte-macrophage lineage, respectively. To detect F480 surface antigen expression, formalin fixed, paraffin embedded 4 µm sections were deparaffinized and hydrated to deionized water. The sections were quenched with 3% hydrogen peroxide, blocked with Protein Block (Lipshaw, Pittsburgh, Pa.), and incubated in rat monoclonal anti-mouse F480 (Harlan, Indianapolis, Ind.). This antibody was detected by biotinylated rabbit anti-rat immunoglobulins, peroxidase conjugated strepavidin (BioGenex San Ramon, Calif.) with DAB as chromagen (BioTek, Santa Barbara, Calif.). Sections were counterstained with hematoxylin.

Upon gross dissection and observation of visceral tissues, no abnormalities were found in the transgene expressors or control littermates. Analysis of organ weight indicate that spleen size increased by approximately 38% in the transgenic mice relative to controls. There was a slight enlargement of platelet size and increased circulating unstained cells in the transgene expressors. There was a marginal decrease in platelet levels in the transgene expressors. In addition, the serum uric acid, urea nitrogen, and alkaline phosphatase levels all trended lower in the transgene expressors. The expressors were found to have increased radiodensity of the skeleton, including long bones (femurs), vertebrae, and flat bones (pelvis). The relative size of femurs in the expressors were not different from the the control mice.

Histological analysis of stained sections of bone from the OPG expressors show severe osteopetrosis with the presence of cartilage remnants from the primary spongiosa seen within bone trabeculae in the diaphysis of the femur. A clearly defined cortex was not identifiable in the sections of femur. In normal animals, the central diaphysis is filled with bone marrow. Sections of vertebra also show osteopetrotic changes implying that the OPG-induced skeletal changes were systemic. The residual bone marrow showed predominantly myeloid elements. Megakaryocytes were present. Reticulin stains showed no evidence for reticulin deposition. Immunohistochemistry for F480, a cell surface antigen expressed by cells of monocyte-macrophage derivation in the mouse, showed the presence of F480 positive cells in the marrow spaces. Focally, flattened F480 positive cells could be seen directly adjacent to trabecular bone surfaces.

The mesenchymal cells lining the bony trabeculae were flattened and appeared inactive. Based on H&E and TRAP stains, osteoclasts were rarely found on the trabecular bone surfaces in the OPG expressors. In contrast, osteoclasts and/or chondroclasts were seen in the region of the growth plate resorbing cartilage, but their numbers may be reduced compared to controls. Also, osteoclasts were present on the cortical surface of the metaphysis where modelling activity is usually robust. The predominant difference between the expressors and controls was the profound decrease in trabecular osteoclasts, both in the vertebrae and femurs. The extent of bone accumulation was directly correlated with the level of OPG transgene mRNA detected by northern blotting of total liver RNA.

The spleens from the OPG expressors had an increased amount of red pulp with the expansion due to increased hematopoiesis. All hematopoietic lineages are represented. F480 positive cells were present in both control and OPG expressors in the red pulp. Two of the expressors (2 and 17) had foci of extramedullary hematopoiesis within the liver and this is likely due to the osteopetrotic marrow.

There were no observable abnormalities in the thymus, lymph nodes, gastrointestinal tract, pancreato-hepatobiliary tract, respiratory tract, reproductive system, genito-urinary system, skin, nervous system, heart and aorta, breast, skeletal muscle and fat.

EXAMPLE 5

Isolation of Mouse and Human OPG cDNA

A cDNA clone corresponding to the 5' end of the mouse OPG mRNA was isolated from a mouse kidney cDNA library (Clontech) by PCR amplification. The oligonucleotides were derived from the rat OPG cDNA sequence and are shown below:

5'-ATCAAAGGCAGGGCATACTTCCTG-3' (SEQ ID NO:13)

5'-GTTGCACTCCTGTTTCACGGTCTG-3' (SEQ ID NO:14)

5'-CAAGACACCTTGAAGGGCCTGATG-3' (SEQ ID NO:15)

5'-TAACTTTTACAGAAGAGCATCAGC-3' (SEQ ID NO:16)

5'-AGCGCGGCCGCATGAACAAGTGGCTGTGCTGCG-3' (SEQ ID NO:17)

5'-AGCTCTAGAGAAACAGCCCAGTGACCATTCC-3' (SEQ ID NO:18)

The partial and full-length cDNA products obtained in this process were sequenced. The full-length product was digested with Not I and xbaI, then directionally cloned into the plasmid vector pRcCMV (Invitrogen). The resulting plasmid was named pRcCMV-Mu-OPG. The nucleotide sequence of the cloned product was compared to the rat OPG cDNA sequence. Over the 1300 bp region spanning the OPG LORF, the rat and mouse DNA sequences are approximately 88% identical. The mouse cDNA sequence contained a 401 aa LORF, which was compared to the rat OPG sequence and found to be about 94% identical without gaps. This indicates that the mouse cDNA sequence isolated encodes the murine OPG, and that the sequence and structure has been highly conserved throughout evolution. The mouse OPG sequence contains an identical putative signal peptide at its N-terminus, and all 4 potential sites of N-linked glycosylation are conserved.

A partial human OPG cDNA was cloned from a human kidney cDNA library using the following rat-specific oligonucleotides:

5'-GTG AAG CTG TGC AAG AAC CTC ATG-3' (SEQ ID NO:19)

5'-ATC AAA GGC AGG GCA TAC TTC CTG-3' (SEQ ID NO:20)

This PCR product was sequenced and used to design primers for amplifying the 3' end of the human cDNA using a human OPG genomic clone in lambda as template:

5'-TCCGTAAGAAACAGCCCAGTGACC-3' (SEQ ID NO:29)

5'-CAGATCCTGAAGCTGCTCAGTTTG-3' (SEQ ID NO: 21)

The amplified PCR product was sequenced, and together with the 5' end sequence, was used to design 5' and 3' human-specific primers useful for amplifying the entire human OPG cDNA coding sequences:

5'-AGCGCGGCCGCGGGGACCACAATGAACAAG TTG-3' (SEQ ID NO:22)

5'-AGCTCTAGAATTGTGAGGAAACAGCTCAAT GGC-3' (SEQ ID NO:23)

The full-length human PCR product was sequenced, then directionally cloned into the plasmid vector pRcCMV (Invitrogen) using Not I and Xba I. The resulting plasmid was named pRcCMV-human OPG. The nucleotide sequence of the cloned product was compared to the rat and mouse OPG cDNA sequences. Over the 1300 bp region spanning the OPG LORF, the rat and mouse DNA sequences are approximately 78–88% identical to the human OPG cDNA. The human OPG cDNA sequence also contained a 401 aa LORF, and it was compared to the rat and mouse protein sequences. The predicted human OPG is approximatley 85% identical, and about 90% identical to the rat and mouse proteins, respectively. Sequence alignment of rat, mouse and human proteins show that they have been highly conserved during evolution. The human protein is predicted to have a N-terminal signal peptide, and 5 potential sites of N-linked glycosylation, 4 of which are conserved between the rat and mouse OPG.

The DNA and predicted amino acid sequence of mouse OPG is shown in FIGS. 9A and 9B (SEQ ID NO:122). The DNA and predicted amino acid sequence of human OPG is shown in FIGS. 9C an 9D (SEQ ID NO:124). A comparison of the rat, mouse and human OPG amino acid sequences is shown in FIGS. 9E and 9F.

Isolation of additional human OPG cDNA clones revealed the presence of a G to C base change at position 103 of the DNA sequence shown in FIG. 9C. This nucleotide change results in substitution of an asparagine for a lysine at position 3 of the amino acid sequence shown in FIG. 9C. The remainder of the sequence in clones having this change was identical to that in FIGS. 9C and 9D.

EXAMPLE 6

OPG Three-dimensional Structure Modelling

The amino-terminal portion of OPG has homology to the extracellular portion of all known members of the TNFR superfamily (FIG. 1C). The most notable motif in this region of TNFR-related genes is an about 40 amino acid, cysteine-rich repeat sequence which folds into distinct structures (Banner et al. (1993), Cell 73: 431–45). This motif is usually displayed in four (range 3–6) tandem repeats (see FIG. 1C), and is known to be involved in ligand binding (Beutler and van Huffel (1994), Science 264: 667–73). Each repeat usually contains six interspaced cysteine residues, which are involved in forming three intradomain disulfide bonds, termed SS1, SS2, and SS3 (Banner et al., ibid). In some receptors, such as TNFR2, CD30 and CD40, some of the repeat domains contain only two intrachain disulfide bonds (SS1 and SS3).

The human OPG sequence was aligned to a TNFR1 extracellular domain profile using methods described by Luethy, et al., id, and the results were graphically displayed using the PrettyPlot program from the Wisconsin Package, version 8.1 (Genetics Computer Group, Madison, Wis.) (FIG. 10). The alignment indicates a clear conservation of cysteine residues involved in formation of domains 1–4. This alignment was then used to construct a three-dimensional (3-D) model of the human OPG N-terminal domain using the known 3-D structure of the extracellular domain of p55 TNFR1 (Banner et al., ibid) as the template. To do this the atomic coordinates of the peptide backbone and side chains of identical residues were copied from the crystal structure coordinates of TNFR1. Following this, the remaining coordinates for the insertions and different side chains were generated using the LOOK program (Molecular Applications Group, Palo Alto, Calif.). The 3-D model was then refined by minimizing its conformational energy using LOOK.

By analogy with other TNFR family members, it is assumed that OPG binds to a ligand. For the purpose of modelling the interaction of OPG with its ligand, the crystal structure of TNF-β was used to simulate a 3-D representation of an "OPG ligand". This data was graphically displayed (see FIG. 11) using Molscript (Kraulis (1991), J. Appl. Cryst. 24: 946–50). A model for the OPG/ligand complex with 3 TNFβ and 3 OPG molecules was constructed where the relative positions of OPG are identical to TNFR1 in the crystal structure. This model was then used to find the residues of OPG that could interact with its ligand using the following approach: The solvent accessible area of all residues in the complex and one single OPG model were calculated. The residues that have different accessibility in the complex than in the monomer are likely to interact with the ligand.

The human and mouse OPG amino acid sequences were realigned using this information to highlight sequences comprising each of the cysteine rich domains 1–4 (FIGS. 12A and 12B). Each domain has individual structural characteristics which can be predicted.

Domain 1: Contains 4 cysteines involved in SS2 (C41 to C54) and SS3 (C44 to C62) disulfide bonds. Although no SS1 bond is evident based on disulfide bridges, the conserved tyrosine at position 28 is homologous to Y20 in TNFR1, which is known to be involved in interacting with H66 to aid in domain formation. OPG has a homologous histidine at position 75, suggesting OPG Y28 and H75 stack together in the native protein, as do the homologous residues in TNFR1. Therefore, both of these residues may indeed be important for biological activity, and N-terminal OPG truncations up to and beyond Y28 may have altered activity. In addition, residues E34 and K43 are predicted to interact with a bound ligand based on our 3-dimensional model.

Domain 2: Contains six cysteines and is predicted to contain SS1 (C65 to C80), SS2 (C83 to C98) and SS3 (C87 to C105) disulfide bonds. This region of OPG also contains an region stretching from P66-Q91 which aligns to the portion of TNFR1 domain 2 which forms close contacts with TNFβ (see above), and may interact with an OPG ligand. In particular residues P66, H68, Y69, Y70, T71, D72, S73, H75, T76, S77, D78, E79, L81, Y82, P85, V86, K88, E89, L90, and Q91 are predicted to interact with a bound ligand based on our structural data.

Domain 3: Contains 4 cysteines involved in SS1 (C107 to C 118) and SS3 (C124 to C142) disulfide bonds, but not an SS2 bond. Based on our structural data, residues E115, L118 and K119 are predicted in to interact with an OPG ligand.

Domain 4: Contains 4 cysteines involved in SS1 (C145 to C160) and SS3 (C166 to C185) disulfide bonds, but not an SS2 bond, similar to domain 3. Our structural data predict that E153 and S155 interact with an OPG ligand.

Thus, the predicted structural model for OPG identifies a number of highly conserved residues which are likely to be important for its biological activity.

EXAMPLE 7

Production of Recombinant Secreted OPG in Mammalian Cells

To determine if OPG is actually a secreted protein, mouse OPG cDNA was fused to the human IgG1 Fc domain as a tag (Capon et al. Nature 337, 525–531 (1989)), and expressed in human 293 fibroblasts. Fc fusions were carried out using the vector pFc-A3. pFc-A3 contains the region encoding the Fc portion of human immunoglobulin IgG-γ1 heavy chain (Ellison et al. ibid) from the first amino acid of the hinge domain (Glu-99) to the carboxyl terminus and is flanked by a 5'-NotI fusion site and 3'-SalI and xbaI sites. The plasmid was constructed by PCR amplification of the human spleen cDNA library (Clontech). PCR reactions were in a final volume of 100 µl and employed 2 units of Vent DNA polymerase (New England Biolabs) in 20 mM Tris-HCl (pH 8.8), 10 mM KCl, 10 µM $(NH_4)2SO_4$, 2 mM $MgSO_4$, 0.1% Triton X-100 with 400 µM each dNTP and 1 ng of the cDNA library to be amplified together with 1 µM of each primer. Reactions were initiated by denaturation at 95° C. for 2 min, followed by 30 cycles of 95° C. for 30 s, 55° C. for 30 s, and 73° C. for 2 min. The 5' primer

5 ' ATAGCGGCCGCTGAGCCCAAATCTTGT-GACAAAACTCAC 3' (SEQ ID NO:24)

incorporated a NotI site immediately 5' to the first residue (Glu-99) of the hinge domain of IgG-γ1. The 3' primer

5'-TCTAGAGTCGACTTATCATTTACCCGGAGACA GGGAGAGGCTCTT-3' (SEQ ID NO:25)

incorporated SalI and xbaI sites. The 717-bp PCR product was digested with NotI and SalI, isolated by electrophoresis through 1% agarose (FMC Corp.),purified by the Geneclean procedure (BIO 101, Inc.) and cloned into NotI, SalI-digested pBluescript II KS vector (Stratagene). The insert in the resulting plasmid, pFc-A3, was sequenced to confirm the fidelity of the PCR reaction.

The cloned mouse cDNA in plasmid pRcCMV-MuOPG was amplified using the following two sets of primer pairs:

Pair 1:
5'-CCTCTGAGCTCAAGCTTCCGAGGACCACAAT GAACAAG-3' (SEQ ID NO:26)
5'-CCTCTGCGGCCGCTAAGCAGCTTATTTTCACG GATTGAACCTG-3' (SEQ ID NO:27)

Pair 2:
5'-CCTCTGAGCTCAAGCTTCCGAGGACCACAAT GAACAAG-3' (SEQ ID NO:28)
5'-CCTCTGCGCCCGCTGTTGCATTTCCTTTCTC-3' (SEQ ID NO:30)

The first pair amplifies the entire OPG LORF, and creates a NotI restriction site which is compatible with the in-frame Not I site in Fc fusion vector pFcA3. pFcA3 was prepared by engineering a NotI restriction site 5' to aspartic acid reside 216 of the human IgG1 Fc cDNA. This construct introduces a linker which encodes two irrelevant amino acids which span the junction between the OPG and IgG Fc region. This product, when linked to the Fc portion, would encode all 401 OPG residues directly followed by all 227 amino acid residues of the human IgG1 Fc region (Fl.Fc). The second primer pair amplifies the DNA sequences encoding the first 180 amino acid residues of OPG, which encompasses its putative ligand binding domain. As above, the 3' primer creates an artificial Not I restriction site which fuses the C-terminal truncated OPG LORF at position threonine 180 directly to the IgG1 Fc domain (CT.fc).

The amino acid sequence junction linking OPG residue 401 and aseptic acid residue 221 of the human Fc region can be modified as follows: The DNA encoding residues 216–220 of the human Fc region can be deleted as described below, or the cysteine residue corresponding to C220 of the human Fc region can be mutated to either serine or alanine. OPF-Fc fusion protein encoded by these modifed vectors can be transfected into human 293 cells, or CHO cells, and recombinant OPG-Fc fusion protein purified as described below.

Both products were directionally cloned into the plasmid vector pCEP4 (Invitrogen). pCEP4 contains the Epstein-Barr virus origin of replication, and is capable of episomal replication in 293-EBNA-1 cells. The parent pCEP4, and pCEP4-Fl.Fc and pCEP4-CT.Fc vectors were lipofected into 293-EBNA-1 cells using the manufacturer's recommended methods. The transfected cells were then selected in 100 µg/ml hygromycin to select for vector expression, and the resulting drug-resistant mass cultures were grown to confluence. The cells were then cultured in serum-free media for 72 hr, and the conditioned media removed and analysed by SDS-PAGE. A silver staining of the polyacrylamide gel detects the major conditioned media proteins produced by the drug resistant 293 cultures. In the pCEP4-Fl.Fc and the pCEP4-CT.Fc conditioned media, unique bands of the predicted sizes were abundantly secreted (see FIGS. 13B and 13C). The full-length Fc fusion protein accumulated to a high concentration, indicating that it may be stable. Both Fc fusion proteins were detected by anti-human IgG1 Fc antibodies (Pierce) on western blots, indicating that they are recombinant OPG products.

The full length OPG-Fc fusion protein was purified by Protein-A column chromatography (Pierce) using the manufacturers recommended procedures. The protein was then subjected to N-terminal sequence analysis by automated Edman degradation as essentially described by Matsudaira et al. (J. Biol. Chem. 262, 10–35 (1987)). The following amino acid sequence was read after 19 cycles:

$NH_2$-E T L P P K Y L H Y D P E T G H Q L L-$CO_2H$ (SEQ ID NO:31)

This sequence was identical to the predicted mouse OPG amino acid sequence beginning at amino acid residue 22, suggesting that the natural mammalian leader cleavage site is between amino acid residues Q21-E22, not between Y31-D32 as originally predicted. The expression experiments performed in 293-EBNA cells with pCEP4-Fl.Fc and pCEP4-CT.Fc demonstrate that OPG is a secreted protein, and may act systemically to bind its ligand.

Procedures similar to those used to construct and express the muOPG[22–180]-Fc and muOPG[22–401]-Fc fusions were employed for additional mouse and human OPG-Fc fusion proteins.

Murine OPG cDNA encoding amino acids 1–185 fused to the Fc region of human IgG1 [muOPG Ct(185).Fc] was constructed as follows. Murine OPG cDNA from plasmid pRcCMv Mu Osteoprotegerin (described in Example 5) was amplified using the following primer pair in a polymerase chain reaction as described above:

1333-82:
5'-TCC CTT GCC CTG ACC ACT CTT-3' (SEQ ID NO:32)
1333-80:
5'-CCT CTG CGG CCG CAC ACA CGT TGT CAT GTG TTG C-3' (SEQ ID NO:33)

This primer pair amplifies the murine OPG cDNA region encoding amino acid residues 63–185 (corresponding to bp 278–645) of the OPG reading frame as shown in FIG. 9A. The 3' primer contains a Not I restriction site which is compatible with the in-frame Not I site of the Fc fusion vector pFcA3. The product also spans a unique EcoRI restriction site located at bp 436. The amplified PCR product was purified, cleaved with NotI and EcoRI, and the resulting EcoRI-NotI restriction fragment was purified. The vector pCEP4 having the murine 1–401 OPG-Fc fusion insert was cleaved with EcoRI and NotI, purified, and ligated to the PCR product generated above. The resulting pCEP4-based expression vector encodes OPG residues 1–185 directly followed by all 227 amino acid residues of the human IgG1 Fc region. The murine OPG 1–185.Fc fusion vector was transfected into 293 cells, drug selected, and conditioned media was produced as described above.

The resulting secreted murine OPG 1–185.Fc fusion product was purified by Protein-A column chromatography (Pierce) using the manufacturers recommended procedures.

Murine OPG DNA encoding amino acid residues 1–194 fused to the Fc region of human IgG1 (muOPG Ct(194).Fc)

was constructed as follows. Mouse OPG cDNA from plasmid pRcCMV Mu-Osteoprotegerin was amplified using the following primer pairs:
1333-82:
5'-TCC CTT GCC CTG ACC ACT CTT-3' (SEQ ID NO:34)
1333-81:
5'-CCT CTG CGG CCG CCT TTT GCG TGG CTT CTC TGT T-3' (SEQ ID NO:35)

This primer pair amplifies the murine OPG cDNA region encoding amino acid residues 70–194 (corresponding to bp 298–672) of the OPG reading frame. The 3' primer contains a Not I restriction site which is compatible with the in-frame Not I site of the Fc fusion vector pFcA3. The product also spans a unique EcORI restriction site located at bp 436. The amplified PCR product was cloned into the murine OPG [1–401] Fc fusion vector as described above. The resulting pCEP4-based expression vector encodes OPG residues 1–194 directly followed by all 227 amino acid residues of the human IgG1 Fc region. The murine OPG 1–194.Fc fusion vector was transfected into 293 cells, drug selected, and conditioned media was produced. The resulting secreted fusion product was purified by Protein-A column chromatography (Pierce) using the manufacturers recommended procedures.

Human OPG DNA encoding amino acids 1–401 fused to the Pc region of human IgG1 was constructed as follows. Human OPG DNA in plasmid pRcCMV-hu osteoprotegerin (described in Example 5) was amplified using the following oligonucleotide primers:
1254-90:
5'CCT CTG AGC TCA AGC TTG GTT TCC GGG GAC CAC AAT G-3' (SEQ ID NO:36)
1254-95:
5'-CCT CTG CGG CCG CTA AGC AGC TTA TTT TTA CTG AAT GG-3' (SEQ ID NO:37)

The resulting PCR product encodes the full-length human OPG and creates a Not I restriction site which is compatible with the in-frame Not I site Fc fusion vector FcA3. The PCR product was directionally cloned into the plasmid vector pCEP4 as described above. The resulting expression vector encodes human OPG residues 1–401 directly followed by 227 amino acid residues of the human IgG1 Fc region. Conditioned media from transfected and drug selected cells was produced and the huOPG Fl.Fc fusion product was purified by Protein-A column chromatography (Pierce) using the manufacturers recommended procedures.

Human OPG DNA encoding amino acid residues 1–201 fused to the FC region of human IgG1 [huOPG Ct(201).Fc] was constructed as follows. The cloned human OPG cDNA from plasmid pRrCMV-hu osteoprotegerin was amplified by PCR using the following oligonucleotide primer pair:
1254-90:
5'-CCT CTG AGC TCA AGC TTG GTT TCC GGG GAC CAC AAT G-3' (SEQ ID NO:38)
1254-92:
5'-CCT CTG CGG CCG CCA GGG TAA CAT CTA TTC CAC-3' (SEQ ID NO:39)

This primer pair amplifies the human OPG cDNA region encoding amino acids 1–201 of the OPG reading frame, and creates a Not I restriction site at the 3' end which is compatable with the in-frame Not I site Fc fusion vector FcA3. This product, when linked to the Fc portion, encodes OPG residues 1–201 directly followed by all 221 amino acid residues of the human IgG1 Fc region. The PCR product was directionally cloned into the plasmid vector pCEP4 as described above. Conditioned media from transfected and drug selected cells was produced, and the hu OPG Ct(201).Fc fusion products purified by Protein-A column chromatography (Pierce) using the manufacturer's recommended procedures.

The following procedures were used to construct and express unfused mouse and human OPG.

A plasmid for mammalian expression of full-length murine OPG (residues 1–401) was generated by PCR amplification of the murine OPG cDNA insert from pRcCMV Mu-Osteoprotegerin and subcloned into the expression vector pDSRα (DeClerck et. atl. J. Biol. Chem. 266, 3893 (1991)). The following oligonucleotide primers were used:
1295-26:
5'-CCG AAG CTT CCA CCA TGA ACA AGT GGC TGT GCT GC-3' (SEQ ID NO:40)
1295-27:
5'-CCT CTG TCG ACT ATT ATA AGC AGC TTA TTT TCA CGG ATT G-3' (SEQ ID NO:41)

The murine OPG full length reading frame was amplified by PCR as described above. The PCR product was purified and digested with restriction endonucleases Hind III and XbaI (Boehringer Mannheim, Indianapolis, Ind.) under the manufacturers recommended conditions, then ligated to Hind III and Xba I digested pDSRα. Recombinant clones were detected by restriction endonuclease digestion, then sequenced to ensure no mutations were produced during the PCR amplification steps.

The resulting plasmid, pDSRα-muOPG was introduced into Chinese hamster ovary (CHO) cells by calcium mediated transfection (Wigler et al. (1977), Cell 11: 233). Individual colonies were selected based upon expression of the dihydrofolate reductase (DHFR) gene in the plasmid vector and several clones were isolated. Expression of the murine OPG recombinant protein was monitored by western blot analysis of CHO cell conditioned media. High expressing cells were selected, and OPG expression was further amplified by treatment with methotrexate as described (DeClerck et al., ibid.). Conditioned media from CHO cell lines was produced for further purification of recombinant secreted murine OPG.

A plasmid for mammalian expression of full-length human OPG (amino acids 1–401) was generated by subcloning the cDNA insert in pRcCMV-hu Osteoprotegerin directly into vector pDSRα (DeClerck et al., ibid). The pRcCMV-OPG plasmid was digested to completion with Not I, blunt ended with Klenow, then digested to completion with XbaI. Vector DNA was digested with HindIII, blunt ended with Klenow, then digested with XbaI, then ligated to the OPG insert. Recombinant plasmids were then sequenced to confirm proper orientation of the human OPG cDNA.

The resulting plasmid pDSRα-huOPG was introduced into Chinese hamster ovary (CHO) cells as described above. Individual colonies were selected based upon expression of the dihydrofolate reductase (DHFR) gene in the plasmid vector and several clones were isolated. Expression of the human OPG recombinant protein was monitored by western blot analysis of CHO cell conditioned media. High expressing clones were selected, and OPG expression was further amplified by treatment with methotrexate. Conditioned media from CHO cell lines expressing human OPG was produced for protein purification.

Expression vectors for murine OPG encoding residues 1–185 were constructed as follows. Murine OPG cDNA from pRcCMV-Mu OPG was amplified using the following oligonucleotide primers:
1333-82:
5'-TCC CTT GCC CTG ACC ACT CTT-3' (SEQ ID NO:42)
1356-12:
5'-CCT CTG TCG ACT TAA CAC ACG TTG TCA TGT GTT GC-3' (SEQ ID NO:43)

This primer pair amplifies the murine OPG cDNA region encoding amino acids 63–185 of the OPG reading frame (bp 278–645) and contains an artificial stop codon directly after the cysteine codon (C185), which is followed by an artificial Sal I restriction endonuclease site. The predicted product contains an internal Eco RI restriction site useful for subcloning into a pre-existing vector. After PCR amplification, the resulting purified product was cleaved with Eco RI and Sal I restriction endonucleases, and the large fragment was gel purified. The purified product was then subcloned into the large restriction fragment of an Eco RI and Sal I digest of pBluescript-muOPG Fl.Fc described above. The resulting plasmid was digested with Hind III and Xho I and the small fragment was gel purified. This fragment, which contains a open reading frame encoding residues 1–185 was then subcloned into a Hind III and Xho I digest of the expression vector pCEP4. The resulting vector, pmuOPG [1–185], encodes a truncated OPG polypeptide which terminates at a cysteine residue located at position 185. Conditioned media from transfected and drug selected cells was produced as described above.

1333-82:

5'-TCC CTT GCC CTG ACC ACT CTT-3' (SEQ ID NO:44)

1356-13:

5'-CCT CTG TCG ACT TAC TTT TGC GTG GCT TCT CTG TT-3' (SEQ ID NO:45)

This primer pair amplifies the murine OPG cDNA region encoding amino acids 70–194 of the OPG reading frame (bp 298–672) and contains an artificial stop codon directly after the lysine codon (K194), which is followed by an artificial Sal I restriction endonuclease site. The predicted product contains an internal Eco RI restriction site useful for subcloning into a pre-existing vector. After PCR amplification, the resulting purified product was cleaved with Eco RI and Sal I restriction endonucleases, and the large fragment was gel purified. The purified product was then subcloned into the large restriction fragment of an Eco RI and Sal I digest of pBluescript-muOPG Fl.Fc described above. The resulting plasmid was digested with Hind III and Xho I and the small fragment was gel purified. This fragment, which contains a open reading frame encoding residues 1–185 was then subcloned into a Hind III and Xho I digest of the expression vector pCEP4. The resulting vector, pmuOPG [1–185], encodes a truncated OPG polypeptide which terminates at a lysine at position 194. Conditioned media from transfected and drug selected cells was produced as described above.

Several mutations were generated at the 5' end of the huOPG [22–401]-Fc gene that introduce either amino acid substitutions, or deletions, of OPG between residues 22 through 32. All mutations were generated with the "Quick-Change™ Site-Directed Mutagenesis Kit" (Stratagene, San Diego, Calif.) using the manfacturer's recommended conditions. Briefly, reaction mix containing huOPG [22–401]-Fc plasmid DNA template and mutagenic primers were treated with Pfu polymerase in the presence of deoxynucleotides, then amplified in a thermocycler as described above. An aliqout of the reaction is then transfected into competent E. coli XL1-Blue by heatshock, then plated. Plasmid DNA from transformants was then sequenced to verify mutations.

The following primer pairs were used to delete residues 22–26 of the human OPG gene, resulting in the production of a huOPG [27–401]-Fc fusion protein:

1436-11:

5'-TGG ACC ACC CAG AAG TAC CTT CAT TAT GAC-3' (SEQ ID NO:140)

1436-12:

5'-GTC ATA ATG AAG GTA CTT CTG GGT GGT CCA-3' (SEQ ID NO:141)

The following primer pairs were used to delete residues 22–28 of the human OPG gene, resulting in the production of a huOPG [29–401]-Fc fusion protein:

1436-17:

5'-GGA CCA CCC AGC TTC ATT ATG ACG AAG AAA C-3' (SEQ ID NO:142)

1436-18:

5'-GTT TCT TCG TCA TAA TGA AGC TGG GTG GTC C-3' (SEQ ID NO:143)

The following primer pairs were used to delete residues 22–31 of the human OPG gene, resulting in the production of a huOPG [32–401]-Fc fusion protein:

1436-27:

5'-GTG GAC CAC CCA GGA CGA AGA AAC CTC TC-3' (SEQ ID NO:144)

1436-28:

5'-CAG AGG TTT CTT CGT CCT GGG TGG TCC AC-3' (SEQ ID NO:145)

The following primer pairs were used to change the codon for tyrosine residue 28 to phenylalanine of the human OPG gene, resulting in the production of a huOPG [22–401]-Fc Y28F fusion protein:

1436-29:

5'-CGT TTC CTC CAA AGT TCC TTC ATT ATG AC-3' (SEQ ID NO:146)

1436-30:

5'-GTC ATA ATG AAG GAA CTT TGG AGG AAA CG-3' (SEQ ID NO: 147)

The following primer pairs were used to change the codon for proline residue 26 to alanine of the human OPG gene, resulting in the production of a huOPG [22–401]-Fc P26A fusion protein:

1429-83:

5'-GGA AAC GTT TCC TGC AAA GTA CCT TCA TTA TG-3' (SEQ ID NO: 148)

1429-84:

5'-CAT AAT GAA GGT ACT TTG CAG GAA ACG TTT CC-3' (SEQ ID NO:149)

Each resulting muOPG [22–401]-Fc plasmid containing the appropriate mutation was then transfected into human 293 cells, the mutant OPG-Fc fusion protein purified from conditioned media as described above. The biological activity of each protein was assessed the in vitro osteoclast forming assay described in Example 11.

EXAMPLE 8

Expression of OPG in E. coli

A. Bacterial Expression Vectors pAMG21

The expression plasmid pAMG21 can be derived from the Amgen expression vector pCFM1656 (ATCC #69576) which in turn be derived from the Amgen expression vector system described in U.S. Pat. No. 4,710,473. The pCFM1656 plasmid can be derived from the described pCFM836 plasmid (U.S. Pat. No. 4,710,473) by: (a) destroying the two endogenous NdeI restriction sites by end filling with T4 polymerase enzyme followed by blunt end ligation; (b) replacing the DNA sequence between the unique AatII and ClaI restriction sites containing the synthetic $P_L$ promoter with a similar fragment obtained from pCFM636 (U.S. Pat. No. 4,710,473) containing the PL promoter

```
AatII
5'    CTAATTCCGCTCTCACCTACCAAACAATGCCCCCCTGCAAAAAATAAATTCATAT-
3'TGCAGATTAAGGCGAGAGTGGATGGTTTGTTACGGGGGACGTTTTTTATTTAAGTATA-

-AAAAAACATACAGATAACCATCTGCGGTGATAAATTATCTCTGGCGGTGTTGACATAAA-
-TTTTTTGTATGTCTATTGGTAGACGCCACTATTTAATAGAGACCGCCACAACTGTATTT-

-TACCACTGGCGGTGATACTGAGCACAT  3' (SEQ ID NO:53)
-ATGGTGACCGCCACTATGACTCGTGTAGC5' (SEQ ID NO:54)
``` and then (c) substituting the small DNA sequence between the unique ClaI and KpnI restriction sites with the following oligonucleotide:

```
5'   CGATTTGATTCTAGAAGGAGGAATAACATATGGTTAACGCGTTGGAATTCGGTAC3'
(SEQ ID NO:48)
3'       TAAACTAAGATCTTCCTCCTTATTGTATACCAATTGCGCAACCTTAAGC   5'
(SEQ ID NO:49)
     ClaI                                                KpnI
```

The expression plasmid pAMG21 can then be derived from pCFM1656 by making a series of site directed base changes by PCR overlapping oligo mutagenesis and DNA sequence substitutions. Starting with the BglII site (plasmid bp # 180) immediately 5' to the plasmid replication promoter PcopB and proceeding toward the plasmid replication genes, the base pair changes are as follows:

TABLE 4

| pAMG21 bp # | bp in pCFM1656 | bp changed to in pAMG21 |
|---|---|---|
| #204 | T/A | C/G |
| #428 | A/T | G/C |
| #509 | G/C | A/T |
| #617 | — | insert two G/C bp |
| #679 | G/C | T/A |
| #980 | T/A | C/G |
| #994 | G/C | A/T |
| #1004 | A/T | C/G |
| #1007 | C/G | T/A |
| #1028 | A/T | T/A |
| #1047 | C/G | T/A |

TABLE 4-continued

| pAMG21 bp # | bp in pCFM1656 | bp changed to in pAMG21 |
|---|---|---|
| #1178 | G/C | T/A |
| #1466 | G/C | T/A |
| #2028 | G/C | bp deletion |
| #2187 | C/G | T/A |
| #2480 | A/T | T/A |
| #2499–2502 | AGTG | GTCA |
|  | TCAC | CAGT |
| #2642 | TCCGAGC | 7 bp deletion |
|  | AGGCTCG |  |
| #3435 | G/C | A/T |
| #3446 | G/C | A/T |
| #3643 | A/T | T/A |

The DNA sequence between the unique AatII (position #4364 in pCFM1656) and SacII (position #4585 in pCFM1656) restriction sites is substituted with the following DNA sequence:

```
[AatII sticky end]        5' GCGTAACGTATGCATGGTCTCC-
(position #4358 in pAMG21) 3' TGCACGCATTGCATACGTACCAGAGG- -CCATGCGAGAGTAGGGAACTGCCAGGCATCAAATAAAACGAAAGGCTCAGTCGAAAGACT-
-GGTACGCTCTCATGCCTTGACGGTCCGTAGTTTATTTTGCTTTCCGAGTCAGCTTTCTGA- -GGGCCTTTCGTTTTATCTGTTGTTTGTCGGTGAACGCTCTCCTGAGTAGGACAAATCCGC-
-CCCGGAAAGCAAAATAGACAACAAACAGCCACTTGCGAGAGGACTCATCCTGTTTAGGCG- -CGGGAGCGGATTTGAACGTTGCGAAGCAACGGCCCGGAGGGTGGCGGGCAGGACGCCCGC-
-GCCCTCGCCTAAACTTGCAACGCTTCGTTGCCGGGCCTCCCACCGCCCGTCCTGCGGGCG- -CATAAACTGCCAGGCATCAAATTAAGCAGAAGGCCATCCTCACGGATGGCCTTTTTGCGT-
-GTATTTGACGGTCCGTAGTTTAATTCGTCTTCCGGTAGGACTGCCTACCGGAAAAACGCA- AaTII
-TTCTACAAACTCTTTTGTTTATTTTTCTAAATACATTCAAATATGGACGTCGTACTTAAC-
-AAGATGTTTGAGAAAACAAATAAAAAGATTTATGTAAGTTTATACCTGCAGCATGAATTG-
```

-continued

```
-TTTTAAAGTATGGGCAATCAATTGCTCCTGTTAAAATTGCTTTAGAAATACTTTGGCAGC-
-AAAATTTCATACCCGTTAGTTAACGAGGACAATTTTAACGAAATCTTTATGAAACCGTCG-

-GGTTTGTTGTATTGAGTTTCATTTGCGCATTGGTTAAATGGAAAGTGACCGTGCGCTTAC-
-CCAAACAACATAACTCAAAGTAAACGCGTAACCAATTTACCTTTCACTGGCACGCGAATG-

-TACAGCCTAATATTTTTGAAATATCCCAAGAGCTTTTTCCTTCGCATGCCCACGCTAAAC-
-ATGTCGGATTATAAAAACTTTATAGGGTTCTCGAAAAAGGAAGCGTACGGGTGCGATTTG-

-ATTCTTTTTCTCTTTTGGTTAAATCGTTGTTTGATTTATTATTTGCTATATTTATTTTTC-
-TAAGAAAAAGAGAAAACCAATTTAGCAACAAACTAAATAATAAACGATATAAATAAAAAG-

-GATAATTATCAACTAGAGAAGGAACAATTAATGGTATGTTCATACACGCATGTAAAAATA-
-CTATTAATAGTTGATCTCTTCCTTGTTAATTACCATACAAGTATGTGCGTACATTTTTAT-

-AACTATCTATATAGTTGTCTTTCTCTGAATGTGCAAAACTAAGCATTCCGAAGCCATTAT-
-TTGATAGATATATCAACAGAAAGAGACTTACACGTTTTGATTCGTAAGGCTTCGGTAATA-

-TAGCAGTATGAATAGGGAAACTAAACCCAGTGATAAGACCTGATGATTTCGCTTCTTTAA-
-ATCGTCATACTTATCCCTTTGATTTGGGTCACTATTCTGGACTACTAAAGCGAAGAAATT-

-TTACATTTGGAGATTTTTTATTTACAGCATTGTTTTCAAATATATTCCAATTAATCGGTG-
-AATGTAAACCTCTAAAAAATAAATGTCGTAACAAAAGTTTATATAAGGTTAATTAGCCAC-

-AATGATTGGAGTTAGAATAATCTACTATAGGATCATATTTTATTAAATTAGCGTCATCAT-
-TTACTAACCTCAATCTTATTAGATGATATGCTAGTATAAAATAATTTAATCGCAGTAGTA-

-AATATTGCCTCCATTTTTTAGGGTAATTATCCAGAATTGAAATATCAGATTTAACCATAG-
-TTATAACGGAGGTAAAAAATCCCATTAATAGGTCTTAACTTTATAGTCTAAATTGGTATC-

-AATGAGGATAAATGATCGCGAGTAAATAATATTCACAATGTACCATTTTAGTCATATCAG-
-TTACTCCTATTTACTAGCGCTCATTTATTATAAGTGTTACATGGTAAAATCAGTATAGTC-

-ATAAGCATTGATTAATATCATTATTGCTTCTACAGGCTTTAATTTTATTAATTATTCTGT-
-TATTCGTAACTAATTATAGTAATAACGAAGATGTCCGAAATTAAAATAATTAATAAGACA-

-AAGTGTCGTCGGCATTTATGTCTTTCATACCCATCTCTTTATCCTTACCTATTGTTTGTC-
-TTCACAGCAGCCGTAAATACAGAAAGTATGGGTAGAGAAATAGGAATGGATAACAAACAG-

-GCAAGTTTTGCGTGTTATATATCATTAAAACGGTAATAGATTGACATTTGATTCTAATAA-
-CGTTCAAAACGCACAATATATAGTAATTTTGCCATTATCTAACTGTAAACTAAGATTATT-

-ATTGGATTTTTGTCACACTATTATATCGCTTGAAATACAATTGTTTAACATAAGTACCTG-
-TAACCTAAAAACAGTGTGATAATATAGGGAACTTTATGTTAACAAATTGTATTCATGGAC-

-TAGGATCGTACAGGTTTACGCAAGAAAATGGTTTGTTATAGTCGATTAATCGATTTGATT-
-ATCCTAGCATGTCCAAATGCGTTCTTTTACCAAACAATATCAGCTAATTAGCTAAACTAA-

-CTAGATTTGTTTTAACTAATTAAAGGAGGAATAACATATGGTTAACGCGTTGGAATTCGA-
-GATCTAAACAAAATTGATTAATTTCCTCCTTATTGTATACCAATTGCGCAACCTTAAGCT-

SacII
-GCTCACTAGTGTGGACCTGCAGGGTACCATGGAAGCTTACTCGAGGATCCGCGGAAAGAA-
-CGAGTGATCACAGCTGGACGTCCCATGGTACCTTCGAATGAGCTCCTAGGCGCCTTTCTT-

-GAAGAAGAAGAAGAAAGCCCGAAAGGAAGCTGAGTTGGCTGCTGCCACCGCTGAGCAATA-
-CTTCTTCTTCTTCTTTCGGGCTTTCCTTCGACTCAACCGACGACGGTGGCGACTCGTTAT-

-ACTAGCATAACCCCTTGGGGCCTCTAAACGGGTCTTGAGGGGTTTTTTGCTGAAAGGAGG-
-TGATCGTATTGGGGAACCCCGGAGATTTGCCCAGAACTCCCCAAAAAACGACTTTCCTCC-

-AACCGCTCTTCACGCTCTTCACGC 3' [SacII sticky end] (SEQ ID NO: 50)
-TTGGCGAGAAGTGCGAGAAGTG 5' (position #5904 in pAMG21) (SEQ ID
NO:46)
```

During the ligation of the sticky ends of this substitution DNA sequence, the outside AatII and SacII sites are destroyed. There are unique AatII and SacII sites in the substituted DNA.

pAMG22-His

The expression plasmid pAMG22-His can be derived from the Amgen expression vector pAMG22 by substituting the small DNA sequence between the unique NdeI (#4795) and EcoRI (#4818) restriction sites of pAMG22 with the following oligonucleotide duplex:

```
NdeI          NheI      EcoRI
5'TATGAAACATCATCACCATCACCATCATGCTAGCGTTAACGCGTTGG   3'      (SEQ ID NO:51)

3'   ACTTTGTAGTAGTGGTAGTGGTAGTACGATCGCAATTGCGCAACCTTAA 5'    (SEQ ID NO:52)

MetLysHisHisHisHisHisHisAlaSerValAsnAlaLeuGlu              (SEQ ID NO:168)
``` pAMG22

The expression plasmid pAMG22 can be derived from the Amgen expression vector pCFM1656 (ATCC #69576) which in turn be derived from the Amgen expression vector system described in U.S. Pat. No. 4,710,473 granted Dec. 1, 1987. The pCFM1656 plasmid can be derived from the described pCFM836 plasmid (U.S. Pat. No. 4,710,473) by: (a) destroying the two endogenous NdeI restriction sites by end filling with T4 polymerase enzyme followed by blunt end ligation; (b) replacing the DNA sequence between the unique AatII and ClaI restriction sites containing the synthetic PL promoter with a similar fragment obtained from pCFM636 (U.S. Pat. No. 4,710,473) containing the PL promoter

```
AatII
5'    CTAATTCCGCTCTCACCTACCAAACAATGCCCCCTGCAAAAAATAAATTCATAT-   (SEQ ID NO:53)
3'TGCAGATTAAGGCGAGAGTGGATGGTTTGTTACGGGGGACGTTTTTTATTTAAGTATA-  (SEQ ID NO:54)

AAAAAACATACAGATAACCATCTGCGGTGATAAATTATCTCTGGCGGTGTTGACATAAA-
TTTTTTGTATGTCTATTGGTAGACGCCACTATTTAATAGAGACCGCCACAACTGTATTT-

TACCACTGGCGGTGATACTGAGCACAT   3'
ATGGTGACCGCCACTATGACTCGTGTAGC5'
``` and then (c) substituting the small DNA sequence between the unique ClaI and KpnI restriction sites with the following oligonucleotide:

```
5'CGATTTGATTCTAGAAGGAGGAATAACATATGGTTAACGCGTTGGAATTCGGTAC   3'    (SEQ ID NO:55)

3'   TAAACTAAGATCTTCCTCCTTATTGTATACCAATTGCGCAACCTTAAGC 5'           (SEQ ID NO:56)
  ClaI                                                KpnI
```

The expression plasmid pAMG22 can then be derived from pCFM1656 by making a series of site directed base changes by PCR overlapping oligo mutagenesis and DNA sequence substitutions. Starting with the BglII site (plasmid bp # 180) immediately 5' to the plasmid replication promoter PcopB and proceeding toward the plasmid replication genes, the base pair changes are as follows:

TABLE 5

| pAMG22 bp # | bp in pCFM1656 | bp changed to in pAMG22 |
|---|---|---|
| #204 | T/A | C/G |
| #428 | A/T | G/C |
| #509 | G/C | A/T |
| #617 | — | insert two G/C bp |
| #679 | G/C | T/A |
| #980 | T/A | C/G |
| #994 | G/C | A/T |
| #1004 | A/T | C/G |
| #1007 | C/G | T/A |
| #1028 | A/T | T/A |
| #1047 | C/G | T/A |

TABLE 5-continued

| pAMG22 bp # | bp in pCFM1656 | bp changed to in pAMG22 |
|---|---|---|
| #1178 | G/C | T/A |
| #1466 | G/C | T/A |
| #2028 | G/C | bp deletion |
| #2187 | C/G | T/A |
| #2480 | A/T | T/A |
| #2499–2502 | AGTG TCAC | GTCA CAGT |
| #2642 | TCCGAGC AGGCTCG | 7 bp deletion |

TABLE 5-continued

| pAMG22 bp # | bp in pCFM1656 | bp changed to in pAMG22 |
|---|---|---|
| #3435 | G/C | A/T |
| #3446 | G/C | A/T |
| #3643 | A/T | T/A |

The DNA sequence between the unique AatII (position #4364 in pCFM1656) and SacII (position #4585 in pCFM1656) restriction sites is substituted with the following DNA sequence:

[AatII sticky end] (position #4358 in pAMG22)

```
5'  GCGTAACGTATGCATGGTCTCCCCATGCGAGAGTAGGGAACTGCCAGGCATCAA-    (SEQ ID NO: 58)
3'  TGCACGCATTGCATACGTACCAGAGGGGTACGCTCTCATCCCTTGACGGTCCGTAGTT- (SEQ ID NO:57)

-ATAAAACGAAAGGCTCAGTCGAAAGACTGGGCCTTTCGTTTTATCTGTTGTTTGTCGGTG-
-TATTTTGCTTTCCGAGTCAGCTTTCTGACCCGGAAAGCAAAATAGACAACAAACAGCCAC-

-AACGCTCTCCTGAGTAGGACAAATCCGCCGGGAGCGGATTTGAACGTTGCGAAGCAACGG-
-TTGCGAGAGGACTCATCCTGTTTAGGCGGCCCTCGCCTAAACTTGCAACGCTTCGTTGCC-

-CCCGGAGGGTGGCGGGCAGGACGCCCGCCATAAACTGCCAGGCATCAAATTAAGCAGAAG-
-GGGCCTCCCACCGCCCGTCCTGCGGGCGGTATTTGACGGTCCGTAGTTTAATTCGTCTTC-

-GCCATCCTGACGGATGGCCTTTTGCGTTTCTACAAACTCTTTTGTTTATTTTTCTAAAT-
-CGGTAGGACTGCCTACCGGAAAAACGCAAAGATGTTTGAGAAAACAAATAAAAAGATTTA-

AatII
-ACATTCAAATATGGACGTCTCATAATTTTTAAAAAATTCATTTGACAAATGCTAAAATTC-
-TGTAAGTTTATACCTGCAGAGTATTAAAAATTTTTTAAGTAAACTGTTTACGATTTTAAG-

-TTGATTAATATTCTCAATTGTGAGCGCTCACAATTTATCGATTTGATTCTAGATTTGTTT-
-AACTAATTATAAGAGTTAACACTCGCGAGTGTTAAATAGCTAAACTAAGATCTAAACTCA-

-TAACTAATTAAAGGAGGAATAACATATGGTTAACGCGTTGGAATTCGAGCTCACTAGTGT-
-ATTGATTAATTTCCTCCTTATTGTATACCAATTGCGCAACCTTAAGCTCGAGTGATCACA-

SacII
-CGACCTGCAGGGTACCATGGAAGCTTACTCGAGGATCCGCGGAAAGAAGAAGAAGAAGAA-
-GCTGGACGTCCCATGGTACCTTCGAATGAGCTCCTAGGCGCCTTTCTTCTTCTTCTTCTT-

-GAAAGCCCGAAAGGAAGCTGAGTTGGCTGCTGCCACCGCTGAGCAATAACTAGCATAACC-
-CTTTCGGGCTTTCCTTCGACTCAACCGACGACGGTGGCGACTCGTTATTGATCGTATTGG-

-CCTTGGGGCCTCTAAACGGGTCTTGAGGGGTTTTTTGCTGAAAGGAGGAACCGCTCTTCA-
-GGAACCCCGGAGATTTGCCCAGAACTCCCCAAAAAACGACTTTCCTCCTTGGCGAGAAGT-

-CGCTCTTCACGC 3'
-GCGAGAAGTG  5'
```

-CGCTCTTCACGC 3' (SEQ ID NO:58)
-GCGAGAAGTG 5' (SEQ ID NO:57)
[SacII sticky end] (position #5024 in pAMG22)

During the ligation of the sticky ends of this substitution DNA sequence, the outside AatII and SacII sites are destroyed. There are unique AatII and SacII sites in the substituted DNA.

B. Human OPG Met[32–401]

In the example, the expression vector used was pAMG21, a derivative of pCFM1656 (ATCC accession no. 69576) which contains appropriate restriction sites for insertion of genes downstream from the lux PR promoter. (See U.S. Pat. No. 5,169,318 for description of the lux expression system). The host cell used was GM120 (ATCC accession no. 55764). This host has the lacIQ promoter and lacI gene integrated into a second site in the host chromosome of a prototrophic E. coli K12 host. Other commonly used E. coli expression vectors and host cells are also suitable for expression.

A DNA sequence coding for an N-terminal methionine and amino acids 32–401 of the human OPG polypeptide was placed under control of the luxPR promoter in the plasmid expression vector pAMG21 as follows. To accomplish this, PCR using oligonucleotides #1257-20 and #1257-19 as primers was performed using as a template plasmid pRcCMV-Hu OPG DNA containing the human OPG cDNA and thermocycling for 30 cycles with each cycle being: 94° C. for 20 seconds, followed by 37° C. for seconds, followed by 72° C. for 30 seconds. The resulting PCR sample was resolved on an agarose gel, the PCR product was excised, purified, and restricted with KpnI and BamHI restriction endonucleases and purified. Synthetic oligonucleotides #1257-21 and #1257-22 were phophorylated individually using T4 polynucleotide kinase and ATP, and were then mixed together, heated at 94° C. and allowed to slow cool to room temperature to form an oligonucleotide linker duplex containing NdeI and KpnI sticky ends. The phosphorylated linker duplex formed between oligonucleotides #1257-21 and #1257-22 containing NdeI and KpnI cohesive ends (see FIG. 14A) and the KpnI and BamHI digested and purified PCR product generated using oligo primers #1257-20 and #1257-19 (see above) was directionally inserted between two sites of the plasmid vector pAMG21, namely the NdeI site and BamHI site, using standard recombinant DNA methodology (see FIG. 14A and sequences below). The synthetic linker utilized E. coli codons and provided for a N-terminal methionine.

Two clones were selected and plasmid DNA isolated, and the human OPG insert was subsequently DNA sequence confirmed. The resulting pAMG21 plasmid containing amino acids 32–401 of the human OPG polypeptide immediately preceded in frame by a methionine is referred to as pAMG21-huOPG met[32–401] or pAMG21-huOPG et[32–401].

Oligo#1257-19:
5'-TACGCACTGGATCCTTATAAGCAGCTTATTTTACTGATTGGAC-3' SEQ ID NO:59)

Oligo#1257-20:
5'-GTCCTCCTGGTACCTACCTAAAACAAC-3' (SEQ ID NO:60)

Oligo#1257-21:
5'-TATGGATGAAGAAACTTCTCATCAGCTGCTGTGTGATAAATGTCCGCCGGGTAC-3' (SEQ ID NO:61)

Oligo#1257-22:
5'-CCGGCGGACATTTATCACACAGCAGCTGATGAGAAGTTTCTTCATCCA-3' (SEQ ID NO:47)

Cultures of pAMG21-huOPG met[32–401] in E. coli l GM120 in 2XYT media containing 20 µg/ml kanamycin were incubated at 30° C. prior to induction. Induction of huOPG met[32–401] gene product expression from the luxPR promoter was achieved following the addition of the synthetic autoinducer N-(3-oxohexanoyl)-DL-homoserine lactone to the culture media to a final concentration of 30 ng/ml and cultures were incubated at either 30° C. or 37° C. for a further 6 hours. After 6 hours, the bacterial cultures were examined by microscopy for the presence of inclusion bodies and were then pelletted by centrifugation. Refractile inclusion bodies were observed in induced cultures indicating that some of the recombinant huOPG met[32–401] gene product was produced insolubly in E. coli.

Figure 14B:
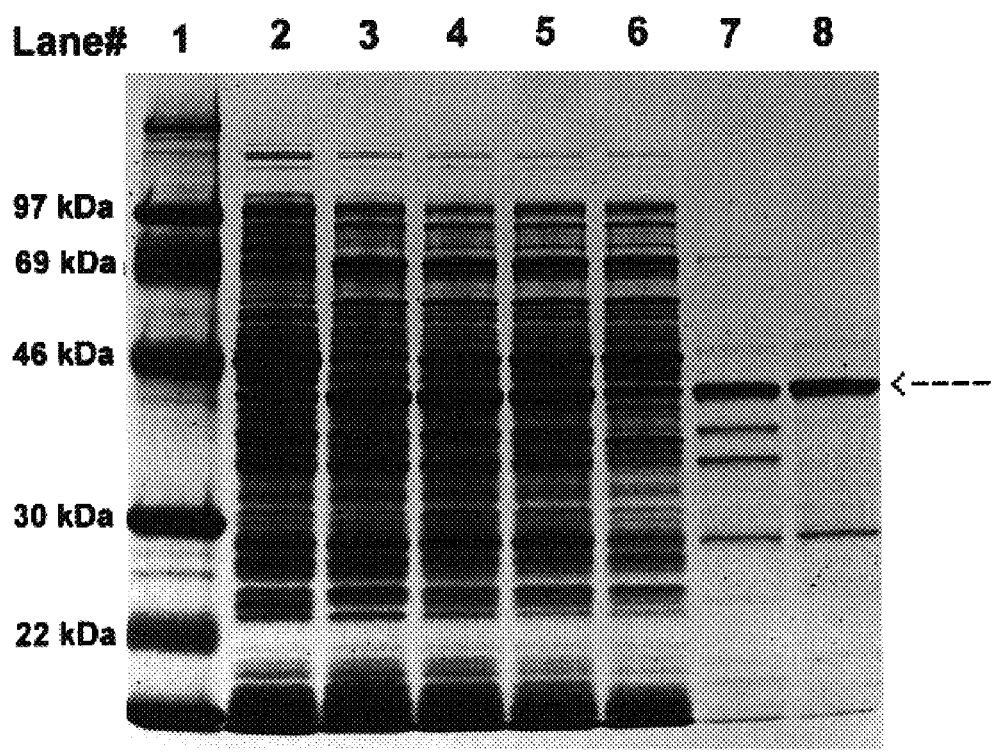

Some bacterial pellets were resuspended in 10 mM Tris-HCl/pH8, 1 mN EDTA and lysed directly by addition of 2×Laemlli sample buffer to 1× final, and β-mercaptoethanol to 5% final concentration, and analyzed by SDS-PAGE. A substantially more intense coomassie stained band of approximately 42 kDa was observed on a SDS-PAGE gel containing total cell lysates of 30° C. and 37° C. induced cultures versus lane 2 which is a total cell lysate of a 30° C. uninduced culture (FIG. 14B). The expected gene product would be 370 amino acids in length and have an expected molecular weight of about 42.2 kDa.

Following induction at 37° C. for 6 hours, an additional culture was pelleted and either processed for isolation of inclusion bodies (see below) or processed by microfluidizing. The pellet processed for microfluidizing was resuspended in 25 mM Tris-HCl/pH8, 0.5M NaCl buffer and passed 20 times through a Microfluidizer Model 1108 (Microfluidics Corp.) and collected. An aliquot was removed of the collected sample (microfluidized total lysate), and the remainder was pelleted at 20,000×g for 20 minutes. The supernatant following centrifugation was removed (microfluidized soluble fraction) and the pellet resuspended in a 25 mM Tris-HCl/pH8, 0.5M NaCl, 6M urea solution (microfluidized insoluble fraction). To an aliquot of either the total soluble, or insoluble fraction was added to an equal volume of 2×Laemalli sample buffer and β-mercaptoethanol to 5% final concentration. The samples were then analyzed by SDS-PAGE. A significant amount of recombinant huOPG met[32–401] gene product appeared to be found in the insoluble fraction.

To purify the recombinant protein, inclusion bodies were purified as follows: Bacterial cells were separated from media by density gradient centrifugation in a Beckman J-6B centrifuge equipped with a JS-4.2 rotor at 4,900×g for 15 minutes at 4° C. The bacterial pellet was resuspended in 5 ml of water and then diluted to a final volume of 10 ml with water. This suspension was transferred to a stainless steel cup cooled in ice and subjected to sonic disruption using a Branson Sonifier equipped with a standard tip (power setting=5, duty cycle=95%, 80 bursts). The sonicated cell suspension was centrifuged in a Beckman Optima TLX ultracentrifuge equipped with a TLA 100.3 rotor at 195,000×g for 5 to 10 minutes at 23° C. The supernatant was discarded and the pellet rinsed with a stream of water from a squirt bottle. The pellets were collected by scraping with a micro spatula and transferred to a glass homogenizer (15 ml capacity). Five ml of Percoll solution (75% liquid Percoll, 0.15 M sodium chloride) was added to the homogenizer and the contents are homogenized until uniformly suspended. The volume was increased to 19.5 ml by the addition of Percoll solution, mixed, and distributed into 3 Beckman Quick-Seal tubes (13×32 mm). Tubes were sealed according to manufacturers instructions. The tubes were spun in a Beckman TLA 100.3 rotor at 23° C., 20,000 rpm (21,600×g), 30 minutes. The tubes were examined for the appropriate banding pattern. To recover the refractile bodies, gradient fractions were recovered and pooled, then diluted with water. The inclusion bodies were pelleted by centrifugation, and the protein concentration estimated following SDS-PAGE.

An aliquot of inclusion bodies isolated as described below was dissolved into 1× Laemlli sample buffer with 5% β-mercaptoethanol and resolved on a SDS-PAGE gel and the isolated inclusion bodies provide a highly purified recombinant huOPG[32–401] gene product. The major ~42 kDa band observed after resolving inclusion bodies on a SDS-polyacrylamide gel was excised from a separate gel and the N-terminal amino acid sequence determined essentially as described (Matsudaira et al. J. Biol. Chem. 262, 10–35 (1987)). The following sequence was determined after 19 cycles:

$NH_2$ -MDEETSHQLLCDKCPPGTY-COOH (SEQ ID NO:62)

This sequence was found to be identical to the first 19 amino acids encoded by the pAMG21 Hu-OPG met[32–401] expression vector, produced by a methionine residue provided by the bacterial expression vector.

C. Human OPG met[22–401]

A DNA sequence coding for an N-terminal methionine and amino acids 22 through 401 of human OPG was placed under control of the luxPR promoter in a prokaryotic plasmid expression vector pAMG21 as follows. Isolated plasmid DNA of pAMG21-huOPG met[32–401] (see Section B) was cleaved with KpnI and BamHI restriction endonucleases and the resulting fragments were resolved on an agarose gel. The B fragment (about 1064 bp fragment) was isolated from the gel using standard methodology. Synthetic oligonucleotides (oligos) #1267-06 and #1267-07 were phosphorylated individually and allowed to form an oligo linker duplex, which contained NdeI and KpnI cohesive ends, using methods described in Section B. The synthetic linker duplex utilized E. coli codons and provided for an N-terminal methionine. The phosphorylated oligo linker containing NdeI and KpnI cohesive ends and the isolated about 1064 bp fragment of pAMG21-huOP met[32–401] digested with KpnI and BamHI restriction endonucleases were directionally inserted between the NdeI and BamHI sites of pAMG21 using standard recombinant DNA methodology. The ligation mixture was transformed into E. coli host 393 by electroporation utilizing the manufacturer's protocol. Clones were selected, plasmid DNA was isolated, and DNA sequencing was performed to verify the DNA sequence of the huOPG-met [22–401] gene. oligo #1267-06:

5'-TAT GGA AAC TTT TCC TCC AAA ATA TCT TCA TTA TGA TGA AGA AAC TTC TCA TCA GCT GCT GTG TGA TAA ATG TCC GCC GGG TAC-3' (SEQ ID NO:63)

Oligo #1267-07:

5'-CCG GCG GAC ATT TAT CAC ACA GCA GCT GAT GAG AAG TTT CTT CAT CAT AAT GAA GAT ATT TTG GAG GAA AAG TTT CCA-3' (SEQ ID NO:64)

Cultures of pAMG21-huOPG-met[22–401] in E. coli host 393 were placed in 2XYT media containing 20 μg/ml kanamycin and were incubated at 30° C. prior to induction. Induction of recombinant gene product expression from the luxPR promoter of vector pAMG21 was achieved following the addition of the synthetic autoinducer N-(3-oxohexanoyl)-DL-homoserine lactone to the culture media to a final concentration of 30 ng/ml and incubation at either 30° C. or 37° C. for a further 6 hours. After 6 hours, bacterial cultures were pelleted by centrifugation (=30° C. I+6 or 37° C. I+6). Bacterial cultures were also either pelleted just prior to induction (=30° C. PreI) or alternatively no autoinducer was added to a separate culture which was allowed to incubate at 30° C. for a further 6 hours to give an uninduced (UI) culture (=30° C. UI). Bacterial pellets of either 30° C. PreI, 30° C. UI, 30° C. I+6, or 37° C. I+6 cultures were resuspended, lysed, and analyzed by SDS-polyacrylamide gel electrophoresis (PAGE) as described in Section B. Polyacrylamide gels were either stained with coomassie blue and/or Western transferred to nitrocellulose and immunoprobed with rabbit anti-mu OPG-Fc polyclonal antibody as described in Example 10. The level of gene product following induction compared to either an uninduced (30° C. UI) or pre-induction (30° C. PreI) sample.

D. Murine OPG met[22–401]

A DNA sequence coding for an N-terminal methionine and amino acids 22 through 401 of the murine (mu) OPG (OPG) polypeptide was placed under control of the luxPR promoter in a prokaryotic plasmid expression vector pAMG21 as follows. PCR was performed using oligonucleotides #1257-16 and #1257-15 as primers, plasmid pRcCMV-Mu OPG DNA as a template and thermocycling conditions as described in Section B. The PCR product was purified and cleaved with KpnI and BamHI restriction endonucleases as described in Section B. Synthetic oligos #1260-61 and #1260-82 were phosphorylated individually and allowed to form an oligo linker duplex with NdeI and KpnI cohesive ends using methods described in Section B. The synthetic linker duplex utilized *E. coli* codons and provided for an N-terminal methionine. The phosphorylated linker duplex formed between oligos #1260-61 and #1260-82 containing NdeI and KpnI cohesive ends and the KpnI and BamHI digested and purified PCR product generated using oligo primers #1257-16 and #1257-15 were directionally inserted between the NdeI and BamHI sites of pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the MuOPG met[22–401] gene.

Expression of recombinant muOPG met[22–401] polypeptide from cultures of 393 cells harboring plasmid pAMG21-MuOPG met[22–401] following induction was determined using methods described in Section C.

Oligo #1257-15:
5'-TAC GCA CTG GAT CCT TAT AAG CAG CTT ATT TTC ACG GAT TGA AC-3' (SEQ ID NO:65)

Oligo #1257-16:
5'-GTG CTC CTG GTA CCT ACC TAA AAC AGC ACT GCA CAG TG-3' (SEQ ID NO:66)

Oligo #1260-61:
5'-TAT GGA AAC TCT GCC TCC AAA ATA CCT GCA TTA CGA TCC GGA AAC TGG TCA TCA GCT GCT GTG TGA TAA ATG TGC TCC GGG TAC-3' (SEQ ID NO:67)

Oligo #1260-82:
5'-CCG GAG CAC ATT TAT CAC ACA GCA GCT GAT GAC CAG TTT CCG GAT CGT AAT GCA GGT ATT TTG GAG GCA GAG TTT CCA-3' (SEQ ID NO:68)

E. Murine OPG met[32–401]

A DNA sequence coding for an N-terminal methionine and amino acids 32 through 401 of murine OPG was placed under control of the luxPR promoter in a prokaryotic plasmid expression vector pAMG21 as follows. To accomplish this, Synthetic oligos #1267-08 and #1267-09 were phosphorylated individually and allowed to form an oligo linker duplex using methods described in Section B. The synthetic linker duplex utilized *E. coli* codons and provided for an N-terminal methionine. The phosphorylated linker duplex formed between oligos #1267-08 and #1267-09 containing NdeI and KpnI cohesive ends, and the KpnI and BamHI digested and purified PCR product described earlier (see Section D), was directionally inserted between the NdeI and BamHI sites of pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the muOPG-met[32–401] gene.

Expression of recombinant muOPG-met [32–401] polypeptide from cultures of 393 cells harboring the pAMG21 recombinant plasmid following induction was determined using methods described in Section C.

Oligo #1267-08:
5'-TAT GGA CCC AGA AAC TGG TCA TCA GCT GCT GTG TGA TAA ATG TGC TCC GGG TAC-3' (SEQ ID NO:69)

Oligo #1267-09:
5'-CCG GAG CAC ATT TAT CAC ACA GCA GCT GAT GAC CAG TTT CTG GGT CCA-3' (SEQ ID NO:70)

F. Murine OPG met-lys[22–401]

A DNA sequence coding for an N-terminal methionine followed by a lysine residue and amino acids 22 through 401 of murine OPG was placed under control of the lux PR promoter in prokaryotic expression vector pAMG21 as follows. Synthetic oligos #1282-95 and #1282-96 were phosphorylated individually and allowed to form an oligo linker duplex using methods described in Section B. The synthetic linker duplex utilized *E. coli* codons and provided for an N-terminal methionine. The phosphorylated linker duplex formed between oligos #1282-95 and #1282-96 containing NdeI and KpnI cohesive ends and the KpnI and BamHI digested and purified PCR product described in Section D was directionally inserted between the NdeI and BamHI sites in pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the MuOPG-Met-Lys[22–401] gene.

Expression of recombinant MuOPG Met-Lys[22–401] polypeptide from transformed 393 cells harboring the recombinant pAMG21 plasmid following induction was determined using methods described in Section C.

Oligo #1282-95:
5'-TAT GAA AGA AAC TCT GCC TCC AAA ATA CCT GCA TTA CGA TCC GGA AAC TGG TCA TCA GCT GCT GTG TGA TAA ATG TGC TCC GGG TAC-3' (SEQ ID NO:71)

Oligo #1282-96:
5'-CCG GAG CAC ATT TAT CAC ACA GCA GCT GAT GAC CAG TTT CCG GAT CGT AAT GCA GGT ATT TTG GAG GCA GAG TTT CTT TCA-3' (SEQ ID NO:72)

G. Murine OPG met-lys-(his)$_7$[22–401]

A DNA sequence coding for N-terminal residues Met-Lys-His-His-His-His-His-His-His (=MKH) followed by amino acids 22 through 401 of Murine OPG was placed under control of the lux PR promoter in prokaryotic expression vector pAMG21 as follows. PCR was performed using oligonucleotides #1300-50 and #1257-15 as primers and plasmid pAMG21-muOPG-met[22–401] DNA as template. Thermocycling conditions were as described in Section B. The resulting PCR sample was resolved on an agarose gel, the PCR product was excised, purified, cleaved with NdeI and BamHI restriction endonucleases and purified. The NdeI and BamHI digested and purified PCR product generated using oligo primers #1300-50 and #1257-15 was directionally inserted between the NdeI and BamHI sites of pAMG21 using standard DNA methodology. The ligation mixture was transformed into *E. coli* host 393 by electroporation utilizing the manufacturer's protocol. Clones were selected, plasmid DNA was isolated, and DNA sequencing performed to verify the DNA sequence of the muOPG-MKH[22–401] gene.

Expression of recombinant MuOPG-MKH[22–401] polypeptide from transformed 393 cultures harboring the recombinant pAMG21 plasmid following induction was determined using methods described in Section C.

Oligo #1300-50:
5'-GTT CTC CTC ATA TGA AAC ATC ATC ACC ATC ACC ATC ATG AAA CTC TGC CTC CAA AAT ACC TGC ATT ACG AT-3' (SEQ ID NO:73)

Oligo #1257-15: see Section D

H. Murine OPG met-lys[22–401] (his)$_7$

A DNA sequence coding for a N-terminal met-lys, amino acids 22 through 401 murine OPG, and seven histidine residues following amino acid 401 (=muOPG MK[22–401]-H$_7$), was placed under control of the lux PR promoter in prokaryotic expression vector pAMG21 as follows. PCR was performed using oligonucleotides #1300-49 and #1300-51 as primers and pAMG21-muOPG met[22–401] DNA as template. Thermocycling conditions were as described in Section B. The resulting PCR sample was resolved on an agarose gel, the PCR product was excised, purified, restricted with NdeI and BamHI restriction endonucleases, and purified. The NdeI and BamHI digested and purified PCR product was directionally inserted between the NdeI and BamHI sites in pAMG21 using standard methodology. The ligation was transformed into *E. coli* host 393 by electroporation utilizing the manufacturer's protocol. Clones were selected, plasmid DNA was isolated, and DNA sequencing was performed to verify the DNA sequence of the muOPG MK[22–401]-H$_7$ gene.

Expression of the recombinant muOPG MK-[22–401]-H$_7$ polypeptide from a transformed 393 cells harboring the recombinant pAMG21 plasmid following induction was determined using methods described in Section C.

Oligo #1300-49:
5'-GTT CTC CTC ATA TGA AAG AAA CTC TGC CTC CAA AAT ACC TGC A-3' (SEQ ID NO:74)

Oligo #1300-51:
5'-TAC GCA CTG GAT CCT TAA TGA TGG TGA TGG TGA TGA TGT AAG CAG CTT ATT TTC ACG GAT TGA ACC TGA TTC CCT A-3' (SEQ ID NO:75)

I. Murine OPG met[27–401]

A DNA sequence coding for a N-terminal methionine and amino acids 27 through 401 of murine OPG was placed under control of the lux PR promoter of prokaryotic expression vector pAMG21 as follows. PCR was performed with oligonucleotides #1309-74 and #1257-15 as primers and plasmid pAMG21-muOPG-met[22–401] DNA as template. Thermocycling conditions were as described in Section B. The resulting PCR sample was resolved on an agarose gel, the PCR product was excised, purified, cleaved with NdeI and BamHI restriction endonucleases, and purified. The NdeI and BamHI digested and purified PCR product was directionally inserted between the NdeI and BamHI sites of pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the muOPG-met [27–401] gene.

Expression of recombinant muOPG-met[27–401] polypeptide from a transfected 393 culture harboring the recombinant pAMG21 plasmid following induction was determined using methods described in Section C.

Oligo#1309-74:
5'-GTT CTC CTC ATA TGA AAT ACC TGC ATT ACG ATC CGG AAA CTG GTC AT-3' (SEQ ID NO:76)

Oligo#1257-15: See Section D

J. Human OPG met[27–401]

A DNA sequence coding for a N-terminal methionine and amino acids 27 through 401 of human OPG was placed under control of the lux PR promoter of prokaryotic expression vector pAMG21 as follows. PCR was performed using oligonucleotides #1309-75 and #1309-76 as primers and plasmid pAMG21-huOPG-met[22–401] DNA as template. Thermocycling conditions were as described in Section B. The resulting PCR sample was resolved on an agarose gel, the PCR product was excised, purified, restricted with AseI and BamHI restriction endonucleases, and purified. The AseI and BamHI digested and purified PCR product above was directionally inserted between the NdeI and BamHI sites of pAMG21 using standard methodology. The ligation mixture was transformed into *E. coli* host 393 by electroporation utilizing the manufacturer's protocol. Clones were selected, plasmid DNA was isolated, and DNA sequencing was performed to verify the DNA sequence of the huOPG-met[27–401] gene.

Expression of the recombinant huOPG-met[27–401] polypeptide following induction of from transfected 393 cells harboring the recombinant pAMG21 plasmid was determined using methods described in Section C.

Oligo #1309-75:
5'-GTT CTC CTA TTA ATG AAA TAT CTT CAT TAT GAT GAA GAA ACT T-3' (SEQ ID NO:77)

Oligo #1309-76:
5'-TAC GCA CTG GAT CCT TAT AAG CAG CTT ATT TTT ACT GAT T-3' (SEQ ID NO:78)

K. Murine OPG met[22–180]

A DNA sequence coding for a N-terminal methionine and amino acids 22 through 180 of murine OPG was placed under control of the lux PR promoter of prokaryotic expression vector pAMG21 as follows. PCR was performed with oligonucleotides #1309-72 and #1309-73 as primers and plasmid pAMG21-muOPG-met[22–401] DNA as template. Thermocycling conditions were as described in Section B. The resulting PCR sample was resolved on an agarose gel, the PCR product was excised, purified, restricted with NdeI and BamHI restriction endonucleases, and purified. The NdeI and BamHI digested and purified PCR product above was directionally inserted between the NdeI and BamHI sites of pAMG21 using standard methodology. The ligation was transformed into *E. coli* host 393 by electroporation utilizing the manufacturer's protocol. Clones were selected, plasmid DNA was isolated, and DNA sequencing was performed to verify the DNA sequence of the muOPG-met [22–180] gene.

Expression of recombinant muOPG-met[22–180] polypeptide from transformed 393 cultures harboring the recombinant pAMG21 plasmid following induction was determined using methods described in Section C.

Oligo #1309-72:
5'-GTT CTC CTC ATA TGG AAA CTC TGC CTC CAA AAT ACC TGC A-3' (SEQ ID NO:79)

Oligo #1309-73:
5'-TAC GCA CTG GAT CCT TAT GTT GCA TTT CCT TTC TGA ATT AGC A-3' (SEQ ID NO:80)

L. Murine OPG met[27–180]

A DNA sequence coding for a N-terminal methionine and amino acids 27 through 180 of murine OPG was placed under the control of the lux PR promoter of prokaryotic expression vector pAMG21 as follows. PCR was performed using oligonucleotides #1309-74 (see Section I) and #1309-73 (see Section K) as primers and plasmid pAMG21-muOPG met[22–401] DNA as template. Thermocycling conditions were as described in Section B. The resulting PCR sample was resolved on an agarose gel, the PCR product excised, purified, restricted with NdeI and BamHI restriction endonucleases, and purified. The NdeI and BamHI digested and purified PCR product above was directionally inserted between the NdeI and BamHI sites in pAMG21 using standard methodology. The ligation mixture was transformed into E. coli host 393 by electroporation utilizing the manufacturer's protocol. Clones were selected, plasmid DNA was isolated, and DNA sequencing was performed to verify the DNA sequence of the muOPG met [27–180] gene.

Expression of recombinant muOPG met[27–180] polypeptide from cultures of transformed 393 cells harboring the recombinant pAMG21 plasmid following induction was determined using methods described in Section C.

M. Murine OPG met[22–189] and met[22–194]

A DNA sequence coding for a N-terminal methionine and either amino acids 22 through 189, or 22 through 194 of murine OPG was placed under control of the lux PR promoter of prokaryotic expression vector pAMG21 as follows. The pair of synthetic oligonucleotides #1337-92 and #1337-93 (=muOPG-189 linker) or #1333-57 and #1333-58 (=muOPG-194 linker) were phosphorylated individually and allowed to form an oligo linker duplex pair using methods described in Section B. Purified plasmid DNA of pAMG21-muOPG-met[22–401] was cleaved with KpnI and BspEI restriction endonucleases and the resulting DNA fragments were resolved on an agarose gel. The ~413 bp B fragment was isolated using standard recombinant DNA methodology. The phosphorylated oligo linker duplexes formed between either oligos #1337-92 and #1337-93 (muOPG-189 linker) or oligos #1333-57 and #1333-58 (muOPG-194 linker) containing BspEI and BamHI cohesive ends, and the isolated ~413 bp B fragment of plasmid pAMG21-muOPG-met[22–401] digested with KpnI and BspEI restriction endonucleases above, was directionally inserted between the KpnI and BamHI sites of pAMG21-muOPG met[22–401] using standard methodology. Each ligation mixture was transformed into E. coli host 393 by electroporation utilizing the manufacturer's protocol. Clones were selected, plasmid DNA was isolated, and DNA sequencing was performed to verify the DNA sequence of either the muOPG-met[22–189] or muOPG-met[22–194] genes.

Expression of recombinant muOPG-met[22–189] and muOPG-met[22–1949] polypeptides from recombinant pAMG21 plasmids transformed into 393 cells was determined using methods described in Section C.

Oligo #1337-92:
5'-CCG GAA ACA GAT AAT GAG-3' (SEQ ID NO:81)
Oligo #1337-93:
5'-GAT CCT CAT TAT CTG TTT-3' (SEQ ID NO:82)
Oligo #1333-57:
5'-CCG GAA ACA GAG AAG CCA CGC AAA AGT AAG-3' (SEQ ID NO:83)
Oligo #1333-58:
5'-GAT CCT TAC TTT TGC GTG GCT TCT CTG TTT-3' (SEQ ID NO:84)

N. Murine OPG met[27–189] and met[27–194]

A DNA sequence coding for a N-terminal methionine and either amino acids 27 through 189, or 27 through 194 of murine OPG was placed under control of the lux PR promoter of prokaryotic expression vector pAMG21 as follows. Phosphorylated oligo linkers either "muOPG-189 linker" or "muOPG-194 linker" (see Section M) containing BspEI and BamHI cohesive ends, and the isolated ~413 bp B fragment of plasmid pAMG21-muOPG-met[22–401] digested with KpnI and BspEI restriction endonucleases were directionally inserted between the KpnI and BamHI sites of plasmid pAMG21-muOPG-met[27–401] using standard methodology. Each ligation was transformed into E. coli host 393 by electroporation utilizing the manufacturer's protocol. Clones were selected, plasmid DNA was isolated, and DNA sequencing was performed to verify the DNA sequence of either the muOPG met[27–189] or muOPG met[27–194] genes.

Expression of recombinant muOPG met[27–189] and muOPG met[27–194] following induction of 393 cells harboring recombinant pAMG21 plasmids was determined using methods described in Section C.

O. Human OPG met[22–185], met[22–189], met[22–194]

A DNA sequence coding for a N-terminal methionine and either amino acids 22 through 185, 22 through 189, or 22 through 194 of the human OPG polypeptide was placed under control of the lux PR promoter of prokaryotic expression vector pAMG21 as follows. The pair of synthetic oligonucleotides #1331-87 and #1331-88 (=huOPG-185 linker), #1331-89 and #1331-90 (=huOPG-189 linker), or #1331-91 & #1331-92 (=huOPG-194 linker) were phosphorylated individually and each allowed to form an oligo linker duplex pair using methods described in Section B. Purified plasmid DNA of pAMG21-huOPG-met[27–401] was restricted with KpnI and NdeI restriction endonucleases and the resulting DNA fragments were resolved on an agarose gel. The ~407 bp B fragment was isolated using standard recombinant DNA methodology. The phophorylated oligo linker duplexes formed between either oligos #1331-87 and #1331-88 (huOPG-185 linker), oligos #1331-89 and #1331-90 (huOPG-189 linker), or oligos #1331-91 and #1331-92 (huOPG-194 linker) [each linker contains NdeI and BamHI cohesive ends], and the isolated ~407 bp B fragment of plasmid pAMG21-huOPG-met[27–401] digested with KpnI and NdeI restriction endonucleases above, was directionally inserted between the KpnI and BamHI sites of plasmid pAMG21-huOPG-met[22–401] using standard methodology. Each ligation was transformed into E. coli host 393 by electroporation utilizing the manufacturer's protocol. Clones were selected, plasmid DNA was isolated, and DNA sequencing was performed to verify the DNA sequence of either the huOPG-met[22–185], huOPG-met[22–189], or huOPG-met[22–194] genes.

Expression of recombinant huOPG-met[22–185], huOPG-met[22–189] or huOPG-met[22–194] in transformed 393 cells harboring recombinant pAMG21 plasmids following induction was determined using methods described in Section C.

Oligo #1331-87:
5'-TAT GTT AAT GAG-3' (SEQ ID NO:85)
Oligo #1331-88:
5'-GAT CCT CAT TAA CA-3' (SEQ ID NO:86)
Oligo #1331-89:
5'-TAT GTT CCG GAA ACA GTT AAG-3' (SEQ ID NO:87)
Oligo #1331-90:
5'-GAT CCT TAA CTG TTT CCG GAA CA-3' (SEQ ID NO:88)
Oligo #1331-91:
5'-TAT GTT CCG GAA ACA GTG AAT CAA CTC A AAT AAG-3' (SEQ ID NO:89)

Oligo #1331-92:
5'-GAT CCT TAT TTT TGA GTT GAT TCA CTG TTT CCG GAA CA-3' (SEQ ID NO:90)

P. Human OPG met[27–185], met[27–189], met [27–194]

A DNA sequence coding for a N-terminal methionine and either amino acids 27 through 185, 27 through 189, or 27 through 194 of the human OPG polypeptide was placed under control of the lux PR promoter of prokaryotic expression vector pAMG21 as follows. Phosphorylated oligo linkers "huOPG-185 linker", "huOPG-189 linker", or "huOPG-194 linker" (See Section O) each containing NdeI and BamHI cohesive ends, and the isolated ~407 bp B fragment of plasmid pAMG21-huOPG-met[27–401] digested with KpnI and NdeI restriction endonucleases (See Section O) were directionally inserted between the KpnI and BamHI sites of plasmid pAMG21-huOPG-met[27–401] (See Section J) using standard methodology. Each ligation was transformed into E. coli host 393 by electroporation utilizing the manufacturer's protocol. Clones were selected, plasmid DNA isolated, and DNA sequencing performed to verify the DNA sequence of either the huOPG-met[27–185], huOPG-met[27–189], or huOPG-met[27–194] genes.

Expression of recombinant huOPG-met[27–185], huOPG-met[27–189], and huOPG-met[27–194] from recombinant pAMG21 plasmids transformed into 393 cells was determined using methods described in Section C.

O. Murine OPG met[27–401] (P33E, G36S, A45P)

A DNA sequence coding for an N-terminal methionine and amino acids 27 through 48 of human OPG followed by amino acid residues 49 through 401 of murine OPG was placed under control of the lux PR promoter of prokaryotic expression vector pAMG21 as follows. Purified plasmid DNA of pAMG21-huOPG-met[27–401] (See Section J) was cleaved with AatII and KpnI restriction endonucleases and a ~1075 bp B fragment isolated from an agarose gel using standard recombinant DNA methodology. Additionally, plasmid pAMG21-muOPG-met[22–401] DNA (See Section D) was digested with KpnI and BamHI restriction endonucleases and the ~1064 bp B fragment isolated as described above. The isolated ~1075 bp pAMG21-huOPG-met [27–401] restriction fragment containing AatII & KpnI cohesive ends (see above), the ~1064 bp pAMG21-muOPG-met[22–401] restriction fragment containing KpnI and BamHI sticky ends and a ~5043 bp restriction fragment containing AatII and BamHI cohesive ends and corresponding to the nucleic acid sequence of pAMG21 between AatII & BamHI were ligated using standard recombinant DNA methodology. The ligation was transformed into E. coli host 393 by electroporation utilizing the manufacturer's protocol. clones were selected, and the presence of the recombinant insert in the plasmid verified using standard DNA methodology. muOPG-27–401 (P33E, G36S, A45P) gene. Amino acid changes in muOPG from proline-33 to glutamic acid-33, glycine-36 to serine-36, and alanine-45 to proline-45, result from replacement of muOPG residues 27 through 48 with huOPG residues 27 through 48.

Expression of recombinant muOPG-met[27–401] (P33E, G36S, A45P) from transformed 393 cells harboring the recombinant pAMG21 plasmid was determined using methods described in Section C.

R. Murine OPG met-lys-(his)$_7$-ala-ser-(asp)$_4$-lys[22–401] (A45T)

A DNA sequence coding for an N-terminal His tag and enterokinase recognition sequence which is ($NH_2$ to COOH terminus): Met-Lys-His-His-His-His-His-His-His-Ala-Ser-Asp-Asp-Asp-Asp-Lys (=HEK), followed by amino acids 22 through 401 of the murine OPG polypeptide was placed under control of the lac repressor regulated Ps4 promoter as follows. pAMG22-His (See Section A) was digested with NheI and BamHI restriction endonucleases, and the large fragment (the A fragment) isolated from an agarose gel using standard recombinant DNA methodology. oligonucleotides #1282-91 and #1282-92 were phosphorylated individually and allowed to form an oligo linker duplex using methods previously described (See Section B). The phosphorylated linker duplex formed between oligos #1282-91 and #1282-92 containing NheI and KpnI cohesive ends, the KpnI and BamHI digested and purified PCR product described (see Section D), and the A fragment of vector pAMG22-His digested with NheI and BamHI were ligated using standard recombinant DNA methodology. The ligation was transformed into E. coli host GM120 by electroporation utilizing the manufacturer's protocol. Clones were selected, plasmid DNA isolated and DNA sequencing performed to verify the DNA sequence of the muOPG-HEK[22–401] gene. DNA sequencing revealed a spurious mutation in the natural muOPG sequence that resulted in a single amino acid change of Alanine-45 of muOPG polypeptide to a Threonine.

Expression of recombinant muOPG-HEK[22–401] (A45T) from GM120 cells harboring the recombinant pAMG21 plasmid was determined using methods similar to those described in Section C, except instead of addition of the synthetic autoinducer, IPTG was added to 0.4 mm final to achieve induction.

Oligo #1282-91:
5'-CTA GCG ACG ACG ACG ACA AAG AAA CTC TGC CTC CAA AAT ACC TGC ATT ACG ATC CGG AAA CTG GTC ATC AGC TGC TGT GTG ATA AAT GTG CTC CGG GTA C-3' (SEQ ID NO:91)

Oligo #1282-92:
5'-CCG GAG CAC ATT TAT CAC ACA GCA GCT GAT GAC CAG TTT CCG GAT CGT AAT GCA GGT ATT TTG GAG GCA GAG TTT CTT TGT CGT CGT CGT CG-3' (SEQ ID NO:92)

S. Human OPG met-arg-gly-ser-(his)$_6$[22–401]

Eight oligonucleotides (1338-09 to 1338-16 shown below) were designed to produce a 175 base fragment as overlapping, double stranded DNA. The oligos were annealed, ligated, and the 5' and 3' oligos were used as PCR primers to produce large quantities of the 175 base fragment. The final PCR gene products were digested with restriction endonucleases ClaI and KpnI to yield a fragment which replaces the N-terminal 28 codons of human OPG. The ClaI and KpnI digested PCR product was inserted into pAMG21-huOPG [27–401] which had also been cleaved with ClaI and KpnI. Ligated DNA was transformed into competent host cells of E. coli strain 393. Clones were screened for the ability to produce the recombinant protein product and to possess the gene fusion having the correct nucleotide sequence. Protein expression levels were determined from 50 ml shaker flask studies. Whole cell lysate and sonic pellet were analyzed for expression of the construct by Coomassie stained PAGE gels and Western analysis with murine anti-OPG antibody. Expression of huOPG Met-Arg-Gly-Ser-(His)$_6$ [22–401] resulting in the formation of large inclusion bodies and the protein was localized to the insoluble (pellet) fraction.

1338-09:
ACA AAC ACA ATC GAT TTG ATA CTA GA (SEQ ID NO:93)

1338-10:
TTT GTT TTA ACT AAT TAA AGG AGG AAT AAA ATA TGA GAG GAT CGC ATC AC (SEQ ID NO:94)

1338-11:
CAT CAC CAT CAC GAA ACC TTC CCG CCG AAA TAC CTG CAC TAC GAC CAA GA (SEQ ID NO:95)
1338-12:
AAC CTC CCA CCA GCT GCT GTG CGA CAA ATG CCC GCC GGG TAC CCA AAC A (SEQ ID NO:96)
1338-13:
TGT TTG GGT ACC CGG CGG GCA TTT GT (SEQ ID NO:97)
1338-14:
CGC ACA GCA GCT GGT GGG AGG TTT CTT CGT CGT AGT GCA GGT ATT TCG CC (SEQ ID NO:98)
1338-15:
GGG AAG GTT TCG TGA TGG TGA TGG TGA TGC GAT CCT CTC ATA TTT TAT T (SEQ ID NO:99)
1338-16:
CCT CCT TTA ATT AGT TAA AAC AAA TCT AGT ATC AAA TCG ATT GTG TTT GT (SEQ ID NO:100)

T. Human OPG met-lys[22–401] and met(lys)$_3$[22–401]

To construct the met-lys and met-(lys)$_3$ versions of human OPG[22–401], overlapping oligonucleotides were designed to add the appropriate number of lysine residues. The two oligos for each construct were designed to overlap, allowing two rounds of PCR to produce the final product. The template for the first PCR reaction was a plasmid DNA preparation containing the human OPG 22–401 gene. The first PCR added the lysine residue(s). The second PCR used the product of the first round and added sequence back to the first restriction site, ClaI.

The final PCR gene products were digested with restriction endonucleases ClaI and KpnI, which replace the N-terminal 28 codons of hu OPG, and then ligated into plasmid pAMG21-hu OPG [27–401] which had been also digested with the two restriction endonucleases. Ligated DNA was transformed into competent host cells of *E coli* strain 393. Clones were screened for the ability to produce the recombinant protein product and to possess the gene fusion having the correct nucleotide sequence. Protein expression levels were determined from 50 ml shaker flask studies. Whole cell lysate and sonic pellet were analyzed for expression of the construct by Coomassie stained PAGE gels and Western analysis with murine anti-OPG antibody. Neither construct had a detectable level of protein expression and inclusion bodies were not visible. The DNA sequences were confirmed by DNA sequencing.

Oligonucleotide primers to prepare Met-Lys huOPG [22–401]:
1338-17:
ACA AAC ACA ATC GAT TTG ATA CTA GAT TTG TTT TAA CTA ATT AAA GGA GGA ATA AAA TG (SEQ ID NO:101)
1338-18:
CTA ATT AAA GGA GGA ATA AAA TGA AAG AAA CTT TTC CTC CAA AAT ATC (SEQ ID NO:102)
1338-20:
TGT TTG GGT ACC CGG CGG ACA TTT ATC ACA C (SEQ ID NO:103)

Oligonucleotide primers to prepare Met-(Lys)$_3$-huOPG [22–401]:
1338-17:
ACA AAC ACA ATC GAT TTG ATA CTA GAT TTC TTT TAA CTA ATT AAA GGA GGA ATA AAA TG (SEQ ID NO:104)
1338-19:
CTA ATT AAA GGA GGA ATA AAA TGA AAA AAA AAG AAA CTT TTC CTC CAA AAT ATC (SEQ ID NO:105)
1338-20:
TGT TTG GGT ACC CGG CGG ACA TTT ATC ACA C (SEQ ID NO:106)

U. Human and Murine OPG [22–401]/Fc Fusions

Four OPG-Fc fusions were constructed where the Fc region of human IgG1 was fused at the N-terminus of either human or murine Osteoprotegerin amino acids 22 to 401 (referred to as Fc/OPG [22–401]) or at the C-terminus (referred to as OPG[22–401]/Fc). Fc fusions were constructed using the fusion vector pFc-A3 described in Example 7.

All fusion genes were constructed using standard PCR technology. Template for PCR reactions were plasmid preparations containing the target genes. overlapping oligos were designed to combine the C-terminal portion of one gene with the N terminal portion of the other gene. This process allows fusing the two genes together in the correct reading frame after the appropriate PCR reactions have been performed. Initially one "fusion" oligo for each gene was put into a PCR reaction with a universal primer for the vector carrying the target gene. The complimentary "fusion" oligo was used with a universal primer to PCR the other gene. At the end of this first PCR reaction, two separate products were obtained, with each individual gene having the fusion site present, creating enough overlap to drive the second round of PCR and create the desired fusion. In the second round of PCR, the first two PCR products were combined along with universal primers and via the overlapping regions, the full length fusion DNA sequence was produced.

The final PCR gene products were digested with restriction endonucleases XbaI and BamHI, and then ligated into the vector pAMG21 having been also digested with the two restriction endonucleases. Ligated DNA was transformed into competent host cells of *E. coli* strain 393. Clones were screened for the ability to produce the recombinant protein product and to possess the gene fusion having the correct nucleotide sequence. Protein expression levels were determined from 50 ml shaker flask studies. Whole cell lysate, sonic pellet, and supernatant were analyzed for expression of the fusion by Coomassie stained PAGE gels and Western analysis with murine anti-OPG antibody.

Fc/huOPG [22–401]

Expression of the Fc/hu OPG [22–401] fusion peptide was detected on a Coomassie stained PAGE gel and on a Western blot. The cells have very large inclusion bodies, and the majority of the product is in the insoluble (pellet) fraction. The following primers were used to construct this OPG-Fc fusion:
1318-48:
CAG CCC GGG TAA AAT GGA AAC GTT TCC TCC AAA ATA TCT TCA TT (SEQ ID NO:107)
1318-49:
CGT TTC CAT TTT ACC CGG GCT GAG CGA GAG GCT CTT CTG CGT GT (SEQ ID NO:108)

Fc/muOPG [22–401]

Expression of the fusion peptide was detected on a Coomassie stained gel and on a Western blot. The cells have very large inclusion bodies, and the majority of the product is in the insoluble (pellet) fraction. The following primers were used to construct this OPG-Fc fusion:
1318-50:
CGC TCA GCC CGG GTA AAA TGG AAA CGT TGC CTC CAA AAT ACC TGC (SEQ ID NO:109)
1318-51:
CCA TTT TAC CCG GGC TGA GCG AGA GGC TCT TCT GCG TGT (SEQ ID NO:110)

muOPG [22–401]/Fc

Expression of the fusion peptide was detected on a Coomassie stained gel and on a Western blot. The amount of recombinant product was less than the OPG fusion proteins having the Fc region in the N terminal position. Obvious inclusion bodies were not detected. Most of the product appeared to be in the insoluble (pellet) fraction. The following primers were used to construct this OPG-Fc fusion:

1318-54:
GAA AAT AAG CTG CTT AGC TGC AGC TCA ACC AAA ATC (SEQ ID NO:111)
1318-55:
CAG CTG CAG CTA AGC AGC TTA TTT TCA CGG ATT G (SEQ ID NO: 112) huOPG [22–401]/Fc

Expression of the fusion peptide was not detected on a Coomassie stained gel, although a faint Western positive signal was present. Obvious inclusion bodies were not detected. The following primers were used to prepare this OPG-Fc fusion:

1318-52:
AAA AAT AAG CTG CTT AGC TGC AGC TGA ACC AAA ATC (SEQ ID NO:113)
1318-53:
CAG CTG CAG CTA AGC AGC TTA TTT TTA CTG ATT GG (SEQ ID NO:114)

V. Human OPG met[22–401]-Fc fusion (P25A)

This construct combines a proline to alanine amino acid change at position 25 (P25A) with the huOPG met[22–401]-Fc fusion. The plasmid was digested with restriction endonucleases ClaI and KpnI, which removes the N-terminal 28 codons of the gene, and the resulting small (less than 200 base pair) fragment was gel purified. This fragment containing the proline to alanine change was then ligated into plasmid pAMG21-huOPG [22–401]-Fc fusion which had been digested with the two restriction endonucleases. The ligated DNA was transformed into competent host cells of *E. coli* strain 393. Clones were screened for the ability to produce the recombinant protein product and to possess the gene fusion having the correct nucleotide sequence. Protein expression levels were determined from 50 ml shaker flask studies. Whole cell lysate and sonic pellet were analyzed for expression of the construct by Coomassie stained PAGE gels and Western analysis with murine anti-OPG antibody. The expression level of the fusion peptide was detected on a Coomassie stained PAGE gel and on a Western blot. The protein was in the insoluble (pellet) fraction. The cells had large inclusion bodies.

W. Human OPG met[22–401] (P25A)

A DNA sequence coding for an N-terminal methionine and amino acids 22 through 401 of human OPG with the proline at position 25 being substituted by alanine under control of the lux PR promoter in prokaryotic expression vector pAMG21 was constructed as follows: Synthetic oligos # 1289-84 and 1289–85 were annealed to form an oligo linker duplex with XbaI and KpnI cohesive ends. The synthetic linker duplex utilized optimal *E. coli* codons and encoded an N-terminal methionine. The linker also included an SpeI restriction site which was not present in the original sequence. The linker duplex was directionally inserted between the xbaI and KpnI sites in pAMG21-huOPG-22–401 using standard methods. The ligation mixture was introduced into *E. coli* host GM221 by transformation. Clones were initially screened for production of the recombinant protein. Plasmid DNA was isolated from positive clones and DNA sequencing was performed to verify the DNA sequence of the HuOPG-Met[22–401] (P25A) gene.

The following oligonucleotides were used to generate the XbaI-KpnI linker:

Oligo #1289-84:
5'-CTA GAA GGA GGA ATA ACA TAT GGA AAC TTT TGC TCC AAA ATA TCT TCA TTA TGA TGA AGA AAC TAG TCA TCA GCT GCT GTG TGA TAA ATG TCC GCC GGG TAC -3' (SEQ ID NO:115)
Oligo #1289-85:
5'-CCG GCG GAC ATT TAT CAC ACA GCA GCT GAT GAC TAG TTT CTT CAT CAT AAT GAA GAT ATT TTG GAG CAA AAG TTT CCA TAT GTT ATT CCT CCT T-3' (SEQ ID NO:116)

X. Human OPG met[22–401] (P26A) and (P26D)

A DNA sequence coding for an N-terminal methionine and amino acids 22 through 401 of human OPG with the proline at position 26 being substituted by alanine under control of the lux $P_R$ promoter in prokaryotic expression vector pAMG21 was constructed as follows: Synthetic oligos # 1289-86 and 1289-87 were annealed to form an oligo linker duplex with XbaI and SpeI cohesive ends. The synthetic linker duplex utilized optimal *E. coli* codons and encoded an N-terminal methionine. The linker duplex was directionally inserted between the XbaI and SpeI sites in pAMG21-huOPG[22–401] (P25A) using standard methods. The ligation mixture was introduced into *E. coli* host GM221 by transformation. Clones were initially screened for production of the recombinant protein. Plasmid DNA was isolated from positive clones and DNA sequencing was performed to verify the DNA sequence of the huOPG-met [22–401] (P26A) gene. One of the clones sequenced was found to have the proline at position 26 substituted by aspartic acid rather than alanine, and this clone was designated huOPG-met[22–401] (P26D). The following oligonucleotides were used to generate the XbaI-SpeI linker:

Oligo #1289-86:
5'-CTA GAA GGA GGA ATA ACA TAT GGA AAC TTT TCC TGC TAA ATA TCT TCA TTA TGA TGA AGA AA-3' (SEQ ID NO:117)
Oligo #1289-87:
5'-CTA GTT TCT TCA TCA TAA TGA AGA TAT TTA GCA GGA AAA GTT TCC ATA TGT TAT TCC TCC TT-3' (SEQ ID NO:118)

Y. Human OPG met[22–194] (P25A)

A DNA sequence coding for an N-terminal methionine nd amino acids 22 through 194 of human OPG with the proline at position 25 being substituted by alanine under control of the lux $P_R$ promoter in prokaryotic expression vector pAMG21 was constructed as follows: The plasmids pAM21-huOPG[27–194] and pAMG21-huOPG[22–401] (P25A) were each digested with KpnI and BamHI endonucleases. The 450 bp fragment was isolated from pAMG21-huOPG[27–194] and the 6.1 kbp fragment was isolated from pAMG21-huOPG[22–401] (P25A). These fragments were ligated together and introduced into *E. coli* host GM221 by transformation. Clones were initially screened for production of the recombinant protein. Plasmid DNA was isolated from positive clones and DNA sequencing was performed to verify the DNA sequence of the huOPG-Met[22–194] (P25A) gene.

EXAMPLE 9

Association of OPG Monomers

CHO cells engineered to overexpress muOPG [22–401] were used to generate conditioned media for the analysis of secreted recombinant OPG using rabbit polyclonal anti-OPG antibodies. An aliquot of conditioned media was concentrated 20-fold, then analysed by reducing and non-reducing SDS-PAGE (FIG. 15). Under reducing conditions, the protein migrated as a Mr 50–55 kd polypeptide, as would be predicted if the mature product was glycosylated at one or more of its consensus N-linked glycosylation sites. Suprisingly, when the same samples were analysed by non-reducing SDS-PAGE, the majority of the protein migrated as an approximately 100 kd polypeptide, twice the size of the reduced protein. In addition, there was a smaller amount of the Mr 50–55 kd polypeptide. This pattern of migration on SDS-PAGE was consistent with the notion that the OPG product was forming dimers through oxidation of a free sulfhydryl group(s).

The predicted mature OPG polypeptide contains 23 cysteine residues, 18 of which are predicted to be involved in forming intrachain disulfide bridges which comprise the four cysteine-rich domains (FIG. 12A). The five remaining C-terminal cysteine residues are not involved in secondary structure which can be predicted based upon homology with other TNFR family members. overall there is a net uneven number of cysteine residues, and it is formally possible that at least one residue is free to form an intermolecular disulfide bond between two OPG monomers.

To help elucidate patterns of OPG kinesis and monomer association, a pulse-chase labelling study was performed. CHO cells expressing muOPG [22–401] were metabolically labelled as described above in serum-free medium containing $^{35}$S methionine and cysteine for 30 min. After this period, the media was removed, and replaced with complete medium containing unlabelled methionine and cysteine at levels approximately 2,000-fold excess to the original concentration of radioactive amino acids. At 30 min, 1 hr, 2 hr, 4 hr, 6 hr and 12 hr post addition, cultures were harvested by the removal of the conditioned media, and lysates of the conditioned media and adherent monolayers were prepared. The culture media and cell lysates were clarified as described above, and then immunoprecipitated using anti-OPG antibodies as described above. After the immunoprecipitates were washed, they were released by boiling in non-reducing SDS-PAGE buffer then split into two equal halves. To one half, the reducing agent β-mercaptothanol was added to 5% (v/v) final concentration, while the other half was maintained in non-reducing conditions. Both sets of immunoprecipitates were analysed by SDS-PAGE as described above, then processed for autoradiography and exposed to film. The results are shown in FIG. 16. The samples analysed by reducing SDS-PAGE are depicted in the bottom two panels. After synthesis, the OPG polypeptide is rapidly processed to a slightly larger polypeptide, which probably represents modification by N-linked glycoslyation. After approximately 1–2 hours, the level of OPG in the cell decreases dramatically, and concomitantly appears in the culture supernatant. This appears to be the result of the vectoral transport of OPG from the cell into the media over time, consistent with the notion that OPG is a naturally secreted protein. Analysis of the same immunoprecipitates under nonreducing conditions reveals the relationship between the formation of OPG dimers and secretion into the conditioned media (FIG. 16, upper panels). In the first 30–60 minutes, OPG monomers are processed in the cell by apparent glycoslylation, followed by dimer formation. Over time, the bulk of OPG monomers are driven into dimers, which subsequently disappear from the cell. Beginning about 60 minutes after synthesis, OPG dimers appear in the conditioned media, and accumulate over the duration of the experiment. Following this period, OPG dimers are formed, which are then secreted into the culture media. OPG monomers persist at a low level inside the cell over time, and small amounts also appear in the media. This does not appear to be the result of breakdown of covalent OPG dimers, but rather the production of sub-stoichiometric amounts of monomers in the cell and subsequent secretion.

Recombinantly produced OPG from transfected CHO cells appears to be predominantly a dimer. To determine if dimerization is a natural process in OPG synthesis, we analysed the conditioned media of a cell line found to naturally express OPG. The CTLL-2 cell line, a murine cytotoxic T lymphocytic cell line (ATCC accession no. TIB-214), was found to express OPG mRNA in a screen of tissue and cell line RNA. The OPG transcript was found to be the same as the cloned and sequenced 2.5–3.0 kb RNA identified from kidney and found to encode a secreted molecule. Western blot analysis of conditioned media obtained from CTLL-2 cells shows that most, if not all, of the OPG secreted is a dimer (FIG. 17). This suggests that OPG dimerization and secretion is not an artifact of over-expression in a cell line, but is likely to be the main form of the product as it is produced by expressing cells.

Normal and transgenic mouse tissues and serum were analysed to determine the nature of the OPG molecule expressed in OPG transgenic mice. Since the rat OPG cDNA was expressed under the control of a hepatocyte control element, extracts made from the parenchyma of control and transgenic mice under non-reducing conditions were analysed (FIG. 18). In extract from transgenic, but not control mice, OPG dimers are readily detected, along with substoichiometric amounts of monomers. The OPG dimers and monomers appear identical to the recombinant murine protein expressed in the genetically engineered CHO cells. This strongly suggests that OPG dimers are indeed a natural form of the gene product, and are likely to be key active components. Serum samples obtained from control and transgenic mice were similarly analysed by western blot analysis. In control mice, the majority of OPG migrates as a dimer, while small amounts of monomer are also detected. In addition, significant amounts of a larger OPG related protein is detected, which migrates with a relative molecular mass consistent with the predicted size of a covalently-linked trimer. Thus, recombinant OPG is expressed predominantly as a dimeric protein in OPG transgenic mice, and the dimer form may be the basis for the osteopetrotic phenotype in OPG mice. OPG recombinant protein may also exist in higher molecular weight "trimeric" forms.

To determine if the five C-terminal cysteine residues of OPG play a role in homodimerization, the murine OPG codons for cytsteine residues 195 (C195), C202, C277, C319, and C400 were changed to serine using the Quick-Change™ Site-Directed Mutagenesis Kit (Stratagene, San Diego, Calif.) as described above. The muOPG gene was subcloned between the Not I and Xba I sites of the pcDNA 3.1 (+) vector (Invitrogen, San Diego, Calif.). The resulting plasmid, pcDNA3.1-muOPG, and mutagenic primers were treated with Pfu polymerase in the presence of deoxynucleotides, then amplified in a thermocycler as described above. An aliqout of the reaction is then transfected into competent *E. coli* XL1-Blue by heatshock, then plated. Plasmid DNA from transformants was then sequenced to verify mutations.

The following primer pairs were used to change the codon for cysteine residue 195 to serine of the murine OPG gene, resulting in the production of a muOPG [22–401] C195S protein:

1389-19:
5'-CAC GCA AAA GTC GGG AAT AGA TGT CAC-3' (SEQ ID NO:150)

1406-38:
5'-GTG ACA TCT ATT CCC GAC TTT TGC GTG-3' (SEQ ID NO:151)

The following primer pairs were used to change the codon for cysteine residue 202 to serine of the murine OPG gene, resulting in the production of a muOPG [22–401] C202S protein:

1389-21:
5'-CAC CCT GTC GGA AGA GGC CTT CTT C-3' (SEQ ID NO:152)

1389-22:
5'-GAA GAA GGC CTC TTC CGA CAG GGT G-3' (SEQ ID NO:153)

The following primer pairs were used to change the codon for cysteine residue 277 to serine of the murine OPG gene, resulting in the production of a muOPG [22–401] C277S protein:

1389-23:
5'-TGA CCT CTC GGA AAG CAG CGT GCA-3' (SEQ ID NO:154)

1389-24:
5'-TGC ACG CTG CTT TCC GAG AGG TCA-3' (SEQ ID NO:155)

The following primer pairs were used to change the codon for cysteine residue 319 to serine of the murine OPG gene, resulting in the production of a muOPG [22–401] C319S protein:

1389-17:
5'-CCT CGA AAT CGA GCG AGC AGC TCC-3' (SEQ ID NO:156)

1389-18:
5'-CGA TTT CGA GGT CTT TCT CGT TCT C-3' (SEQ ID NO:157)

The following primer pairs were used to change the codon for cysteine residue 400 to serine of the murine OPG gene, resulting in the production of a muOPG [22–401] C400S protein:

1406-72:
5'-CCG TGA AAA TAA GCT CGT TAT AAC TAG GAA TGG-3' (SEQ ID NO:158)

1406-75:
5'-CCA TTC CTA GTT ATA ACG AGC TTA TTT TCA CGG-3' (SEQ ID NO:159)

Each resulting muOPG [22–401] plasmid containing the appropriate mutation was then transfected into human 293 cells, the mutant OPG-Fc fusion protein purified from conditioned media as described above. The biological activity of each protein was assessed the in vitro osteoclast forming assay described in example 11. Conditioned media from each transfectant was analysed by non-reducing SDS-PAGE and western blotting with anti-OPG antibodies.

Mutation of any of the five C-terminal cysteine residues results in the production of predominantly (>90%) monomeric 55 kd OPG molecules. This strongly suggests that the C-terminal cysteine residues together play a role in OPC homodimerization.

C-terminal OPG deletion mutants were constructed to map the region(s) of the OPG C-terminal domain which are important for OPG homodimerization. These OPG mutants were constructed by PCR amplification using primers which introduce premature stop translation signals in the C-terminal region of murine OPG. The 5' oligo was designed to the MuOPG start codon (containing a HindIII restriction site) and the 3' oligonucleotides (containing a stop codon and XhoI site) were designed to truncate the C-terminal region of muOPG ending at either threonine residue 200 (CT 200), proline 212 (CT212), glutamic acid 293 (CT-293), or serine 355 (CT-355).

The following primers were used to construct muOPG [22–200]:

1091-39:
5'-CCT CTG AGC TCA AGC TTC CGA GGA CCA CAA TGA ACA AG-3' (SEQ ID NO:160)

1391-91:
5'-CCT CTC TCG AGT CAG GTG ACA TCT ATT CCA CAC TTT TGC GTG GC-3' (SEQ ID NO:161)

The following primers were used to construct muOPG [22–212]:

1091-39:
5'-CCT CTG AGC TCA AGC TTC CGA GGA CCA CAA TGA ACA AG-3' (SEQ ID NO:162)

1391-90:
5'-CCT CTC TCG AGT CAA GGA ACA CCA AAC CTG AAG AAG GC-3' (SEQ ID NO:163)

The following primers were used to construct muOPG [22–293]:

1091-39:
5'-CCT CTG AGC TCA AGC TTC CGA GGA CCA CAA TGA ACA AG-3' (SEQ ID NO:164)

1391-89:
5'-CCT CTC TCG AGT CAC TCT GTG GTG AGG TTC GAG TGG CC-3' (SEQ ID NO:165)

The following primers were used to construct muOPG [22–355]:

1091-39:
5'-CCT CTG AGC TCA AGC TTC CGA GGA CCA CAA TGA ACA AG-3' (SEQ ID NO:166)

1391-88:
5' CCT CTC TCG AGT CAG GAT GTT TTC AAG TGC TTG AGG GC-3' (SEQ ID NO:167)

Each resulting muOPG-CT plasmid containing the appropriate truncation was then transfected into human 293 cells, the mutant OPG-Fc fusion protein purified from conditioned media as described above. The biological activity of each protein was assessed the in vitro osteoclast forming assay described in example 11. The conditioned medias were also analysed by non-reducing SDS-PAGE and western blotting using anti-OPG antibodies.

Truncation of the C-terminal region of OPG effects the ability of OPG to form homodimers. CT 355 is predominantly monomeric, although some dimer is formed. CT 293 forms what appears to be equal molar amounts of monomer and dimer, and also high molecular weight aggregates. However, CT 212 and CT 200 are monomeric.

EXAMPLE 10

Purification of OPG

A. Purification of Mammalian OPG-Fc Fusion Proteins 5 L of conditioned media from 293 cells expressing an OPG-Fc fusion protein were prepared as follows. A frozen sample of cells was thawed into 10 ml of 293S media (DMEM-high glucose, 1× L-glutamine, 10% heat inactivated fetal bovine serum (FBS) and 100 ug/ml hygromycin) and fed with fresh media after one day. After three days, cells were split into two T175 flasks at 1:10 and 1:20 dilutions. Two additional 1:10 splits were done to scale up to 200 T175 flasks. Cells were at days post-thawing at this point. Cells were grown to near confluency (about three days) at which time serum-containing media was aspirated, cells were washed one time with 25 ml PBS per flask and 25 ml of SF media (DMEM-high glucose, 1× L-glutamine) was added to each flask. Cells were maintained at 5% CO2 for three days at which point the media was harvested, centrifuged, and filtered through 0.45 m cellulose nitrate filters (Corning).

OPG-Fc fusion proteins were purified using a Protein G Sepharose column (Pharmacia) equilibrated in PBS. The column size varied depending on volume of starting media. Conditioned media prepared as described above was loaded onto the column, the column washed with PBS, and pure protein eluted using 100 mM glycine pH 2.7. Fractions were collected into tubes containing 1M Tris pH 9.2 in order to neutralize as quickly as possible. Protein containing fractions were pooled, concentrated in either an Amicon Centricon 10 or Centriprep 10 and diafiltered into PBS. The pure protein is stored at −80° C.

Murine [22–401]-Fc, Murine [22–180]-Fc, Murine [22–194]-Fc, human [22–401]-Fc and human [22–201]Fc were purified by this procedure. Murine [22–185]-Fc is purified by this procedure.

B. Preparation of Anti-OPG Antibodies

Three New Zealand White rabbits (5–8 lbs initial wt) were injected subcutaneously with muOPG[22–401]-Fc fusion protein. Each rabbit was immunized on day 1 with 50 µg of antigen emulsified in an equal volume of Freunds complete adjuvant. Further boosts (Days 14 and 28) were performed by the same procedure with the substitution of Freunds incomplete adjuvant. Antibody titers were monitored by EIA. After the second boost, the antisera revealed high antibody titers and 25 ml production bleeds were obtained from each animal. The sera was first passed over an affinity column to which murine OPG-Fc had be immobilized. The anti-OPG antibodies were eluted with Pierce Gentle Elution Buffer containing 1% glacial acetic acid. The eluted protein was then dialyzed into PBS and passed over a FC column to remove any antibodies specific for the Fc portion of the OPG fusion protein. The run through fractions containing anti-OPG specific antibodies were dialyzed into PBS.

C. Purification of Murine OPG[22–401]

Antibody Affinity Chromatography

Affinity purified anti-OPG antibodies were diafiltered into coupling buffer (0.1M sodium carbonate pH 8.3, 0.5M NaCl), and mixed with CNBr-activated sepharose beads (Pharmacia) for two hours at room temperature. The resin was then washed with coupling buffer extensively before blocking unoccupied sited with 1M ethanolamine (pH 8.0) for two hours at room temperature. The resin was then washed with low pH (0.1M sodium acetate pH 4.0, 0.5M NaCl) followed by a high pH wash (0.1M Tris-HCl pH 8.0, 0.5M NaCl). The last washes were repeated three times. The resin was finally equilibrated with PBS before packing into a column. Once packed, the resin was washed with PBS. A blank elution was performed with 0.1M glycine-HCl, pH 2.5), followed by re-equilibration with PBS.

Concentrated conditioned media from CHO cells expressing muOPG[22–410] was applied to the column at a low flow rate. The column was washed with PBS until UV absorbance measured at 280 nm returned to baseline. The protein was eluted from the column first with 0.1M glycine-HCl (pH 2.5), re-equilibrated with PBS, and eluted with a second buffer (0.1M CAPS, pH 10.5) , 1M NaCl). The two elution pools were diafiltered separately into PBS and sterile filtered before freezing at −20° C.

Conventional Chromatography

CHO cell conditioned media was concentrated 23× in an Amicon spiral wound cartridge (S10Y10) and diafiltered into 20 mM tris pH 8.0. The diafiltered media was then applied to a Q-sepharose HP (Pharmacia) column which had been equilibrated with 20 mM tris pH 8.0. The column was then washed until absorbance at 280 nm reached baseline. Protein was eluted with a 20 column volume gradient of 0–300 mM NaCl in tris pH 8.0. OPG was detected using a western blot of column fractions.

Fractions containing OPG were pooled and brought to a final concentration of 300 mM NaCl, 0.2 mM DTT. A NiNTA superose (Qiagen) column was equilibrated with 20 mM tris pH 8.0, 300 mM NaCl, 0.2 mM DTT after which the pooled fractions were applied. The column was washed with equilibration buffer until baseline absorbence was reached. Proteins were eluted from the column with a 0–30 mM Imidazole gradient in equilibration buffer. Remaining proteins were washed off the column with 1M Imidazole. Again a western blot was used to detect OPG containing fractions.

Pooled fractions from the NiNTA column were dialyzed into 10 mm potassium phosphate pH 7.0, 0.2 mM DTT. The dialyzed pool was then applied to a ceramic hydroxyapatite column (Bio-Rad) which had been equilibrated in 10 mM phosphate buffer. After column washing, the protein was eluted with a 10–100 mM potassium phosphate gradient over 20 column volumes. This was then followed by a 20 column volume gradient of 100–400 mM phosphate.

OPG was detected by coomassie blue staining of SDS-polyacrylamide gels and by western blotting. Fractions were pooled and diafiltered onto PBS and frozen at −80° C. The purified protein runs as a monomer and will remain so after diafiltration into PBS. The monomer is stable when stored frozen or at pH 5 at 4° C. However if stored at 4° C. in PBS, dimers and what appears to be trimers and tetramers will form after one week.

D. Purification of Human OPG met[22–401] from *E. coli*

The bacterial cell paste was suspended into 10 mM EDTA to a concentration of 15% (w/v) using a low shear homogenizer at 5° C. The cells were then disrupted by two homogenizations at 15,000 psi each at 5° C. The resulting homogenate was centrifuged at 5,000×g for one hour at 5° C. The centrifugal pellet was washed by low shear homogenization into water at the original homogenization volume followed by centrifugation as before. The washed pellet was then solubilized to 15% (w/v) by a solution of (final concentration) 6 M guanidine HCl, 10 mM dithiothreitol, 10 mM TrisHCl, pH 8.5 at ambient temperature for 30 minutes. This solution was diluted 30-fold into 2M urea containing 50 mM CAPS, pH 10.5, 1 mM reduced glutathione and then stirred for 72 hours at 5° C. The OPG was purified from this solution at 25° C. by first adjustment to pH 4.5 with acetic acid and then chromatography over a column of SP-HP Sepharose resin equilibrated with 25 mM sodium acetate, pH 4.5. The column elution was carried out with a linear sodium chloride gradient from 50 mM to 550 mM in the same buffer using 20 column volumes at a flow rate of 0.1 column volumes/minute. The peak fractions containing only the desired OPG form were pooled and stored at 5° C. or buffer exchanged into phosphate buffered saline, concentrated by ultrafiltration, and then stored at 50° C. This material was analyzed by reverse phase HPLC, SDS-PAGE, limulus amebocyte lysate assay for the presence of endotoxin, and N-terminal sequencing. In addition, techniques such as mass spectrometry, pH/temperature stability, fluoresence, circular dichroism, differential scanning calorimetry, and protease profiling assays may also be used to examine the folded nature of the protein.

EXAMPLE 11

Biological Activity of Recombinant OPG Based on histology and histomorphometry, it appeared that hepatic overexpression of OPG in transgenic mice markedly decreased the numbers of osteoclasts leading to a marked increase in bone tissue (see Example 4). To gain further insight into potential mechanism(s) underlying this in vivo effect, various forms of recombinant OPG have been tested in an in vitro culture model of osteoclast formation (osteoclast forming assay). This culture system was originally devised by Udagawa (Udagawa et al. Endocrinology 125, 1805–1813 (1989), Proc. Natl. Acad. Sci. USA 87, 7260–7264 (1990)) and employs a combination of bone marrow cells and cells from bone marrow stromal cell lines. A description of the modification of this culture system used for these studies has been previously published (Lacey et al. Endocrinology 136, 2367–2376 (1995)). In this method, bone marrow cells, flushed from the femurs and tibiae of mice, are cultured overnight in culture media (alpha MEM with 10% heat inactivated fetal bovine serum) supplemented with 500 U/ml CSF-1 (colony stimulating factor 1, also called M-CSF), a hematopoietic growth factor specific for cells of the monocyte/macrophage family lineage. Following this incubation, the non-adherent cells are collected, subjected to gradient purification, and then cocultured with cells from the bone marrow cell line ST2 ($1\times10^6$ non-adherent cells: $1\times10^5$ ST2 cells/ml media). The media is supplemented with dexamethasone (100 nM) and the biologically-active metabolite of vitamin D3 known as 1,25 dihydroxyvitamin D3 (1,25 (OH)2 D3, 10 nM). To enhance osteoclast appearance, prostaglandin E2 (250 nM) is added to some cultures. The coculture period usually ranges from 8–10 days and the media, with all of the supplements freshly added, is renewed every 3–4 days. At various intervals, the cultures are assessed for the presence of tartrate acid phosphatase (TRAP) using either a histochemical stain (Sigma Kit # 387A, Sigma, St. Louis, Mo.) or TRAP solution assay. The TRAP histochemical method allows for the identification of osteoclasts phenotypically which are multinucleated (° 3 nuclei) cells that are also TRAP+. The solution assay involves lysing the osteoclast-containing cultures in a citrate buffer (100 mM, pH 5.0) containing 0.1% Triton X-100. Tartrate resistant acid phosphatase activity is then measured based on the conversion of p-nitrophenylphosphate (20 nM) to p-nitrophenol in the presence of 80 mM sodium tartrate which occurs during a 3–5 minute incubation at RT. The reaction is terminated by the addition of NaOH to a final concentration of 0.5 M. The optical density at 405 nm is measured and the results are plotted.

Previous studies (Udagawa et al. ibid) using the osteoclast forming assay have demonstrated that these cells express receptors for $^{125}$I-calcitonin (autoradiography) and can make pits on bone surfaces, which when combined with TRAP positivity confirm that the multinucleated cells have an osteoclast phenotype. Additional evidence in support of the osteoclast phenotype of the multinucleated cells that arise in vitro in the osteoclast forming assay are that the cells express αv and β3 integrins by immunocytochemistry and calcitonin receptor and TRAP mRNA by in situ hybridization (ISH).

Figure 19A:
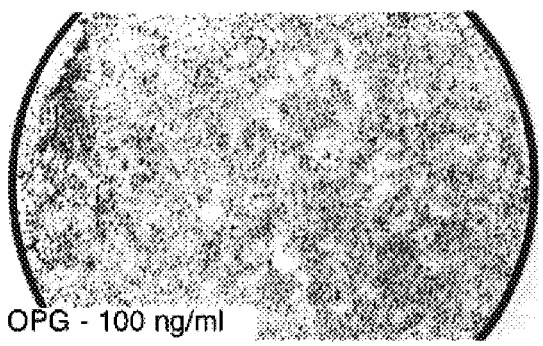
Figure 19B:
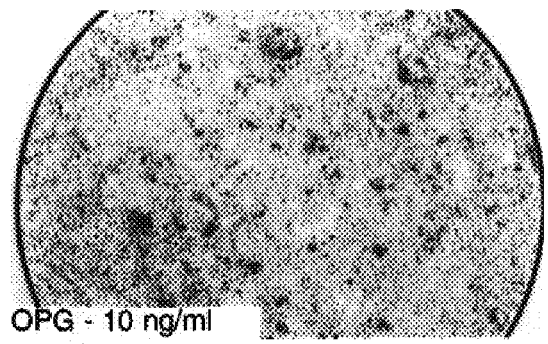
Figure 19C:
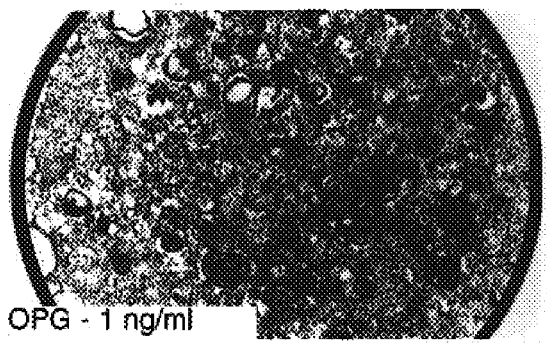
Figure 19D:
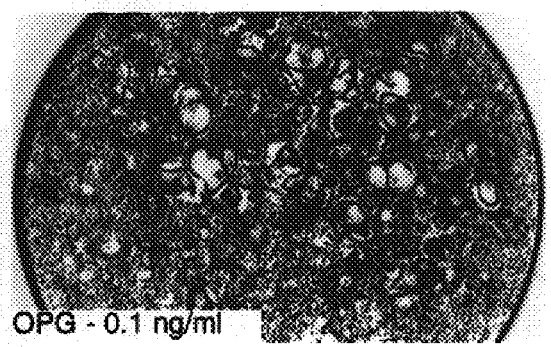
Figure 19E:
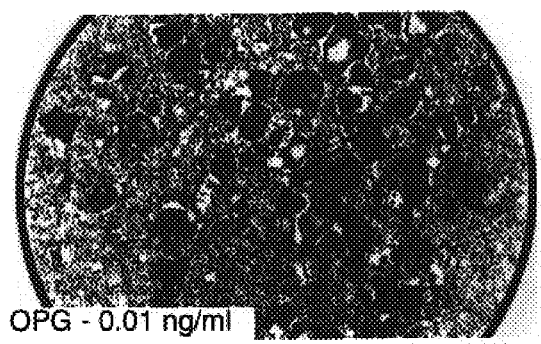
Figure 19F:
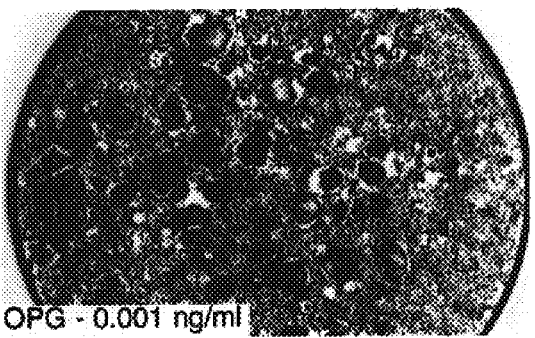
Figure 19G:

The huOPG [22–401]-Fc fusion was purified from CHO cell conditioned media and subsequently utilized in the osteoclast forming assay. At 100 ng/ml of huOPG [22–401]-Fc, osteoclast formation was virtually 100% inhibited (FIG. 19A). The levels of TRAP measured in lysed cultures in microtitre plate wells were also inhibited in the presence of OPG with an $ID_{50}$ of approximately 3 ng/ml (FIG. 20). The level of TRAP activity in lysates appeared to correlate with the relative number of osteoclasts seen by TRAP cytochemistry (compare FIGS. 19A–19G and 20). Purified human IgG1 and TNF-α inhibitor were also tested in this model and were found to have no inhibitory or stimulatory effects suggesting that the inhibitory effects of the huOPG [22–401]-Fc were due to the OPG portion of the fusion protein. Additional forms of the human and murine molecules have been tested and the cumulative data are summarized in Table 3.

TABLE 3

Effects of various OPG forms on in vitro osteoclast formation

| OPG Construct | Relative Bioactivity in vitro |
|---|---|
| muOPG [22-401]-Fc | +++ |
| muOPG [22-194]-Fc | +++ |
| muOPG [22-185]-Fc | ++ |
| muOPG [22-180]-Fc | – |
| muOPG [22-401] | +++ |
| muOPG [22-401] C195 | +++ |
| muOPG [22-401] C202 | + |
| muOPG [22-401] C277 | – |
| muOPG [22-401] C319 | + |
| muOPG [22-401] C400 | + |
| muOPG [22-185] | – |
| muOPG [22-194] | ++ |
| muOPG [22-200] | ++ |
| muOPG [22-212] | – |
| muOPG [22-293] | +++ |
| muOPG [22-355] | +++ |
| huOPG [22-401]-Fc | +++ |
| huOPG [22-201]-Fc | +++ |
| huOPG [22-401]-Fc P26A | +++ |
| huOPG [22-401]-Fc Y28F | +++ |
| huOPG [22-401] | +++ |
| huOPG [27-401]-Fc | ++ |
| huOPG [29-401]-Fc | ++ |
| huOPG [32-401]-Fc | +/– |

+++, $ED_{50}$ = 0.4–2 ng/ml
++, $ED_{50}$ = 2–10 ng/ml
+, $ED_{50}$ = 10–100 ng/ml
–, $ED_{50}$ > 100 ng/ml

The cumulative data suggest that murine and human OPG amino acid sequences 22–401 are fully active in vitro, when either fused to the Fc domain, or unfused. They inhibit in a dose-dependent manner and possess half-maximal activities in the 2–10 ng/ml range. Truncation of the murine C-terminus at threonine residue 180 inactivates the molecule, whereas truncations at cysteine 185 and beyond have full activity. The cysteine residue located at position 185 is predicted to form an SS3 bond in the domain 4 region of OPG. Removal of this residue in other TNFR-related proteins has previously been shown to abrogate biological activity (Yan et al. (1994), *J. Biol. Chem.* 266: 12099–104). Our finding that muOPG[22–180]-Fc is inactive while muOPG[22–185]-Fc is active is consistent with these findings. This suggests that amino acid residues 22–185 define a region for OPG activity.

These findings indicate that like transgenically-expressed OPG, recombinant OPG also suppressed osteoclast formation as tested in the osteoclast forming assay. Time course experiments examining the appearance of TRAP+ cells, β3+ cells, F480+ cells in cultures continuously exposed to OPG demonstrate that OPG blocks the appearance TRAP+ and β3+ cells, but not F480+ cells. In contrast, TRAP+ and β3+ cells begin to appear as early as day 4 following culture establishment in control cultures. Only F480+ cells can be found in OPG-treated cultures and they appear to be present at qualitatively the same numbers as the control cultures. Thus, the mechanism of OPG effects in vitro appears to involve a blockade in osteoclast differentiation at a step beyond the appearance of monocyte-macrophages but before the appearance of cells expressing either TRAP or β3 integrins. Collectively these findings indicate that OPG does not interfere with the general growth and differentiation of monocyte-macrophage precursors from bone marrow, but rather suggests that OPG specifically blocks the selective differentiation of osteoclasts from monocyte-macrophage precursors.

To determine more specifically when in the osteoclast differentiation pathway that OPG was inhibitory, a variation of the in vitro culture method was employed. This variation, described in (Lacey et al. supra), employs bone marrow macrophages as osteoclast precursors. The osteoclast precursors are derived by taking the nonadherent bone marrow cells after an overnight incubation in CSF-1/M-CSF, and culturing the cells for an additional 4 days with 1,000–2,000 U/ml CSF-1. Following 4 days of culture, termed the growth phase, the non-adherent cells are removed. The adherent cells, which are bone marrow macrophages, can then be exposed for up to 2 days to various treatments in the presence of 1,000–2,000 U/ml CSF-1. This 2 day period is called the intermediate differentiation period. Thereafter, the cell layers are again rinsed and then ST-2 cells ($1 \times 10^5$ cell/ml), dexamethasone (100 nM) and 1,25 (OH)2 D3 (10 nM) are added for the last 8 days for what is termed the terminal differentiation period. Test agents can be added during this terminal period as well. Acquisition of phenotypic markers of osteoclast differentiation are acquired during this terminal period (Lacey et al. ibid).

huOPG [22–401]-Fc (100 ng/ml) was tested for its effects on osteoclast formation in this model by adding it during either the intermediate, terminal or, alternatively, both differentiation periods. Both TRAP cytochemistry and solution assays were performed. The results of the solution assay are shown in FIG. 21. HuOPG [22–401]-Fc inhibited the appearance of TRAP activity when added to both the intermediate and terminal or only the terminal differentiation phases. When added to the intermediate phase and then removed from the cultures by rinsing, huOPG [22–401]-Fc did not block the appearance of TRAP activity in culture lysates. The cytochemistry results parallel the solution assay data. Collectively, these observations indicate that huOPG [22–401]-Fc only needs to be present during the terminal differentiation period for it to exert its all of its suppressive effects on osteoclast formation.

B. In Vivo IL-1-α and IL-1-β Challenge Experiments

IL-1 increases bone resorption both systemically and locally when injected subcutaneously over the calvaria of mice (Boyce et al. (1989), *Endocrinology* 125: 1142–50). The systemic effects can be assessed by the degree of hypercalcemia and the local effects histologically by assessing the relative magnitude of the osteoclast-mediated response. The aim of these experiments was to determine if recombinant muOPG [22–401]-Fc could modify the local and/or systemic actions of IL-1 when injected subcutaneously over the same region of the calvaria as IL-1.

IL-1β Experiment

Male mice (ICR Swiss white) aged 4 weeks were divided into the following treatment groups (5 mice per group): Control group: IL-1 treated animals (mice received 1 injection/day of 2.5 ug of IL-1β); Low dose muOPG [22–401]-Fc treated animals (mice received 3 injections/day of 1 μg of muOPG [22–401]-Fc); Low dose MuOPG [22–401]-Fc and IL-1-β; High dose muOPG [22–401]-Fc treated animals (mice receive 3 injections/day of 10 μg muOPG [22–401]-Fc); High dose muOPG [22–401]-Fc and IL-1-β. All mice received the same total number of injections of either active factor or vehicle (0.1% bovine serum albumin in phosphate buffered saline). All groups are sacrificed on the day after the last injection. The weights and blood ionized calcium levels are measured before the first injections, four hours after the second injection and 24 hours after the third IL-1 injection, just before the animals were sacrificed. After sacrifice the calvaria were removed and processed for paraffin sectioning.

IL-1α Experiment

Male mice (ICR Swiss white) aged 4 weeks were divided into the following treatment groups (5 mice per group): Control group; IL-1-α treated animals (mice received 1 injection/day of 5 ug of IL-1-α); Low dose muOPG [22–401]-Fc treated animals (mice received 1 injection/day of 10 μg of muOPG [22–401]-Fc; Low dose muopg [22–401]-Fc and IL-1-α, (dosing as above); High dose muopg [22–401]-Fc treated animals (mice received 3 injections/day of 10 μg muOPG [22–401]-Fc; High dose muOPG [22–401]-Fc and IL-1-α. All mice received the same number of injections/day of either active factor or vehicle. All groups were sacrificed on the day after the last injection. The blood ionized calcium levels were measured before the first injection, four hours after the second injection and 24 hours after the third IL-1 injection, just before the animals were sacrificed. The animal weights were measured before the first injection, four hours after the second injection and 24 hours after the third IL-1 injection, just before the animals were sacrificed. After sacrifice the calvaria were removed and processed for paraffin sectioning.

Histological Methods

Calvarial bone samples were fixed in zinc formalin, decalcified in formic acid, dehydrated through ethanol and mounted in paraffin. Sections (5 μm thick) were cut through the calvaria adjacent to the lambdoid suture and stained with either hematoxylin and eosin or reacted for tartrate resistant acid phosphatase activity (Sigma Kit# 387A) and counterstained with hematoxylin. Bone resorption was assessed in the IL-1α treated mice by histomorphometric methods using the Osteomeasure (Osteometrics, Atlanta, Ga.) by tracing histologic features onto a digitizor platen using a microscope-mounted camera lucida attachment. Osteoclast numbers, osteoclast lined surfaces, and eroded surfaces were determined in the marrow spaces of the calvarial bone. The injected and non-injected sides of the calvaria were measured separately.

Results

Figure 22A:
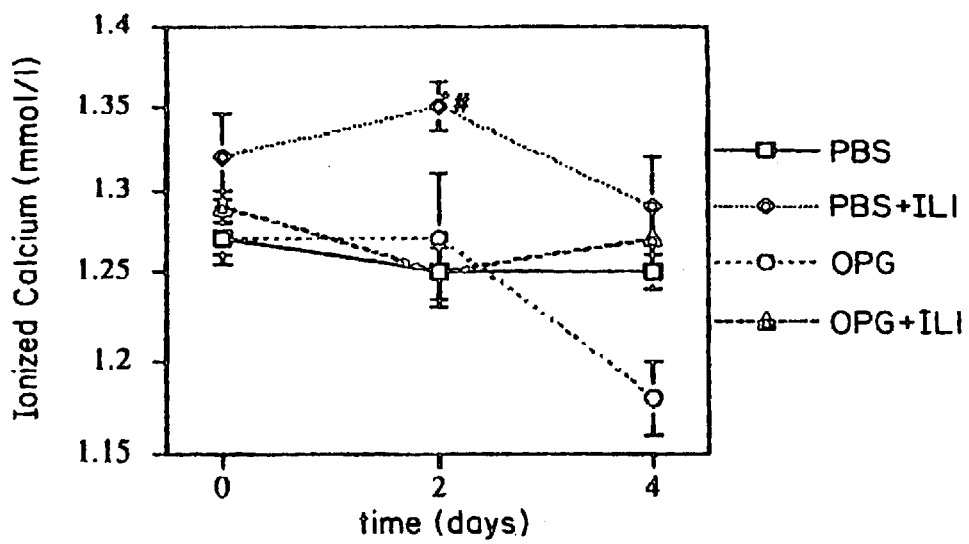
Figure 22B:
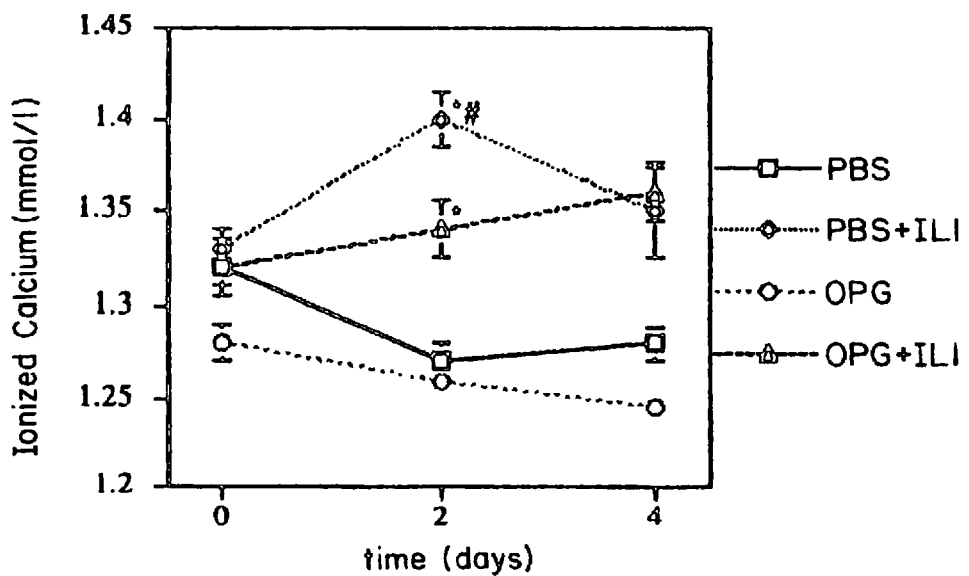

IL-1α and IL-1β produced hypercalcemia at the doses used, particularly on the second day, presumably by the induction of increased bone resorption systemically. The hypercalcemic response was blocked by muOPG [22–401]-Fc in the IL-1 beta treated mice and significantly diminished in mice treated with IL-1-α, an effect most apparent on day 2 (FIGS. 22A–22B).

Figure 23A:
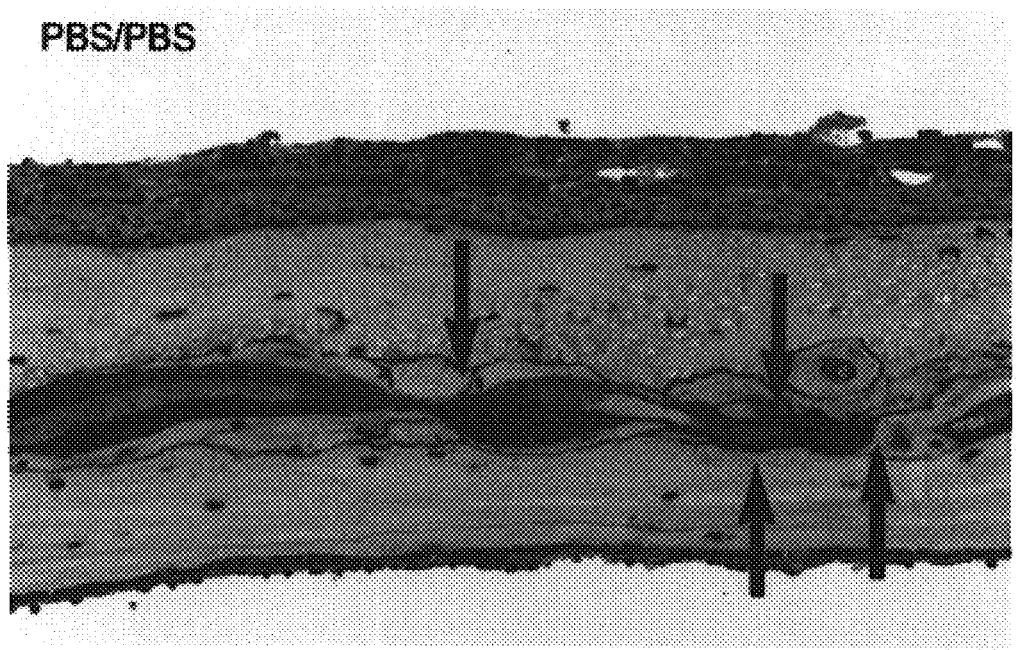
Figure 23B:
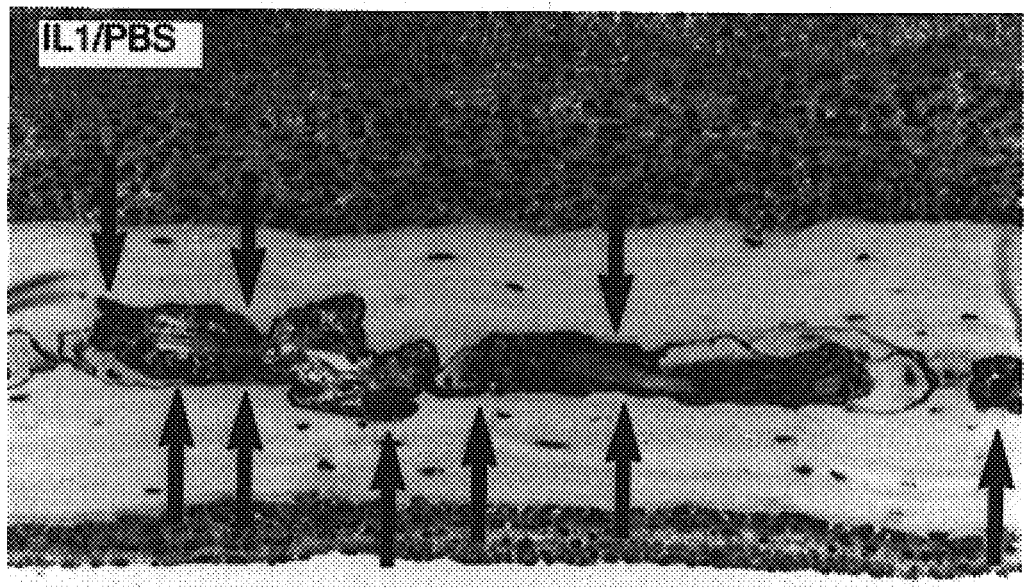
Figure 23C:
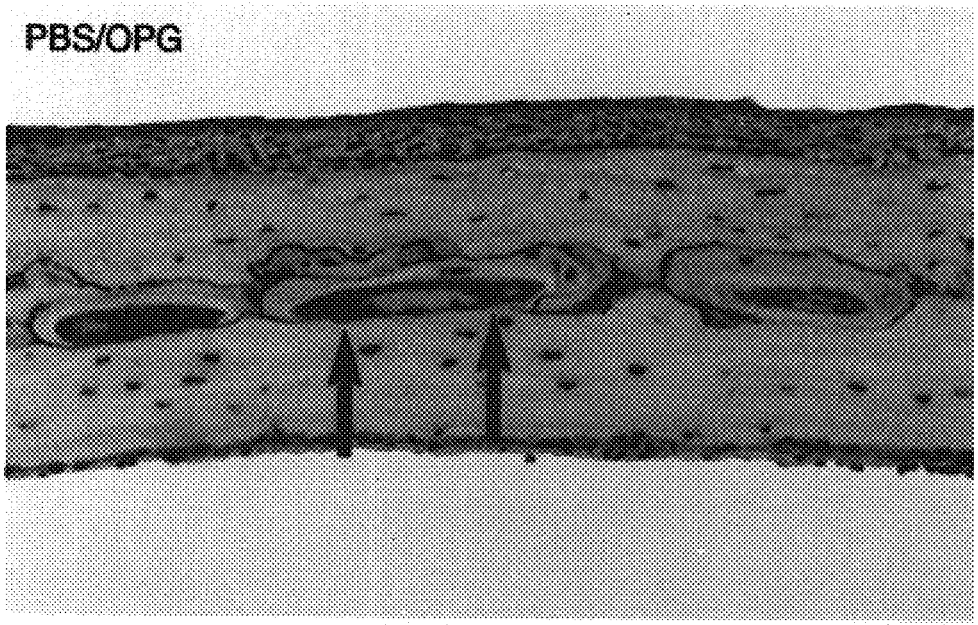
Figure 23D:
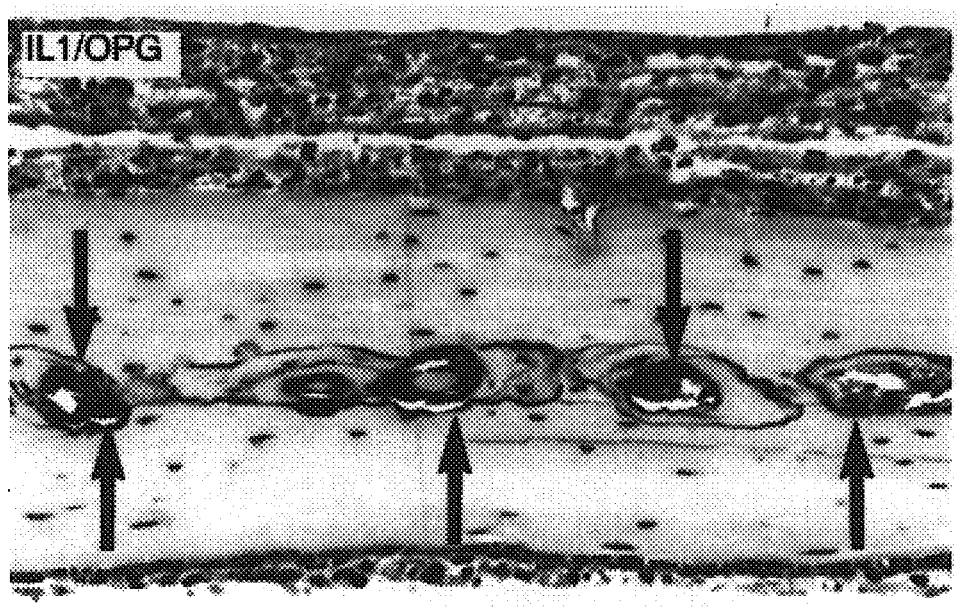

Histologic analysis of the calvariae of mice treated with IL-1-α and beta shows that IL-1 treatments alone produce a marked increase in the indices of bone resorption including: osteoclast number, osteoclast lined surface, and eroded surface (surfaces showing deep scalloping due to osteoclastic action (FIG. 23B). In response to IL-1α or IL-1β, the increases in bone resorption were similar on the injected and non-injected sides of the calvaria. Muopg [22–401]-Fc injections reduced bone resorption in both IL-1-α and beta treated mice and in mice receiving vehicle alone but this reduction was seen only on the muopg [22–401]-Fc injected sides of the calvariae.

The most likely explanation for these observations is that muOPG [22–401]-Fc inhibited bone resorption, a conclusion supported by the reduction of both the total osteoclast number and the percentage of available bone surface undergoing bone resorption, in the region of the calvaria adjacent to the muOPG [22–401]-Fc injection sites. The actions of muOPG [22–401]-Fc appeared to be most marked locally by histology, but the fact that muOPG [22–401]-Fc also blunted IL-1 induced hypercalcemia suggests that muOPG [22–401]-Fc has more subtle effects on bone resorption systemically.

C. Systemic Effects of muOPG [22–401]-Fc in Growing Mice

Male BDF1 mice aged 3–4 weeks, weight range 9.2–15.7 g were divided into groups of ten mice per group. These mice were injected subcutaneously with saline or muOPG [22–401]-Fc 2.5 mg/kg bid for 14 days (5 mg/kg/day). The mice were radiographed before treatment, at day 7 and on day 14. The mice were sacrificed 24 hours after the final injection. The right femur was removed, fixed in zinc formalin, decalcified in formic acid and embedded in paraffin. Sections were cut through the mid region of the distal femoral metaphysis and the femoral shaft. Bone density, by histomorphometry, was determined in six adjacent regions extending from the metaphyseal limit of the growth plate, through the primary and secondary spongiosa and into the femoral diaphysis (shaft). Each region was 0.5×0.5 mm$^2$.

Radiographic Changes

After seven days of treatment there was evidence of a zone of increased bone density in the spongiosa associated with the growth plates in the OPG treated mice relative to that seen in the controls. The effects were particularly striking in the distal femoral and the proximal tibial metaphases (FIGS. 24A–24B). However bands of increased density were also apparent in the vertebral bodies, the iliac crest and the distal tibia. At 14 days, the regions of opacity had extended further into the femoral and tibial shafts though the intensity of the radio-opacity was diminished. Additionally, there were no differences in the length of the femurs at the completion of the experiment or in the change in length over the duration of the experiment implying that OPG does not alter bone growth.

Histological Changes

Figure 26A:
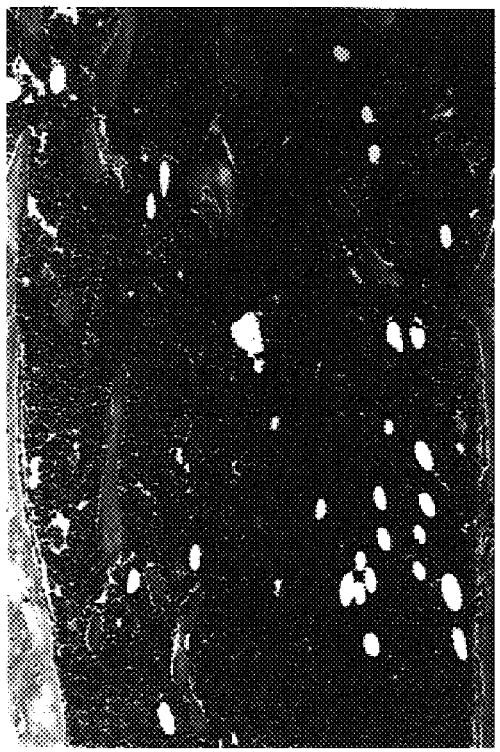
Figure 26B:

The distal femoral metaphysis showed increased bone density in a regions 1.1 to 2.65 mm in distance from the growth plate (FIGS. 25 and 26A–26B). This is a region where bone is rapidly removed by osteoclast-mediated bone resorption in mice. In these rapidly growing young mice, the increase in bone in this region observed with OPG treatment is consistent with an inhibition of bone resorption.

D. Effects of Osteoprotegerin on Bone Loss Induced by Ovariectomy in the Rat

Twelve week old female Fisher rats were ovariectomized (OVX) or sham operated and dual xray absorptiometry (DEXA) measurements made of the bone density in the distal femoral metaphysis. After 3 days recovery period, the animals received daily injections for 14 days as follows: Ten sham operated animals received vehicle (phosphate buffered saline); Ten OVX animals received vehicle (phosphate buffered saline); Six OVX animals received OPG-Fc 5 mg/kg SC; Six OVX animals received pamidronate (PAM) 5 mg/kg SC; Six OVX animals received estrogen (ESTR) 40 ug/kg SC. After 7 and 14 days treatment the animals had bone density measured by DEXA. Two days after the last injection the animals were killed and the right tibia and femur removed for histological evaluation.

The DEXA measurements of bone density showed a trend to reduction in the bone density following ovariectomy that was blocked by OPG-Fc. Its effects were similar to the known antiresorptive agents estrogen and pamidronate. (FIG. 27). The histomorphometric analysis confirmed these observations with OPG-Fc treatment producing a bone density that was significantly higher in OVX rats than that seen in untreated OVX rats (FIG. 28). These results confirm the activity of OPG in the bone loss associated with withdrawal of endogenous estrogen following ovariectomy.

In Vivo Summary

The in vivo actions of recombinant OPG parallel the changes seen in OPG transgenic mice. The reduction in osteoclast number seen in the OPG transgenic is reproduced by injecting recombinant OPG locally over the calvaria in both normal mice and in mice treated with IL-1α or IL-1β. The OPG transgenic mice develop an osteopetrotic phenotype with progressive filling of the marrow cavity with bone and unremodelled cartilage extending from the growth plates from day 1 onward after birth. In normal three week old (growing) mice, OPG treatments also led to retention of bone and unremodelled cartilage in regions of endochondral bone formation, an effect observed radiographically and confirmed histologically. Thus, recombinant OPG produces phenotypic changes in normal animals similar to those seen in the transgenic animals and the changes are consistent with OPG-induced inhibition of bone resorption. Based on in vitro assays of osteoclast formation, a significant portion of this inhibition is due to impaired osteoclast formation. Consistent with this hypothesis, OPG blocks ovariectomy-induced osteoporosis in rat. Bone loss in this model is known to be mediated by activated osteoclasts, suggesting a role for OPG in treatment of primary osteoporosis.

EXAMPLE 12

Pegylation Derivatives of OPG Preparation of N-terminal PEG-OPG Conjugates by Reductive Alkylation HuOPG met [22–194] P25A was buffer exchanged into 25–50 mM NaOAc, pH 4.5–4.8 and concentrated to 2–5 mg/ml. This solution was used to conduct OPG reductive alkylation with monofunctional PEG aldehydes at 5–7 C. PEG monofunctional aldehydes, linear or branched, MW=1 to 57 kDa (available from Shearwater Polymers) were added to the OPG solution as solids in amounts constituting 2–4 moles of PEG aldehyde per mole of OPG. After dissolution of polymer into the protein solution, sodium cyanoborohydride was added to give a final concentration of 15 to 20 mM in the reaction mixture from 1–1.6 M freshly prepared stock solution in cold DI water. The progress of the reaction and the extent of OPG PEGylation was monitored by size exclusion HPLC on a G3000SW$_{XL}$ column (Toso Haas) eluting with 100 mM NaPO$_4$, 0.5 M NaCl, 10% ethanol, pH 6.9. Typically the reaction was allowed to proceed for 16–18 hours, after which the reaction mixture was diluted 6–8 times and the pH lowered to 3.5–4. The reaction mixture was fractionated by ion exchange chromatography (HP SP HiLoad 16/10, Pharmacia) eluting with 20 mM NaOAc pH 4 with a linear gradient to 0.75M NaCl over 25 column volumes at a flow rate of 30 cm/h. Fractions of mono-, di- or poly-PEGylated OPG were pooled and characterized by SEC HPLC and SDS-PAGE. By N-terminal sequencing, it was determined that the monoPEG-OPG conjugate, the major reaction product in most cases, was 98% N-terminally PEG-modified OPG.

This procedure was generally used to prepare the following N-terminal PEG-OPG conjugates (where OPG is HuOPG met [22–194] P25A: 5 kD monoPEG, 10 kD mono branched PEG, 12 kD monoPEG, 20 kD monoPEG, 20 kD mono branched PEG, 25 kD monoPEG, 31 kD monoPEG, 57 kD monoPEG, 12 kD diPEG, 25 kD diPEG, 31 kD diPEG, 57 kD diPEG, 25 kD triPEG.

Preparation of PEG-OPG Conjugates by Acylation

HuOPG met [22–194] P25A was buffer exchanged into 50 mM BICINE buffer, pH 8 and concentrated to 2–3 mg/ml. This solution was used to conduct OPG acylation with monofunctional PEG N-hydroxysuccinimidyl esters at room temperature. PEG N-hydroxysuccinimidyl esters, linear or branched, MW=1 to 57 kDa (available from Shearwater Polymers) were added to the OPG solution as solids in amounts constituting 4–8 moles of PEG N-hydroxysuccinimidyl ester per mole of OPG. The progress of the reaction and the extent of OPG PEGylation was monitored by size exclusion HPLC on a G3000SW$_{XL}$ column (Toso Haas) eluting with 100 mM NaPO4, 0.5 M NaCl, 10% ethanol, pH 6.9. Typically the reaction was allowed to proceed for 1 hour, after which the reaction mixture was diluted 6–8 times and the pH lowered to 3.5–4. The reaction mixture was fractionated by ion exchange chromatography (HP SP HiLoad 16/10, Pharmacia) eluting with 20 mM NaOAc pH 4 with a linear gradient to 0.75M NaCl over 25 column volumes at a flow rate of 30 cm/h. Fractions of mono-, di- or poly- PEGylated OPG were pooled and characterized by SEC HPLC and SDS-PAGE.

This procedure was generally used to prepare the following PEG-OPG conjugates: 5 kD polyPEG, 20 kD polyPEG, 40 kD poly branched PEG, 50 kD poly PEG.

Preparation of Dimeric PEG-OPG

HuOPG met [22–194] P25A is prepared for thiolation at 1–3 mg/ml in a phosphate buffer at near neutral pH. S-acetyl mecaptosuccinic anhydride (AMSA) is added in a 3–7 fold molar excess while maintaining pH at 7.0 and the rxn stirred at 4·C. for 2 hrs. The monothiolated-OPG is separated from unmodified and polythiolated OPG by ion exchange chromatography and the protected thiol deprotected by treatment with hydroxylamine. After deprotection, the hydroxylamine is removed by gel filtration and the resultant monothiolated-OPG is subjected to a variety of thiol specific crosslinking chemistries. To generate a disulfide bonded dimer, the thiolated OPG at >1 mg/ml is allowed to undergo air oxidation by dialysis in slightly basic phosphate buffer. The covalent thioether OPG dimer was prepared by reacting the bis-maleimide crosslinker, N,N-bis(3-maleimido propianyl)-2-hydroxy 1,3 propane with the thiolated OPG at >1 mg/ml at a 0.6× molar ratio of crosslinker:OPG in phosphate buffer at pH 6.5. Similarly, the PEG dumbbells are produced by reaction of substoichiometric amounts of bis-maleimide PEG crosslinkers with thiolated OPG at >1 mg/ml in phosphate buffer at pH 6.5. Any of the above dimeric conjugates may be further purified using either ion exchange or size exclusion chromatographies.

Dimeric PEG-OPG conjugates (where OPG is HuOPG met [22–194] P25A prepared using the above procedures include disulfide-bonded OPG dimer, covalent thioether OPG dimer with an aliphatic amine type crosslinker, 3.4 kD and 8 kD PEG dumbbells and monobells.

PEG-OPG conjugates were tested for activity in vitro using the osteoclast maturation assay described in Example 11A and for activity in vivo by measuring increased bone density after injection into mice as described in Example 11C. The in vivo activity is shown below in Table 2.

TABLE 2

In vivo biological activity of Pegylated OPG

| OPG Construct | Increase in Tibial Bone Density |
|---|---|
| muOPG met [22-194] | − |
| muOPG met [22-194]5k PEG | + |
| muOPG met [22-194]20k PEG | + |
| huOPG met [22-194] P25A | − |
| huOPG met [22-194] P25A 5k PEG | + |
| huOPG met [22-194] P25A 20k PEG | + |
| huOPG met [22-194] P25A 31k PEG | + |
| huOPG met [22-194] P25A 57k PEG | + |
| huOPG met [22-194] P25A 12k PEG | + |
| huOPG met [22-194] P25A 20k Branched PEG | + |
| huOPG met [22-194] P25A 8k PEG dimer | + |
| huOPG met [22-194] P25A disulfide crosslink | + |

EXAMPLE 13

Effects of OPG-Fc During the Course of Adjuvant Arthritis in Lewis rats

The aim of these studies is to investigate whether CHO produced OPG-Fc protects against adjuvant arthritis-associated bone mineral density loss in male Lewis rats.

Animals

Male Lewis rats (Charles River, Wilmington Mass.) 8–9 weeks of age (n=6) at the time of *mycobacteria* in oil injection, were used. Two rats were housed per cage in an air conditioned environment (room temperature 23±2 C, relative humidity 50+20%) that illuminated from 6:30 am to 6:30 p.m. Animals were fed a commercial rodent chow (#8640, Tek Lab, Madison Wis.); calcium and phosphorus contents were 1.2% and 1.0%, respectively. All animals were sacrificed by carbon dioxide inhalation.

Induction and Measurement of Adjuvant Arthritis

Adjuvant arthritis (AdA) was induced by a single injection of a suspension of *Mycobacterium tuberculosis* (Difco Laboratories, Detroit Mich.) in paraffin oil (Crescent Chemical Co., Hauppauge, N.Y.). *Mycobacteria* were grounded in a mortar to fine powder and suspended in paraffin oil (10 mg/ml). The suspension was dispersed evenly just before injection of 0.05 ml at the base of tail. Severity of inflammation was monitored by measuring the volume of hind-paws using volume displacement technique. The extent of inflammation was calculated as increase in paw volume compared to Day 0. In addition, body weight was measured daily.

OPG Treatment and DEXA Bone Mass Measurement

Male Lewis (normal and adjuvant-induced) rats received varying doses of OPG-Fc (22–194) by subcutaneous daily injection (See graphs below for dosing) from day 9 to day 15. At the end of the experiment (day 16) bone mass measurement (DexaScans) of the tibiotarsal region was performed with a Hologic QDR 4500 dual-energy x-ray absorptiometer.

Statistical Analysis

All results were expressed as the mean±standard deviation of the mean. The p value of 0.05 was used in the calculation to determine whether there were any significant differences between any two groups. Statistical significance of difference was assessed by analysis of variance based on a Mann Whitney U test using Statsoft software (Statsoft, Tulsa, Okla.).

Results
OPG-Fc Inhibits Loss of Bone Mineral Density in Adjuvant Arthritis

To study the effects of OPG-Fc on BMD in adjuvant arthritis, paws from two experiments were analyzed by DEXA. The results of BMD measurements on the tibiotarsal region are shown in FIGS. 30A and 30B. Bone protective effects were observed in rats with adjuvant-arthritis treated with OPG-Fc via subcutaneous daily injection (from day 9 to day 15 after *mycobacteria* injection). Treatment with OPG-Fc at 4, 1, 0.25, 0.06, 0.016, and 0.004 mg/kg showed 100%, 100%, 100%, 86%, 22, and 22% inhibition of bone mineral density loss respectively. Treatment of the intermediate and high doses of OPG-Fc (4–0.06 mg/kg) showed a statistically significant difference in BMD when compared to the OPG placebo treated control group (P<0.05).

However, treatment with OPG-Fc (at all doses) had no statistically significant effect on the severity of inflammation (FIGS. 31A and 31B, AUC) or loss of body weight (data on file).

Conclusion

In conclusion, the results demonstrate that OPG-Fc have great efficacy in preventing bone density loss in the tibiotarsal region in arthritic rats. The inhibitory effects of OPG-Fc against bone changes occurred without any anti-inflammatory actions.

EXAMPLE 14

Combination Treatment with OPG-Fc and sTNF-RI on Adjuvant Arthritis in Male Lewis Rats Male Lewis rats were injected with 0.5 mg heat-killed *Mycobacterium tuberculosis* H37Ra in mineral oil at the base of the tail. Rats were monitored for paw swelling and weight loss. Arthritis (paw swelling) developed after about 10 days. Paw swelling was calculated daily relative to paw volume on day 9 (beginning of treatment) and the area under the curve (AUC) from day 9 to 15 is given in the graph (FIG. 31A). On day 16 at the end of the experiment DexaScans of the rats were taken and the calcaneus was evaluated for loss of bone mineral density (BMD) as shown in FIG. 31B.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. A method of treating bone loss, which comprises administering an IL-1 inhibitor, a TNF-α inhibitor, and an OPG protein, wherein "OPG protein" refers to a polypeptide comprising conserved residues from residues 22 to 185 of SEQ ID NOS: 121, 123, or 125.

2. The method of claim 1, wherein the TNF-α inhibitor comprises sTNFR-I, sTNFR-II, an sTNFR fragment, or sTNFR-Fc, wherein "sTNFR" refers to sTNFR-I or sTNFR-II.

3. The method of claim 2, wherein the sTNFR fragment is a 2.6 kD sTNFR-I fragment.

4. The method of claim 3, wherein the sTNFR-I fragment comprises 30 kD PEG.

5. The method of claim 1, wherein the TNF-α inhibitor comprises 30 kD PEG-sTNFR-I.

6. The method of claim 1, wherein the TNFα inhibitor comprises sTNFR-II linked to an Fc region.

7. The method of claim 1, wherein the TNF-α inhibitor is etanercept.

8. The method of claim 1, wherein the OPG protein is OPG-Fc.

9. The method of any of claims 1 to 8, wherein the bone loss results from rheumatoid arthritis.

10. The method of any of claims 1 to 8, wherein the bone loss results from multiple sclerosis.

11. The method of any of claims 1 to 8, wherein the bone loss results from osteoporosis.

12. The method of any of claims 1 to 8, wherein the bone loss results from osteomyelitis.

13. The method of claim 1, wherein the OPG protein comprises residues 22 to 185 of SEQ ID NO: 121.

14. The method of claim 1, wherein the OPG protein comprises residues 22 to 185 of SEQ ID NO: 123.

15. The method of claim 1, wherein the OPG protein comprises residues 22 to 185 of SEQ ID NO: 125.

* * * * *